US012234299B2

(12) United States Patent
Mignolet et al.

(10) Patent No.: US 12,234,299 B2
(45) Date of Patent: Feb. 25, 2025

(54) PEPTIDES FOR INDUCING BACTERIOCIN SYNTHESIS AND METHODS TO IDENTIFY AND/OR SELECT AND/OR OPTIMIZE THE SAME

(71) Applicants: SYNGULON S.A., Seraing (BE); Université catholique de Louvain, Louvain-la-neuve (BE)

(72) Inventors: Johann Mignolet, Saint-Gérard (BE); Pascal Hols, Vedrin (BE); Laura Ledesma García, Ixelles (BE)

(73) Assignees: SYNGULON S.A., Seraing (BE); Université catholique de Louvain, Louvain-la-Neuve (BE)

( * ) Notice: Subject to any disclaimer, the term of this patent is extended or adjusted under 35 U.S.C. 154(b) by 458 days.

(21) Appl. No.: 17/309,375

(22) PCT Filed: Nov. 22, 2019

(86) PCT No.: PCT/EP2019/082242
§ 371 (c)(1),
(2) Date: May 21, 2021

(87) PCT Pub. No.: WO2020/104662
PCT Pub. Date: May 28, 2020

(65) Prior Publication Data

US 2022/0017573 A1 Jan. 20, 2022

(30) Foreign Application Priority Data

Nov. 22, 2018 (EP) .................................... 18207694

(51) Int. Cl.
*C07K 7/06* (2006.01)
*C07K 1/06* (2006.01)
*C07K 14/195* (2006.01)

(52) U.S. Cl.
CPC .............. *C07K 7/06* (2013.01); *C07K 14/195* (2013.01); *C07K 1/061* (2013.01)

(58) Field of Classification Search
None
See application file for complete search history.

(56) References Cited

U.S. PATENT DOCUMENTS 7,662,592 B2 2/2010 Stern et al.

OTHER PUBLICATIONS

International Search Report Dated Jan. 22, 2020 in International Application No. PCT/EP2019/082242 In 11 pages.

Svetoch, Edward A et al., "Inducer Bacteria, Unique Signal Peptides, and Low-Nutrient Media Stimulate in Vitro Bacteriocin Production by *Lactobacillus* spp. and *Enterococcus* spp. Strains", Journal of Agricultural and Food Chemistry, vol. 58, No. 10, pp. 6033-6038, 2010.

Database UniProt [Online] May 1, 2000 (May 1, 2000), "SubName: Full=ORF10S {ECO:0000313: EMBL:BAA85070.1}; Flags: Fragment;", XP002790693, retrieved from EBI accession No. UniProt:Q9S0U6 Database accession No. Q9S0U6 sequence.

Database UniProt [Online] Aug. 30, 2017 (Aug. 30, 2017), "SubName: Full=PH domain-containing protein {ECO:0000313:EMBL:SMQ79867.1};", XP002790691, retrieved from EBI accession No. UniProt:A0A1Y6FVS5 Database accession No. A0A1Y6FVS5 sequence.

Database UniProt [Online] Jul. 18, 2018 (Jul. 18, 2018), "SubName: Full=TIGR03758 family integrating conjugative element protein {ECO:0000313: EMBL:POV42023.1};", XP002790692, retrieved from EBI accession No. UniProt:A0A2S4STJ7 Database accession No. A0A2S4STJ7 sequence.

Database UniProt [Online] Apr. 1, 2015 (Apr. 1, 2015), "SubName: Full=Uncharacterized protein {ECO:0000313: EMBL:KIL79283.1};", XP002790700, retrieved from EBI accession No. UniProt:A0A0C2YCN2 Database accession No. A0A0C2YCN2 sequence.

Mignolet, Johann et al: "Circuitry Rewiring Directly Couples Competence to Predation in the Gut Dweller *Streptococcus salivarius*", Cell Reports, vol. 22, No. 7, pp. 1627-1638, 2018.

Franz C M et al.: "Simple Method To Identify Bacteriocin Induction Peptides and to Auto-Induce Bacteriocin Production at Low Cell Density", FEMS Microbiology Letters, Wiley-Blackwell Publishing Ltd, GB, vol. 186, No. 2, pp. 181-185, 2000.

Database UniProt [Online] Apr. 12, 2017 (Apr. 12, 2017), "SubName: Full=Uncharacterized protein {ECO:0000313:EMBL:SDC97056.1};", XP002790694, retrieved from EBI accession No. UniProt:A0A1G6QZH3 Database accession No. A0A1G6QZH3 sequence.

Database UniProt [Online] Mar. 15, 2017 (Mar. 15, 2017), "RecName: Full=Putative fluoride ion transporter CrcB {ECO:0000256:HAMAP-Rule:MF 00454};", XP002790695,—retrieved from EB accession No. UniProt:A0A1M5S5D2 Database accession No. A0A1M5S5D2 sequence.

Database UniProt [Online] Nov. 7, 2018 (Nov. 7, 2018), "SubName: Full=DUF805 domain-containing protein {ECO:0000313:EMBL:AXS39116.1};", XP002790696, retrieved from EBI accession No. UniProt:A0A346QY07 Database accession No. A0A346QY07 sequence.

Database UniProt [Online] May 14, 2014 (May 14, 2014), "SubName: Full=Uncharacterized protein {ECO:0000313: EMBL:GAI68768.1}; Flags: Fragment;", XP002790697, retrieved from EBI accession No. UniProt:X1QKI4 Database accession No. X1QKI4 sequence.

Database UniProt [Online] Jul. 24, 2013 (Jul. 24, 2013), "SubName: Full=Uncharacterized protein {ECO:0000313:EMBL:CDC57668.1};", XP002790698, retrieved from EBI accession No. UniProt:R6S903 Database accession No. R6S903 sequence.

(Continued)

*Primary Examiner* — Thomas S Heard
(74) *Attorney, Agent, or Firm* — KNOBBE, MARTENS, OLSON & BEAR, LLP

(57) ABSTRACT

Described herein is a peptide or peptidomimetic with a length of at least 6 residues comprising, consisting essentially of, or consisting of the sequence motif $Xaa_1$-Trp-$Xaa_2$-$Xaa_3$-$Xaa_4$-$Xaa_5$ (SEQ ID NO:1), wherein: $Xaa_1$ represents an aromatic residue (Phe, Tyr, Trp, His), Cys or Ser; $Xaa_2$, $Xaa_3$ and $Xaa_4$ represent any residue; and $Xaa_5$ represents Gly, lie or Val.

14 Claims, 13 Drawing Sheets

Specification includes a Sequence Listing.

(56) References Cited

OTHER PUBLICATIONS

Database UniProt [Online] Oct. 10, 2018 (Oct. 10, 2018), "RecName: Full=3',5'-cyclic adenosine monophosphate phosphodiesterase CpdA {ECO:0000256: HAMAP-Rule:MF 00905}; Short=3',5'-cyclic AMP phosphodiesterase {ECO:0000256: HAMAP-Rule:MF 00905}; Short= cAMP phosphodiesterase {ECO:0000256:HAMAP-Rule:MF 00905}; EC=3.1.4.53—{ECO: 0000256: HAMAP-Rule:MF 00905};", XP002790699,—retrieved from EBI accession No. UniProt:A0A328X1S3 Database accession No. A0A328X1S3 sequence.
Database UniProt [Online] Jun. 27, 2006 (Jun. 27, 2006), "SubName: Full=Cytochrome C oxidase subunit IV {ECO:0000313:EMBL:ABF65019.1};", XP002790701, retrieved from EBI accession No. UniProt:Q1GE97 Database accession No. Q1GE97 sequence.
Database UniProt [Online] Jan. 31, 2018 (Jan. 31, 2018), "SubName: Full=Uncharacterized protein {ECO:0000313:EMBL:PIE05801. 1}; Flags: Fragment;", XP002790702, retrieved from EBI accession No. UniProt:A0A2G613RI Database accession No. A0A2G613RI sequence.
Database UniProt [Online] Oct. 25, 2017 (Oct. 25, 2017), "SubName: Full=Uncharacterized protein {ECO:0000313:EMBL:ASV17796. 1};", XP002790703, retrieved from EBI accession No. UniProt:A0A223U4A6 Database accession No. A0A223U4A6 sequence.
Database UniProt [Online] Mar. 15, 2017 (Mar. 15, 2017), "SubName: Full=Uncharacterized protein {ECO:0000313:EMBL:OJU66760. 1};", XP002790704, retrieved from EBI accession No. UniProt:A0A1M3AIY8 Database accession No. A0A1M3AIY8 sequence.
Database UniProt [Online] Dec. 20, 2017 (Dec. 20, 2017), "SubName: Full=Tellurite resistance protein TehA-like permease {ECO:0000313:EMBL:PFG32060.1};", XP002790705, retrieved from EBIaccession No. UniProt:A0A2A9EIJ4 Database accession No. A0A2A9E1J4 sequence.
Database UniProt [Online] Nov. 7, 2018 (Nov. 7, 2018), "SubName: Full=Uncharacterized protein {ECO:0000313:EMBL:HAZ30760. 1}; Flags: Fragment;", XP002790706, retrieved from EBI accession No. UniProt:A0A351JWU0 Database accession No. A0A351JWU0 sequence.
Database UniProt [Online] Mar. 4, 2015 (Mar. 4, 2015), "SubName: Full=Uncharacterized protein {ECO:0000313:EMBL:JAD30899. 1};", XP002790707, retrieved from EBI accession No. UniProt:A0A0A8YUT1 Database accession No. A0A0A8YUT1 sequence.
Database UniProt [Online] May 29, 2013 (May 29, 2013), "SubName: Full=Uncharacterized protein {ECO:0000313:EMBL:CCO29484. 1};", XP002790708, retrieved from EBI accession No. Uni Prot:M5BQK2 Database accession No. M5BQK2 sequence.
Database UniProt [Online] Jan. 18, 2017 (Jan. 18, 2017), "SubName: Full=Uncharacterized protein {ECO:0000313:EMBL:ODN65441. 1};", XP002790709, retrieved from EBI accession No. UniProt:A0A1E3GPU9 Database accession No. A0A1E3GPU9 sequence.
Database UniProt [Online] Sep. 7, 2016 (Sep. 7, 2016), "SubName: Full=Uncharacterized protein {ECO:0000313:EMBL:OAG75443. 1};", XP002790710, retrieved from EBI accession No. UniProt:A0A177G535 Database accession No. A0A177G535 sequence.
Database UniProt [Online] Jan. 31, 2018 (Jan. 31, 2018), "SubName: Full=Uncharacterized protein {ECO:0000313:EMBL:PIC05503. 1};", XP002790711, retrieved from EBI accession No. UniProt:A0A2G5RS15 Database accession No. A0A2G5RS15 sequence.
Database UniProt [Online] May 14, 2014 (May 14, 2014), "SubName: Full=Uncharacterized protein {ECO:0000313:EMBL:GAI10111. 1};", XP002790712, retrieved from EBI accession No. UniProt:X1LWE7 Database accession No. X1LWE7 sequence.
Database UniProt [Online] Apr. 25, 2018 (Apr. 25, 2018) "SubName: Full=DoxX-like family protein {ECO:0000313: EMBL:PJZ25793. 1};", XP002790713, retrieved from EBI accession No. UniProt:A0A2M9XDL6 Database accession No. A0A2M9XDL6 sequence.
Database UniProt [Online] Jan. 31, 2018 (Jan. 31, 2018), "SubName: Full=Uncharacterized protein {EC0:0000313:EMBL:MAR57216. 1};", XP002790714, retrieved from EBI accession No. UniProt: A0A2E0EP50 Database accession No. A0A2EOEP50 sequence.
DATABASE UniProt [Online] Mar. 15, 2017 (Mar. 15, 2017), "SubName: Full=Uncharacterized protein {EC0:0000313: EMBL:SI019486.1};", XP002790715, retrieved from EBI accession No. UniProt:A0A1N6HIC8 Database accession No. A0A1N6HIC8sequence.
Database UniProt [Online] Apr. 16, 2014 (Apr. 16, 2014), "SubName: Full=D-alanine/D-serine/glycine permease {EC0:0000313:EMBL:EUK19008.1};", XP002790716, retrieved from EBI accession No. UniProt:W7DXS3 Database accession No. W7DXS3 sequence.
Anonymous: "DOE-type integrase/transposase/recombinase [Polyangium spumosum]—Protein—NCBI", Nov. 18, 2019 (Nov. 18, 2019), XP055660871, Retrieved from the Internet: URL:https//www.ncbi.nlm.nih.gov/protein/1 775721868?sat=5&satkey=410645985 [retrieved on Jan. 22, 2020].
Mignolet, Johann et al: "Subtle Selectivity in a Pheromone Sensor Triumvirate Desynchronizes Competence and Predation in a Human Gut Commensal", ELI FE, pp. 1-23, 2019.

PEPTIDES FOR INDUCING BACTERIOCIN SYNTHESIS AND METHODS TO IDENTIFY AND/OR SELECT AND/OR OPTIMIZE THE SAME

CROSS REFERENCE TO RELATED APPLICATIONS

This application is a U.S. national phase application under 35 U.S.C. § 371 of International Application No. PCT/EP2019/082242, filed on Nov. 22, 2019, which claims the benefit of European Application No. 18207694.3, filed Nov. 22, 2018. The content of each of these related applications is hereby incorporated in its entirety by reference, for all purposes.

REFERENCE TO SEQUENCE LISTING

The present application is being filed along with a Sequence Listing in electronic format. The Sequence Listing is provided as a file entitled SEQLIST_NLO003_001APC.txt, created May 18, 2021 which is 350 KB in size. The information in the electronic format of the Sequence Listing is incorporated herein by reference in its entirety.

FIELD

Aspects herein relate generally to peptides and peptide-responsive regulators. More particularly, some aspects herein relate to peptides, culture media, compositions, methods and uses for inducing bacteriocin production in a microbial organism. Some other aspects herein relate to a method for identifying, selecting and/or optimizing peptide ligands of peptide-responsive regulators.

BACKGROUND

Populations of microbial organisms are involved in maintaining the health and metabolic functions of multicellular organisms, for example as the microbiota associated with the gut and skin of humans, or the roots of the plants. In addition, populations of microbial organisms are used for various industrial processes. Accordingly, tuning populations of microbial organisms, for example to reduce or eliminate or neutralize undesired microbial organisms, can be useful for maintaining robustness and consistency of industrial processes and maintaining the health of tissues that comprise microbial organisms. For example, WO 2015/024855 describes systems, methods and microbial cells for the controlled growth of microorganisms.

Extensive and widespread use of antimicrobial drugs to reduce or eliminate or neutralize undesired microbial organisms has led to the emergence of resistant strains of microbial organisms. These microbial organisms are no longer susceptible to the currently available antimicrobial drugs. Bacteriocins are proteinaceous or peptidic toxins produced by microbial organisms, typically to inhibit the growth of similar or closely related strain(s). Bacteriocins are able to overcome at least some of the drawbacks associated with antimicrobials, as they are still active against antimicrobial-resistant microbial organisms.

It is well known that regulation of bacteriocin production is tightly coupled to regulation of competence. Competence has its customary and ordinary meaning as understood by one of skill in the art in view of this disclosure. It refers to a physiological state enabling bacteria to bind and take up high-molecular-weight exogenous DNA (transformation). Concomitant induction of competence upon inducing bacteriocin production may be disadvantageous, as it places a fitness burden on the microbial population, and increases the likelihood of unwanted genetic changes occurring in the microbial organisms in the population. For example, competence may increase the spread of antibiotic resistance genes and/or bacteriocin immunity genes.

Accordingly, to expand the currently available arsenal of compounds that can be used to tune populations of microbial organisms, there is a need for compounds which can activate bacteriocin production in microbial cells, preferably without concomitantly inducing competence to avoid the disadvantages thereof as indicated above.

SUMMARY

In a first aspect, there is provided a peptide or peptidomimetic with a length of at least 6 residues comprising, consisting essentially of, or consisting of the sequence motif $Xaa_1$-Trp-$Xaa_2$-$Xaa_3$-$Xaa_4$-$Xaa_5$ (SEQ ID NO: 1), wherein:

- $Xaa_1$ represents an aromatic residue (Phe, Tyr, Trp, His), Cys or Ser;
- $Xaa_2$, $Xaa_3$ and $Xaa_4$ represent any residue; and
- $Xaa_5$ represents Gly, Ile or Val.

In a preferred embodiment, there is provided a peptide or peptidomimetic able to induce bacteriocin production in a microbial organism with a length of at least 6 residues comprising, consisting essentially of, or consisting of the sequence motif $Xaa_1$-Trp-$Xaa_2$-$Xaa_3$-$Xaa_4$-$Xaa_5$ (SEQ ID NO:1), wherein the sequence motif is located at the C-terminus of said peptide or peptidomimetic or located so that it is followed by 1, 2, 3, 4 or 5 additional C-terminal residues, and wherein:

- $Xaa_1$ represents an aromatic residue (Phe, Tyr, Trp, His), Cys or Ser;
- $Xaa_2$, $Xaa_3$ and $Xaa_4$ represent any residue; and
- $Xaa_5$ represents Gly, Ile or Val.

Preferably, the sequence motif is located at the C-terminus of said peptide or peptidomimetic. Preferably, the peptide or peptidomimetic fulfills at least one or at least two or all of the following conditions:

- the sequence motif is preceded immediately by a Pro residue
- $Xaa_1$ represents an aromatic residue (Phe, Tyr, Trp, His)
- $Xaa_5$ represents Gly The sequence motif is preferably Phe-Trp-Leu-Val-Leu-Gly (SEQ ID NO: 2). Preferably, the peptide or peptidomimetic comprises, consists essentially of, or consists of any of the following sequences:

```
                                   (SEQ ID NO: 3)
Ala-Phe-Trp-Leu-Ile-Leu-Gly

                                   (SEQ ID NO: 4)
Thr-Trp-Trp-Leu-Ile-Leu-Gly

                                   (SEQ ID NO: 5)
Pro-Tyr-Trp-Leu-Gly-Leu-Gly

                                   (SEQ ID NO: 6)
Pro-Trp-Trp-Val-Ser-Val-Gly

                                   (SEQ ID NO: 7)
Pro-Phe-Trp-Leu-Ile-Leu-Gly

                                   (SEQ ID NO: 8)
Pro-Tyr-Trp-Leu-Leu-Ile-Gly
```

-continued (SEQ ID NO: 9)
Pro-Phe-Trp-Leu-Val-Leu-Gly (SEQ ID NO: 10)
Pro-Phe-Trp-Val-Val-Ala-Gly (SEQ ID NO: 11)
Pro-Phe-Trp-Leu-Ser-Val-Gly (SEQ ID NO: 12)
Pro-Tyr-Trp-Leu-Asp-Met-Gly (SEQ ID NO: 13)
Pro-Tyr-Trp-Val-Thr-Met-Gly (SEQ ID NO: 14)
Pro-Tyr-Trp-Val-Val-Leu-Gly (SEQ ID NO: 15)
Pro-Ser-Trp-Leu-Val-Val-Gly (SEQ ID NO: 16)
Pro-His-Trp-Ile-Thr-Ile-Gly (SEQ ID NO: 17)
Pro-His-Trp-Cys-Val-Leu-Gly (SEQ ID NO: 18)
Pro-Phe-Trp-Leu-Ala-Leu-Gly (SEQ ID NO: 19)
Pro-Phe-Trp-Cys-Val-Leu-Gly (SEQ ID NO: 20)
Phe-Trp-Val-Glu-Leu-Gly (SEQ ID NO: 21
Tyr-Trp-Ala-Thr-Thr-Gly-Leu (SEQ ID NO: 22)
Trp-Trp-Gly-Thr-Met-Ile (SEQ ID NO: 23)
Pro-Tyr-Trp-Leu-Cys-Ile-Ile (SEQ ID NO: 24)
Thr-Cys-Trp-Val-Cys-Ile-Val (SEQ ID NO: 749)
Leu-Ala-Phe-Trp-Asp-Ser-Leu-Gly Preferably, the peptide or peptidomimetic is able to induce bacteriocin production in a microbial organism, preferably without concomitantly inducing competence.

In a preferred embodiment, the peptide or peptidomimetic has a maximum length of 30 amino acids. In another preferred embodiment, the peptide or peptidomimetic has a maximum length of 20 amino acids. In another preferred embodiment, the peptide or peptidomimetic has a maximum length of 10 amino acids.

In a second aspect, there is provided a polypeptide able to induce bacteriocin production in a microbial organism, preferably without concomitantly inducing competence, comprising a peptide or peptidomimetic as described in the first aspect, wherein the peptide or peptidomimetic can be released from the polypeptide by natural, chemical or biological peptide hydrolysis.

In a third aspect, there is provided a culture medium comprising a peptide or peptidomimetic as described in the first aspect. Also provided is a culture medium comprising a peptide or peptidomimetic according to the first aspect and/or a polypeptide according to the second aspect. The culture medium may further comprise a signaling molecule and/or a quenching molecule and/or an antimicrobial peptide and/or a bacteriocin.

In a fourth aspect, there is provided a composition for inducing bacteriocin production in a microbial organism, comprising a peptide or peptidomimetic as described in the first aspect and a solvent. Also provided is a composition for inducing bacteriocin production in a microbial organism, comprising a peptide or peptidomimetic according to the first aspect and/or polypeptide according to the second aspect. The composition may further comprise a signaling molecule and/or a quenching molecule and/or an antimicrobial peptide and/or a bacteriocin.

In a fifth aspect, there is provided a microbial organism able to produce and/or secrete a peptide or peptidomimetic according to the first aspect and/or a polypeptide according to the second aspect.

In a sixth aspect, there is provided a method for inducing bacteriocin production in a microbial organism, preferably without concomitantly inducing competence, comprising administering a peptide or peptidomimetic according to the first aspect to the microbial organism, and/or culturing the microbial organism in a culture medium according to the third aspect, and/or administering a composition according to the fourth aspect to the microbial organism. The bacteriocin production in the microbial organism can neutralize a second, undesired microbial organism. According to some embodiments, the microbial organism is a Gram-positive bacterium, for example a lactic acid bacterium, such as a *Streptococcus* species, such as *Streptococcus salivarius*.

Also provided is a method for inducing bacteriocin production in a microbial organism, preferably without concomitantly inducing competence, comprising administering a peptide or peptidomimetic according to the first aspect and/or a polypeptide according to the second aspect to the microbial organism, and/or culturing the microbial organism in a culture medium according to the third aspect, and/or administering a composition according to the fourth aspect to the microbial organism. Also provided is a method for inducing bacteriocin production in a first microbial organism, preferably without concomitantly inducing competence, comprising administering to the first microbial organism a second microbial organism according to the fifth aspect and/or co-culturing the first microbial organism with the second microbial organism according to the fifth aspect. Preferably, the bacteriocin-producing microbial organism belongs to the microbiota. Preferably the bacteriocin-producing microbial organism also produces a desired product. Preferably, the bacteriocin-producing microbial organism is a Gram-positive bacterium, for example a lactic acid bacterium, such as a *Streptococcus* species, such as *Streptococcus salivarius*. Preferably the undesired microbial organism is a pathogenic microbial organism or a contaminant.

In a seventh aspect, there is provided a method for identifying, selecting, and/or optimizing peptide ligands of peptide-responsive transcriptional regulators, comprising the following steps:

- generating a library of randomized genes, wherein said genes are operably linked to an inducible promoter, inducible by an inducer molecule;
- transforming the library into a microbial organism which comprises a nucleic acid encoding a selectable marker conferring resistance to a selection agent, operably linked to a promoter which is controlled by the peptide-responsive transcriptional regulator; and
- selecting or enriching positive clones by growing the microbial organism in the presence of the inducer molecule and the selection agent.

Preferably, the nucleotide sequences of the randomized genes comprise both fixed-sequence codons and degenerate codons.

Description

The present inventors have surprisingly developed a method, by which they have identified a group of peptide ligands inducing a unique peptide-responsive regulator of bacteriocin production. Particularly, as elaborated in the experimental part, the present inventors have surprisingly found that a peptide or peptidomimetic according to the invention can act as a ligand of the peptide-responsive regulators ScuR and/or SarF, thereby inducing the production of a group of class II type bacteriocins without necessarily inducing competence. Accordingly, the aspects and embodiments of the present invention as described herein solve at least some of the problems and needs as discussed herein.

Peptide

In a first aspect, there is provided a peptide or peptidomimetic with a length of at least 6 residues comprising, consisting essentially of, or consisting of the sequence motif $Xaa_1$-Trp-$Xaa_2$-$Xaa_3$-$Xaa_4$-$Xaa_5$ (SEQ ID NO:1), wherein:

$Xaa_1$ represents an aromatic residue (Phe, Tyr, Trp, His), Cys or Ser;

$Xaa_2$, $Xaa_3$ and $Xaa_4$ represent any residue; and $Xaa_5$ represents Gly, Ile or Val.

The sequence motif $Xaa_1$-Trp-$Xaa_2$-$Xaa_3$-$Xaa_4$-$Xaa_5$ may also be denoted as a sequence pattern or, simply, a sequence. A "sequence motif" or "sequence pattern" has its customary and ordinary meaning as understood by one of skill in the art in view of this disclosure. It refers to an amino-acid (or nucleotide) sequence that recurs, with a certain degree of variation, on several sites of a molecule or several different molecules and has, or is conjectured to have or is assumed to be linked to, a biological significance or exhibit a biological activity as described herein. A biological significance or biological activity of the peptide of the invention is preferably to be able to induce bacteriocin production in a microbial organism, more preferably without concomitantly inducing competence.

In some embodiments, a peptide or peptidomimetic according to the invention may have a length of at least 6, at least 7, at least 8, at least 9, at least 10, at least 11, at least 12, at least 13, at least 14, at least 15, at least 16, at least 17, at least 18, at least 19 or at least 20 residues, or at least 25 residues, or at least 30 residues, or at least 35 residues, or at least 40 residues, or at least 45 residues, or at least 50 residues. Accordingly, in other embodiments, a peptide or peptidomimetic according to the invention may have a minimal length of 6, 7, 8, 9, 10, 11, 12, 13, 14, 15, 16, 17, 18, 19 or 20 residues and a maximal length of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 residues.

As used herein, a "peptide" should be understood to encompass any peptide, regardless of whether it is generated through recombinant protein synthesis, purified from a native producer microbial organism or generated by means of chemical peptide synthesis. In some embodiments, the peptide comprises, consists essentially of, or consists of a non-naturally occurring amino acid sequence, a naturally occurring amino acid sequence, or a combination of these. Accordingly, there is also provided a vector comprising a nucleic acid encoding a peptide according to the invention. The term "vector" as used herein has its customary and ordinary meaning as understood by one of skill in the art in view of this disclosure. It refers to a nucleic acid molecule, such as a plasmid, bacteriophage or animal virus, capable of introducing a heterologous nucleic acid sequence into a host cell. Further provided is a recombinant host cell comprising a vector according to the invention. The recombinant host cell can be a microbial host cell. Exemplary microbial host cells that can be used in this context are described later herein.

A "synthetic peptide" has its customary and ordinary meaning as understood by one of skill in the art in view of this disclosure. It refers to a peptide which is generated by means of chemical peptide synthesis. Accordingly, in some embodiments, a peptide may be a synthetic peptide. A synthetic peptide according to the invention may be prepared or synthesized using conventional methods that are well known in the art. For instance, peptides can be synthesized by commonly used solid-phase synthesis methods such as those that involve a tert-butyloxycarbonyl protecting group (t-BOC) or fluorenylmethyloxycarbonyl protecting group (FMOC) for protection of alpha-amino groups. In such methods, amino acids are added sequentially to a growing amino acid chain. Such methods are, for instance, described in Merrifield (1963), J. Am. Chem. Soc. 85(14): 2149-2154; and Atherton & Sheppard, Solid Phase Peptide Synthesis: A practical Approach (IRL Press, Oxford, UK, 1999), both of which are incorporated herein by reference. A peptide may further be modified by natural processes, such as post-translational processing, or by chemical modification techniques. Such modifications may be inserted in the peptide at any location, including in the backbone, amino acid side-chains and at the N- or C-terminus. Multiple types of modifications may occur in a single peptide, or a peptide may comprise several modifications of a single type. Illustrative but non-limiting examples of modifications are alkylation, acetylation, amidation, acylation, phosphorylation, methylation, demethylation, ADP-ribosylation, disulfide bond formation, ubiquitination, gamma-carboxylation, glycosylation, hydroxylation, iodination, oxidation, pegylation, succinylation and sulfation.

As used herein, a "peptidomimetic" is understood to encompass all compounds whose essential elements (pharmacophore) mimic a natural peptide and which retain the ability to interact with the biological target and produce the same biological effect. In some embodiments, the peptidomimetic comprises, consists essentially of, or consists of a non-naturally occurring amino acid sequence. In an embodiment, the peptidomimetic does not occur in nature and is considered to be man-made. They typically arise either from modification of an existing peptide, or by designing similar systems that mimic peptides, such as peptoids and β-peptides. Structures and synthesis of peptidomimetics are for instance described in William D. Lubell (ed.), Peptidomimetics I and II, Topics in Heterocyclic Chemistry (Book 48), Springer 1st ed. 2017, XVI, 310 p, which is incorporated herein by reference. Modification of an existing peptide may be the result of natural processes, such as post-translational processing, or chemical modification techniques. In general, a peptidomimetic typically refers to a compound containing non-peptidic structural elements. Typical but non-limiting examples of non-peptidic structural elements are modifications of one or more existing amino acids, conformational restraints, cyclization of the polypeptide, isosteric replacement or other modifications. In some embodiments, a peptidomimetic may contain one or more or all substitutions of an amino acid by the corresponding D-amino acid. As used herein, "corresponding D-amino acid" denotes the D-amino acid counterpart of an L-amino acid. In some embodiments, a peptidomimetic may also contain non-natural amino acids. As used herein, "non-natural amino acid" has its customary and ordinary meaning as understood by one of skill in the art in view of this disclosure. It refers to non-genetically encoded amino acids, irrespective of whether they appear in nature or not. Non-natural amino acids that can be present in a peptidomimetic as described herein include: β-amino acids; p-acyl-L-phenylalanine; N-acetyl lysine; O-4-allyl-L-tyrosine; 2-aminoadipic acid; 3-aminoadipic acid; beta-alanine; 4-tert-butyl hydrogen 2-azidosuccinate; beta-amino-propionic acid; 2-aminobutyric acid; 4-aminobutyric acid; 2,4-diamino butyric acid; 6-aminocaproic acid; 2-aminoheptanoic acid; 2-aminoisobutyric acid; 3-aminoisobutyric acid; 2-aminopimelic acid; p-aminophenylalanine; 2,3-diaminobutyric acid; 2,3-diamino propionic acid; 2,2'-diaminopimelic acid; p-amino-L-phenylalanine; p-azido-L-phenylalanine; D-allyl glycine; p-benzoyl-L-phenylalanine; 3-benzothienyl alanine p-bromophenylalanine; t-butylalanine; t-butylglycine; 4-chlorophenylalanine; cyclohexylalanine; cysteic acid; D-citrulline; thio-L-citrulline; desmosine; epsilon-amino hexanoic acid; N-ethylglycine; N-ethylasparagine; 2-fluorophenylalanine; 3-fluorophenylalanine; 4-fluorophenylalanine; homoarginine; homocysteine; homoserine; hydroxy lysine; alio-hydroxy lysine; 3-(3-methyl-4-nitrobenzyl)-L-histidine methyl ester; isodesmosine; allo-isoleucine; isopropyl-L-phenylalanine; 3-methyl-phenylalanine; N-methylglycine; N-methylisoleucine; 6-N-methyllysine; O-methyl-L-tyrosine; N-methylvaline; methionin sulfoxide; 2-napthylalanine; L-3-(2-naphthyl)alanine; isoserine; 3-phenylserine; norvaline; norleucine; 5,5,5-trifluoro-DL-leucine; ornithine; 3-chloro-tyrosine; N5-carbamoylornithine; penicillamine; phenylglycine; piperidinic acid; pyridylalanine; 1,2,3,4-tetrahydro-isoquinoline-3-carboxylic acid; beta-2-thienylalanine; γ-carboxy-DL-glutamic acid; 4-fluoro-DL-glutamic acid; D-thyroxine; allo-threonine; 5-hydroxy-tryptophan; 5-methoxy-tryptophan; 5-fluoro-tryptophan; 3-fluoro-valine. In some embodiments, a natural amino acid of a peptide or peptidomimetic according to the invention is substituted by a corresponding non-natural amino acid. As used herein, a "corresponding non-natural amino acid" refers to a non-natural amino acid that is a derivative of the reference natural amino acid. For instance, a natural amino acid can be substituted by the corresponding β-amino acid, which have their amino group bonded to the β-carbon rather than the α-carbon. According to some embodiments, a peptide or peptidomimetic of the invention can further be provided with a targeting moiety. It is known that peptidomimetics are able to circumvent some of the disadvantages associated with natural peptides: e.g. stability against proteolysis (duration of activity) and poor bioavailability. Certain other properties, such as receptor selectivity or potency, often can be substantially improved.

As used herein, a "peptide or peptidomimetic" is understood to refer to a chain of a limited number of amino acids, generally between 2 and 50.

In a preferred embodiment, the sequence motif as described herein is located at the C-terminus of the peptide or peptidomimetic. In some other embodiments, the sequence motif as described herein may be located so that it is followed by 1, 2, 3, 4 or 5 additional C-terminal residues.

In some embodiments, a peptide or peptidomimetic as described herein does not comprise, consist essentially of, or consist of the amino acid sequence TNVTKSWWVLAGCNQWASNCNCGNVKGLT (SEQ ID NO: 751) as disclosed in U.S. Pat. No. 7,662,592.

In some embodiments, a peptide or peptidomimetic as described herein does not comprise, consist essentially of, or consist of the sequence VKGLT. In some embodiments, a peptide or peptidomimetic as described herein does not comprise a VKGLT sequence (SEQ ID NO: 752) at its C-terminus or at its C-terminus followed by 1, 2, 3, 4 or 5 additional C-terminal residues.

In some embodiments, a peptide or peptidomimetic according to the invention may be comprised in a polypeptide. In certain embodiments, the polypeptide can be processed by natural, chemical or biological peptide hydrolysis, including proteolysis mediated by recombinant or natural (endo- and exo-) proteases, in order to generate a peptide as described herein. Accordingly, in some embodiments there is provided a polypeptide able to induce bacteriocin production in a microbial organism, preferably without concomitantly inducing competence, comprising a peptide sequence as described herein, wherein the peptide or peptidomimetic can be released from the polypeptide by natural, chemical or biological peptide hydrolysis. Such polypeptide can be referred to as a "pro-polypeptide".

In some embodiments a "pro-polypeptide", i.e. a polypeptide able to induce bacteriocin production in a microbial organism, preferably without concomitantly inducing competence, comprising a peptide sequence as described herein may be a precursor peptide or peptidomimetic. Accordingly, in some embodiments there is provided a precursor peptide or peptidomimetic able to induce bacteriocin production in a microbial organism, preferably without concomitantly inducing competence, comprising a peptide or peptidomimetic as described herein, wherein the peptide or peptidomimetic can be released from the protein by natural, chemical or biological peptide hydrolysis. In some embodiments, a precursor peptide or peptidomimetic may comprise, consist essentially of, or consist of any of the sequences of SEQ ID NO: 3-24 and 749 followed by a tail of 1, 2, 3, 4, 5, 6, 7, 8, 9, 10 or more additional amino acids, for example a triple leucine tail. In some embodiments, a precursor peptide or peptidomimetic may comprise, consist essentially of, or consist of the sequence LAFWDSLGLLL (SEQ ID NO: 750).

In some embodiments, a polypeptide ("pro-polypeptide') or a precursor peptide or peptidomimetic as described herein may have a length of at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, or at least 50 residues. Accordingly, in other embodiments, a polypeptide ("pro-polypeptide") or a precursor peptide or peptidomimetic as described herein may have a minimal length of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 residues and a maximal length of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 residues. In some embodiments, a polypeptide ("pro-polypeptide') may have a length of at least 50, at least 75, at least 100, at least 125, at least 150, at least 175, at least 200, at least 250, at least 300, at least 350, at least 400, at least 450, at least 500, at least 600, at least 700, at least 800, at least 900, or at least 1000 residues.

In some embodiments, processing occurs in or by a microbial cell. In other embodiments, processing occurs in an animal or human host. In certain embodiments, a peptide or peptidomimetic according to the invention may be comprised in a polypeptide which is a "pro-polypeptide", further containing one or more other peptides with a specific activity separated by cleavage sites. As used herein, "cleavage site" has its customary and ordinary meaning as understood by one of skill in the art in view of this disclosure. It refers to a polypeptide sequence that mediates the cleavage of a polypeptide (for example by hydrolysis of a peptide bond) to separate a single polypeptide into two or more discrete polypeptides. In some embodiments, a cleavage site comprises, consists essentially of, or consists of a consensus polypeptide sequence for cleavage by a "cleavage enzyme," such as a peptidase. In some embodiments, the cleavage enzyme is a wild-type, a variant, or a synthetic cleavage enzyme, for example a wild-type, variant, or synthetic endopeptidase. In some embodiments, the cleavage sites are for a cleavage enzyme selected from the group consisting of: Arg-C proteinase, Asp-N endopeptidase, BNPS-Skatole, Caspase 1, Caspase 2, Caspase 3, Caspase 4, Caspase 5, Caspase 6, Caspase 7, Caspase 8, Caspase 9, Caspase 10, Chymotrypsin-high specificity, Clostripain (Clostridiopeptidase B), CNBr, Enterokinase, Factor Xa, Formic acid, Glutamyl endopeptidase, GranzymeB, Hydroxylamine, lodosobenzoic acid, LysC, Neutrophil elastase, NTCB (2-nitro-5-thiocyanobenzoic acid), Pepsin (pH 1.3), Pepsin (pH>2), Proline-endopeptidase, Proteinase K, Staphylococcal peptidase I, Thermolysin, Thrombin, or Trypsin. The one or more other peptides with a specific activity can be signal molecules and/or quenching molecules and/or antimicrobial peptides and/or bacteriocins as described herein. Upon processing, such pro-polypeptide releases the peptide or peptidomimetic according to the invention as well as the one or more other peptides with a specific activity. A possible advantage of a peptide or peptidomimetic according to the invention when it is comprised in a precursor peptide or peptidomimetic or in a polypeptide and can be released by natural, chemical or biological peptide hydrolysis, is that the released peptides are able to induce bacteriocins while precursor peptide or peptidomimetic or the full protein is not. Therefore, this constitutes an inducible or switchable system. In some embodiments, the inducible/switchable system may comprise, consist essentially of, or consist of a protease released in the environment (culture medium, microbiota, . . . ). In some embodiments, the inducible/switchable system may comprise, consist essentially of, or consist of a sensor protein directly or indirectly coupled to the activation of a transcriptional regulator. Activation of the transcriptional regulator would result in the net production/secretion of a protease that will cleave the precursor and release the active part of the inducibles peptide or peptidomimetic. The sensor may be capable to perceive stimuli from physico-chemical (temperature, pH, . . . ) changes in the culture condition or from the addition of biological or chemical compounds (preferentially sugar, peptides or peptidomimetics). Inducible promoters as described herein, such as xylose-, arabinose-, nickel-, nisin-, IPTG-, and pheromone-inducible promoters, may also be used. In some specific cases, the active peptide or peptidomimetic released might be the stimulus by itself, creating a positive feedback loop that promotes a rapid and sharp accumulation of the peptide or peptidomimetic in the environment (culture medium, microbiota, . . . ).

In a preferred embodiment, a peptide or peptidomimetic as described herein fulfills at least one or at least two or all of the following conditions:

the sequence motif is preceded immediately by a Pro residue;

$Xaa_1$ represents an aromatic residue (Phe, Tyr, Trp, His);

$Xaa_5$ represents Gly.

In some embodiments, if all of the above-defined conditions are fulfilled, a peptide or peptidomimetic according to the invention may thus comprise, consist essentially of, or consist of the sequence motif $Xaa_1$-Trp-$Xaa_2$-$Xaa_3$-$Xaa_4$-Gly (SEQ ID NO: 25), wherein:

$Xaa_1$ represents an aromatic residue (Phe, Tyr, Trp, His); and $Xaa_2$, $Xaa_3$ and $Xaa_4$ represent any residue.

In some embodiments, $Xaa_2$, $Xaa_3$ and $Xaa_4$ may be hydrophobic residues.

Sequence motifs may be represented by a consensus sequence: a single sequence consisting of the most commonly encountered residues at each site. Hence, a peptide or peptidomimetic according to an embodiment of the invention may comprise, consist essentially of, or consist of a sequence motif having the consensus sequence Phe-Trp-Leu-Val-Leu-Gly (SEQ ID NO: 2). Thus, in some embodiments, a peptide or peptidomimetic according to the invention may comprise, consist essentially of, or consist of the sequence motif Phe-Trp-Leu-Val-Leu-Gly (SEQ ID NO: 2). In some embodiments, the sequence motif Phe-Trp-Leu-Val-Leu-Gly (SEQ ID NO: 2) may contain amino acid substitutions at 1, 2, 3, 4 or up to 5 positions. Amino acid substitutions can be conservative amino acid substitutions, as described herein. Examples of suitable amino acid substitutions in this context include the substitution of Phe for Tyr, Trp or His, and/or the substitution of Gly for Val or Ile. In some embodiments, the sequence motif Phe-Trp-Leu-Val-Leu-Gly (SEQ ID NO: 2) may contain amino acid substitutions at 1, 2, 3, 4 or up to 5 positions, wherein Trp is not substituted. In some embodiments, the sequence motif Phe-Trp-Leu-Val-Leu-Gly (SEQ ID NO: 2) contains amino acid substitutions at 1, 2, 3, 4 or up to 5 positions, wherein Trp is not substituted and Gly is substituted by Val or Ile. In some embodiments, the sequence motif Phe-Trp-Leu-Val-Leu-Gly (SEQ ID NO: 2) may contain amino acid substitutions at 1, 2, 3 or up to 4 positions, wherein Trp and Gly are not substituted. In some embodiments, the sequence motif Phe-Trp-Leu-Val-Leu-Gly (SEQ ID NO: 2) may contain amino acid substitutions at 1, 2, 3 or up to 4 positions, wherein Trp and Gly are not substituted and Phe is substituted by Tyr, Trp or His. In some embodiments, the sequence motif Phe-Trp-Leu-Val-Leu-Gly (SEQ ID NO: 2) may contain amino acid substitutions at 1, 2, or up to 3 positions, wherein Trp, Gly and Phe are not substituted.

It will be appreciated that a consensus sequence can also be represented by a sequence logo. A sequence logo is a graphical representation of the consensus sequence, in which the size of a symbol is related to the frequency that a given nucleotide or amino acid occurs at a certain position. The more conserved the residue, the larger the symbol for that residue is drawn; the less conserved the residue, the smaller the symbol is drawn. Sequence logos can for example be generated using WebLogo, available at on the world wide web at weblogo.berkely.edu. In some embodiments, the sequence motif $Xaa_1$-Trp-$Xaa_2$-$Xaa_3$-$Xaa_4$-$Xaa_5$ as described herein, can be represented by a sequence logo as depicted in FIG. 2C.

According to a preferred embodiment, a peptide or peptidomimetic as described herein comprises, consists essentially of, or consists of one of the following sequences:

```
                                     (SEQ ID NO: 3)
Ala-Phe-Trp-Leu-Ile-Leu-Gly

                                     (SEQ ID NO: 4)
Thr-Trp-Trp-Leu-Ile-Leu-Gly

                                     (SEQ ID NO: 5)
Pro-Tyr-Trp-Leu-Gly-Leu-Gly

                                     (SEQ ID NO: 6)
Pro-Trp-Trp-Val-Ser-Val-Gly

                                     (SEQ ID NO: 7)
Pro-Phe-Trp-Leu-Ile-Leu-Gly

                                     (SEQ ID NO: 8)
Pro-Tyr-Trp-Leu-Leu-Ile-Gly

                                     (SEQ ID NO: 9)
Pro-Phe-Trp-Leu-Val-Leu-Gly

                                    (SEQ ID NO: 10)
Pro-Phe-Trp-Val-Val-Ala-Gly

                                    (SEQ ID NO: 11)
Pro-Phe-Trp-Leu-Ser-Val-Gly

                                    (SEQ ID NO: 12)
Pro-Tyr-Trp-Leu-Asp-Met-Gly

                                    (SEQ ID NO: 13)
Pro-Tyr-Trp-Val-Thr-Met-Gly

                                    (SEQ ID NO: 14)
Pro-Tyr-Trp-Val-Val-Leu-Gly

                                    (SEQ ID NO: 15)
Pro-Ser-Trp-Leu-Val-Val-Gly

                                    (SEQ ID NO: 16)
Pro-His-Trp-Ile-Thr-Ile-Gly

                                    (SEQ ID NO: 17)
Pro-His-Trp-Cys-Val-Leu-Gly

                                    (SEQ ID NO: 18)
Pro-Phe-Trp-Leu-Ala-Leu-Gly

                                    (SEQ ID NO: 19)
Pro-Phe-Trp-Cys-Val-Leu-Gly

                                    (SEQ ID NO: 20)
Phe-Trp-Val-Glu-Leu-Gly

                                     (SEQ ID NO: 21
Tyr-Trp-Ala-Thr-Thr-Gly-Leu

                                    (SEQ ID NO: 22)
Trp-Trp-Gly-Thr-Met-Ile

                                    (SEQ ID NO: 23)
Pro-Tyr-Trp-Leu-Cys-Ile-Ile

                                    (SEQ ID NO: 24)
Thr-Cys-Trp-Val-Cys-Ile-Val

                                   (SEQ ID NO: 749)
Leu-Ala-Phe-Trp-Asp-Ser-Leu-Gly
```

In some embodiments, there is also provided a peptide or peptidomimetic which comprises, consists essentially of, or consists of a sequence in which 1, 2, 3, 4 or up to 5 residues are deleted, added or substituted compared to any of the sequences of SEQ ID NO's: 3-24 and 749. Amino acid substitutions can be conservative amino acid substitutions, as described herein.

In a preferred embodiment, a peptide or peptidomimetic according to the invention is able to induce bacteriocin production in a microbial organism, preferably without concomitantly inducing competence.

Natural DNA transformation, or just "transformation", refers to a lateral gene transfer mechanism during which bacteria take up naked DNA from their environment and stably integrate it in their genome. The physiological state during which bacteria become able to take up DNA is named competence. Although natural transformation drives genome plasticity and adaptability, competence induction may also be associated with several disadvantages. For example, competence induction is likely to cause deleterious effects in the chromosome of the recipient bacteria and negatively impact cell growth by imposing an important energy burden on the recipient cells (Fontaine et al. Infection, Genetics and Evolution 2015, 33:343-360). Competence is also associated with a suppression of basal metabolism, which may have consequences for the microbe's resilience to fluctuations in the environment, as competence is costly in terms of use of energy and protein translation (Zaccaria et al. Plos One 2016, 11(5):e0153571). Also, competence induction may contribute to the unwanted spread of antibiotic resistance or bacteriocin immunity genes. The competence window is thus generally tightly regulated in response to species-specific environmental conditions or signaling oligopeptides called competence pheromones and limited to a proportion of the cell population.

In some embodiments, a peptide or peptidomimetic according to the invention is able to induce bacteriocin production in a microbial organism, preferably without concomitantly inducing competence, by inducing a peptide-responsive regulator that regulates genes involved in the synthesis of bacteriocins. Within the context of this disclosure, "inducing bacteriocin production" may be assessed by a skilled person at the nucleic acid level and/or at the amino acid level using common known techniques. As soon as a bacteriocin is detectable using common known techniques, the peptide or peptidomimetic according to embodiments of the invention will be said to exhibit a biological activity. A bacteriocin may be detectable using common known techniques after 1, 2, 3, 5, 10, 20, 30, 45, 60 or 90 minutes or also after 2, 3, 4, 5, 6, 8, 10, 12, 16, 20 or 24 hours, including intervals between any two of the listed values. In a preferred embodiment, the peptide-responsive regulator that regulates genes involved in the synthesis of bacteriocins does not regulate genes involved with competence, such as the central regulator of competence ComX (also denoted alternative sigma factor X, SigX or $\sigma^X$), ComK, SigH (also denoted alternative sigma factor H or $\sigma^H$) and TfoX (also denoted Sxy). As used herein, regulation includes both direct regulation as well as indirect regulation. Preferred peptide-responsive regulators regulate genes involved in the synthesis of bacteriocins but do not regulate genes involved with competence, such as ScuR and SarF.

A peptide or peptidomimetic as described herein is a ligand of a peptide-responsive regulator, preferably a peptide-responsive regulator that regulates genes involved in the synthesis of bacteriocins. Examples of suitable peptide-responsive regulators in this context are RRNPP type peptide-responsive regulators, such as ScuR and SarF.

Exemplary bacteriocins in this context are bacteriocins as described herein. Preferred bacteriocins in this context comprise, consist essentially of, or consist of class II bacteriocins, for example salivaricins.

Culture Medium

In a further aspect, there is provided a culture medium comprising a peptide or peptidomimetic as described herein, and/or a polypeptide as described herein. A culture medium can be either a liquid culture medium or a solid culture medium, such as an agar-based solid culture medium.

A preferred culture medium as described herein induces bacteriocin production in a microbial organism, preferably without concomitantly inducing competence, when the microbial organism is cultured in the culture medium. Exemplary bacteriocins in this context are bacteriocins as described herein. Preferred bacteriocins in this context comprise, consist essentially of, or consist of class II bacteriocins, for example salivaricins.

Typically, a culture medium as described herein comprises a peptide or peptidomimetic as described herein in a concentration ranging from 1 nM (0.001 μM) to 10 μM. Thus, a suitable concentration may be at least 0.001 μM, at least 0.01 μM, at least 0.1 μM, at least 1 μM or at least 10 μM. Accordingly, in other embodiments, a suitable concentration may lie between a minimum of 0.001 μM, 0.01 μM, 0.1 μM, 1 μM or 10 μM and a maximum of 0.001 μM, 0.01 μM, 0.1 μM, 1 μM or 10 μM.

In some embodiments, a suitable concentration is a concentration which induces bacteriocin production in a microbial organism that is cultured in the culture medium. A skilled person knows how to determine such suitable concentrations, for example based on an assay as used in the experimental part.

In some embodiments, the culture medium further comprises a signal molecule and/or a quenching molecule and/or an antimicrobial peptide and/or a bacteriocin as described herein.

Composition

In a further aspect, there is provided a composition comprising a peptide or peptidomimetic as described herein, and/or a polypeptide as described herein, and a solvent.

Suitable solvents include any solvent or mixture of solvents in which a peptide or peptidomimetic or polypeptide as described herein can be dissolved at a suitable concentration. The number and types of ionic charges in the peptide determine its solubility in aqueous solutions. In general, the more charged residues the peptide possesses, the more soluble it is in aqueous solutions. In addition, peptides generally have more charges at pH 6-8 than at pH 2-6. It is for this reason that peptides are better dissolved at near neutral pH. Among the many exceptions to the rule are peptide sequences that are very hydrophobic and those that tend to aggregate. While the hydrophobicity of the sequence is the primary cause of aggregation, peptides can also aggregate or "gel" through extensive hydrogen bonding network. Non-limiting examples of solvents that can be used in the context of the invention are water, ethanol, ammoniumhydroxide, dimethylsulfoxide (DMSO), acetic acid, acetonitrile and dimethylformamide (DMF). Dissolution can be enhanced by sonication.

A peptide or peptidomimetic or polypeptide according to the invention exhibits a number of activities that can be advantageously used in a wide range of applications, including therapeutic or agricultural applications, and applications in probiotics, cosmetology, cleaning of surfaces (including surfaces of chemically fragile medical devices), biotechnology, biofermentation processes, and food preservation. Provided therefore are compositions comprising a peptide or peptidomimetic or polypeptide as described herein or an acceptable salt thereof, and an acceptable carrier, diluent and/or excipient. Each of the acceptable salt, carrier, diluent and/or excipient can be a salt, carrier, diluent and/or excipient which is suitable for the intended use or application, for example pharmaceutical or agricultural.

A peptide or peptidomimetic or polypeptide according to the invention exhibits a number of activities that can be advantageously used in agricultural applications. Provided therefore are agricultural compositions comprising a peptide or peptidomimetic or polypeptide as described herein or an agriculturally acceptable salt thereof, and an agriculturally acceptable carrier, diluent and/or excipient.

Pharmaceutically and/or agriculturally acceptable salts include, but are not limited to, acid addition salts and base addition salts. As used herein, "pharmaceutically acceptable salt" of a peptide refers to a salt that retains the desired function of the peptide, and is suitable for administration to humans or animals. As used herein, "agriculturally acceptable salt" of a peptide refers to a salt that retains the desired function or activity of the peptide at least to some extent, and is suitable for use in the environment including animals, plants, water, air and/or soil. Within the context of the application, "at least to some extent" means that at least 10%, 20%, 30%, 40%, 50%, 60%, 70%, 80%, 90% or more of the initial desired function or activity is retained. Methods for the preparation of salts of peptides are known in the art and generally involve mixing of the peptide with a pharmaceutically and/or agriculturally acceptable acid or base, for instance, by reacting the free acid or free base forms of the product with one or more equivalents of the appropriate acid or base in a solvent or medium in which the salt is insoluble, or in a solvent such as water, which is then removed by vacuum or by freeze-drying, or by exchanging the cations of an existing salt for another cation on a suitable ion exchange resin. Non-limiting examples of pharmaceutically and/or agriculturally acceptable acids and bases are organic and inorganic acids such as formic acid, acetic acid, propionic acid, lactic acid, glycolic acid, oxalic acid, pyruvic acid, succinic acid, maleic acid, malonic acid, trifluoroacetic acid, cinnamic acid, sulfuric acid, hydrochloric acid, hydrobromic acid, nitric acid, perchloric acid, phosphoric acid, and thiocyanic acid, which form ammonium salts with free amino groups of polypeptides, and bases that form carboxylate salts with free carboxylic groups of polypeptides, such as ethylamine, methylamine, dimethylamine, triethylamine, isopropylamine, diisopropylamine, and other mono-, di- and trialkylamines, and arylamines.

Preferred compositions, pharmaceutical compositions and agricultural compositions as described herein induce bacteriocin production in a microbial organism, preferably without concomitantly inducing competence. Thus, compositions, pharmaceutical compositions and agricultural compositions as described herein include compositions, pharmaceutical compositions and agricultural compositions for inducing bacteriocin production in a microbial organism, preferably without concomitantly inducing competence. Preferred bacteriocins in this context comprise, consist essentially of, or consist of class II bacteriocins, for example salivaricins.

Typically, compositions, pharmaceutical compositions and agricultural compositions as described herein comprise a peptide or peptidomimetic or polypeptide as earlier described herein at a concentration ranging from 0.001 to 10 μM. Thus, a suitable concentration may be at least 0.001 μM, at least 0.01 μM, at least 0.1 μM, at least 1 μM or at least 10 μM. Accordingly, in other embodiments, a suitable concentration may lie between a minimum of 0.001 μM, 0.01 μM, 0.1 μM, 1 μM or 10 μM and a maximum of 0.001 μM, 0.01 μM, 0.1 μM, 1 μM or 10 μM.

In some embodiments, a suitable concentration is a concentration which induces bacteriocin production in a microbial organism when the composition is administered to the microbial organism. A skilled person knows how to determine such suitable concentrations, for example based on an assay as used in the experimental part.

In some embodiments, the composition further comprises a signal molecule and/or a quenching molecule and/or an antimicrobial peptide and/or a bacteriocin.

Within the context of culture media and compositions and methods according to embodiments of the invention, a "signal molecule" as used herein has its customary and ordinary meaning as understood by one of skill in the art in view of this disclosure. It refers to a secreted or released molecule that is capable of modulating, inducing, or inhibiting an activity or process in the cell that produced it, or in a different cell (a subject cell can be a microbial cell or a non-microbial cell, for example a cell of a multicellular organism such as an animal or plant).

In some embodiments, a signal molecule may be selected from the group consisting of: quorum sensing molecules, signal transduction receptor ligands, growth factors, hormones, and cytokines. A signal molecule as described herein can be wild-type, mutant, or synthetic. Examples of suitable signal molecules include quorum sensing peptides (also called pheromones). In some embodiments, a signal molecule comprises, consists essentially of, or consists of a signaling peptides, quorum sensing molecules (for example, quorum sensing peptides), signal transduction receptor ligands, growth factors, hormones, or cytokine. In some embodiments, a signal molecule comprises, consists essentially of, or consists of a combination of two or more of signaling peptides, quorum sensing molecules (for example, quorum sensing peptides), signal transduction receptor ligands, growth factors, hormones, and cytokines, which can include combinations of two or more of the same type of molecule (for example a combination of two signaling peptides or a combination of two receptor ligands), as well as combinations of two or more different kinds of molecules (e.g., a combination of a cytokine and a hormone). In some embodiments, the signal molecule stimulates, inhibits, increases, or decreases the production of bacteriocins and/or the growth rate of a subpopulation of a microbiota. In some embodiments, the signal molecule comprises, consists essentially of, or consists of a quorum sensing peptide, or a variant thereof as described herein.

Examples of quorum sensing peptides suitable for culture media and compositions according to embodiments of the invention include, but are not limited to, quorum sensing peptides such as the peptides shown in Table 1 below, including variants of these peptides, and combinations of two or more of any of these peptides.

In some embodiments, the quorum sensing peptides are naturally-occurring. In some embodiments, the quorum sensing peptide comprises, consists essentially of, or consists of a variant of a naturally-occurring quorum sensing peptide. In some embodiments, the quorum sensing peptide comprises, consists essentially of, or consists of a synthetic peptide. Information on quorum sensing peptides, including example sequences, can be found on the quorumpeps database, accessible on the world wide web at quorumpeps.ugent.be, which is hereby incorporated by reference in its entirety.

TABLE 1

| Name | Species | SEQ ID NO: |
|---|---|---|
| phrANTH3 | *Bacillus anthracis* | — |
| phrANTH1 | *Bacillus anthracis* | — |
| phrANTH2 | *Bacillus anthracis* | — |
| PapR5I | *Bacillus cereus* | — |
| PapR5IV | *Bacillus cereus* | — |
| PapR5II | *Bacillus cereus* | — |
| PapR7III | *Bacillus cereus* | — |
| PapR7IV | *Bacillus cereus* | — |
| PapR7II | *Bacillus cereus* | — |
| PapR5III | *Bacillus cereus* | — |
| PapR7I | *Bacillus cereus, Bacillus thuringiensis* | — |
| Phr0662 | *Bacillus halodurans* | — |
| phr1988 | *Bacillus halodurans* | — |
| Phr-pPL10-1, PhrPUM | *Bacillus pumilus* | — |
| PHRBST1 | *Bacillus stearothermophilus* | — |
| PhrA | *Bacillus subtilis* | — |
| Mersacidin | *Bacillus subtilis* | — |
| PhrI | *Bacillus subtilis* | — |
| PhrG | *Bacillus subtilis* | — |
| PhrK | *Bacillus subtilis* | — |
| Subtilin | *Bacillus subtilis* | — |
| Phr-pLS20 | *Bacillus subtilis* | — |
| PhrF | *Bacillus subtilis* | — |
| Phr-pTA1040 | *Bacillus subtilis* | — |
| Phr-pPOD2000, Phr-pTA1060 | *Bacillus subtilis* | — |
| PhrE | *Bacillus subtilis* | — |
| BsEDF | *Bacillus subtilis* | — |
| Entianin | *Bacillus subtilis* | — |
| NprRB | *Bacillus thuringiensis* | — |
| PisN | *Carnobacterium maltaromaticum* | — |
| CbaX | *Carnobacterium maltaromaticum* | — |
| Carnobacteriocin B2, CB2, CbnB2 | *Carnobacterium piscicola* | — |
| CbnS, CS | *Carnobacterium piscicola, Carnobacterium maltaromaticum* | — |
| AIP, Autoinducing peptide | *Clostridium acetobutylicum* | — |
| PHRCACET4 | *Clostridium acetobutylicum* | — |

TABLE 1-continued

| Name | Species | SEQ ID NO: |
|---|---|---|
| PHRCACET1 | *Clostridium acetobutylicum* | — |
| AgrD2, AIP, Autoinducing peptide | *Clostridium botulinum* | — |
| AgrD2, AIP, Autoinducing peptide | *Clostridium botulinum* | — |
| AgrD2, AIP, Autoinducing peptide | *Clostridium botulinum* | — |
| AgrD2, AIP, Autoinducing peptide | *Clostridium botulinum* | — |
| AgrD1, AIP, Autoinducing peptide | *Clostridium botulinum* | — |
| AgrDCp | *Clostridium perfringens* | — |
| WS9326A | *Clostridium perfringens* | — |
| WS9326B | *Clostridium perfringens* | — |
| Cochinmicin II/III | *Clostridium perfringens* | — |
| AgrD2, AIP, Autoinducing peptide | *Clostridium sporogenes* | — |
| AgrD1, AIP, Autoinducing peptide | *Clostridium sporogenes* | — |
| AgrD | *Clostridium thermocellum* | — |
| QSP1 | *Cryptococcus neoformans* | — |
| QSP24 | *Cryptococcus neoformans* | — |
| QSP2 | *Cryptococcus neoformans* | — |
| — | *Eikenella corodens* | — |
| cAM373 | *Enterococcus faecalis* | — |
| iCF10 | *Enterococcus faecalis* | — |
| iPD1 | *Enterococcus faecalis* | — |
| cPD1 | *Enterococcus faecalis* | — |
| GBAP, Gelatinase Biosynthesis-Activating Pheromone | *Enterococcus faecalis* | — |
| cAD1 | *Enterococcus faecalis* | — |
| iAD1 | *Enterococcus faecalis* | — |
| cCF10 | *Enterococcus faecalis* | — |
| iAM373 | *Enterococcus faecalis* | — |
| cOB1 | *Enterococcus faecalis* | — |
| EntF | *Enterococcus faecium* | — |
| EDF, Extracellular death factor | *Escherichia coli* | — |
| LamD | *Lactobacillus plantarum* | — |
| PltA | *Lactobacillus plantarum* | — |
| Plantaricin A, PlnA | *Lactobacillus plantarum* | — |
| IP-TX | *Lactobacillus sakei* | — |
| IP-673 | *Lactobacillus sakei* | — |
| Orf4 | *Lactobacillus sakei* | — |
| Nisin A | *Lactococcus lactis* | — |
| AIP | *Listeria monocytogenes* | — |
| PaEDF-1 | *Pseudomonas aeruginosa* | — |
| PaEDF-2 | *Pseudomonas aeruginosa* | — |
| PaEDF-3 | *Pseudomonas aeruginosa* | — |
| AIP, Autoinducing peptide | *Staphylococcus arlettae* | — |
| AIP2, Autoinducing peptide 2 | *Staphylococcus aureus* | — |
| AIP3, Autoinducing peptide 3 | *Staphylococcus aureus* | — |
| AIP1, Autoinducing peptide 1 | *Staphylococcus aureus* | — |
| AIP4, Autoinducing peptide 4 | *Staphylococcus aureus* | — |
| AIP, Autoinducing peptide | *Staphylococcus auricularis* | — |
| AIP, Autoinducing peptide | *Staphylococcus auricularis* | — |
| AIP, Autoinducing peptide | *Staphylococcus capitis* | — |
| AIP, Autoinducing peptide | *Staphylococcus capitis* | — |
| AIP, Autoinducing peptide | *Staphylococcus caprae* | — |
| AIP, Autoinducing peptide | *Staphylococcus caprae* | — |
| AIP, Autoinducing peptide | *Staphylococcus caprae* | — |
| AIP, Autoinducing peptide | *Staphylococcus carnosus* | — |
| AIP, Autoinducing peptide | *Staphylococcus cochnii* subsp. *cochnii* | — |
| AIP, Autoinducing peptide | *Staphylococcus cochnii* subsp. *urealyticum* | — |
| AIP2, Autoinducing peptide 2 | *Staphylococcus epidermidis* | — |
| AIP, Autoinducing peptide | *Staphylococcus epidermidis* | — |
| AIP, Autoinducing peptide | *Staphylococcus epidermidis* | — |
| AIP, Autoinducing peptide | *Staphylococcus epidermidis* | — |
| Pep5 | *Staphylococcus epidermidis* | — |
| AIP4, Autoinducing peptide 4 | *Staphylococcus epidermidis* | — |
| AIP1, Autoinducing peptide 1 | *Staphylococcus epidermidis* | — |
| AIP3, Autoinducing peptide 3 | *Staphylococcus epidermidis* | — |
| AIP-II | *Staphylococcus epidermidis* | — |
| AIP-III | *Staphylococcus epidermidis* | — |
| AIP, Autoinducing peptide | *Staphylococcus gallinarum* | — |
| AIP, Autoinducing peptide | *Staphylococcus lugdunensis* | — |
| AIP, Autoinducing peptide | *Staphylococcus lugdunensis* | — |
| AIP, Autoinducing peptide | *Staphylococcus simulans* | — |

TABLE 1-continued

| Name | Species | SEQ ID NO: |
|---|---|---|
| AIP, Autoinducing peptide | *Staphylococcus simulans* | — |
| AIP, Autoinducing peptide | *Staphylococcus simulans* | — |
| AIP, Autoinducing peptide | *Staphylococcus warneri* | — |
| AIP, Autoinducing peptide | *Staphylococcus xylosus* | — |
| Short Hydrophobic Peptide 3, SHP3 | *Streptococcus agalactiae* | — |
| SilCR | *Streptococcus dysgalactiae* | — |
| Short Hydrophobic Peptide, SHP1509 | *Streptococcus mutans* | — |
| Bacteriocin Inducing Peptide, BIP | *Streptococcus pneumoniae* | — |
| Bacteriocin Inducing Peptide, BIP, BIP-2, BIpC | *Streptococcus pneumoniae* | — |
| Bacteriocin Inducing Peptide, BIP-1, BIpC | *Streptococcus pneumoniae* | — |
| Streptin 1 | *Streptococcus pyogenes* | — |
| SHP2-C10 | *Streptococcus pyogenes* | — |
| SHP2-C9 | *Streptococcus pyogenes* | — |
| SHP2-C7 | *Streptococcus pyogenes* | — |
| SHP3-C10 | *Streptococcus pyogenes* | — |
| SHP3-C9 | *Streptococcus pyogenes* | — |
| SHP3-C7 | *Streptococcus pyogenes* | — |
| STP | *Streptococcus thermophilus* | — |
| SHP1358(15-23) | *Streptococcus thermophilus* | — |
| Short Hydrophobic Peptide; SHP1299 | *Streptococcus thermophilus* | — |
| Siamycin I | *Streptomyces* species | — |
| TM0504 | *Thermotoga maritima* | — |
| Synthetic RAP-binding peptide, RBP | Synthetic (FHWWQTSPAHFS) | 184 |
| Synthetic RAP-binding peptide, RBP | Synthetic (WPFAHWPWQYPR) | 185 |
| Synthetic AgrC ligand | Synthetic (GDSVCASYF, thiolacton linkage between C5 and F9) | 186 |
| Synthetic AgrC ligand | Synthetic (SVCASYF, thiolacton linkage between C3 and F7) | 187 |
| Synthetic Cry1Aa ligand | Synthetic (SKADT) | 188 |
| Synthetic Cry1Aa ligand | Synthetic (SKPAD) | 189 |
| Synthetic Fsr ligand | Synthetic (benzyloxycarbonyl-QNSAAAFAAWA, lacton linkage between S3 and A11) | 190 |
| Synthetic Fsr ligand | Synthetic (benzyloxycarbonyl-QNSAAAFGQWA, lacton linkage between S3 and A11) | 191 |
| Synthetic AgrC1, AgrC2 | Synthetic (YSTC(alpha-aminobutyric acid)FIM, thiolacton linkage between C4 and M7) | 192 |
| Synthetic AgrC1, AgrC2 | Synthetic (N-4-(4-benzoylphenoxy)butyryl-STCAFIM, thiolacton linkage between C3 and M7) | 193 |

Within the context of culture media and compositions and methods according to embodiments of the invention, a “quenching molecule” as used herein has its customary and ordinary meaning as understood by one of skill in the art in view of this disclosure. It refers to (peptidic) quenching molecules that prevent the signal molecules to reach their cognate receptors by enzymatic activity such as proteolysis, addition of inactivating chemical groups or by competition with the signal molecule.

Within the context of culture media and compositions and methods according to embodiments of the invention, an “antimicrobial peptide” as used herein has its customary and ordinary meaning as understood by one of skill in the art in view of this disclosure. It refers to a class of peptides that confer innate immune activity to kill or arrest the growth of microbial organisms. Classically, antimicrobial peptides have been described as peptides produced by the innate immune systems of invertebrates and vertebrates. Thus, while bacteriocins have classically been referred to a class of microbial gene products that target microbial organisms, antimicrobial peptides have classically been referred to as a class of invertebrate and vertebrate gene products that target microbial organisms.

Examples of antimicrobial peptides suitable for peptides or peptidomimetics, culture media, compositions, methods and uses according to the invention are known in the art, and can be found, for example, at The Antimicrobial Peptide Database accessible on the world wide web at aps.unmc.edu/AP/main.php, which is incorporated herein by reference in its entirety. Over 1000 antimicrobial peptides and variants thereof have been identified and cataloged. The Antimicrobial Peptide Database is described in Wang et al. (2016), Nucleic Acids Res. 44:D1087-D1093, which is incorporated herein by reference in its entirety.

Over 1000 antimicrobial peptides and variants thereof have been identified and cataloged. The Antimicrobial Peptide Database is described in Wang et al. (2016), Nucleic Acids Res. 44 (Database issue): D1087-D1093, which is incorporated herein by reference in its entirety. Examples of antimicrobial peptides include bacteriocins, antibacterial, antiviral, anti-HIV, antifungal, antiparasitic and anticancer peptides, such as Dermaseptin-B2, Abaecin, Ct-AMPI, Andropin, Aurein 1.1, Lactofericin B, and Heliomicin. Methods, culture media, and compositions of some embodiments comprise naturally occurring antimicrobial peptides, or a nucleic acid encoding the same, and/or nonnaturally occurring antimicrobial peptides, or a nucleic acid encoding the same. Methods, culture media, and compositions of some embodiments include antimicrobial peptides that comprise a mutation or variation in a naturally-occurring antimicrobial peptide, or a nucleic acid encoding the same. Methods, culture media, and compositions of some embodiments comprise antimicrobial peptides comprising, consisting essentially of, or consisting of non-naturally occurring peptide sequences, or nucleic acids encoding the same.

It is further contemplated that methods, culture media, and compositions of some embodiments herein can be in conjunction with naturally occurring antimicrobial peptides, variants of naturally occurring antimicrobial peptides, and/or synthetic antimicrobial peptides. As such, antimicrobial peptides of methods, culture media, and compositions of some embodiments can comprise, consist essentially of, or consist of naturally occurring antimicrobial peptides, variants of naturally occurring antimicrobial peptides, and/or synthetic antimicrobial peptides. In some embodiments, a variant antimicrobial peptide has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to a reference antimicrobial peptide (for example Dermaseptin-B2, Abaecin, Ct-AMPI, Andropin, Aurein 1.1, Lactoferricin B, or Heliomicin).

Microbial Organism

In a further aspect, there is provided a microbial organism able to produce and/or secrete a peptide or peptidomimetic and/or a precursor peptide or peptidomimetic and/or a protein as described herein. A variety of bacterial species and strains can be used in accordance with embodiments herein, as explained in the section "General descriptions". In some embodiments, the microbial organism is a Gram-positive bacterium, preferably a lactic acid bacterium. In some embodiments, the microbial organism is a *Streptococcus* sp., preferably *Streptococcus salivarius*. In some embodiments, the microbial organism is "generally recognized as safe" (GRAS). In some embodiments, the microbial organism is a commensal bacterium from the microbiota.

Method and Use

In a further aspect, there is provided a method for inducing bacteriocin production in a microbial organism, preferably without concomitantly inducing competence, comprising administering a peptide or peptidomimetic or polypeptide as described herein to the microbial organism, and/or culturing the microbial organism in a culture medium as described herein, and/or administering a composition as described herein to the microbial organism. In some embodiments of a method according to the invention, administering a peptide or peptidomimetic or polypeptide as described herein to the microbial organism and administering a composition as described herein to the microbial organism may optionally be followed by a culturing step. In some embodiments, a peptide or peptidomimetic or polypeptide or a composition as described herein can be administered to a microbial organism in a host, such as a patient having an infection or an imbalance in the microbiome.

Also provided is a use of a peptide or peptidomimetic or polypeptide as described herein, a culture medium as described herein, or a composition as described herein for inducing bacteriocin production in a microbial organism. The use can be without concomitantly inducing competence. In a further aspect, there is provided a method for inducing bacteriocin production in a first microbial organism, preferably without concomitantly inducing competence, comprising administering to the first microbial organism a second microbial organism able to produce and/or secrete a peptide or peptidomimetic and/or a polypeptide as described herein and/or co-culturing the first microbial organism with the second microbial organism able to produce and/or secrete a peptide or peptidomimetic and/or a polypeptide as described herein.

Also provided is a use of a microbial organism able to produce and/or secrete a peptide or peptidomimetic and/or a polypeptide as described herein for inducing bacteriocin production in a microbial organism. The use can be without concomitantly inducing competence.

In some embodiments of a method and/or a use as described herein, the bacteriocin production in the microbial organism neutralizes a second, undesired microbial organism.

As used herein, "neutralizes" and variations to this root term has its customary and ordinary meaning as understood by one of skill in the art in view of this disclosure. It includes any form of inhibition or arrest of microbial growth and/or division (bacteriostatic effect), as well as any cytotoxic or bactericidal effect (killing). Neutralization can be fully or partially. For example, the whole population or only a part of the targeted population may be growth-inhibited or killed. More particularly, partial neutralization may mean that at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% of the microbial organisms is growth-inhibited or killed. A skilled person knows how to assess growth inhibition and killing, for example based on assays that are used in the experimental part. "Undesired" microbial organism as used herein refers to any microbial organism that is targeted for neutralization. For example, an undesired microbial organism may be a pathogenic microbial organism or a contaminant.

In some embodiments of a method and/or a use as described herein, the microbial organism that produces bacteriocin is a bacterium. In some embodiments, the microbial organism that produces bacteriocin is a Gram-negative bacterium. According to some embodiments, the microbial organism that produces bacteriocin is a Gram-positive bacterium, for example a lactic acid bacterium, such as a *Streptococcus* species, such as *Streptococcus salivarius*.

In the context of a method and/or a use according to the invention, the undesired microbial organism may be a pathogenic microbial organism, preferably a pathogenic microbial organism that is susceptible to neutralization by a bacteriocin as described herein. In some embodiments, the undesired microbial organism is a Gram-positive bacterium. In still some embodiments, the undesired microbial organism is a pathogenic Gram-positive bacteria. The pathogenic Gram-positive bacteria can be selected from the group consisting of the following genera: *Staphylococcus, Enterococcus, Streptococcus, Listeria, Bacillus, Brochothrix, Clostridium, Mycobacterium, Propionibacterium*, or *Corynebacterium*. Accordingly, Gram-positive bacterial species may be *Staphylococcus aureus, Enterococcus faecium, Streptococcus agalactiae, Streptococcus pneumoniae, Streptococcus pyogenes, Listeria monocytogenes, Bacillus cereus, Brocho-*

*thrix thermosphacta, Staphylococcus epidermidis, Clostridium difficile, Clostridium perfringens, Mycobacterium tuberculosis, Propionibacterium acnes*, and *Corynebacterium diphteriae.*

In some embodiments, a method and/or a use as described herein may be a method and/or a use wherein the microbial organism belongs to the microbiota. In other words, the microbial organism that produces bacteriocin is a microbial organism that belongs to the microbiota. In this context, a microbiota can be the microbiota of human, for example the microbiota of the skin and/or the gut and/or the mouth and/or the vagina, the microbiota of an animal, for example the microbiota of the skin and/or the gut and/or the mouth and/or the vagina, and/or the microbiota of a plant, for example the microbiota of the roots.

In other embodiments, a method and/or a use as described herein may be a method and/or a use wherein the microbial organism produces a desired product. In other words, the microbial organism that produces bacteriocin is a microbial organism that also produces a desired product. In this context, the microbial organism can exist in a number in commercially useful environments such as industrial cultures, fermenters, pharmaceutical, biological, and cosmetic manufacturing and in products, such as foods (for human and/or animals), drug products, and cosmetic products. Hence, in some embodiments, the undesired microbial organism may be a contaminant in commercially useful environments such as industrial cultures, fermenters, pharmaceutical, biological, and cosmetic manufacturing and in products, such as foods (for human and/or animals), drug products, and cosmetic products.

Exemplary bacteriocins in this context are bacteriocins as described herein. In the context of a method and/or a use according to the invention, the bacteriocin may be a class II bacteriocin, for example salivaricin.

Method

In a further aspect, there is provided a method for identifying, selecting and/or optimizing peptide ligands of peptide-responsive transcriptional regulators, comprising the following:

- generating a library of randomized genes, wherein said genes are operably linked to an inducible promoter, inducible by an inducer molecule;
- transforming the library into a microbial organism which encodes a selectable marker conferring resistance to a selection agent, operably linked to a promoter which is controlled by the peptide-responsive transcriptional regulator; and
- selecting or enriching positive clones by growing the microbial organism in the presence of the inducer molecule and the selection agent.

In a preferred embodiment, there is provided a method for identifying, selecting and/or optimizing peptide ligands of peptide-responsive transcriptional regulators, comprising the following steps:

- generating a library of randomized genes, wherein said genes are operably linked to an inducible promoter, inducible by an inducer molecule;
- transforming the library into a microbial organism which encodes a selectable marker conferring resistance to a selection agent, operably linked to a promoter which is controlled by the peptide-responsive transcriptional regulator; and
- selecting or enriching positive clones by growing the microbial organism in the presence of the inducer molecule and the selection agent.

In a preferred embodiment, the peptide-responsive transcriptional regulator belongs to the RRNPP family. RRNPP proteins are named after the different sensors described: Rgg, Rap, NprR, PlcR, and PrgX. They are characterized at the structural level by tetratricopeptide repeat (TPR) domains, which are involved in the regulator/peptide interaction.

In a preferred embodiment, the peptide responsive regulator is a regulator of bacteriocin synthesis. The peptide responsive regulator of bacteriocin synthesis may be ScuR or SarF.

In a preferred embodiments, a method as described herein may be a method wherein the nucleotide sequences of the randomized genes comprise both fixed-sequence codons and degenerate codons. As used herein, degenerate codons include mixtures of nucleotides at one, two or three positions and are used for introducing random diversity in the genes during oligonucleotide synthesis. For example, the complete set of standard amino acids can be encoded using NNK or NNS codons, where N=A or T or G or C, K=G or T and S=C or G.

In some embodiments, the randomized genes are optionally further operably linked to a selectable marker. Accordingly, the transforming step of a method as described herein optionally involves a selection step for successful transformants by selecting or enriching transformants in the presence of the selectable marker.

In some embodiments, the selectable marker encoded by the microbial organism is different from the selectable marker operably linked to the randomized genes. Exemplary selectable markers useful in some embodiments herein are antibiotic-resistance conferring genes such as cat (chloramphenicol acetyl transferase), erm (erythromycin ribosome methylation) and spec (spectinomycine resistance gene). Other suitable selectable markers may be bacteriocin immunity genes.

Inducible promoters are promoters which drive transcription only in the presence of a suitable inducer molecule. Inducible promoters useful in some embodiments herein are xylose-, arabinose-, nickel-, nisin-, IPTG-, and pheromone-inducible promoters. More exemplary promoters suitable for embodiments herein are given in Tables 2 and 3 below.

TABLE 2

Exemplary metal-sensitive promoters

| SEQ ID NO: | Name | Description |
|---|---|---|
| 194 | BBa_I721001 | Lead Promoter |
| 195 | BBa_I731004 | FecA promoter |
| 196 | BBa_I760005 | Cu-sensitive promoter |
| 197 | BBa_I765000 | Fe promoter |
| 198 | BBa_I765007 | Fe and UV promoters |
| 199 | BBa_J3902 | PrFe (PI + PII rus operon) |

TABLE 3

| Exemplary Cell Signaling-Responsive Promoters | | |
|---|---|---|
| SEQ ID NO: | Name | Description |
| 200 | BBa_I1051 | Lux cassette right promoter |
| 201 | BBa_I14015 | P(Las) TetO |
| 202 | BBa_I14016 | P(Las) CIO |
| 203 | BBa_I14017 | P(Rhl) |
| 204 | BBa_I739105 | Double Promoter (LuxR/HSL, positive/cl, negative) |
| 205 | BBa_I746104 | P2 promoter in agr operon from *S. aureus* |
| 206 | BBa_I751501 | plux-cl hybrid promoter |
| 207 | BBa_I751502 | plux-lac hybrid promoter |
| 208 | BBa_I761011 | CinR, CinL and glucose controlled promotor |
| 209 | BBa_J06403 | RhIR promoter repressible by Cl |
| 210 | BBa_J102001 | Reverse Lux Promoter |
| 211 | BBa_J64000 | rhII promoter |
| 212 | BBa_J64010 | lasI promoter |
| 213 | BBa_J64067 | LuxR + 3OC6HSL independent R0065 |
| 214 | BBa_J64712 | LasR/LasI Inducible & RHLR/RHLI repressible Promoter |
| 215 | BBa_K091107 | pLux/cl Hybrid Promoter |
| 216 | BBa_K091117 | pLas promoter |
| 217 | BBa_K091143 | pLas/cl Hybrid Promoter |
| 218 | BBa_K091146 | pLas/Lux Hybrid Promoter |
| 219 | BBa_K091156 | pLux |
| 220 | BBa_K091157 | pLux/Las Hybrid Promoter |
| 221 | BBa_K145150 | Hybrid promoter: HSL-LuxR activated, P22 C2 repressed |
| 222 | BBa_K266000 | PAI + LasR -> LuxI (AI) |
| 223 | BBa_K266005 | PAI + LasR -> LasI & AI + LuxR --\| LasI |
| 224 | BBa_K266006 | PAI + LasR -> LasI + GFP & AI + LuxR --\| LasI + GFP |
| 225 | BBa_K266007 | Complex QS -> LuxI & LasI circuit |
| 226 | BBa_K658006 | position 3 mutated promoter lux pR-3 (luxR & HSL regulated) |
| 227 | BBa_K658007 | position 5 mutated promoter lux pR-5 (luxR & HSL regulated) |
| 228 | BBa_K658008 | position 3&5 mutated promoter lux pR-3/5 (luxR & HSL regulated) |
| 229 | BBa_R0061 | Promoter (HSL-mediated luxR repressor) |
| 230 | BBa_R0062 | Promoter (luxR & HSL regulated -- lux pR) |
| 231 | BBa_R0063 | Promoter (luxR & HSL regulated -- lux pL) |
| 232 | BBa_R0071 | Promoter (RhIR & C4-HSL regulated) |
| 233 | BBa_R0078 | Promoter (cinR and HSL regulated) |
| 234 | BBa_R0079 | Promoter (LasR & PAI regulated) |
| 235 | BBa_R1062 | Promoter, Standard (luxR and HSL regulated -- lux pR) |

In some embodiments, the randomized genes may also be operably linked to a sequence which is homologous to a sequence of the microbial organism's genome to allow recombination at a desired locus in the microbial organism's genome. In some embodiments, the homologous sequence has a length of 50-2000 nucleotides, for example 100-1000 nucleotides, 200-800 nucleotides, or 500 nucleotides. In some embodiments of a method as described herein, the microbial organism that encodes a selectable marker is a bacterium. In some embodiments, the microbial organism that encodes a selectable marker is a Gram-negative bacterium. According to some embodiments, the microbial organism that encodes a selectable marker is a Gram-positive bacterium, for example a lactic acid bacterium, such as a *Streptococcus* species, such as *Streptococcus salivarius.*

Within the context of peptides or peptidomimetics, polypeptides, culture media, compositions, microbial organisms, and methods and uses according to embodiments of the invention, a "bacteriocin" as used herein has its customary and ordinary meaning as understood by one of skill in the art in view of this disclosure. It refers to proteinaceous toxins produced by bacteria to inhibit the growth of similar or closely related bacterial strain(s). A bacteriocin can neutralize at least one cell other than the individual host cell in which the polypeptide is made, including cells clonally related to the host cell and other microbial cells. Neutralization can be fully or partially as described herein. As used herein, bacteriocin also encompasses a cell-free or chemically synthesized version of such a polypeptide. A synthetic variant of a bacteriocin may be derived from the bacteriocin secreted by a host cell in any way as long as the synthetic variant still exhibits at least 10%, 20%, 30%, 40%, 50%, 60%, 70%, 80%, 90% of the activity of the corresponding bacteriocin secreted by a host cell.

Detailed descriptions of bacteriocins, including methods and compositions for using bacteriocins to control the growth of microbial cells can be found, for example, in U.S. Pat. No. 9,333,227, which is hereby incorporated by reference. "Bacteriocin" is not limited by the origin of the polypeptide, and by way of example is contemplated to encompass any bacteriocin, such as naturally-occurring bacteriocins, synthetic bacteriocins, and variants and combinations thereof.

A cell that expresses a particular "immunity modulator" is immune to the neutralizing effects of a particular bacteriocin or group of bacteriocins. As such, bacteriocins can neutralize a cell producing the bacteriocin and/or other microbial cells, so long as these cells are "susceptible", i.e. do not produce an appropriate immunity modulator. As such, a bacteriocin can exert cytotoxic or growth-inhibiting effects on a plurality of other microbial organisms. In an embodiment, a bacteriocin is produced by the translational machinery (e.g. a ribosome, etc.) of a microbial cell. In another embodiment, a bacteriocin is chemically synthesized. Some bacteriocins can be derived from a polypeptide precursor. The polypeptide precursor can undergo cleavage (for example processing by a protease) to yield the polypeptide of the bacteriocin itself. As such, in some embodiments, a bacteriocin is produced from a precursor polypeptide. In some embodiments, a bacteriocin comprises, consists essentially of, or consists of a polypeptide that has undergone post-translational modifications, for example cleavage, or the addition of one or more functional groups.

Neutralizing activity of bacteriocins can include inhibition or arrest of microbial growth and/or division, or cytotoxicity. Some bacteriocins have cytotoxic activity (e.g. "bacteriocide" effects), and thus can kill microbial organisms, for example bacteria, yeast, algae, synthetic micoorganisms, and the like. Some bacteriocins can inhibit the growth and/or division of microbial organisms (e.g. "bacteriostatic" effects), for example bacteria, yeast, algae, synthetic microorganisms, and the like, for example by arresting the cell cycle.

A number of bacteriocins have been identified and characterized (see Table 4 and 5). Without being limited by any particular theory, exemplary bacteriocins can be classified as "class I" bacteriocins, which typically undergo post-translational modification, and "class II" bacteriocins, which are typically unmodified. Additionally, exemplary bacteriocins in each class can be categorized into various subgroups, as summarized in Cotter, P. D. et al. "Bacteriocins—a viable alternative to antibiotics" Nature Reviews Microbiology 11(2): 95-105, hereby incorporated by reference. Without being limited by any particular theory, bacteriocins can effect neutralization of a target microbial cell in a variety of ways. For example, a bacteriocin can permeabilize a cell wall, thus depolarizing the cell wall and interfering with respiration.

TABLE 4

Classification of Exemplary Bacteriocins

| Group | Distinctive feature | Examples |
|---|---|---|
| Class I (typically modified) | | |
| MccC7-C51-type bacteriocins | Is covalently attached to a carboxy-terminal aspartic acid | MccC7-C51 |
| Lasso peptides | Have a lasso structure | MccJ25 |
| Linear azole- or azoline-containing peptides | Possess heterocycles but not other modifications | MccB17 |
| Lantibiotics | Possess lanthionine bridges | Nisin, planosporicin, mersacidin, actagardine, mutacin 1140 |
| Linaridins | Have a linear structure and contain dehydrated amino acids | Cypemycin |
| Proteusins | Contain multiple hydroxylations, epimerizations and methylations | Polytheonamide A |
| Sactibiotics | Contain sulphur-α-carbon linkages | Subtilosin A, thuricin CD |
| Patellamide-like cyanobactins | Possess heterocycles and undergo macrocyclization | Patellamide A |
| Anacyclamide-like cyanobactins | Cyclic peptides consisting of proteinogenic amino acids with prenyl attachments | Anacyclamide A10 |
| Thiopeptides | Contain a central pyridine, dihydropyridine or piperidine ring as well as heterocycles | Thiostrepton, nocathiacin I, GE2270 A, philipimycin |
| Bottromycins | Contain macrocyclic amidine, a decarboxylated carboxy-terminal thiazole and carbon-methylated amino acids | Bottromycin A2 |
| Glycocins | Contain S-linked glycopeptides | Sublancin 168 |
| Class II (typically unmodified or cyclic) | | |
| IIa peptides (pediocin PA-1-like bacteriocins) | Possess a conserved YGNGV motif (in which N represents any amino acid) | Pediocin PA-1, enterocin CRL35, carnobacteriocin BM1 |
| IIb peptides | Two unmodified peptides are required for activity | ABP118, lactacin F |
| IIc peptides | Cyclic peptides | Enterocin AS-48 |
| IId peptides | Unmodified, linear, non-pediocin-like, single-peptide bacteriocins | MccV, MccS, epidermicin NI01, lactococcin A |
| IIe peptides | Contain a serine-rich carboxy-terminal region with a non-ribosomal siderophore-type modification | MccE492, MccM |

A number of bacteriocins can be used in accordance with embodiments herein. Exemplary bacteriocins are shown in Table 5. In some embodiments, at least one bacteriocin comprising, consisting essentially of, or consisting of a polypeptide sequence of Table 5 is provided. As shown in Table 5, some bacteriocins function as pairs of molecules. As such, it will be understood that unless explicitly stated otherwise, when a functional "bacteriocin" or "providing a bacteriocin," or the like is discussed herein, functional bacteriocin pairs are included along with bacteriocins that function individually. With reference to Table 5, "organisms of origin" listed in parentheses indicate alternative names and/or strain information for organisms known to produce the indicated bacteriocin.

Embodiments herein also include peptides and proteins with identity to bacteriocins described in Table 5. The term "identity" is meant to include nucleic acid or protein sequence homology or three-dimensional homology. Several techniques exist to determine nucleic acid or polypeptide sequence homology and/or three-dimensional homology to polypeptides. These methods are routinely employed to discover the extent of identity that one sequence, domain, or model has to a target sequence, domain, or model. A vast range of functional bacteriocins can incorporate features of bacteriocins disclosed herein, thus providing for a vast degree of identity to the bacteriocins in Table 5. In some embodiments, a bacteriocin has at least 50% identity, for example, at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any one of the polypeptides of Table 5.

While the bacteriocins in Table 5 are naturally-occurring, the skilled artisan will appreciate that variants of the bacteriocins of Table 5, naturally-occurring bacteriocins other than the bacteriocins of Table 5 or variants thereof, or synthetic bacteriocins can be used according to some embodiments herein. In some embodiments, such variants have enhanced or decreased levels of cytotoxic or growth inhibition activity on the same or a different microorganism or species of microorganism relative to the wild type protein. Several motifs have been recognized as characteristic of bacteriocins. For example, the motif YGXGV (SEQ ID NO: 236), wherein X is any amino acid residue, is an N-terminal consensus sequence characteristic of class IIa bacteriocins. Accordingly, in some embodiments, a synthetic bacteriocin comprises an N-terminal sequence with at least 50% identity to SEQ ID NO: 236, for example at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 236. In some embodiments, a synthetic bacteriocin comprises a N-terminal sequence comprising SEQ ID NO: 236. Additionally, some class IIb bacteriocins comprise a GXXXG motif (SEQ ID NO: 237) (X means any amino acid). Without being limited by any particular theory, it is believed that the GXXXG (SEQ ID NO: 237) motif can mediate association between helical proteins in the cell membrane, for example to facilitate bacteriocin-mediated neutralization through cell membrane interactions. As such, in some embodiments, the bacteriocin comprises a motif that facilitates interactions with the cell membrane. In some embodiments, the bacteriocin comprises a GXXXG (SEQ ID NO: 237) motif. Optionally, the bacteriocin comprising a GXXXG (SEQ ID NO: 237) motif can comprise a helical structure. In addition to structures described herein, "bacteriocin" as used herein also encompasses structures that have substantially the same effect on microbial cells as any of the bacteriocins explicitly provided herein.

It has been shown that fusion polypeptides comprising, consisting essentially of, or consisting of two or more bacteriocins or portions thereof can have neutralizing activity against a broader range of microbial organisms than either individual bacteriocin. For example, it has been shown that a hybrid bacteriocin, Ent35-MccV (GKYYGNGVSCNKKGCSVDWGRAIGIIGNNSAANLATGGAAGWKSGGGASGRD IAMAIGTLSGQFVAGGIGAAAGGVAGGAIYDYASTHKPNPAMSPSGLGGTIKQKP EGIPSE AWNYAAGRLCNWSPNNLSDVCL, SEQ ID NO: 238) displays antimicrobial activity against pathogenic Gram-positive and Gram-negative bacteria (Acuna et al. (2012), FEBS Open Bio, 2: 12-19). It is noted that that Ent35-MccV fusion bacteriocin comprises, from N-terminus to C-terminus, an N-terminal glycine, Enterocin CRL35, a linker comprising three glycines, and a C-terminal Microcin V. It is contemplated herein that bacteriocins can comprise fusions of two or more polypeptides having bacteriocin activity. In some embodiments, a fusion polypeptide of two or more bacteriocins is provided. In some embodiments, the two or more bacteriocins comprise, consist essentially of, or consist of polypeptides from Table 5, or modifications thereof. In some embodiments, the fusion polypeptide comprising of two or more bacteriocins has a broader spectrum of activity than either individual bacteriocin, for example having neutralizing activity against more microbial organisms, neutralizing activity under a broader range of environmental conditions, and/or a higher efficiency of neutralization activity. In some embodiments, a fusion of two or more bacteriocins is provided, for example two, three, four, five, six, seven, eight, nine, or ten bacteriocins. In some embodiments, two or more bacteriocin polypeptides are fused to each other via a covalent bond, for example a peptide linkage. In some embodiments, a linker is positioned between the two bacteriocin polypeptides. In some embodiments, the linker comprises, consists essentially of, or consists of one or more glycines, for example 1, 2, 3, 4, 5, 6, 7, 8, 9, 10, 11, 12, 13, 14, 15, 16, 17, 18, 19, or 20 glycines. In some embodiments, the linker is cleaved within the cell to produce the individual bacteriocins included in the fusion protein. In some embodiments, a bacteriocin as provided herein is modified to provide a desired spectrum of activity relative to the unmodified bacteriocin. For example, the modified bacteriocin may have enhanced or decreased activity against the same organisms as the unmodified bacteriocin. Alternatively, the modified bacteriocin may have enhanced activity against an organism against which the unmodified bacteriocin has less activity or no activity.

TABLE 5

| Exemplary Bacteriocins | | | | |
|---|---|---|---|---|
| Poly-peptide SEQ ID NO: | Name | Class | Organism of origin | Poly-nucleotide SEQ ID NO: |
| 239 | Acidocin 8912 | Unclassified | *Lactobacillus acidophilus* | 240 |
| 241 | Acidocin A | class IIA/YGNGV | *Lactobacillus acidophilus* | 242 |
| 243 | Acidocin B (AcdB) | Unclassified | *Lactobacillus acidophilus* | 244 |
| 245 | Acidocin LF221B (Gassericin K7B) | Unclassified | *Lactobacillus gasseri* | 246 |
| 247 | Aureocin A53 | Unclassified | *Staphylococcus aureus* | 248 |
| 249 | Avicin A | class IIA/YGNGV | *Enterococcus avium* (*Streptococcus avium*) | 250 |
| 251 | Bacteriocin 31 | Unclassified | *Enterococcus faecalis* (*Streptococcus faecalis*) | 252 |
| 253 | Bacteriocin J46 | Unclassified | *Lactococcus lactis* | 254 |
| 255 | Bacteriocin T8 | class IIa | *Enterococcus faecium* (*Streptococcus faecium*) | 256 |
| 257 | Boticin B | Unclassified | *Clostridium botulinum* | 258 |
| 259 | Bovicin HJ50 | Lantibiotic | *Streptococcus equinus* (*Streptococcus bovis*) | 260 |
| 261 | Brochocin-c | Unclassified | *Brochothrix campestris* | 262 |
| 263 | Butyrivibriocin AR10 | Unclassified | *Butyrivibrio fibrisolvens* | 264 |
| 265 | Butyrivibriocin OR79 | Lantibiotic | *Butyrivibrio fibrisolvens* | 266 |
| 267 | Carnobacteriocin B2 (Carnocin CP52) | class IIA/YGNGV | *Carnobacterium maltaromaticum* (*Carnobacterium piscicola*) | 268 |
| 269 | Carnobacteriocin BM1 (Carnobacteriocin B1) | class IIA/YGNGV | *Carnobacterium maltaromaticum* (*Carnobacterium piscicola*) | 270 |
| 271 | Carnobacteriocin-A (Piscicolin-61) | class IIc, non subgrouped bacteriocins (problematic) | *Carnobacterium maltaromaticum* (*Carnobacterium piscicola*) | 272 |
| 273 | Carnocyclin-A | Unclassified | *Carnobacterium maltaromaticum* (*Carnobacterium piscicola*) | 274 |
| 275 | Carocin D | Unclassified | *Pectobacterium carotovorum* subsp. *carotovorum* (*Erwinia carotovora* subsp. *carotovora*) | 276 |
| 277 | Cerein 7B | Unclassified | *Bacillus cereus* | 278 |
| 279 | Cinnamycin (Lanthiopeptin) | Lantibiotic | *Streptoverticillium griseoverticillatum* | 280 |
| 281 | Circularin A | Unclassified | *Geobacillus kaustophilus* (strain HTA426) | 282 |
| 283 | Closticin 574 | Unclassified | *Clostridium tyrobutyricum* | 284 |
| 285 | Coagulin A | Unclassified | *Bacillus coagulans* | 286 |
| 287 | Colicin-10 | Unclassified | *Escherichia coli* | 288 |
| 289 | Colicin-E1 | Unclassified | *Escherichia coli* | 290 |
| 291 | Colicin-Ia | Unclassified | *Escherichia coli* | 292 |
| 293 | Colicin-Ib | Unclassified | *Escherichia coli* | 294 |
| 295 | Colicin-M | Unclassified | *Escherichia coli* | 296 |
| 297 | Colicin-N | Unclassified | *Escherichia coli* | 298 |
| 299 | Colicin-V (Microcin-V) | Unclassified | *Escherichia coli* | 300 |
| 301 | Columbicin A | Lantibiotic | *Enterococcus columbae* | 302 |
| 303 | Curvacin-A | class IIA/YGNGV | *Lactobacillus curvatus* | 304 |
| 305 | Cypemycin | Unclassified | *Streptomyces* sp. | 306 |
| 307 | Cytolysin | Lantibiotic | *Bacillus halodurans* (strain ATCC BAA-125/DSM 18197/FERM 7344/JCM 9153/C-125) | 308 |
| 309 | Divercin V41 | class IIa/YGNGV | *Carnobacterium divergens* (*Lactobacillus divergens*) | 310 |
| 311 | Divergicin 750 | Unclassified | *Carnobacterium divergens* (*Lactobacillus divergens*) | 312 |
| 313 | Divergicin A | Class IIc | *Carnobacterium divergens* (*Lactobacillus divergens*) | 314 |
| 315 | Durancin Q | Unclassified | *Enterococcus durans* | 316 |
| 317 | Durancin TW-49M | Unclassified | *Enterococcus durans* | 318 |
| 319 | Dysgalacticin | Unclassified | *Streptococcus dysgalactiae* subsp. *equisimilis* (*Streptococcus equisimilis*) | 320 |
| 321 | Enterocin 1071A | Unclassified | *Enterococcus faecalis* (*Streptococcus faecalis*) | 322 |
| 323 | Enterocin 7A (Enterocin L50A) | bacteriocins without sequence leader | *Enterococcus faecalis* (*Streptococcus faecalis*) | 324 |

TABLE 5-continued

| Exemplary Bacteriocins | | | | |
|---|---|---|---|---|
| Poly-peptide SEQ ID NO: | Name | Class | Organism of origin | Poly-nucleotide SEQ ID NO: |
| 325 | Enterocin 7B | Unclassified | *Enterococcus faecalis* (*Streptococcus faecalis*) | 326 |
| 327 | Enterocin 96 | Class II | *Enterococcus faecalis* (strain ATCC 700802/V583) | 328 |
| 329 | Enterocin A | Class IIa, IIc (problematic) | *Enterococcus faecium* (*Streptococcus faecium*) | 330 |
| 331 | Enterocin AS-48 (BACTERIOCIN AS-48) | Unclassified | *Enterococcus faecalis* (*Streptococcus faecalis*) | 332 |
| 333 | Enterocin B | class IIc, non subgrouped bacteriocins (problematic) | *Enterococcus faecium* (*Streptococcus faecium*) | 334 |
| 335 | Enterocin CRL35 (Mundticin KS) | Class IIa | *Enterococcus mundtii* | 336 |
| 337 | Enterocin EJ97 | Unclassified | *Enterococcus faecalis* (*Streptococcus faecalis*) | 338 |
| 339 | Enterocin P | Class IIa, IIb and IIc (problematic) | *Enterococcus faecium* (*Streptococcus faecium*) | 340 |
| 341 | Enterocin Q | Class IIc | *Enterococcus faecium* (*Streptococcus faecium*) | 342 |
| 343 | Enterocin SE-K4 | Class IIa | *Enterococcus faecalis* (*Streptococcus faecalis*) | 344 |
| 345 | Enterocin W alfa | Class IIb | *Enterococcus faecalis* (*Streptococcus faecalis*) | 346 |
| 347 | Enterocin W beta | Class IIb | *Enterococcus faecalis* (*Streptococcus faecalis*) | 348 |
| 349 | Enterocin Xalpha | Class IIb | *Enterococcus faecium* (*Streptococcus faecium*) | 350 |
| 351 | Enterocin Xbeta | Class IIb | *Enterococcus faecium* (*Streptococcus faecium*) | 352 |
| 353 | Enterolysin A | class III | *Enterococcus faecalis* (*Streptococcus faecalis*) | 354 |
| 355 | Epicidin 280 | Lantibiotic | *Staphylococcus epidermidis* | 356 |
| 357 | Epidermicin NI01 | Unclassified | *Staphylococcus epidermidis* | 358 |
| 359 | Epidermin | Lantibiotic | *Staphylococcus epidermidis* | 360 |
| 361 | Epilancin K7 | Lantibiotic | *Staphylococcus epidermidis* | 362 |
| 363 | Gallidermin | Lantibiotic | *Staphylococcus gallinarum* | 364 |
| 365 | Garvicin A | IId | *Lactococcus garvieae* | 366 |
| 367 | Garvicin ML | Unclassified | *Lactococcus garvieae* | 368 |
| 369 | Gassericin A | Unclassified | *Lactobacillus gasseri* | 370 |
| 371 | Gassericin T (gassericin K7B) | Unclassified | *Lactobacillus gasseri* | 372 |
| 373 | Glycocin F | Unclassified | *Lactobacillus plantarum* | 374 |
| 375 | Halocin H4 | Unclassified | *Haloferax mediterranei* (strain ATCC 33500/DSM 1411/JCM 8866/NBRC 14739/NCIMB 2177/R-4) (*Halobacterium mediterranei*) | 376 |
| 377 | Halocin-S8 | Unclassified | *Haloarchaeon S8a* | 378 |
| 379 | Helveticin-J | Unclassified | *Lactobacillus helveticus* (*Lactobacillus suntoryeus*) | 380 |
| 381 | Hiracin JM79 | Class II sec-dependent | *Enterococcus hirae* | 382 |
| 383 | Lactacin-F (lafA) | class IIB | *Lactobacillus johnsonii* (strain CNCM I-12250/La1/NCC 533) | 384 |
| 385 | Lactacin-F (lafX) | class IIB | *Lactobacillus johnsonii* (strain CNCM I-12250/La1/NCC 533) | 386 |
| 387 | Lacticin 3147 A1 | Lantibiotic | *Lactococcus lactis* subsp. *lactis* (*Streptococcus lactis*) | 388 |
| 389 | Lacticin 3147 A2 | Lantibiotic | *Lactococcus lactis* subsp. *lactis* (*Streptococcus lactis*) | 390 |
| 391 | Lacticin 481 (Lactococcin DR) | Lantibiotic | *Lactococcus lactis* subsp. *lactis* (*Streptococcus lactis*) | 392 |
| 393 | Lacticin Q | Unclassified | *Lactococcus lactis* | 394 |
| 395 | Lacticin Z | Unclassified | *Lactococcus lactis* | 396 |
| 397 | Lactobin-A (Amylovorin-L471) | class IIB | *Lactobacillus amylovorus* | 398 |
| 399 | Lactocin-S | Lantibiotic | *Lactobacillus sakei L45* | 400 |
| 401 | Lactococcin 972 | Unclassified | *Lactococcus lactis* subsp. *lactis* (*Streptococcus lactis*) | 402 |
| 403 | Lactococcin-A | Unclassified | *Lactococcus lactis* subsp. *cremoris* (*Streptococcus cremoris*) | 404 |

TABLE 5-continued

Exemplary Bacteriocins

| Poly-peptide SEQ ID NO: | Name | Class | Organism of origin | Poly-nucleotide SEQ ID NO: |
|---|---|---|---|---|
| 405 | Lactococcin-B | Unclassified | *Lactococcus lactis* subsp. *cremoris* (*Streptococcus cremoris*) | 406 |
| 407 | Lactocyclicin Q | Unclassified | *Lactococcus* sp. QU 12 | 408 |
| 409 | Laterosporulin | Unclassified | *Brevibacillus* sp. GI-9 | 410 |
| 411 | Leucocin N | Class IId | *Leuconostoc pseudomesenteroides* | 412 |
| 413 | Leucocin Q | Class IId | *Leuconostoc pseudomesenteroides* | 414 |
| 415 | Leucocin-A (Leucocin A-UAL 187) | class IIA/YGNGV | *Leuconostoc gelidum* | 416 |
| 417 | Leucocin-B (Leucocin B-Ta11a) | class IIA/YGNGV | *Leuconostoc carnosum* | 418 |
| 419 | Leucocyclicin Q | Unclassified | *Leuconostoc mesenteroides* | 420 |
| 421 | Lichenicidin A1 | Lantibiotic (two-peptide) | *Bacillus licheniformis* (strain DSM 13/ATCC 14580) | 422 |
| 423 | Linocin M18 | Unclassified | *Brevibacterium linens* | 424 |
| 425 | Listeriocin 743A | Class IIa | *Listeria innocua* | 426 |
| 427 | Mersacidin | Lantibiotic, type B | *Bacillus* sp. (strain HIL-Y85/54728) | 428 |
| 429 | Mesentericin Y105 | class IIA/YGNGV | *Leuconostoc mesenteroides* | 430 |
| 431 | Michiganin-A | Lantibiotic | *Clavibacter michiganensis* subsp. *michiganensis* | 432 |
| 433 | Microcin B17 (MccB17) | Unclassified | *Escherichia coli* | 434 |
| 435 | Microcin C7 | Unclassified | *Escherichia coli* | 436 |
| 437 | Microcin E492 | Unclassified | *Klebsiella pneumoniae* | 438 |
| 439 | Microcin H47 | Unclassified | *Escherichia coli* | 440 |
| 441 | Microcin J25 | Unclassified | *Escherichia coli* | 442 |
| 443 | Microcin-24 | Unclassified | *Escherichia coli* | 444 |
| 445 | Mundticin KS | Unclassified | *Enterococcus mundtii* | 446 |
| 447 | Mundticin L | class IIA/YGNGV | *Enterococcus mundtii* | 448 |
| 449 | Mutacin 1140 (Mutacin III) | Lantibiotic | *Streptococcus mutans* | 450 |
| 451 | Mutacin-2 | Lantibiotic | *Streptococcus mutans* | 452 |
| 453 | Nisin A | Lantibiotic | *Lactococcus lactis* subsp. *lactis* (*Streptococcus lactis*) | 454 |
| 455 | Nisin F | Lantibiotic | *Lactococcus lactis* | 456 |
| 457 | Nisin Q | Lantibiotic | *Lactococcus lactis* | 458 |
| 459 | Nisin U | Lantibiotic | *Streptococcus uberis* | 460 |
| 461 | Nisin Z | Lantibiotic | *Lactococcus lactis* subsp. *lactis* (*Streptococcus lactis*) | 462 |
| 463 | Nukacin ISK-1 | Lantibiotic | *Staphylococcus warneri* | 464 |
| 465 | Paenicidin A | Lantibiotic | *Paenibacillus polymyxa* (*Bacillus polymyxa*) | 466 |
| 467 | Pediocin PA-1 (Pediocin ACH) | class IIA/YGNGV | *Pediococcus acidilactici* | 468 |
| 469 | Penocin A | class IIA/YGNGV | *Pediococcus pentosaceus* (strain ATCC 25745/183-1w) | 470 |
| 471 | Pep5 | Lantibiotic | *Staphylococcus epidermidis* | 472 |
| 473 | Piscicolin 126 | class IIA/YGNGV | *Carnobacterium maltaromaticum* (*Carnobacterium piscicola*) | 474 |
| 475 | Plantaricin 1.25 β | Unclassified | *Lactobacillus plantarum* | 476 |
| 477 | Plantaricin 423 | class IIa | *Lactobacillus plantarum* | 478 |
| 479 | Plantaricin ASM1 | Unclassified | *Lactobacillus plantarum* | 480 |
| 481 | Plantaricin E | Unclassified | *Lactobacillus plantarum* | 482 |
| 483 | Plantaricin F | Class IIb | *Lactobacillus plantarum* | 484 |
| 485 | Plantaricin J | Class IIb | *Lactobacillus plantarum* | 486 |
| 487 | Plantaricin K | Unclassified | *Lactobacillus plantarum* | 488 |
| 489 | Plantaricin NC8 α | Unclassified | *Lactobacillus plantarum* | 490 |
| 491 | Plantaricin NC8 β | Unclassified | *Lactobacillus plantarum* | 492 |
| 493 | Plantaricin S α | Unclassified | *Lactobacillus plantarum* | 494 |
| 495 | Plantaricin S β | Unclassified | *Lactobacillus plantarum* | 496 |
| 497 | Plantaricin W α | Lantibiotic (two-peptide) | *Lactobacillus plantarum* | 498 |
| 499 | Plantaricin W β | Lantibiotic (two-peptide) | *Lactobacillus plantarum* | 500 |
| 501 | Plantaricin-A | Unclassified | *Lactobacillus plantarum* (strain ATCC BAA-793/NCIMB 8826/WCFS1) | 502 |
| 503 | Propionicin SM1 | Unclassified | *Propionibacterium jensenii* | 504 |

TABLE 5-continued

| Exemplary Bacteriocins | | | | |
|---|---|---|---|---|
| Poly-peptide SEQ ID NO: | Name | Class | Organism of origin | Poly-nucleotide SEQ ID NO: |
| 505 | Propionicin T1 | Unclassified | *Propionibacterium thoenii* | 506 |
| 507 | Propionicin-F | Unclassified | *Propionibacterium freudenreichii* subsp. *freudenreichii* | 508 |
| 509 | Pyocin S1 | Unclassified | *Pseudomonas aeruginosa* | 510 |
| 511 | Pyocin S2 | colicin/pyosin nuclease family | *Pseudomonas aeruginosa* (strain ATCC 15692/PAO1/1C/PRS 101/LMG 12228) | 512 |
| 513 | Ruminococcin-A | Lantibiotic | *Ruminococcus gnavus* | 514 |
| 515 | Sakacin G | Class IIa | *Lactobacillus sakei* | 516 |
| 517 | Sakacin-A | class IIA/YGNGV | *Lactobacillus sakei* | 518 |
| 519 | Sakacin-P (Sakacin 674) | class IIA/YGNGV | *Lactobacillus sakei* | 520 |
| 521 | Salivaricin 9 | lantibiotic | *Streptococcus salivarius* | 522 |
| 523 | Salivaricin A | Lantibiotic | *Streptococcus pyogenes* serotype M28 (strain MGAS6180) | 524 |
| 525 | Salivaricin A3 | Lantibiotic | *Streptococcus salivarius* | 526 |
| 527 | Salivaricin-A sa | Lantibiotic | *Streptococcus salivarius* | 528 |
| 529 | Staphylococcin C55 alpha | Lantibiotic (two-peptide) | *Staphylococcus aureus* | 530 |
| 531 | Staphylococcin C55 beta | Lantibiotic (two-peptide) | *Staphylococcus aureus* | 532 |
| 533 | Streptin | lantibiotic | *Streptococcus pyogenes* | 534 |
| 535 | Streptococcin A-FF22 | Lantibiotic | *Streptococcus pyogenes* | 536 |
| 537 | Streptococcin A-M49 | Lantibiotic | *Streptococcus pyogenes* serotype M49 | 538 |
| 539 | Sublancin 168 | Lantibiotic | *Bacillus subtilis* (strain 168) | 540 |
| 541 | Subtilin | Lantibiotic | *Bacillus subtilis* | 542 |
| 543 | Subtilosin | Unclassified | *Bacillus subtilis* (strain 168) | 544 |
| 545 | Subtilosin-A | Unclassified | *Bacillus subtilis* (strain 168) | 546 |
| 547 | Thermophilin 1277 | Lantibiotic | *Streptococcus thermophilus* | 548 |
| 549 | Thermophilin 13 | Unclassified | *Streptococcus thermophilus* | 550 |
| 551 | Thermophilin A | Unclassified | *Streptococcus thermophilus* | 552 |
| 553 | Thiocillin (Micrococcin P1) (Micrococcin P2) (Thiocillin I) (Thiocillin II) (Thiocillin III) (Thiocillin IV) (Antibiotic YM-266183) (Antibiotic YM-266184) | Unclassified | *Bacillus cereus* (strain ATCC 14579/ DSM 31) | 554 |
| 555 | Thuricin CD alpha | two-peptide lantibiotic | *Bacillus cereus* 95/8201 | 556 |
| 557 | Thuricin CD beta | two-peptide lantibiotic | *Bacillus cereus* 95/8201 | 558 |
| 559 | Thuricin-17 | Class IId | *Bacillus thuringiensis* | 560 |
| 561 | Trifolitoxin | Unclassified | *Rhizobium leguminosarum* bv. *trifolii* | 562 |
| 563 | Ubericin A | Class IIa | *Streptococcus uberis* | 564 |
| 565 | Uberolysin | Unclassified | *Streptococcus uberis* | 566 |
| 567 | UviB | Unclassified | *Clostridium perfringens* | 568 |
| 569 | Variacin | Lantibiotic, Type A | *Micrococcus varians* | 570 |
| 571 | Zoocin A | Unclassified | *Streptococcus equi* subsp. *zooepidemicus* | 572 |
| 573 | Fulvocin-C | Unclassified | *Myxococcus fulvus* | 574 |
| 575 | Duramycin-C | Lantibiotic | *Streptomyces griseoluteus* | 576 |
| 577 | Duramycin (duramycin-B) (Leucopeptin) | Lantibiotic B | *Streptoverticillium griseoverticillatum* | 578 |
| 579 | Carnocin UI49 | lantibiotic | *Carnobacterium* sp. (strain UI49) | 580 |
| 581 | Lactococcin-G α | Unclassified | *Lactococcus lactis* subsp. *lactis* (*Streptococcus lactis*) | 582 |
| 583 | Lactococcin-G β | Unclassified | *Lactococcus lactis* subsp. *lactis* (*Streptococcus lactis*) | 584 |
| 585 | Ancovenin | Lantibiotic | *Streptomyces* sp. (strain A647P-2) | 586 |
| 587 | Actagardine (Gardimycin) | Lantibiotic | *Actinoplanes liguriae* | 588 |
| 589 | Curvaticin FS47 | Unclassified | *Lactobacillus curvatus* | 590 |
| 591 | Bavaricin-MN | class IIA/YGNGV | *Lactobacillus sakei* | 592 |
| 593 | Mutacin B-Ny266 | Lantibiotic | *Streptococcus mutans* | 594 |
| 595 | Mundticin | class IIA/YGNGV | *Enterococcus mundtii* | 596 |
| 597 | Bavaricin-A | class IIA/YGNGV | *Lactobacillus sakei* | 598 |

TABLE 5-continued

Exemplary Bacteriocins

| Poly-peptide SEQ ID NO: | Name | Class | Organism of origin | Poly-nucleotide SEQ ID NO: |
|---|---|---|---|---|
| 599 | Lactocin-705 | Class IIb | *Lactobacillus paracasei* | 600 |
| 601 | Leucocin-B | Unclassified | *Leuconostoc mesenteroides* | 602 |
| 603 | Leucocin C | class IIA/YGNGV | *Leuconostoc mesenteroides* | 604 |
| 605 | LCI | Unclassified | *Bacillus subtilis* | 606 |
| 607 | Lichenin | Unclassified | *Bacillus licheniformis* | 608 |
| 609 | Lactococcin MMFII | class IIA/YGNGV | *Lactococcus lactis* subsp. *lactis* (*Streptococcus lactis*) | 610 |
| 611 | Serracin-P | Phage-Tail-Like | *Serratia plymuthica* | 612 |
| 613 | Halocin-C8 | Unclassified | *Halobacterium* sp. (strain AS7092) | 614 |
| 615 | Subpeptin JM4-B | Unclassified | *Bacillus subtilis* | 616 |
| 617 | Curvalicin-28a | Unclassified | *Lactobacillus curvatus* | 618 |
| 619 | Curvalicin-28b | Unclassified | *Lactobacillus curvatus* | 620 |
| 621 | Curvalicin-28c | Unclassified | *Lactobacillus curvatus* | 622 |
| 623 | Thuricin-S | Unclassified | *Bacillus thuringiensis* subsp. *entomocidus* | 624 |
| 625 | Curvaticin L442 | Unclassified | *Lactobacillus curvatus* | 626 |
| 627 | Divergicin M35 | class IIa/YGNGV | *Carnobacterium divergens* (*Lactobacillus divergens*) | 628 |
| 629 | Enterocin E-760 | class IIb | *Enterococcus* sp. | 630 |
| 631 | Bacteriocin E50-52 | Unclassified | *Enterococcus faecium* (*Streptococcus faecium*) | 632 |
| 633 | Paenibacillin | Unclassified | *Paenibacillus polymyxa* (*Bacillus polymyxa*) | 634 |
| 635 | Epilancin 15x | Unclassified | *Staphylococcus epidermidis* | 636 |
| 637 | Enterocin-HF | class IIa | *Enterococcus faecium* (*Streptococcus faecium*) | 638 |
| 639 | Bacillocin 602 | Class IIa | *Paenibacillus polymyxa* (*Bacillus polymyxa*) | 640 |
| 641 | Bacillocin 1580 | Class IIa | *Bacillus circulans* | 642 |
| 643 | Bacillocin B37 | Unclassified | *Paenibacillus polymyxa* (*Bacillus polymyxa*) | 644 |
| 645 | Rhamnosin A | Unclassified | *Lactobacillus rhamnosus* | 646 |
| 647 | Lichenicidin A2 | Lantibiotic (two-peptide) | *Bacillus licheniformis* (strain DSM 13/ATCC 14580) | 648 |
| 649 | Plantaricin C19 | Class IIa | *Lactobacillus plantarum* | 650 |
| 651 | Acidocin J1132 β | Class IIb | *Lactobacillus acidophilus* | 652 |
| 653 | factor with anti-*Candida* activity | Unclassified | *Enterococcus faecalis* | 654 |
| 655 | Ava_1098 (putative heterocyst differentiation protein) | Unclassified | *Anabaena variabilis* ATCC 29413 | 656 |
| 657 | alr2818 (putative heterocyst differentiation protein) | Unclassified | *Nostoc* sp 7120 | 658 |
| 659 | Aazo_0724 (putative heterocyst differentiation protein) | Unclassified | *Nostoc azollae* 0708 | 660 |
| 661 | AM1_4010 (putative heterocyst differentiation protein) | Unclassified | *Acaryochloris marina* MBIC11017 | 662 |
| 663 | PCC8801_3266 (putative heterocyst differentiation protein) | Unclassified | *Cyanothece* PCC 8801 | 664 |
| 665 | Cyan8802_2855 (putative heterocyst differentiation protein) | Unclassified | *Cyanothece* PCC 8802 | 666 |
| 667 | PCC7424_3517 | Unclassified | *Cyanothece* PCC 7424 | 668 |
| 669 | cce_2677(putative HetP protein) | Unclassified | *Cyanothece* ATCC 51142 | 670 |

TABLE 5-continued

| Exemplary Bacteriocins | | | | |
|---|---|---|---|---|
| Poly-peptide SEQ ID NO: | Name | Class | Organism of origin | Poly-nucleotide SEQ ID NO: |
| 671 | CY0110_11572 (putative heterocyst differentiation protein) | Unclassified | *Cyanothece* CCY0110 | 672 |
| 673 | MC7420_4637 | Unclassified | *Microcoleus chthonoplastes* PCC 7420 | 674 |
| 675 | asr1611 (putative DUF37 family protein) | Unclassified | *Nostoc* sp 7120 | 676 |
| 677 | Ava_4222 (putative DUF37 family protein) | Unclassified | *Anabaena variabilis* ATCC 29413 | 678 |
| 679 | N9414_07129 (putative DUF37 family protein) | Unclassified | *Nodularia spumigena* CCY9414 | 680 |
| 681 | Aazo_0083 (putative DUF37 family protein) | Unclassified | *Nostoc azollae* 0708 | 682 |
| 683 | S7335_3409 (putative DUF37 family protein) | Unclassified | *Synechococcus* PCC 7335 | 684 |
| 685 | P9303_21151 (putative DUF37 family protein) | Unclassified | *Prochlorococcus marinus* MIT 9303 | 686 |
| 687 | Curvalicin-28c | Unclassified | *Lactobacillus curvatus* | 688 |
| 689 | thruicin-S | Unclassified | *Bacillus thuringiensis* | 690 |
| 691 | curvaticin L442 | Unclassified | *Lactobacillus curvatus* L442 | 692 |
| 693 | Bacteriocin divergicin M35 | P84962 | *Carnobacterium divergens* (*Lactobacillus divergens*) | 694 |
| 695 | Lantibiotic 107891 | P85065 | *Microbispora* sp. (strain 107891) | 696 |
| 697 | Enterocin E-760 (Bacteriocin E-760) | P85147 | *Enterococcus* sp. | 698 |
| 699 | Bacteriocin E50-52 | P85148 | *Enterococcus faecium* (*Streptococcus faecium*) | 700 |
| 701 | Lantibiotic paenibacillin | P86013 | *Paenibacillus polymyxa* (*Bacillus polymyxa*) | 702 |
| 703 | Lantibiotic epilancin 15X | P86047 | *Staphylococcus epidermidis* | 704 |
| 705 | Enterocin-HF | P86183 | *Enterococcus faecium* (*Streptococcus faecium*) | 706 |
| 707 | Bacteriocin SRCAM 602 | P86393 | *Paenibacillus polymyxa* (*Bacillus polymyxa*) | 708 |
| 709 | Bacteriocin SRCAM 1580 | P86394 | *Bacillus circulans* | 710 |
| 711 | Bacteriocin SRCAM 37 | P86395 | *Paenibacillus polymyxa* (*Bacillus polymyxa*) | 712 |
| 713 | Bacteriocin rhamnosin A (Fragment) | P86526 | *Lactobacillus rhamnosus* | 714 |
| 715 | Lantibiotic lichenicidin A2 (LchA2) (BliA2) | P86720 | *Bacillus licheniformis* (strain ATCC 14580/DSM 13/JCM 2505/ NBRC 12200/NCIMB 9375/NRRL NRS-1264/Gibson 46) | 716 |
| 717 | Pyocin-S2 (EC 3.1.-.-) (Killer protein) | | *Pseudomonas aeruginosa* (strain ATCC 15692/DSM 22644/CIP 104116/JCM 14847/LMG 12228/ 1C/PRS 101/PAO1) | 718 |
| 719 | Plantaricin C19 (Fragment) | | *Lactobacillus plantarum* | 720 |
| 721 | LsbB | | *Lactococcus lactis* subsp. *lactis* (*Streptococcus lactis*) | 722 |
| 723 | ACIDOCIN J1132 beta peptide (Fragment) | | *Lactobacillus acidophilus* | 724 |
| 725 | Uncharacterized protein | | *Lactobacillus salivarius* cp400 | 726 |

For example, in some embodiments, an anti-fungal activity (such as anti-yeast activity) is desired. A number of bacteriocins with anti-fungal activity have been identified. For example, bacteriocins from *Bacillus* have been shown to have neutralizing activity against yeast strains (Adetunji and Olaoye (2013) Malaysian Journal of Microbiology 9: 130-13, hereby incorporated by reference), an *Enterococcus faecalis* peptide (WLPPAGLLGRCGRWFRPWLLWLQ SGAQY KWLGNLFGLGPK, SEQ ID NO: 727) has been shown to have neutralizing activity against *Candida* species {see Shekh and Roy (2012) BMC Microbiology 12: 132, hereby incorporated by reference in its entirety), and bacteriocins from Pseudomonas have been shown to have neutralizing activity against fungi such as *Curvularia lunata, Fusarium* species, *Helminthosporium* species, and *Biopolaris* species (Shalani and Srivastava (2008) The Internet Journal of Microbiology. Volume 5 Number 2, hereby incorporated by reference). By way of example, botrycidin AJ1316 (Zuber, P et al. (1993) Peptide Antibiotics. In *Bacillus subtilis* and Other Gram-Positive Bacteria: Biochemistry, Physiology, and Molecular Genetics ed Sonenshein et al., pp. 897-916, American Society for Microbiology, hereby incorporated by reference) and alirin BI (Shenin et al. (1995) Antibiot Khimioter 50: 3-7, hereby incorporated by reference) from *B. subtilis* have been shown to have antifungal activities. As such, in some embodiments, for example embodiments in which neutralization of a fungal microbial organism is desired, a bacteriocin comprises at least one of botrycidin AJ1316 or alirin B 1.

For example, in some embodiments, bacteriocin activity in a culture of cyanobacteria is desirable. In some embodiments, bacteriocins are provided to neutralize cyanobacteria. In some embodiments, bacteriocins are provided to neutralize invading microbial organisms typically found in a cyanobacteria culture environment. Clusters of conserved bacteriocin polypetides have been identified in a wide variety of cyanobacteria species. For example, at least 145 putative bacteriocin gene clusters have been identified in at least 43 cyanobacteria species, as reported in Wang et al. (2011), Genome Mining Demonstrates the Widespread Occurrence of Gene Clusters Encoding Bacteriocins in Cyanobacteria. PLoS ONE 6(7): e22384, hereby incorporated by reference in its entirety. Exemplary cyanobacteria bacteriocins are shown in Table 5 as SEQ ID NO's 655, 657, 659, 661, 663, 665, 667, 669, 671, 673, 675, 677, 679, 681, 683, and 685.

General Descriptions

Unless stated otherwise, all technical and scientific terms used herein have the same meaning as customarily and ordinarily understood by a person of ordinary skill in the art to which this invention belongs, and read in view of this disclosure.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer.

As used herein, a "regulator" or "transcriptional regulator" is a protein that controls the rate of transcription of genetic information from DNA to messenger RNA, by binding to a specific DNA sequence.

The term "selectable marker" is a term familiar to one of ordinary skill in the art and is used herein to describe any genetic entity which, when expressed, can be used to select for a cell or cells containing the selectable marker. Selectable markers may be dominant or recessive or bidirectional.

As used herein, the term "operably linked" refers to a linkage of polynucleotide elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

The terms "protein" or "polypeptide" are used interchangeably and refer to molecules consisting of a chain of amino acids, without reference to a specific mode of action, size, 3-dimensional structure or origin.

The term "gene" means a DNA fragment comprising a region (transcribed region), which is transcribed into an RNA molecule (e.g. an mRNA) in a cell, operably linked to suitable regulatory regions (e.g. a promoter). A gene will usually comprise several operably linked fragments, such as a promoter, a 5' leader sequence, a coding region and a 3'-nontranslated sequence (3'-end) e.g. comprising a polyadenylation- and/or transcription termination site.

"Expression of a gene" refers to the process wherein a DNA region which is operably linked to appropriate regulatory regions, particularly a promoter, is transcribed into an RNA, which is biologically active, i.e. which is capable of being translated into a biologically active protein or peptide.

In amino acid sequences as described herein, amino acids or "residues" are denoted by three-letter symbols. These three-letter symbols as well as the corresponding one-letter symbols are well known to the person skilled in the art and have the following meaning: A (Ala) is alanine, C (Cys) is cysteine, D (Asp) is aspartic acid, E (Glu) is glutamic acid, F (Phe) is phenylalanine, G (Gly) is glycine, H (His) is histidine, I (Ile) is isoleucine, K (Lys) is lysine, L (Leu) is leucine, M (Met) is methionine, N (Asn) is asparagine, P (Pro) is proline, Q (Gln) is glutamine, R (Arg) is arginine, S (Ser) is serine, T (Thr) is threonine, V (Val) is valine, W (Trp) is tryptophan, Y (Tyr) is tyrosine. A residue may be any proteinogenic amino acid, but also any non-proteinogenic amino acid such as D-amino acids and modified amino acids formed by post-translational modifications, and also any non-natural amino acid, as described herein.

Sequence Identity

The terms "homology", "sequence identity" and the like are used interchangeably herein. Sequence identity is described herein as a relationship between two or more amino acid (polypeptide or protein) sequences or two or more nucleic acid (polynucleotide) sequences, as determined by comparing the sequences. In a preferred embodiment, sequence identity is calculated based on the full length of two given SEQ ID NO's or on a part thereof. Part thereof preferably means at least 50%, 60%, 70%, 80%, 90%, or 100% of both SEQ ID NO's. In the art, "identity" also refers to the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods, including but not limited to those described in Bioinformatics and the Cell: Modern Computational Approaches in Genomics, Proteomics and transcriptomics, Xia X., Springer International Publishing, New York, 2018; and Bioinformatics: Sequence and Genome Analysis, Mount D., Cold Spring Harbor Laboratory Press, New York, 2004.

"Sequence identity" and "sequence similarity" can be determined by alignment of two peptide or two nucleotide sequences using global or local alignment algorithms, depending on the length of the two sequences. Sequences of similar lengths are preferably aligned using a global alignment algorithms (e.g. Needleman-Wunsch) which aligns the sequences optimally over the entire length, while sequences of substantially different lengths are preferably aligned using a local alignment algorithm (e.g. Smith-Waterman). Sequences may then be referred to as "substantially identical" or "essentially similar" when they (when optimally aligned by for example the program EMBOSS needle or EMBOSS water using default parameters) share at least a certain minimal percentage of sequence identity (as described below).

A global alignment is suitably used to determine sequence identity when the two sequences have similar lengths. When sequences have a substantially different overall length, local alignments, such as those using the Smith-Waterman algorithm, are preferred. EMBOSS needle uses the Needleman-Wunsch global alignment algorithm to align two sequences over their entire length (full length), maximizing the number of matches and minimizing the number of gaps. EMBOSS water uses the Smith-Waterman local alignment algorithm. Generally, the EMBOSS needle and EMBOSS water default parameters are used, with a gap open penalty=10 (nucleotide sequences)/10 (proteins) and gap extension penalty=0.5 (nucleotide sequences)/0.5 (proteins). For nucleotide sequences the default scoring matrix used is DNAfull and for proteins the default scoring matrix is Blosum62 (Henikoff & Henikoff, 1992, PNAS 89, 915-919).

Alternatively percentage similarity or identity may be determined by searching against public databases, using algorithms such as FASTA, BLAST, etc. Thus, the nucleic acid and protein sequences of some embodiments of the present invention can further be used as a "query sequence" to perform a search against public databases to, for example, identify other family members or related sequences. Such searches can be performed using the BLASTn and BLASTx programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to oxidoreductase nucleic acid molecules of the invention. BLAST protein searches can be performed with the BLASTx program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTx and BLASTn) can be used. See the homepage of the National Center for Biotechnology Information accessible on the world wide web at www.ncbi.nlm.nih.gov/.

Optionally, in determining the degree of amino acid similarity, the skilled person may also take into account so-called conservative amino acid substitutions.

As used herein, "conservative" amino acid substitutions refer to the interchangeability of residues having similar side chains. Examples of classes of amino acid residues for conservative substitutions are given in the Tables below.

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

Alternative Conservative Amino Acid Residue Substitution Classes:

| | | | |
|---|---|---|---|
| 1 | A | S | T |
| 2 | D | E | |
| 3 | N | Q | |
| 4 | R | K | |
| 5 | I | L | M |
| 6 | F | Y | W |

Alternative Physical and Functional Classifications of Amino Acid Residues:

| | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P and T |
| Flexible residues | Q, T, K, S, G, P, D, E, and R |

Microbial Organism

As used herein, "microbial organism", "microorganism", "microbial cell" or "microbial host" and variations of these root terms (such as pluralizations and the like) have their customary and ordinary meanings as understood by one of skill in the art in view of this disclosure, including any naturally-occurring species or synthetic or fully synthetic prokaryotic or eukaryotic unicellular organism. Thus, this expression can refer to cells of any of the three domains Bacteria, Archaea and Eukarya. Exemplary microorganisms that can be used in accordance with embodiments herein include, but are not limited to, bacteria, yeast, filamentous fungi, and algae, for example photosynthetic microalgae. Furthermore, fully synthetic microorganism genomes can be synthesized and transplanted into single microbial cells, to produce synthetic microorganisms capable of continuous self-replication (see Gibson et al. (2010), "Creation of a Bacterial Cell Controlled by a Chemically Synthesized Genome," Science 329: 52-56, which is incorporated herein by reference). As such, in some embodiments, the microorganism is fully synthetic. A desired combination of genetic elements, including elements that regulate gene expression, and elements encoding gene products (for example immunity modulators, poison, antidote, and industrially useful molecules also called product of interest) can be assembled on a desired chassis into a partially or fully synthetic microorganism. Description of genetically engineered microbial organisms for industrial applications can also be found in Wright, et al. (2013) "Building-in biosafety for synthetic biology" Microbiology 159: 1221-1235, incorporated herein by reference.

A variety of bacterial species and strains can be used in accordance with embodiments herein, and genetically modified variants, or synthetic bacteria based on a "chassis" of a known species can be provided. Exemplary bacteria with industrially applicable characteristics, which can be used in accordance with embodiments herein include, but are not limited to, *Bacillus* species (for example *Bacillus coagulans, Bacillus subtilis*, and *Bacillus licheniformis*), *Paenibacillus* species, *Streptomyces* species, *Micrococcus* species, *Corynebacterium* species, *Acetobacter* species, *Cyanobacteria* species, *Salmonella* species, *Rhodococcus* species, *Pseudomonas* species, *Lactobacillus* species, *Enterococcus* species, *Alcaligenes* species, *Klebsiella* species, *Paenibacillus* species, *Arthrobacter* species, *Corynebacterium* species, *Brevibacterium* species, *Thermus aquaticus, Pseudomonas stutzeri, Clostridium thermocellus*, and *Escherichia coli*. A variety of yeast species and strains can be used in accordance with embodiments herein, and genetically modified variants, or synthetic yeast based on a "chassis" of a known species can be provided. Exemplary yeast with industrially applicable characteristics, which can be used in accordance with embodiments herein include, but are not limited to *Saccharomyces* species (for example, *Saccharomyces cerevisiae, Saccharomyces bayanus, Saccharomyces boulardii*), *Candida* species (for example, *Candida utilis, Candida krusei*), *Schizosaccharomyces* species (for example *Schizosaccharomyces pombe, Schizosaccharomyces japonicus*), *Pichia* or *Hansenula* species (for example, *Pichia pastoris* or *Hansenula polymorpha*) species, and *Brettanomyces* species (for example, *Brettanomyces claussenii*).

A variety of algae species and strains can be used in accordance with embodiments herein, and genetically modified variants, or synthetic algae based on a "chassis" of a known species can be created. In some embodiments, the algae comprises, consists essentially of, or consists of photosynthetic microalgae. Exemplary algae species that can be useful for biofuels, and can be used in accordance with embodiments herein, include *Botryococcus braunii, Chlorella* species, *Dunaliella tertiolecta, Gracilaria* species, *Pleurochrysis carterae*, and *Sargassum* species. Additionally, many algaes can be useful for food products, fertilizer products, waste neutralization, environmental remediation, and carbohydrate manufacturing (for example, biofuels).

A variety of filamentous fungal species and strains can be used in accordance with embodiments herein, and genetically modified variants, or synthetic filamentous fungi based on a "chassis" of a known species can be provided. Exemplary filamentous fungi with industrially applicable characteristics, which can be used in accordance with embodiments herein include, but are not limited to an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocaffimastix, Neurospora, Paecilomyces, Peniciffium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria*.

Species include *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenaturn, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei*, or *Trichoderma viride*.

In this document and in its claims, the verb "to comprise" and its conjugations is used in its non-limiting sense to mean that items following the word are included, but items not specifically mentioned are not excluded. In addition, the verb "to consist" may be replaced by "to consist essentially of" meaning that a peptide or peptidomimetic, a polypeptide, a culture medium, a microbial organism or a composition as described herein may comprise additional component(s) than the ones specifically identified, said additional component(s) not altering the unique characteristic of the invention. In addition, the verb "to consist" may be replaced by "to consist essentially of" meaning that a method as described herein may comprise additional step(s) than the ones specifically identified, said additional step(s) not altering the unique characteristic of the invention.

Reference to an element by the indefinite article "a" or "an" does not exclude the possibility that more than one of the element is present, unless the context clearly requires that there be one and only one of the elements. The indefinite article "a" or "an" thus usually means "at least one".

As used herein, with "at least" a particular value means that particular value or more. For example, "at least 2" is understood to be the same as "2 or more" i.e., 2, 3, 4, 5, 6, 7, 8, 9, 10, 11, 12, 13, 14, 15, . . . , etc.

The word "about" or "approximately" when used in association with a numerical value (e.g. about 10) preferably means that the value may be the given value (of 10) more or less 0.1% of the value.

As used herein, the term "and/or" indicates that one or more of the stated cases may occur, alone or in combination with at least one of the stated cases, up to with all of the stated cases.

Each embodiment as identified herein may be combined together unless otherwise indicated.

All patent applications, patents, and printed publications cited herein are incorporated herein by reference in the entireties, except for any definitions, subject matter disclaimers or disavowals, and except to the extent that the incorporated material is inconsistent with the express disclosure herein, in which case the language in this disclosure controls.

One skilled in the art will recognize many methods and materials similar or equivalent to those described herein, which could be used in the practice of the present invention. Indeed, the present invention is in no way limited to the methods and materials described.

The present invention is further described by the following examples which should not be construed as limiting the scope of the invention.

(A) Scheme of genomic organization and transcriptional dependencies (dashed arrows) between competence activation (comX) and bacteriocins production (blpK, slvX, . . . ) in *S. salivarius*. Promoters are depicted with broken arrows. Regulators and the ComS pheromone are stained according to their encoding genes. The ComS precursor is produced (curled arrow) as an intracellular precursor (square) before secretion, maturation and import as an active pheromone (ellipses). The newly described two-Rgg system is shaded and the T arrow pinpoints the inhibitory role of SarF on ScuR.

(B, C, D and E) Maximum luciferase activity/$OD_{600}$ ratio (RLU/OD; logarithmic scale) of various competence or bacteriocin production-involved promoters fused to a luxAB reporter system in WT or overexpressing backgrounds. (B) Promoter activation of genes upon sComS addition (full bars) vs mock condition (striped bars) in WT (light grey bars) or scuR overexpression mutant ($scuR^{++}$; dark grey bars). (C) Activity of sptA, comS and slvX promoters in WT strain, and $scuR^{++}$ or sarF ($sarF^{++}$) overexpression mutants. (D) Activity of sptA and comS promoters in WT and $scuR^{++}$ mutant deleted or not for comR gene. (E) Activity of sptA and comS promoters in overexpression of scuR or sarF in a scuR locus (ΔscuR-sarF) deletion background. Experimental values represent the averages (with standard error of the mean, SEM) of at least three independent biological replicates.

(F) Maximum luciferase activity/$OD_{600}$ ratio (RLU/OD) of comS, blpK and slvX promoters fused to a luxAB reporter system in WT (open bars) or ΔscuR-sarF (grey bars) strain activated with sComS. Experimental values represent the averages (with standard error of the mean, SEM) of at least three independent biological replicates.

Figure 2:
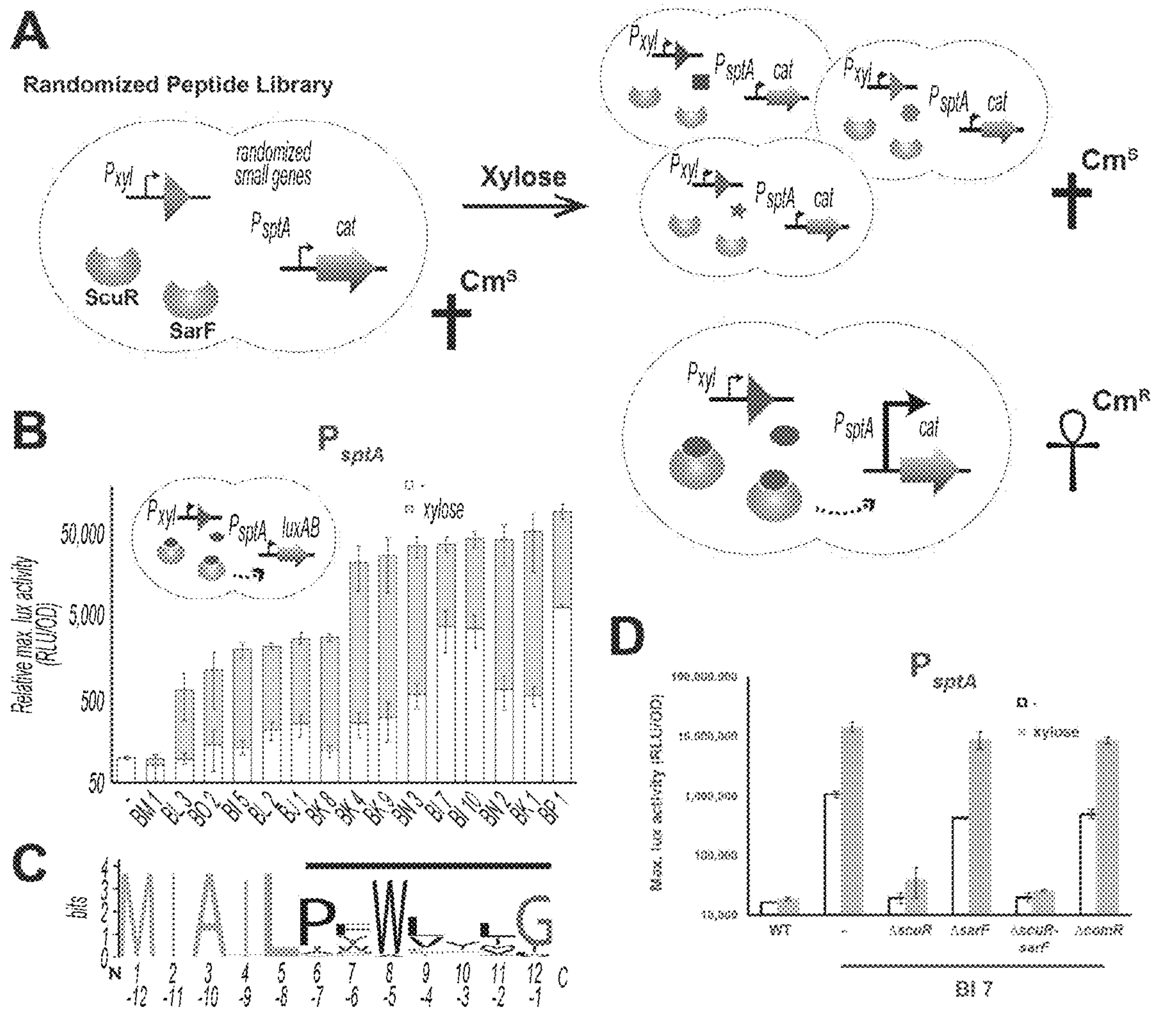

FIG. 2. ScuR/SarF Activating Peptide Identification (A) Cartoon portraying the rational strategy for the peptide randomization-based screen. A library of randomized small genes under inducible promoter controls ($P_{xyl}$) is transformed in a reporter strain in which the chloramphenicol resistance gene (cat) is translationally fused to sptA promoter. In absence of xylose or upon xylose induction of irrelevant peptides (square, hexagon and star), sptA promoter is maintained OFF and does not initiate cat transcription, causing cell sensitivity ($Cm^S$) on chloramphenicol-supplemented media. The xylose-driven intracellular production of a cognate peptide (ellipse) promotes chloramphenicol resistance ($Cm^R$), through $P_{sptA}$ activation by ScuR/SarF (dashed arrow).

(B) Activity of sptA promoter in WT strains and various mutants expressing intracellularly activating peptides (cartoon) in medium supplemented with xylose (0.1% or 1%; grey bars) vs mock conditions (open bars). The BM 1 clone is an irrelevant peptide (negative control). Magnitude is expressed in percentage compared to the WT $P_{sptA}$-luxAB reporter strain (Relative maximal luciferase activity). Experimental values represent the averages (with standard error of the mean, SEM) of at least three independent biological replicates.

(C) Weighted consensus sequence for the suite of 22 activating peptides identified in the randomization-based screen. Randomized residues are crowned with a horizontal black bar while the non-variable amino acids are grey-coloured. The Bits represent the relative frequency of residues. Information content is plotted as a function of residues position and reckoned from the N-terminus (1 to 12) or the C-terminus (−1 to −12). The sequence logo image was generated using the WebLogo application (accessible on the world wide web at weblogo.berkeley.edu/logo.cgi).

(D) Promoter activity of the sptA gene in response to the BI7 encoded peptide in various rgg mutant backgrounds. Media were supplemented with 0.1% xylose (open bars) or water (grey bars). Experimental values represent the averages (with standard error of the mean, SEM) of at least three independent biological replicates.

Figure 3:
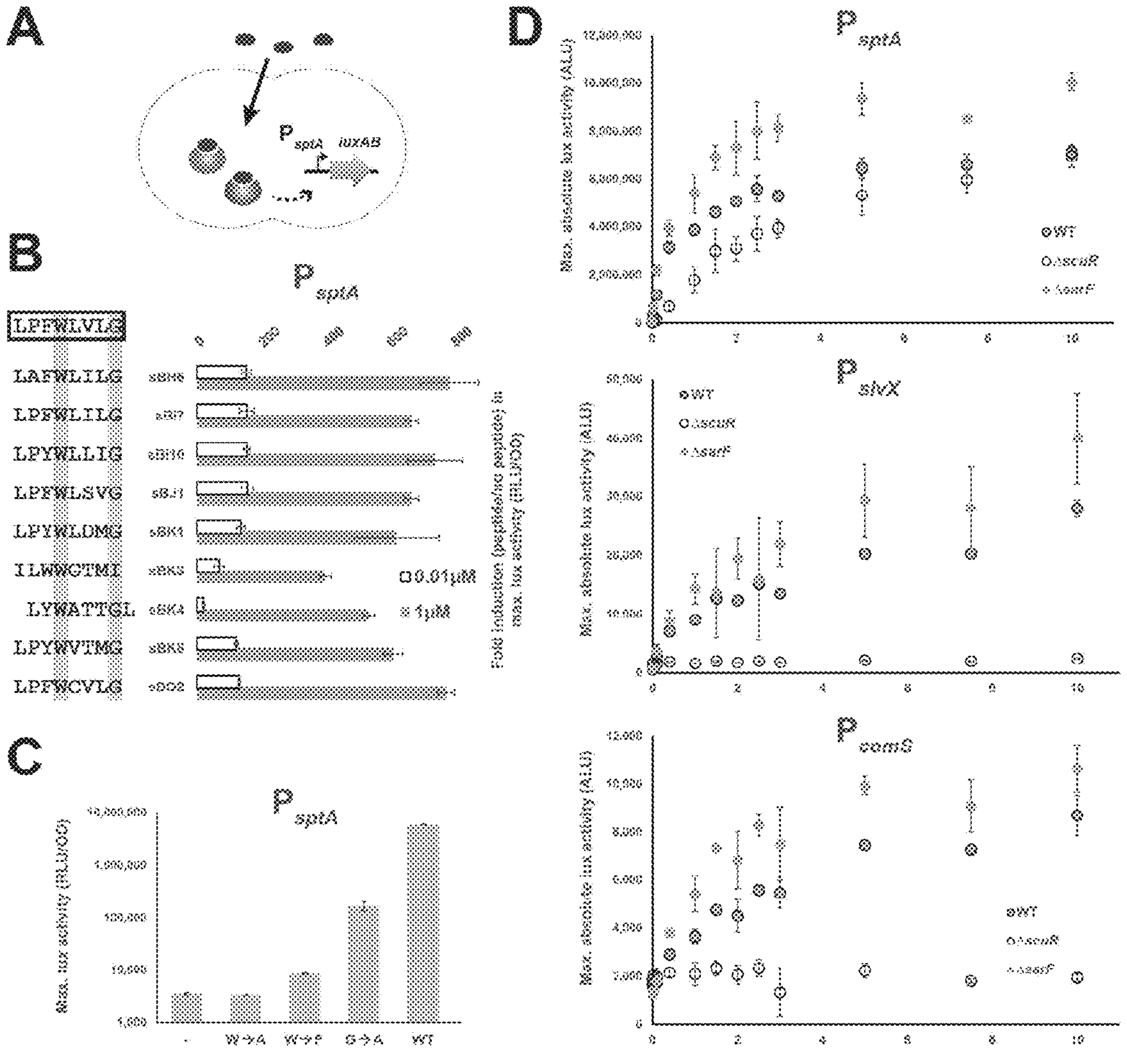
Figure 3:
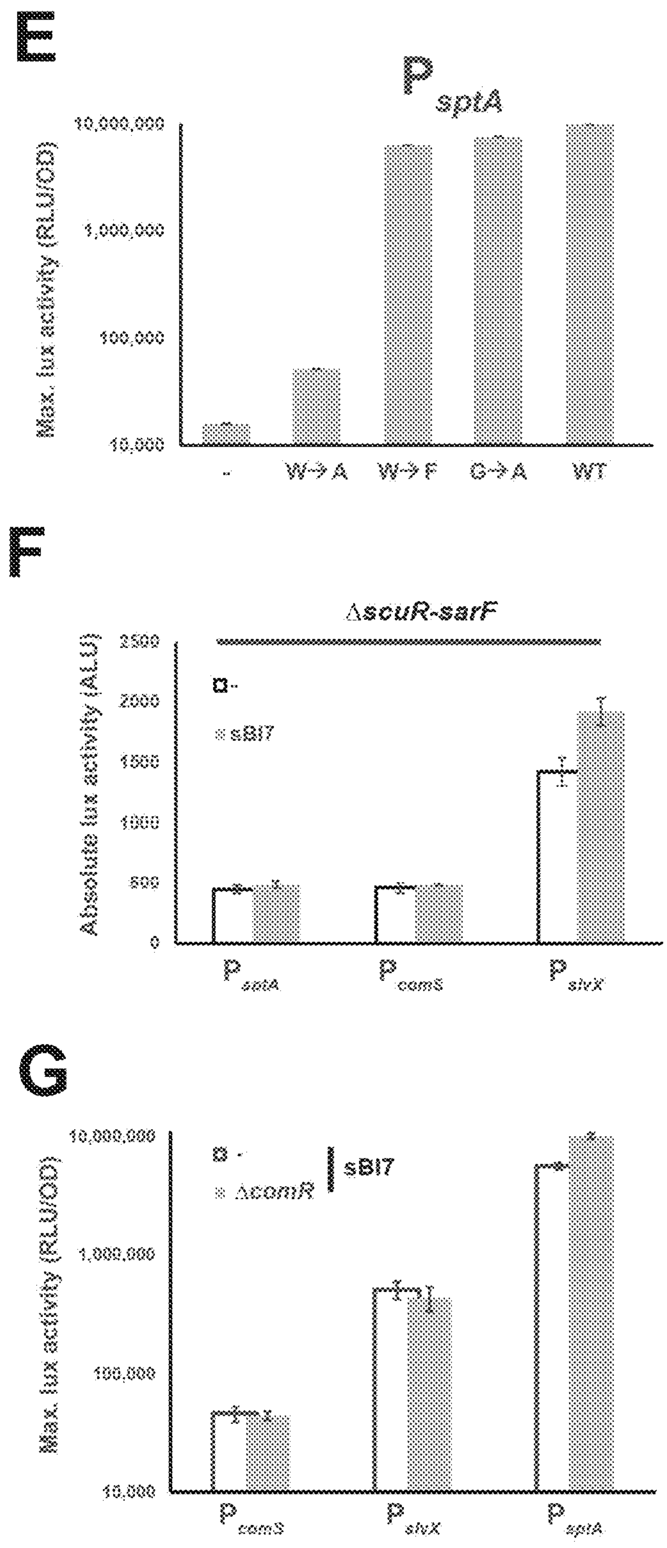

FIG. 3. The ScuR/SarF System Responds to Exogenous Peptides (A) Cartoon depicting the ScuR/SarF-mediated activation of $P_{sptA}$ upon addition of exogenous synthetic peptides.

(B) Fold increase in maximal $P_{sptA}$ activity upon addition of representative synthetic peptide (0.01 or 1 μM) vs mock conditions. Peptide sequences are correlated to peptide name and compared to the consensus motive (SEQ ID NO: 728) (open box). sBH6: SEQ ID NO: 729; sBI7: SEQ ID NO: 730; sBI10: SEQ ID NO: 731; sBJ1: SEQ ID NO: 732; sBK1: SEQ ID NO: 733; sBK3: SEQ ID NO: 734; sBK4: SEQ ID NO: 735; sBK8: SEQ ID NO: 736; sBO2: SEQ ID NO: 737. The crucial W and G residues are highlighted with grey boxes.

(C) Maximal activity of $P_{sptA}$ exposed to sBI7 WT and mutant peptides (1 nM).

(D) Dose response dot plot of sptA, slvX and comS promoter activity upon sBI7 induction at various concentrations (nM). Promoters were tested in WT strain and, ΔscuR or ΔsarF deletants.

(B, C and D) Experimental values represent the averages (with standard error of the mean, SEM) of at least three independent biological replicates.

(E) Maximal activity of PsptA (RLU/OD; logarithmic scale) exposed to WT and mutant sBI7 peptides (1 μM). Experimental values represent the averages (with standard error of the mean, SEM) of at least three independent biological replicates.

(F) Activity of sptA, comS and slvX promoters (absolute maximal luciferase activity; ALU) in ΔscuR-sarF challenged with sBI7 synthetic peptide (grey bars) vs mock conditions (open bars). Experimental values represent the averages (with standard error of the mean, SEM) of at least three independent biological replicates.

(G) Maximum luciferase activity/OD600 ratio (RLU/OD; logarithmic scale) of comS, slvX and sptA promoters fused to a luxAB reporter system in WT (open bars) or ΔcomR (grey bars) strain activated with the sBI7 synthetic peptide. Experimental values represent the averages (with standard error of the mean, SEM) of at least three independent biological replicates.

Figure 4:
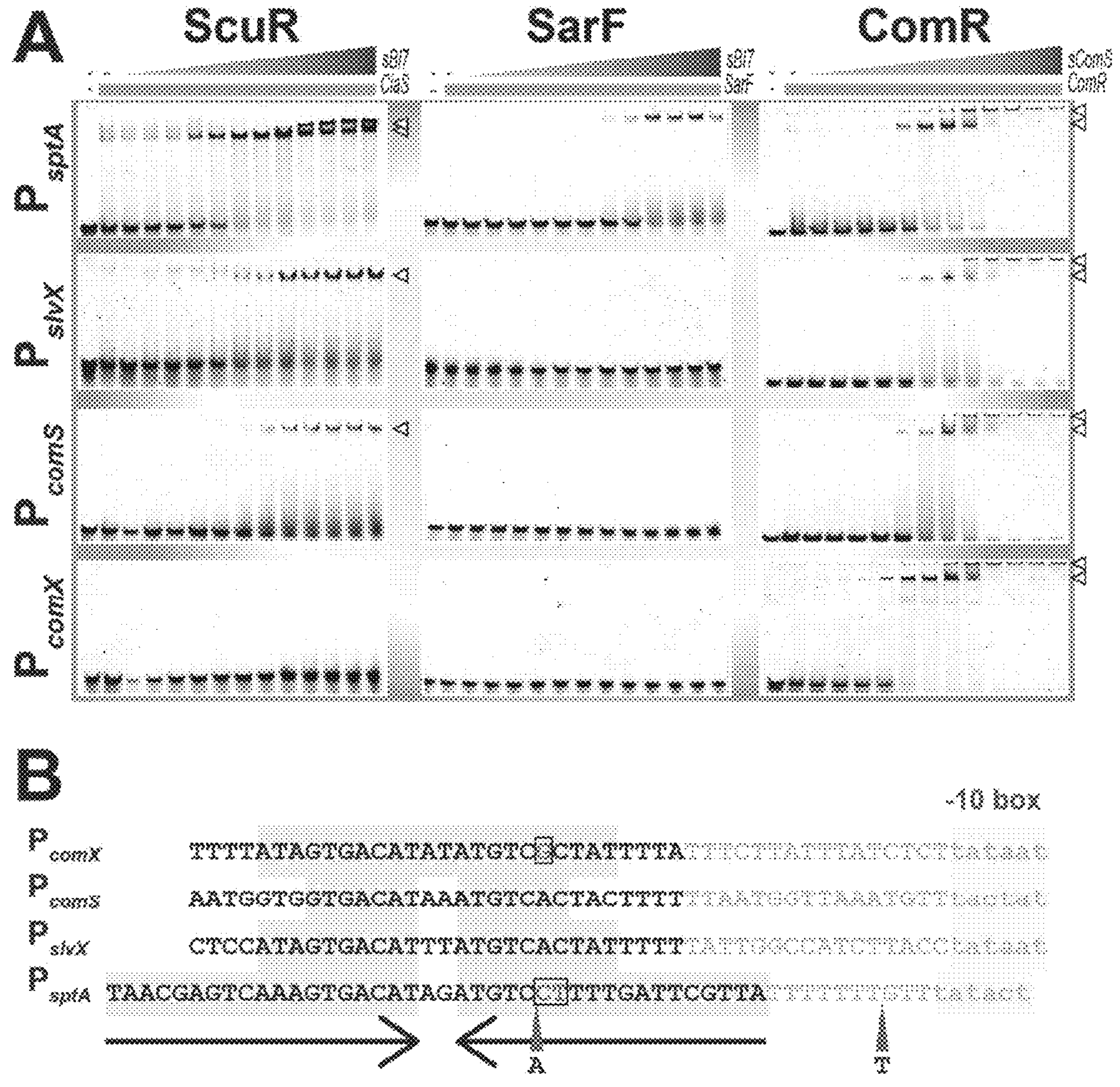
Figure 4:
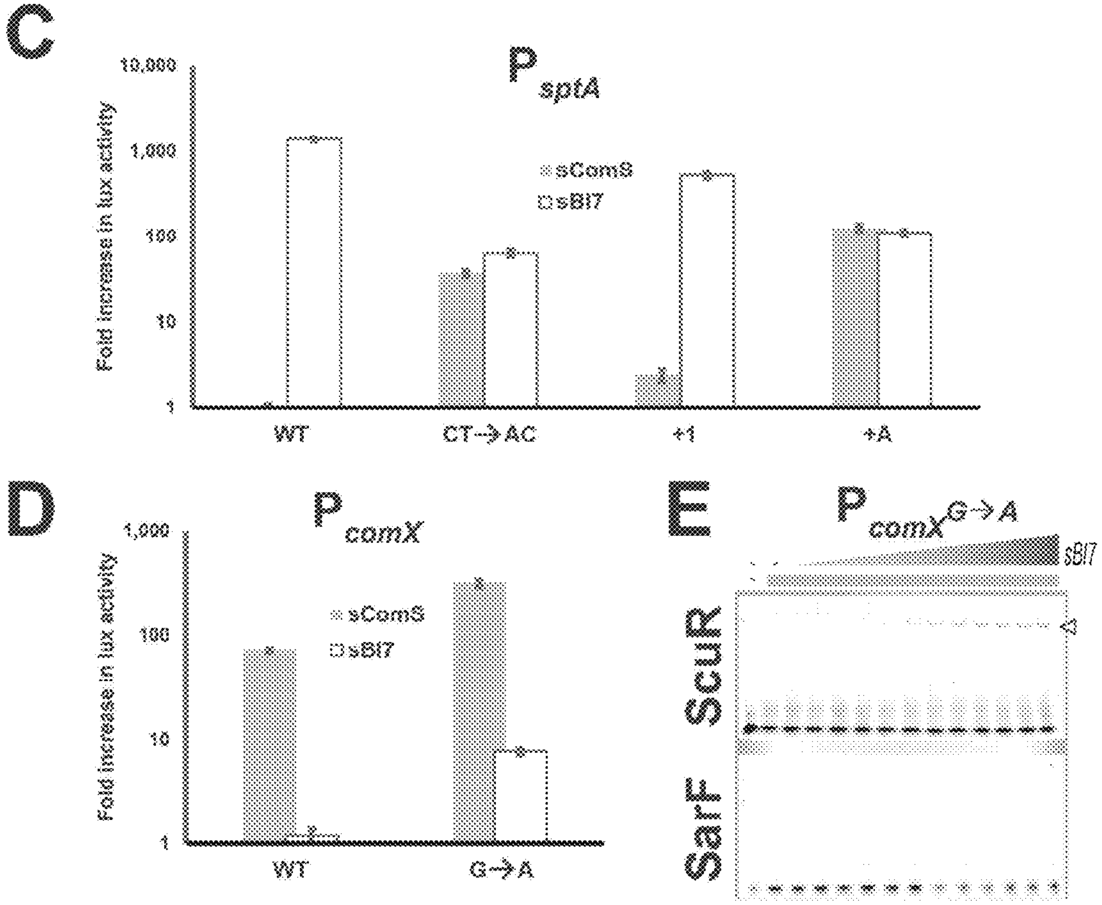
Figure 4:
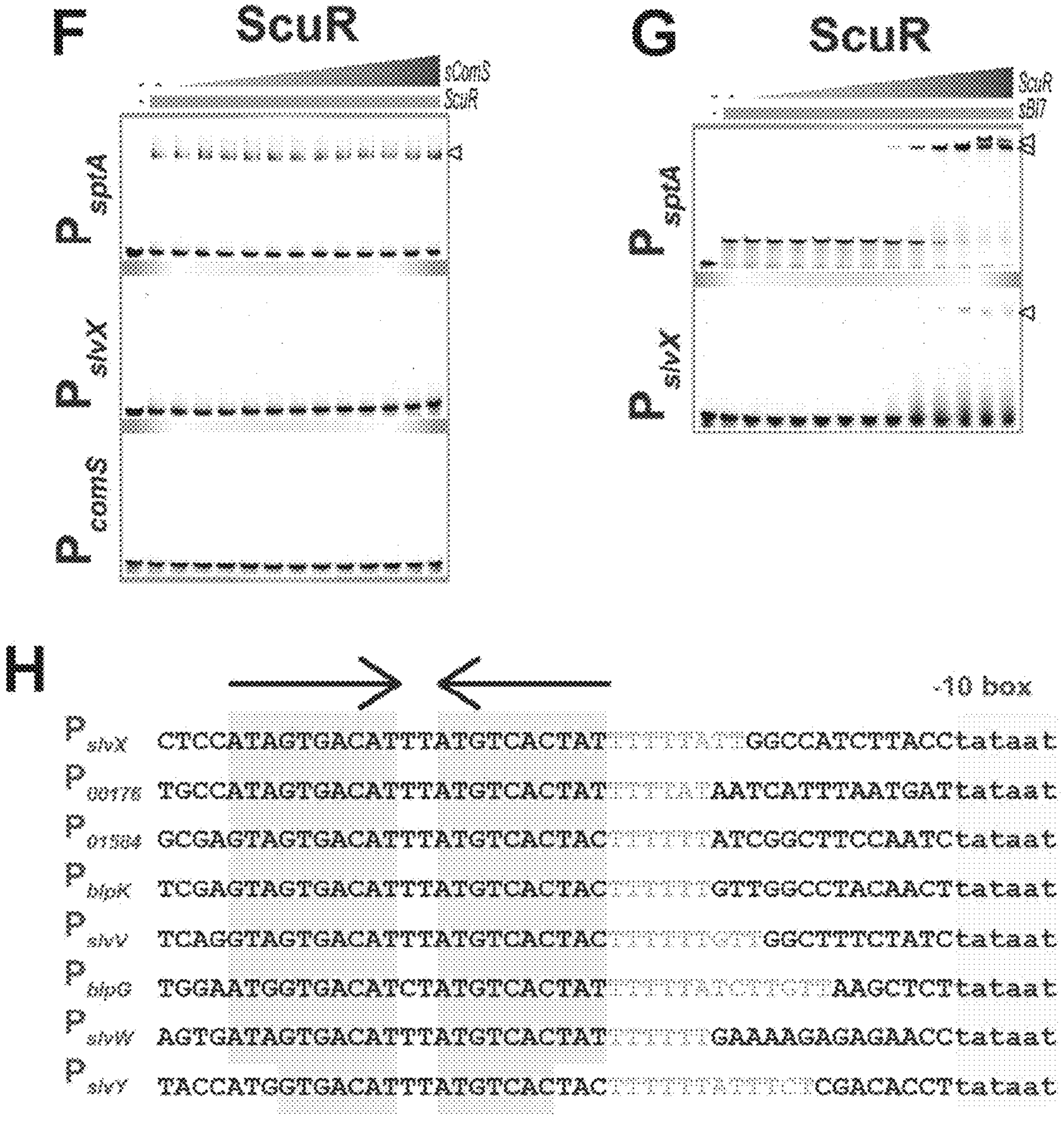

FIG. 4. Singularities in Promoter Recognition of Rgg Paralogs (A) Mobility shift assays of comX, comS, slvX and sptA promoter probes conducted with purified Rgg paralogs and decreasing concentrations of their cognate peptide (grey triangles; 2:2 dilutions from 20 μM). Probes are 30 bp (or 40 bp for $P_{sptA}$), were Cy3-conjugated and used at 40 ng. Protein concentration remains constant (grey boxes; 4 μM). Open triangles showcase ternary complexes (peptide-Rgg-DNA).

(B) Nucleotide alignment of promoters of comX (SEQ ID NO: 738), comS (SEQ ID NO: 739), slvX (SEQ ID NO: 740) and sptA (SEQ ID NO: 741). The palindromic stretches (inverted arrows) and the sigma-bound DNA sequence (−10 boxes) are shaded in grey. Boxed nucleotides highlight the potential mismatches in the hairpin structure of $P_{comX}$ or $P_{sptA}$ that were substituted to restore a genuine dyad symmetry sequence (see FIGS. 4C and 4D). A and T represent the position and nature of single nucleotide insertion in the sptA promoter (see FIG. 4C).

(C and D) Fold increase in maximal activity of WT and mutated promoters of sptA (C) or comX (D) exposed to sBI7 or sComS (1 μM). Nucleotides substitutions and insertions are disclosed in FIG. 4B. Experimental values represent the averages (with standard error of the mean, SEM) of at least three independent biological replicates.

(E) Mobility shift assays of mutated comX promoter probes conducted with a unique concentration of ScuR or SarF (grey boxes; 4 μM) and decreasing concentrations of sBI7 peptide (grey triangles; 2:2 dilutions from 20 μM). Open triangles showcase ternary complexes (peptide-Rgg-DNA).

(F) Mobility shift assays of comS, slvX and sptA promoter probes conducted with purified ScuR and decreasing concentrations of the non-cognate sComS peptide (grey triangles; 2:2 dilutions from 20 μM). Probes are 30 bp (or 40 bp for $P_{sptA}$), were Cy3-conjugated and used at 40 ng. Protein concentration remains constant (grey boxes; 4 μM). Open triangle showcases binary complexes (ScuR-DNA).

(G) Mobility shift assays of slvX and sptA promoter probes conducted with sBI7 peptide and decreasing concentrations of purified ScuR (grey triangles; 2:2 dilutions from 8 μM). Probes are 30 bp ($P_{slvX}$) or 40 bp ($P_{sptA}$), were Cy3-conjugated and used at 40 ng. Peptide concentration remains constant (grey boxes; 1 μM). Open triangles showcase ternary complexes (sBI7-ScuR-DNA).

(H) Nucleotide alignment of bacteriocin-related gene promoters. $P_{slvX}$: SEQ ID NO: 740; $P_{00176}$: SEQ ID NO: 742; $P_{01584}$: SEQ ID NO: 743; $P_{blpK}$: SEQ ID NO: 744; $P_{slvV}$: SEQ ID NO: 745; $P_{blpG}$: SEQ ID NO: 746; $P_{slvW}$: SEQ ID NO: 747; $P_{slvY}$: SEQ ID NO: 748. The palindromic stretches (inverted arrows) and the sigma-bound DNA sequence (−10 boxes) are shaded in grey. The characteristic T-rich region is grey font.

Figure 5:
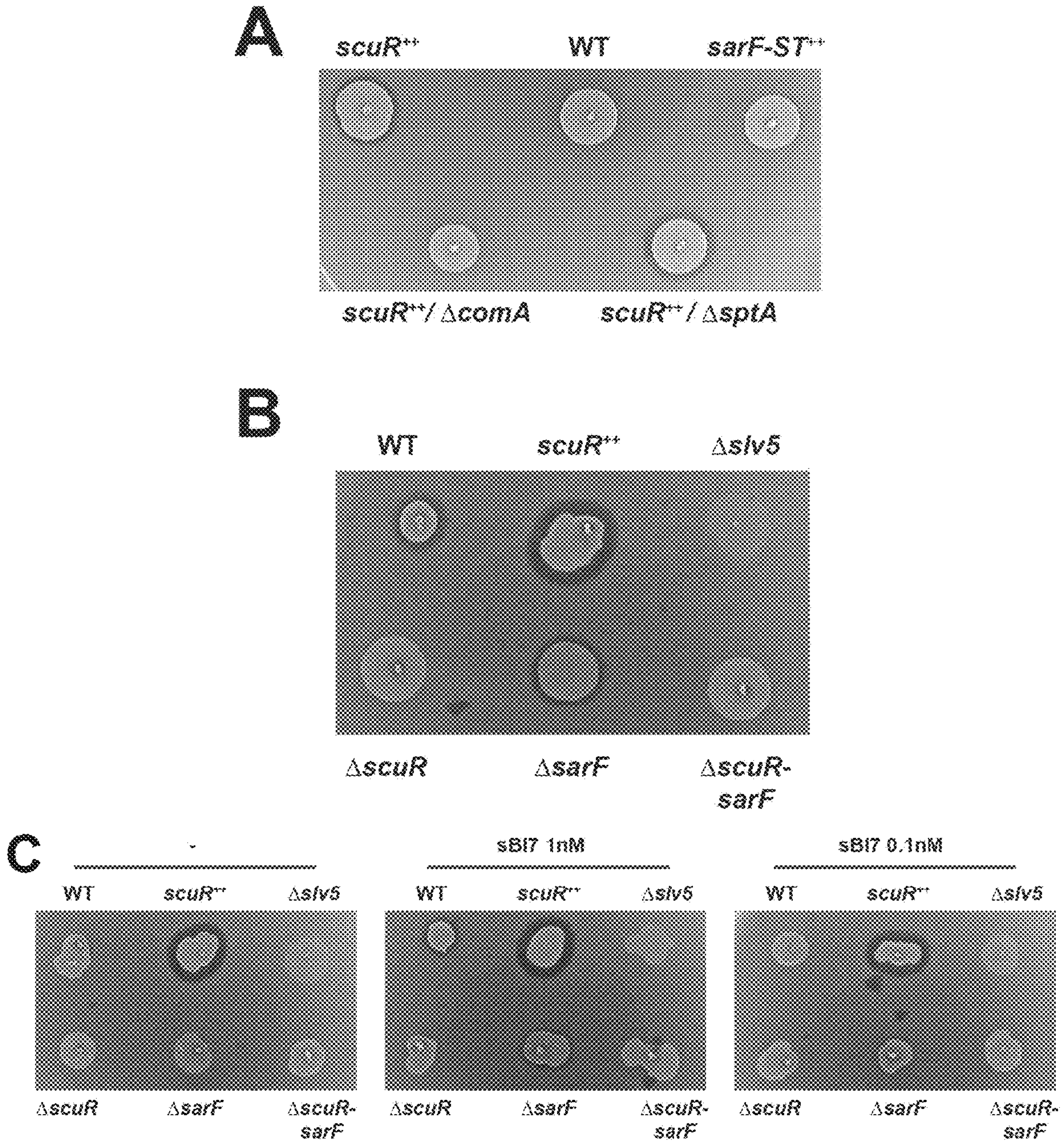

FIG. 5. Activated ScuR Drives Bacteriocin Secretion (A and B) Bacteriocin inhibition assay of *S. salivarius* WT and mutant derivatives. Indicator strains (*L. lactis*) were embedded in the top soft agar layer, while sBI7 was supplemented into the bottom agar layer as required. Producer strains were spotted on top of the two agar layers. (A) Killing properties of scuR or sarF overexpression mutants compared WT. (B) Effect of sBI7 addition (1 μM) on WT strain and scuR/sarF various mutants. $scuR^{++}$ and bacteriocin null mutant (Δslv5) were used as positive and negative control, respectively.

(C) Bacteriocin inhibition assay of *S. salivarius* WT and scuR/sarF mutant derivatives. Indicator strains (*L. lactis*) were embedded in the top soft agar layer, while sBI7 was supplemented or not into the bottom agar layer as stated. Producer strains were spotted on top of the two agar layers. $scuR^{++}$ and bacteriocin null mutant (Δslv5) were used as positive and negative control, respectively.

Figure 6:
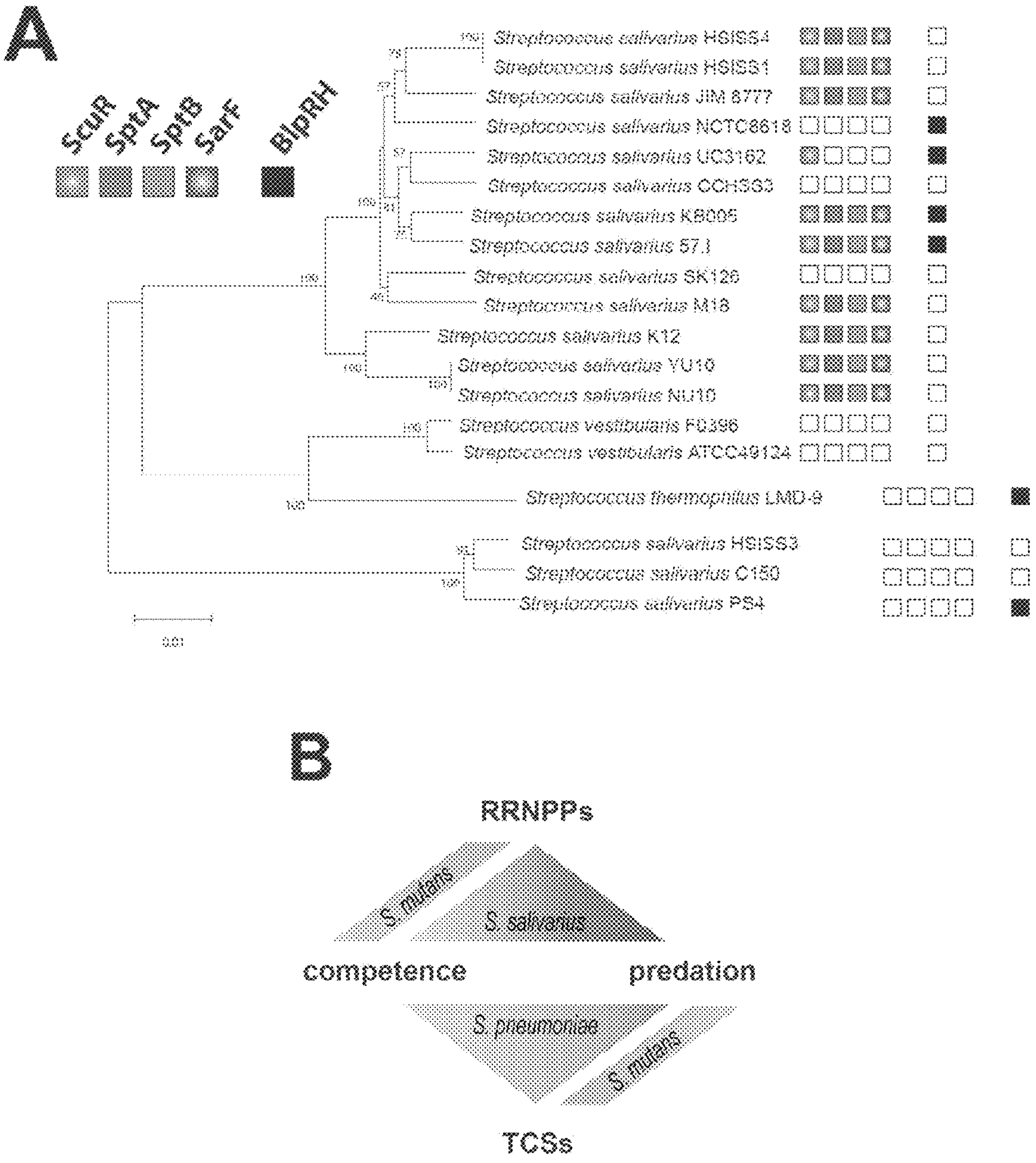

FIG. 6. Rgg Members Requisition Predation Control in *S. salivarius*

(A) Conservation of ScuR locus, and BIpRH system across *S. salivarius*. Functional BIpRH pair, ScuR, SptA, SptB, and SarF were sought for homologs in various *S. salivarius* strains. The phylogenetic tree (100 bootstrap replicates) was adapted from (Yu et al., 2015). An empty box means that no functional ortholog was found in the species genome. Scale bar: 0.01 substitution per site.

(B) Figurative illustration of RRNPPs vs two-component systems (TCSs) drift toward competence and predation regulation in paradigmatic streptococci (*S. pneumoniae, S. mutans* and *S. salivarius*).

Figure 7:
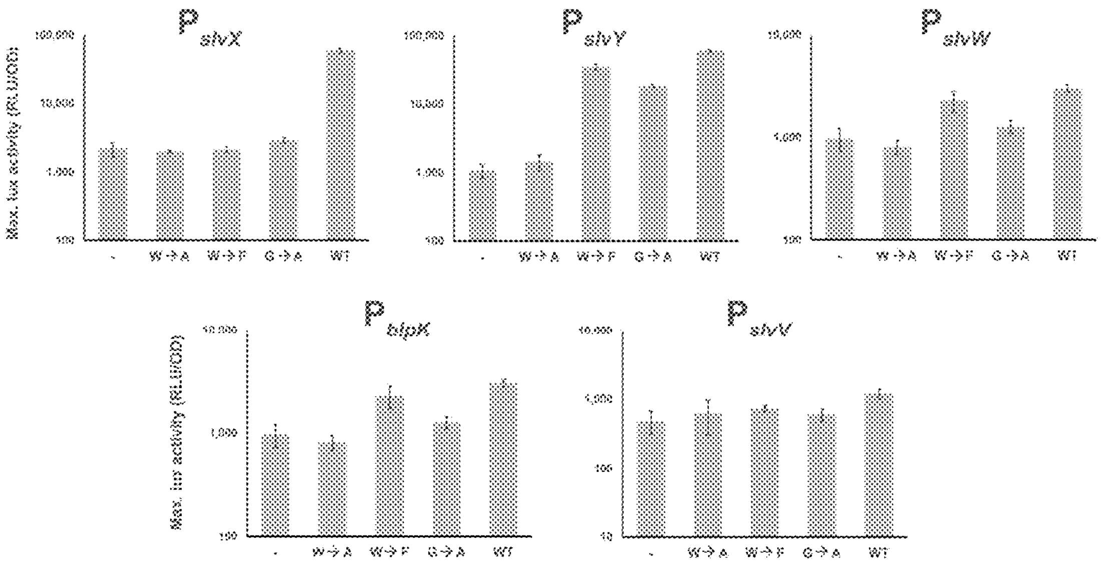

FIG. 7. Amino Acid Requirements for the sBI7-Mediated Effect

Maximal activity of salivaricin promoters (RLU/OD; logarithmic scale) exposed to sBI7 (WT) (SEQ ID NO: 36) and mutant peptides (1 μM). Experimental values represent the averages (with standard error of the mean, SEM) of at least three independent biological replicates.

Figure 8:
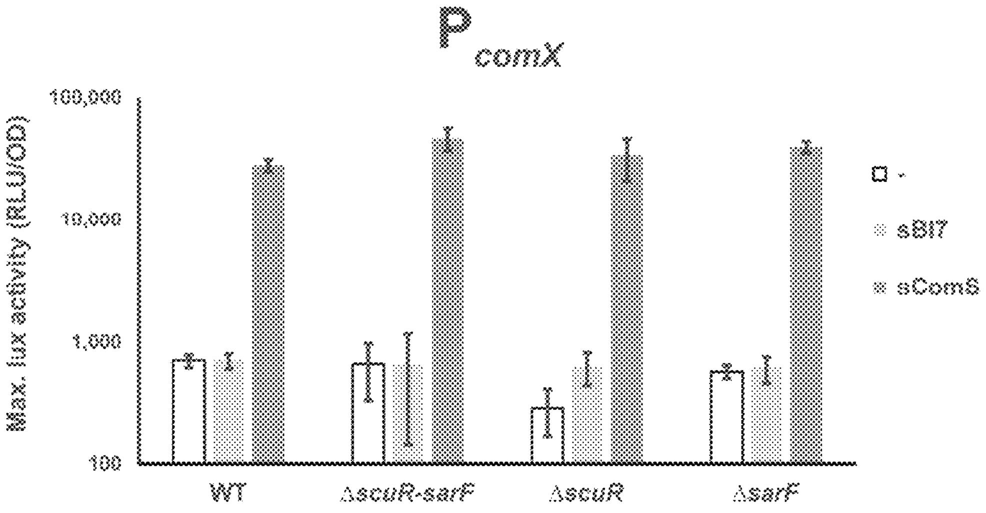

FIG. 8. sBI7 Has No Effect on the comX Promoter Activation

Maximal activity of $P_{comX}$ exposed to the sComS or sBI7 peptide (1 μM) (SEQ ID NO: 36) in WT strain and ΔscuR and/or ΔsarF mutants. Experimental values represent the averages (with standard error of the mean, SEM) of at least three independent biological replicates.

Figure 9:
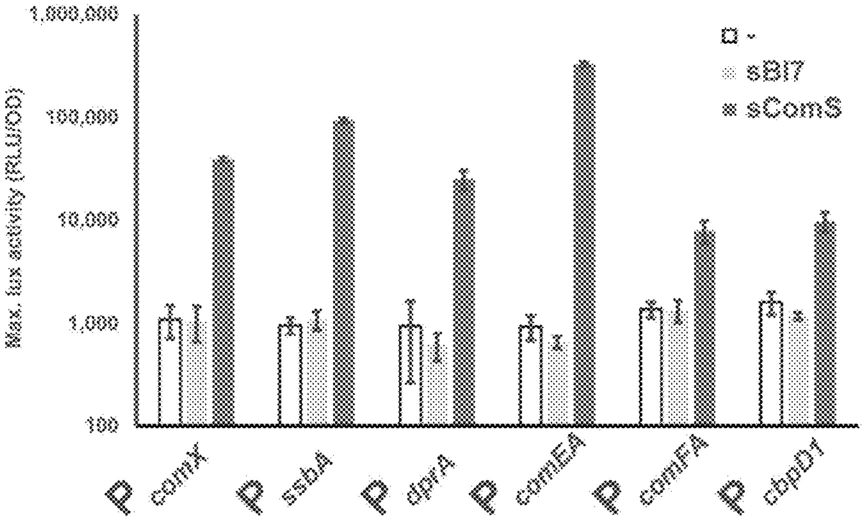

FIG. 9. No Activation of comX or Late Competence Genes Under ComX Control by sBI7

Maximal activity of $P_{comX}$ and ComX-dependent promoters exposed to the sComS (light grey) or sBI7 peptide (SEQ ID NO: 36) (dark grey) (1 μM) in comparison to basal activity (open box). Experimental values represent the averages (with standard error of the mean, SEM) of at least three independent biological replicates.

Figure 10:
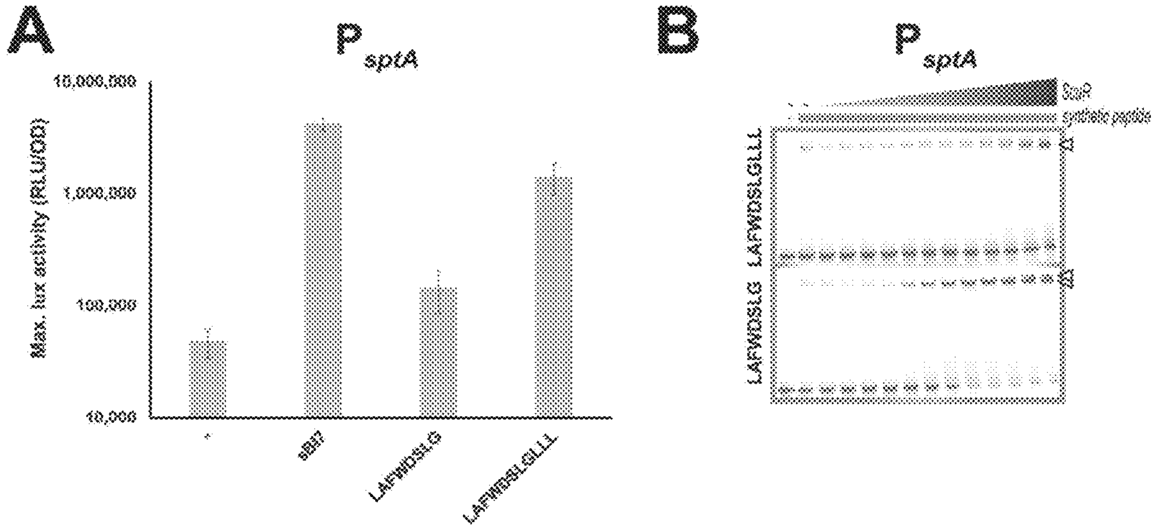

FIG. 10. C-Terminal Tolerance of Synthetic Peptides (A) Maximal activity of $P_{sptA}$ exposed to LAFWDSLG (SEQ ID NO: 749), LAFWDSLGLLL (SEQ ID NO: 750) or the peptide sBI7 (SEQ ID NO: 36) (1 μM) in comparison to basal activity. Experimental values represent the averages (with standard error of the mean, SEM) of at least three independent biological replicates.

(B) Mobility shift assays of the sptA promoter probe conducted with purified ScuR and decreasing concentrations of the peptides LAFWDSLG (SEQ ID NO: 749) or LAFWDSLGLLL (SEQ ID NO: 750) (grey triangles; 2:2 dilutions from 20 μM). The probe is 40 bp, Cy3-conjugated and used at 40 ng. Protein concentration remains constant (grey boxes; 4 μM). Open triangle showcases single or binary complexes (ScuR-DNA).

EXAMPLES

Experimental Procedures

Bacterial Strains, Plasmids, Oligonucleotides, and Growth Conditions

Bacterial strains, plasmids and oligonucleotides used in the Examples are listed and described in the tables below. *Streptococcus salivarius* HSISS4 and derivatives were grown at 37° C. without shaking in M17 (Difco Laboratories, Detroit, MI) or in CDM (Fontaine et al. Mol Microbiol 2013, 87:1113-1132) supplemented with 1% (w/v) glucose (M17G, CDMG, respectively). *Escherichia coli* TOP10 (Invitrogen) were cultivated with shaking at 37° C. in LB. Electrotransformation of *E. coli* was performed as previously described (Mignolet et al. Elife 2016, 5:e18647). *Lactococcus lactis* was grown in M17 broth with 1% glucose at 30° C. without shaking. We added 1.5% (w/v) agar into M17 and LB plates, and bacteriocin inhibition tests were assayed on M17 plates containing 0.2% agar. We added D-xylose (0.1 or 1%; w/v), ampicillin (250 μg/ml), spectinomycin (200 μg/ml), chloramphenicol (5 μg/ml; except if otherwise stated) or erythromycin (10 μg/ml), 5-FOA (1 mg/ml) (Melford Laboratories), as required. Synthetic peptides and sComS (purity of 95%; 1 μM, except if otherwise stated) were supplied by Peptide 2.0 Inc. (Chantilly, VA, USA) and resuspended in DMSO. Solid plates inoculated with streptococci cells were incubated anaerobically (BBL GasPak systems, Becton Dickinson, Franklin lakes, N.J.) at 37° C.

TABLE 1

List of bacterial strains used in the Examples

| | Characteristics | Reference/source |
|---|---|---|
| | *Escherichia coli* | |
| TOP10 | mcrA, Δ(mrr-hsdRMS-mcrBC), Phi80lacZ(del)M15, ΔlacX74, deoR, recA1, araD139, Δ(ara-leu)7697, galU, galK, rpsL(SmR), endA1, nupG | Invitrogen |
| | *Streptococcus salivarius* | |
| HSISS4 | Wild-type gastro-intestinal tract isolate | (Van den Bogert et al., 2014) |
| JM1004 | HSISS4 ΔcomA::cat | (Mignolet et al., 2018) |
| JM1013 | HSISS4 Δslv5 | (Mignolet et al., 2018) |
| JM1019 | HSISS4 $tRNA^{Thr}$::$P_{comS}$-luxAB-cat | (Mignolet et al., 2018) |
| JM1020 | HSISS4 $tRNA^{Thr}$::$P_{comX}$-luxAB-cat | (Mignolet et al., 2018) |
| JM1021 | HSISS4 $tRNA^{Thr}$::$P_{blpK}$-luxAB-cat | (Mignolet et al., 2018) |
| JM1022 | HSISS4 $tRNA^{Thr}$::$P_{HSISS4\_00176}$-luxAB-cat | (Mignolet et al., 2018) |
| JM1023 | HSISS4 $tRNA^{Thr}$::$P_{HSISS4\_01584}$-luxAB-cat | (Mignolet et al., 2018) |
| JM1024 | HSISS4 $tRNA^{Thr}$::$P_{slvV}$-luxAB-cat | (Mignolet et al., 2018) |
| JM1025 | HSISS4 $tRNA^{Thr}$::$P_{blpG}$-luxAB-cat | (Mignolet et al., 2018) |
| JM1026 | HSISS4 $tRNA^{Thr}$::$P_{slvW}$-luxAB-cat | (Mignolet et al., 2018) |
| JM1027 | HSISS4 $tRNA^{Thr}$::$P_{slvX}$-luxAB-cat | (Mignolet et al., 2018) |
| JM1028 | HSISS4 $tRNA^{Thr}$::$P_{slvY}$-luxAB-cat | (Mignolet et al., 2018) |
| JM1100 | HSISS4 $tRNA^{Thr}$::$P_{sptA}$-luxAB-cat | This work |
| JM1101 | HSISS4 $tRNA^{Ser}$::$P_{32}$-scuR-spec ($scuR^{++}$) | This work |
| JM1102 | HSISS4 $tRNA^{Ser}$::$P_{32}$-sarF-ST-spec ($sarF\text{-}ST^{++}$) | This work |
| JM1103 | JM1019 $tRNA^{Ser}$::$P_{32}$-scuR-spec | This work |
| JM1104 | JM1020 $tRNA^{Ser}$::$P_{32}$-scuR-spec | This work |
| JM1105 | JM1021 $tRNA^{Ser}$::$P_{32}$-scuR-spec | This work |
| JM1106 | JM1022 $tRNA^{Ser}$::$P_{32}$-scuR-spec | This work |
| JM1107 | JM1023 $tRNA^{Ser}$::$P_{32}$-scuR-spec | This work |
| JM1108 | JM1024 $tRNA^{Ser}$::$P_{32}$-scuR-spec | This work |
| JM1109 | JM1025 $tRNA^{Ser}$::$P_{32}$-scuR-spec | This work |
| JM1110 | JM1026 $tRNA^{Ser}$::$P_{32}$-scuR-spec | This work |
| JM1111 | JM1027 $tRNA^{Ser}$::$P_{32}$-scuR-spec | This work |
| JM1112 | JM1028 $tRNA^{Ser}$::$P_{32}$-scuR-spec | This work |
| JM1113 | JM1100 $tRNA^{Ser}$::$P_{32}$-scuR-spec | This work |
| JM1114 | JM1019 $tRNA^{Ser}$::$P_{32}$-sarF-spec | This work |
| JM1115 | JM1027 $tRNA^{Ser}$::$P_{32}$-sarF-spec | This work |
| JM1116 | JM1100 $tRNA^{Ser}$::$P_{32}$-sarF-spec | This work |
| JM1117 | JM1113 ΔcomR::ery | This work |
| JM1118 | HSISS4 ΔscuR-sarF::ery | This work |
| JM1119 | JM1113 ΔscuR-sarF::ery | This work |
| JM1120 | JM1116 ΔscuR-sarF::ery | This work |
| JM1121 | HSISS4 $tRNA^{Thr}$::$P_{sptA}$-cat-spec | This work |
| JM1122 | HSISS4 $tRNA^{Thr}$::$P_{sptA}$-cat-lox72 | This work |
| JM1123 | JM1122 $tRNA^{Ser}$::$P_{xyl1}$-comR-spec | This work |
| JM1124 | JM1013 $tRNA^{Thr}$::$P_{sptA}$-cat-lox72 | This work |
| JM1125 | JM1122 $tRNA^{Ser}$::$P_{xyl2}$-BH6-spec | This work |
| JM1126 | JM1122 $tRNA^{Ser}$::$P_{xyl1}$-BI1-spec | This work |
| JM1127 | JM1122 $tRNA^{Ser}$::$P_{xyl1}$-BI2-spec | This work |
| JM1128 | JM1122 $tRNA^{Ser}$::$P_{xyl1}$-BI5-spec | This work |
| JM1129 | JM1122 $tRNA^{Ser}$::$P_{xyl1}$-BI6-spec | This work |
| JM1130 | JM1122 $tRNA^{Ser}$::$P_{xyl1}$-BI7-spec | This work |
| JM1131 | JM1122 $tRNA^{Ser}$::$P_{xyl1}$-BI9-spec | This work |
| JM1132 | JM1122 $tRNA^{Ser}$::$P_{xyl1}$-BI10-spec | This work |
| JM1133 | JM1122 $tRNA^{Ser}$::$P_{xyl1}$-BI11-spec | This work |
| JM1134 | JM1122 $tRNA^{Ser}$::$P_{xyl1}$-BI12-spec | This work |
| JM1135 | JM1122 $tRNA^{Ser}$::$P_{xyl2}$-BJ1-spec | This work |

TABLE 1-continued

| List of bacterial strains used in the Examples | | |
|---|---|---|
| | Characteristics | Reference/source |
| JM1136 | JM1122 $tRNA^{Ser}$::$P_{xyl1}$-BK1-spec | This work |
| JM1137 | JM1122 $tRNA^{Ser}$::$P_{xyl1}$-BK2-spec | This work |
| JM1138 | JM1122 $tRNA^{Ser}$::$P_{xyl1}$-BK3-spec | This work |
| JM1139 | JM1122 $tRNA^{Ser}$::$P_{xyl1}$-BK4-spec | This work |
| JM1140 | JM1122 $tRNA^{Ser}$::$P_{xyl1}$-BK5-spec | This work |
| JM1141 | JM1122 $tRNA^{Ser}$::$P_{xyl1}$-BK6-spec | This work |
| JM1142 | JM1122 $tRNA^{Ser}$::$P_{xyl1}$-BK7-spec | This work |
| JM1143 | JM1122 $tRNA^{Ser}$::$P_{xyl1}$-BK8-spec | This work |
| JM1144 | JM1122 $tRNA^{Ser}$::$P_{xyl1}$-BK9-spec | This work |
| JM1145 | JM1124 $tRNA^{Ser}$::$P_{xyl1}$-BL1-spec | This work |
| JM1146 | JM1124 $tRNA^{Ser}$::$P_{xyl1}$-BL2-spec | This work |
| JM1147 | JM1124 $tRNA^{Ser}$::$P_{xyl1}$-BL3-spec | This work |
| JM1148 | JM1124 $tRNA^{Ser}$::$P_{xyl2}$-BM1-spec | This work |
| JM1149 | JM1124 $tRNA^{Ser}$::$P_{xyl1}$-BN1-spec | This work |
| JM1150 | JM1124 $tRNA^{Ser}$::$P_{xyl1}$-BN2-spec | This work |
| JM1151 | JM1124 $tRNA^{Ser}$::$P_{xyl1}$-BN3-spec | This work |
| JM1152 | JM1124 $tRNA^{Ser}$::$P_{xyl1}$-BN4-spec | This work |
| JM1153 | JM1122 $tRNA^{Ser}$::$P_{xyl2}$-BO1-spec | This work |
| JM1154 | JM1122 $tRNA^{Ser}$::$P_{xyl2}$-BO2-spec | This work |
| JM1155 | JM1122 $tRNA^{Ser}$::$P_{xyl1}$-BP1-spec | This work |
| JM1156 | JM1100 $tRNA^{Ser}$::$P_{xyl1}$-BI5-spec | This work |
| JM1157 | JM1100 $tRNA^{Ser}$::$P_{xyl1}$-BI7-spec | This work |
| JM1158 | JM1100 $tRNA^{Ser}$::$P_{xyl1}$-BI10-spec | This work |
| JM1159 | JM1100 $tRNA^{Ser}$::$P_{xyl2}$-BJ1-spec | This work |
| JM1160 | JM1100 $tRNA^{Ser}$::$P_{xyl1}$-BK1-spec | This work |
| JM1161 | JM1100 $tRNA^{Ser}$::$P_{xyl1}$-BK4-spec | This work |
| JM1162 | JM1100 $tRNA^{Ser}$::$P_{xyl1}$-BK8-spec | This work |
| JM1163 | JM1100 $tRNA^{Ser}$::$P_{xyl1}$-BK9-spec | This work |
| JM1164 | JM1100 $tRNA^{Ser}$::$P_{xyl1}$-BL2-spec | This work |
| JM1165 | JM1100 $tRNA^{Ser}$::$P_{xyl1}$-BL3-spec | This work |
| JM1166 | JM1100 $tRNA^{Ser}$::$P_{xyl2}$-BM1-spec | This work |
| JM1167 | JM1100 $tRNA^{Ser}$::$P_{xyl1}$-BN2-spec | This work |
| JM1168 | JM1100 $tRNA^{Ser}$::$P_{xyl1}$-BN3-spec | This work |
| JM1169 | JM1100 $tRNA^{Ser}$::$P_{xyl2}$-BO2-spec | This work |
| JM1170 | JM1100 $tRNA^{Ser}$::$P_{xyl1}$-BP1-spec | This work |
| JM1171 | JM1157 ΔscuR::ery | This work |
| JM1172 | JM1157 ΔsarF::ery | This work |
| JM1173 | JM1157 ΔscuR-sarF::ery | This work |
| JM1174 | JM1157 ΔcomR::ery | This work |
| JM1175 | JM1100 ΔscuR::ery | This work |
| JM1176 | JM1100 ΔsarF::ery | This work |
| JM1177 | JM1027 ΔscuR::ery | This work |
| JM1178 | JM1027 ΔsarF::ery | This work |
| JM1179 | JM1019 ΔscuR::ery | This work |
| JM1180 | JM1019 ΔsarF::ery | This work |
| JM1181 | HSISS4 $tRNA^{Thr}$::${P_{sptA}}^{CT\rightarrow AC}$-luxAB-cat | This work |
| JM1182 | HSISS4 $tRNA^{Thr}$::${P_{sptA}}^{+1}$-luxAB-cat | This work |
| JM1183 | HSISS4 $tRNA^{Thr}$::${P_{sptA}}^{+A}$-luxAB-cat | This work |
| JM1184 | HSISS4 $tRNA^{Thr}$::${P_{comX}}^{G\rightarrow A}$-luxAB-cat | This work |
| JM1185 | JM1101 ΔcomA::cat | This work |
| JM1186 | JM1101 ΔsptA::cat | This work |
| JM1187 | HSISS4 ΔscuR | This work |
| JM1188 | HSISS4 ΔsarF | This work |
| JM1189 | HSISS4 ΔsptA::cat | This work |
| JM1190 | JM1019 ΔscuR-sarF::ery | This work |
| JM1191 | JM1021 ΔscuR-sarF::ery | This work |
| JM1192 | JM1027 ΔscuR-sarF::ery | This work |
| JM1193 | JM1100 ΔscuR-sarF::ery | This work |
| | *Lactococcus lactis* subsp. *lactis* | |
| IL1403 | Laboratory strain | (Chopin et al., 1984) |

TABLE 2

| List of plasmids used in the Examples | | |
|---|---|---|
| | Characteristics | Reference/source |
| pGhostcre | Thermosensitive replication origin vector in *S. salivarius*, encoding the Cre recombinase; $ery^R$ | (Fontaine et al., 2010) |
| pGIUD0855ery | pUC18 derivative containing the erm gene | (Fontaine et al., 2010) |
| pSEUDO-$P_{usp45}$-$_{sf}$gfp(Bs) | erm-oroP containing vector | (Overkamp et al., 2013) |
| pGILFspec | pG$^+$host9 derivative containing the spectinomycin resistance cassette $P_{spec}$-spec downstream of luxAB | (Haustenne et al., 2015) |
| pJUDspecmut1 | pGILFspec derivative in which a SpeI restriction site was mutated | (Mignolet et al., 2018) |
| pJUDspecmut1-gfp$^+$ter | Terminator associated-gfp$^+$ ORF cloned in pJUDspecmut1 | (Mignolet et al., 2018) |
| pNZ5319 | pACYC184 derivative containing the cat gene under the control of the P32 constitutive promoter from Lactococcus lactis | (Lambert et al., 2007) |
| pJIMcat | pG$^+$host9 containing the luxAB genes of Photorhabdus luminescens, a transcriptional terminator with a cat cassette | (Mignolet et al., 2018) |
| pBAD-comR-ST | pBADhisA derivative encoding ComR fused to a C-terminal StreptagII | (Mignolet et al., 2018) |
| pBAD-scuR-ST | pBADhis4 derivative encoding ScuR fused to a C-terminal StreptagII | This work |
| pBAD-sarF-ST | pBADhis4 derivative encoding SarF fused to a C-terminal StreptagII | This work |

TABLE 3

| List of oligonucleotides used in the Examples | | |
|---|---|---|
| Names | Sequences | SEQ ID NO |
| rggD_NcoI SS | 5'-AAAAAACCATGGCAGAAGATATTAAAATCAAGA-3' | 88 |
| rggD_MunI | 5'-AAAAAACAATTGCTTTGACTCGTTACTTGTAT-3' | 89 |
| rggC_NcoI SS | 5'-AAAAAACCATGGCTGAAGATATTAAAATCGAGA-3' | 90 |
| rggC_RI SS | 5'-AAAAAAGAATTCTTCTATATTTAAATCTTTTT-3' | 91 |
| Uplox66 | 5'-TAAGGAAGATAAATCCCATAAGG-3' | 92 |
| DNlox71 | 5'-TTCACGTTACTAAAGGGAATGTA-3' | 93 |
| lox66-ery | 5'-TAAGGAAGATAAATCCCATAAGGTACCTAATAATTTATCTACATTCC-3' | 94 |
| lox71-ery | 5'-TTCACGTTACTAAAGGGAATGTAAAATGATACACCAATCAGTGC-3' | 95 |
| F_spec | 5'-TAATAAGGCCGGCCAATAAA-3' | 96 |
| R_spec | 5'-ATAGGATGAGAACTCCCATG-3' | 97 |
| UPery-oroP | 5'-AAGGTTGATGTTACTGCTGATA-3' | 98 |
| DNery-oroP | 5'-TGCTGACTTGCACCATATCATA-3' | 99 |
| UF_tRNAser | 5'-CAAGATTAACCATGACCTTC-3' | 100 |
| UR_tRNAser | 5'-AGTAATTAAAAAGAAGATGG-3' | 101 |
| DF_tRNAser | 5'-TACCTAAAAAGTGTCCCTTC-3' | 102 |

TABLE 3-continued

| List of oligonucleotides used in the Examples | | |
|---|---|---|
| Names | Sequences | SEQ ID NO |
| DR2_tRNAser | 5'-TTGGATAAGGTCTTGACTTC-3' | 103 |
| UF_tRNAthr | 5'-TGTCAAAGGATTAGGAAAAC-3' | 104 |
| UR_tRNAthr | 5'-TTGATTTATACCTCTCAATTT-3' | 105 |
| DF_tRNAthr | 5'-AAATCAACCTCTTTGAACATA-3' | 106 |
| DR_tRNAthr | 5'-AAAAAAGAATTCATTCATGATGAGCGGGTTCGTGAGA-3' | 107 |
| F_pZX9 | 5'-CCATCTTCTTTTTAATTACTTCTAGATTATATATGATATGATC-3' | 108 |
| R_pZX9_ATG | 5'-CATATTTACCTCCTTTGATTTA-3' | 109 |
| F_luxAB_ATG | 5'-ATGAAATTTGGAAACTTTTTGC-3' | 110 |
| R_cat_tRNAthr | 5'-TATGTTCAAAGAGGTTGATTTCACGTTACTAAAGGGAATGTA-3' | 111 |
| UFcomRJIM-SS1-4 | 5'-GCAGTACCACTCTATGCTAAATTTGCCAACTTTGA-3' | 112 |
| URcomRJIM-SS1-4 | 5'-CCTTATGGGATTTATCTTCCTTAGAGACACTCCTTTATTTC-3' | 113 |
| DFcomRJIM-SS1-4 | 5'-TACATTCCCTTTAGTAACGTGAAAAATGGTGGTGACATAAA-3' | 114 |
| DRcomRJIM-SS1-4 | 5'-TGACGTGATTTCACCAGTACGACGTGAACTAAAGA-3' | 115 |
| Up_comR SS1-4 | 5'-TTGCTTACAGTTGCTATGGT-3' | 116 |
| Down_comR_SS1-4 | 5'-TCATCACAATGGTCACATCT-3' | 117 |
| UFrggC JIM | 5'-AAAACTGCAAGTAGAGTCGCCGAATTAGAA-3' | 118 |
| URrggC_JIM | 5'-CCTTATGGGATTTATCTTCCTTAACATAATTCCTTATGATTTAGA-3' | 119 |
| DFrggC JIM | 5'-TACATTCCCTTTAGTAACGTGAAGACATTGATGTCCTTTTGA-3' | 120 |
| DRrggD SS | 5'-TAGCTTCATTCATGTCATGTGTCGTCAAAA-3' | 121 |
| Up_rggC JIM | 5'-AAATATCGTCATTGCCAGTA-3' | 122 |
| Down_rggD SS | 5'-CTGAATAAGTTCAGCAGGTT-3' | 123 |
| Down_rggD SS | 5'-TCACTTTGACTCGTTACTTGTGATTTTAATATCTTCTGACAT-3' | 124 |
| rggD_S4_3 | 5'-ATGTCAGAAGATATTAAAATCACAAGTAACGAGTCAAAGTGA-3' | 125 |

TABLE 3-continued

List of oligonucleotides used in the Examples

| Names | Sequences | SEQ ID NO |
|---|---|---|
| rggD_S4_4 | 5'-TATCAGCAGTAACATCAACCTTCATGTCATGTGTCGTCAAAA-3' | 126 |
| rggD_S4_5 | 5'-TATGATATGGTGCAAGTCAGCATCATGAAGTCTCCTGTCTAT-3' | 127 |
| rggD_S4_6 | 5'-GGCTAGTACAGTAGCTGTAT-3' | 128 |
| UFrggC SS | 5'-CTGTTTAGCCCTATCTTTGAGTTTATCAGT-3' | 129 |
| URrggD JIM | 5'-CCTTATGGGATTTATCTTCCTTATGTATTCCCCTTGAGTTTT-3' | 130 |
| DFrggD JIM | 5'-TACATTCCCTTTAGTAACGTGAAGAAAATATATCAGCAACAT-3' | 131 |
| DRrggC SS | 5'-CAGTGGTTTGACGTTGTTTTTGAATACGGT-3' | 132 |
| Up_rggC SS | 5'-AAGGTAGCCTAAACAACTCA-3' | 133 |
| Down_rggC SS | 5'-TTTATTGGTACCAAACGCCA-3' | 134 |
| rggC_S4_2 | 5'-CTATTCTATATTTAAATCTTTGATTTTAATATCTTCAGACAT-3' | 135 |
| rggC_S4_3 | 5'-ATGTCTGAAGATATTAAAATCAAAGATTTAAATATAGAATAG-3' | 136 |
| rggC_S4_4 | 5'-TATCAGCAGTAACATCAACCTTGACGTTGTTTTTGAATACGGT-3' | 137 |
| rggC_S4_5 | 5'-TATGATATGGTGCAAGTCAGCAACTAGACATTCCTGAAGACT-3' | 138 |
| rggC_S4_6 | 5'-TCCGCTAGTAGGATAGCTTT-3' | 139 |
| UF_PcomR_luxAB | 5'-TAATTGAGGAGGTCTATGAG-3' | 140 |
| UR_comA | 5'-CCTTATGGGATTTATCTTCCTTAATATGGATATTTTGACATGG-3' | 141 |
| DF_comA | 5'-TACATTCCCTTTAGTAACGTGAAGCTAATTTCAATCCATTCCAG-3' | 142 |
| DR_comA | 5'-ACAGTACTCTTTATTTGGTG-3' | 143 |
| F_comR | 5'-CTAGAGGAGGAATTTAGATGAACATAAAAGACAGCATTG-3' | 144 |
| Down_PcomS_JIMSS1-4 | 5'-GACAAAGTAGTCAAGACCGT-3' | 145 |
| UF_potA2 | 5'-ATACTATACCTTTCAATGTC-3' | 146 |
| UR_potA2 | 5'-CCTTATGGGATTTATCTTCCTTAATAAGGTTTGTCATATCTTG-3' | 147 |
| DF_potA2 | 5'-TACATTCCCTTTAGTAACGTGAAGGAAAACTTAATGTTTAACC-3' | 148 |

TABLE 3-continued

List of oligonucleotides used in the Examples

| Names | Sequences | SEQ ID NO |
|---|---|---|
| DR_potA2 | 5'-ACTGATCCCTGAAAGCATTG-3' | 149 |
| Up_potA2 | 5'-AGAGTATACCTTAAATGACC-3' | 150 |
| Down_potA2 | 5'-GATTTAAAGATTTCGTGAAC-3' | 151 |
| F_PpotA2_ tRNAthr | 5'- AAATTGAGAGGTATAAATCAATCATTTT GGAAGCAAAATAC-3' | 152 |
| R_PpotA2_luxAB_ ATG | 5'- GCAAAAAGTTTCCAAATTTCATATCTTG ATTTCTCCAATTTG-3' | 153 |
| F_rggD | 5'- CTAGAGGAGGAATTTAGATGTCAGAA GATATTAAAATC-3' | 154 |
| R_rggD | 5'- TTTATTGGCCGGCCTTATTATCACTTT GACTCGTTACTTG-3' | 155 |
| F_rggC | 5'- CTAGAGGAGGAATTTAGATGTCTGAAG ATATTAAAATC-3' | 156 |
| R_StrepTag | 5'- TTTATTGGCCGGCCTTATTACTATTTCT CGAACTGCGG-3' | 157 |
| F_P32- gfp + ter_spec | 5'- CCATCTTCTTTTTAATTACTGTCCTCGG GATATGATAAG-3' | 158 |
| R_P32 | 5'-CATCTAAATTCCTCCTCTAG-3' | 159 |
| F_cat_ATG | 5'-ATGAACTTTAATAAAATTGATT-3' | 160 |
| R_cat_(spec) | 5'- TTTATTGGCCGGCCTTATTATAAAAGC CAGTCATTAGGC-3' | 161 |
| R_PpotA2_cat_ ATG | 5'- AATCAATTTTATTAAAGTTCATATCTTG ATTTCTCCAATTTG-3' | 162 |
| Pxyl_seq | 5'-TTGTTTATCCTCCTCTAGTC-3' | 163 |
| spec2 | 5'-AACTCCTGATCCAAACATGTA-3' | 164 |
| Cy3_F_PpotA2_ EMSA | 5'-Cy3- TAACGAGTCAAAGTGACATAGATGTCC TTTTGATTCGTTA-3' | 165 |
| R_PpotA2_ EMSA | 5'- TAACGAATCAAAAGGACATCTATGTCA CTTTGACTCGTTA-3' | 166 |
| Cy3_F_P01665_ EMSA | 5'-Cy3- CTCCATAGTGACATTTATGTCACTATTT TT-3' | 167 |
| R_P01665_ EMSA | 5'- AAAAATAGTGACATAAATGTCACTATG GAG-3' | 168 |
| Cy3_F_PcomS_ EMSA | 5'-Cy3- AATGGTGGTGACATAAATGTCACTACT TTT-3' | 169 |
| R_PcomS_ EMSA | 5'- AAAAGTAGTGACATTTATGTCACCACC ATT-3' | 170 |

TABLE 3-continued

List of oligonucleotides used in the Examples

| Names | Sequences | SEQ ID NO |
|---|---|---|
| Cy3_F_PcomX_EMSA | 5'-Cy3-TTTTATAGTGACATATATGTCGCTATTTTA-3' | 171 |
| R_PcomX_EMSA | 5'-TAAAATAGCGACATATATGTCACTATAAAA-3' | 172 |
| Cy3_F_PcomX_EMSArev | 5'-Cy3-TTTTATAGTGACATATATGTCACTATTTTA-3' | 173 |
| R_PcomX_EMSArev | 5'-TAAAATAGTGACATATATGTCACTATAAAA-3' | 174 |
| F_PcomX_mut | 5'-CATATATGTCACTATTTTATT-3' | 175 |
| R_PcomX_mut | 5'-AATAAAATAGTGACATATATG-3' | 176 |
| F_PpotA2_mut2 | 5'-ACATAGATGTCACTTTGATTCGT-3' | 177 |
| R_PpotA2_mut2 | 5'-ACGAATCAAAGTGACATCTATGT-3' | 178 |
| F_PpotA2_mut + 1 | 5'-TGATTCGTTATTTTTTTTGTTT-3' | 179 |
| R_PpotA2_mut + 1 | 5'-AAACAAAAAAAATAACGAATCA-3' | 180 |
| F_PpotA2_mut + A | 5'-CATAGATGTCACTTTTGATTC-3' | 181 |
| R_PpotA2_mut + A | 5'-GAATCAAAAGTGACATCTATG-3' | 182 |
| F_pept_xyl | 5'-TAAATCAAAGGAGGTAAATATGATCGCAATCCTANNNNNNNNNNNNNNNNNNNNNNTGATAATAAGGCCGGCCAATAAA-3' | 183 |

TABLE 4

List of EMSA annealings, overlapping and cloning PCR subfragments amplified in this study

| PCR/annealing | Primer 1 | Primer 2 |
|---|---|---|
| scuR amplification for pBAD-scuR-ST cloning | rggD_NcoI SS | rggD_MunI |
| sarF amplification for pBAD-sarF-ST cloning | rggC_NcoI SS | rggC_R1 SS |
| P$_{32}$-cat cassette amplification | Uplox66 | DNlox71 |
| Erm cassette amplification | lox66-ery | lox71-ery |
| spec cassette amplification for tRNA$^{Ser}$ locus | F_spec | R_spec |
| Random peptide gene and spec for tRNA$^{Ser}$ locus | F_pept_xyl | R_spec |
| erm-oroP cassette amplification | UPery-oroP | DNery-oroP |
| P$_{xyl1}$ amplification | F_pZX9 | R_pZX9 ATG |
| P$_{xyl2}$ amplification | F_pZX9 | R_pZX9 ATG |
| luxAB-cat amplification | F_luxAB_ATG | R_cat_tRNAthr |
| P$_{32}$ amplification | F_P32-gfp + ter_spec | R_P32 |
| spec cassette amplification for tRNA$^{Thr}$ locus | F_spec | R_cat_tRNAthr |
| Upstream homologous region of tRNA$^{Ser}$ locus | UF_tRNAser | UR_tRNAser |
| Downstream homologous region of tRNA$^{Ser}$ locus | DF_tRNAser | DR2_tRNAser |
| Upstream homologous region of tRNA$^{Thr}$ locus | UF_tRNAthr | UR_tRNAthr |
| Downstream homologous region of tRNA$^{Thr}$ locus | DF_tRNAthr | DR_tRNAthr |
| scuR amplification for P$_{32}$-scuR fusion at tRNA$^{Ser}$ locus | F_rggD | R_rggD |
| sarF-ST amplification for P$_{32}$-sarF-ST fusion at tRNA$^{Ser}$ locus | F_rggC | R_StrepTag |
| Promoter of sptA for luxAB fusion | F_PpotA2_tRNAthr | R_PpotA2_luxAB_ATG |
| Promoter of sptA$^{CT \to AC}$ for luxAB fusion | F_PpotA2_mut2 | R_PpotA2_mut2 |
| Promoter of sptA$^{+1}$ for luxAB fusion | F_PpotA2_mut + 1 | R_PpotA2_mut + 1 |
| Promoter of sptA$^{+A}$ for luxAB fusion | F_PpotA2_mut + A | R_PpotA2_mut + A |
| Promoter of comX$^{G \to A}$ for luxAB fusion | F_PcomX_mut | R_PcomX_mut |
| Promoter of sptA for cat fusion (screen) | F_PpotA2_tRNAthr | R_PpotA2_cat_ATG |

TABLE 4-continued

List of EMSA annealings, overlapping and cloning PCR subfragments amplified in this study

| PCR/annealing | Primer 1 | Primer 2 |
|---|---|---|
| cat cassette amplification for $P_{sptA}$ fusion (screen) | F_cat_ATG | R_cat_(spec) |
| Diagnostic PCR for random peptide sequencing | Pxyl_seq | spec2 |
| PCR for random peptide backcross | UF_tRNAser | DR2_tRNAser |
| PCR for $tRNA^{Ser}$::$P_{xyl1}$-comR-spec amplification | UF_tRNAser | DR2_tRNAser |
| Upstream homologous region of scuR gene | UFrggC JIM | URrggC JIM |
| Downstream homologous region of scuR gene | DFrggC JIM | DRrggD SS |
| Upstream homologous region of scuR gene (in-frame deletion) | UFrggC JIM | rggD_S4_2 |
| Downstream homologous region1 of scuR gene (in-frame deletion) | rggD_S4_3 | rggD_S4_4 |
| Downstream homologous region2 of scuR gene (in-frame deletion) | rggD_S4_5 | rggD_S4_6 |
| Diagnostic PCR for scuR deletion | Up_rggC JIM | Down_rggD SS |
| Upstream homologous region of sarF gene | UFrggC SS | URrggD JIM |
| Downstream homologous region of sarF gene | DFrggD JIM | DRrggC_SS |
| Upstream homologous region of sarF gene (in-frame deletion) | UFrggC SS | rggC_S4_2 |
| Downstream homologous region1 of sarF gene (in-frame deletion) | rggC_S4_3 | rggC_S4_4 |
| Downstream homologous region2 of sarF gene (in-frame deletion) | rggC_S4_5 | rggC_S4_6 |
| Diagnostic PCR for sarF deletion | Up_rggC SS | Down_rggC_SS |
| Diagnostic PCR for scuR-sarF deletion | Up_rggC JIM | Down_rggC_SS |
| Upstream homologous region of comR gene | UFcomRJIM-SS1-4 | URcomRJIM-SS1-4 |
| Downstream homologous region of comR gene | DFcomRJIM-SS1-4 | DRcomRJIM-SS1-4 |
| Diagnostic PCR for comR deletion | Up_comR_SS1-4 | Down_comR_SS1-4 |
| Upstream homologous region of comA gene | UF_PcomR_luxAB | UR_comA |
| Downstream homologous region of comA gene | DF_comA | DR_comA |
| Diagnostic PCR for comA deletion | F_comR | Down_PcomS_JIMSS1-4 |
| Upstream homologous region of sptA gene | UF_potA2 | UR_potA2 |
| Downstream homologous region of sptA gene | DF_potA2 | DR_potA2 |
| Diagnostic PCR for sptA deletion | Up_potA2 | Down_potA2 |
| Promoter of sptA annealing for EMSA | Cy3_F_PpotA2_EMSA | R_PpotA2_EMSA |
| Promoter of slvX annealing for EMSA | Cy3_F_P01665_EMSA | R_P01665_EMSA |
| Promoter of comS annealing for EMSA | Cy3_F_PcomS_EMSA | R_PcomS_EMSA |
| Promoter of comX annealing for EMSA | Cy3_F_PcomX_EMSA | R_PcomX_EMSA |
| Promoter of $comX^{G \rightarrow A}$ annealing for EMSA | Cy3_F_PcomX_EMSArev | R_PcomXE_EMSArev |

Randomized Peptide Screen

To generate the two DNA libraries encoding randomized sequence of small peptides, we performed overlapping PCRs to graft fragments encompassing the follow features: (1) a 5' recombination arm (for the ectopic $tRNA^{ser}$ locus); (2) the xylR gene that codes for the xylose responsive regulator; (3) either $P_{xyl1}$ (library I) or $P_{xyl2}$ (library II) translationally-fused to a 12 codon long gene, for which the last 7 are randomized; (4) the spec gene; (5) a 3' recombination arm (for the ectopic $tRNA^{ser}$ locus). To obtain the randomized DNA stretch, we used a 78 nucleotide long primer degenerated on 21 contiguous positions. Next, we transformed these two libraries in strains containing the sptA promoter translationally-fused to the cat gene (chloramphenicol resistance) in which the associated spec gene was excised by the previously described cre-lox method. The initial background of these strains were either a comR-overexpressing ($P_{xyl1}$-comR) or a salivaricin-deprived (Δslv5) strain. We plated transformed cells on solid medium supplemented with xylose (either 0.1 or 1%), chloramphenicol (2 mg/ml) and spectinomycin (200 mg/ml) and grew overnight. We restreaked single colonies on fresh chloramphenicol and spectinomycin solid medium supplemented or not with xylose. We finally collected clones that displayed an increased in growth on xylose vs non xylose medium (except for the clone BM1 that we used as a negative control).

Mobility Shift Assays (EMSA)

All double-stranded DNA fragments (30 or 40 bp) were obtained from annealing of single-stranded Cy3-labelled (at 5' end) and unlabeled oligonucleotides. Primers used are listed in Table 3. Typically, a gel shift reaction (20 μl) was performed in a binding buffer (20 mM Tris-HCl pH 8.0, 150 mM NaCl, 1 mM EDTA, 1 mM DTT, 10% glycerol, 1 mg ml-1 BSA) and contained 150 ng labelled probe and 4 mM StrepTag proteins. When necessary, 8 mM of ComS peptides (unless otherwise stated) are added. The reaction is incubated at 37° C. for 10 min prior to loading of the samples on a native TBE 5% gel. The gel is next subjected to 80 V for approximately 1 h in TBE buffer. DNA complexes were detected by fluorescence on the Ettan DIGE Imager with bandpass excitation filters (nm): 540/25 (Cy3) or 635/30 (Cy5) and bandpass emission filters: 595/25 (Cy3) or 680/30 (Cy5) (GE Healthcare, Waukesha, WI).

Bacteriocin Detection Assay

The spot-on lawn (multilayer) detection method was performed as followed: 10 μl of overnight cultures of producer strains were diluted in fresh M17G medium and grown to reach mid-log phase ($OD_{600}$=~0.5). In parallel, we casted plates with a bottom feeding layer (M17G 1.5% agar) supplemented with a synthetic peptide where required. Next, we mixed 100 μl of an overnight culture of *Lactococcus lactis* IL1403 (indicator strain) in pre-warmed soft M17G medium (0.3% agar) and casted it as a top layer. Finally, we incubated mid-log phase cultures for 30 minutes with the corresponding synthetic peptides and spotted 3 μl of the producer strains on the top layer. Plates were incubated overnight before analysis of the inhibition zones surrounding the producer colonies.

Competence Induction, Transformation Rate and Engineering of Mutants

To induce competence, overnight CDMG precultures were diluted at a final $OD_{600}$ of 0.05 in 300 μl (10 ml concerning the randomized peptide screen) of fresh CDMG and incubated 75 min at 37° C. Then, we added the pheromone sComS as well as DNA (overlapping PCRs or plasmids) and let the cells recover for 3 h at 37° C. before plating on M17G agar supplemented with antibiotics where required. Null-mutants were constructed by exchanging (double homologous recombination) the coding sequences (CDS) of target genes (sequence between start and stop codons) for either chloramphenicol or erythromycin resistance cassette. If stated, mutants were cleaned for the lox site-flanked resistance cassette, as previously described (Fontaine et al. Mol Microbiol 2010; 87:1113-1132). In case of deletion of multiple CDSs, the region between the start codon of the first CDS and the stop codon of the last CDS was deleted. Integration of the antibiotic resistance cassette at the right location was subsequently checked by PCR. The promoters of sptA genes was fused to the luxAB reporter genes and inserted with a chloramphenicol resistance cassette at the permissive tRNA threonine locus (HSISS4_r00061) by double homologous recombination. In case of ΔscuR and ΔsarF in-frame deletion, we used the two-step selection/counter-selection strategy previously described (Mignolet et al. Cell Rep 2018, 22:1627-1638). We transformed the wild-type strain with an overlapping PCR product composed of 4 fragments: (I) the upstream region of scuR or sarF genes, (II) the downstream region of scuR or sarF genes, (III) a cassette that includes the erythromycin resistance gene (erm) and a gene encoding the orotate transporter oroP, and finally (IV) the downstream region of scuR or sarF genes. We selected a first event of double recombination on medium supplemented with erythromycin. Next, we selected an intramolecular recombination between region (I) and (IV) that excises the erm-oroP cassette by growing cells on M17G supplemented with the toxic 5-fluoro-orotic acid (5-FOA) compound. In absence of oroP, 5-FOA is not able to cross the membrane and penetrate the cytoplasm where it is deleteriously incorporated in the nucleotide metabolic pathway (Overkamp et al., 2013). At final, we engineered an in-frame deletion mutant of scuR or sarF in which the first seven codons were fused to the last six codons without any cassette scar (see below for detailed cloning method).

ComR, ScuR and SarF Purification

The PCR-amplified scuR-StrepTag and gene sarF-StrepTag were cloned into the pBAD-comR-ST vector (see supplemental information). The ComR-StrepTag, ScuR-StrepTag and SarF-StrepTag recombinant proteins were overproduced in *E. coli* and purified as previously described (Fontaine et al., 2013) in standard native conditions on Strep-Tactin agarose beads (IBA).

Measurements of Growth and Luciferase Activity

Overnight precultures were diluted at a final $OD_{600}$ of 0.05. A volume of 300 μl of culture samples was incubated in the wells of a sterile covered white microplate with a transparent bottom (Greiner, Alphen a/d Rijn, The Netherlands) for 75 min at 37° C. and then supplemented with synthetic peptides (1 μM, except if otherwise stated) or DMSO, and xylose where required. Growth ($OD_{600}$) and luciferase (Lux) activity (expressed in relative light units) was monitored at 10 min intervals during 24 h in a multi-wells plate reader (Hidex Sense, Hidex, Turku, Finland) as previously described (Fontaine et al., 2013).

Deep Sequencing (RNAseq) and Data Processing

*S. salivarius* WT, ΔscuR, ΔsarF, $scuR^{++}$ or ΔsarF-$ST^{++}$ strains were pre-cultured overnight in CDMG at 37° C. They were resuspended in 50 ml of fresh pre-warmed CDMG to a final $OD_{600}$ of 0.05 and grown for approximately 2 h 30 min ($OD_{600}$=0.3) at 37° C. Cells were harvested by centrifugation (10 min; 4,050×g), the supernatant were discarded and the cell pellets were frozen with liquid nitrogen. Finally, RNA was extracted using the RiboPure bacteria kit (Ambion-Life Technologies) and the protocol provided by the manufacturer, with protocol changes to cell lysis and RNA precipitation. For lysis, cells were resuspended in RNAwiz buffer (Ambion-Life Technologies) supplemented with Zirconia beads and shaked for 40 sec (4 times) in a fastPrep homogenizer device (MP biomedicals). For RNA precipitation, a 1.25-ethanol volume (instead of 0.5) was added to partially purified RNAs. Total RNA was checked for quality on a RNA Nano chip (Agilent technologies) and concentration was measured using Ribogreen assay (Life technologies). rRNA depletion was performed on 2 μg total RNA with the Ribo-Zero rRNA removal kit for Gram-positive bacteria (Illumina) according to manufacturer's instructions. Total stranded mRNA libraries were prepped with the NEBNext Ultra Directional RNA Library Prep kit for Illumina (New England Biolabs). Library PCR was executed for 15 cycles. Quality of the libraries was evaluated with the use of a High sensitivity DNA chip (Agilent technologies) and concentrations were determined through qPCR according to Illumina protocol. Libraries were sequenced on a NextSeq 500 high-throughput run with 76 bp single reads. 2.3 pM of the library was loaded on the flowcell with a Phix spike-in of 5%. Sequenced mRNAs generated several million reads that were mapped on the WT *S. salivarius* chromosome and processed with both bowties V0.12.9 (http://bowtie-bio.sourceforge.net/bowtie2) and samtools V0.1.18 (http://samtools.sourceforge.net/) algorithms to yield BAM files containing the read coordinates. We imported these files into SeqMonk V0.23.0 (www.bioinformatics.babraham.ac.uk/projects/) to assess the total number of reads for each coding sequence (CDS). The dataset was exported into an excel file for further analyses. First, the dataset was standardized to CDS-mapped reads per million overall reads. Then, we estimated a ratio of CDS-mapped reads in mutants vs WT. All RNAseq data was deposited in the GEO database under accession number GSE120640.

Plasmid and Linear DNA Fragment Constructions

All DNA fragments were amplified by PCR using the Phusion high fidelity polymerase (www.thermoscientificbio.com/) following a protocol as recommended by the manufacturer. Overlapping PCR products were transferred in competence-induced HSISS4 derivatives (Mignolet at al. Genome Announc 2016, 4:e01637-01615). cat, erm, spec, erm-oroP, $P_{xyl1}$, $P_{xyl2}$, and luxAB-cat cassettes were amplified from pNZ5319, pGIUD0855ery, pJUDspecmut1-gfp$^{+}$ ter, pSEUDO-$P_{usp45-sf}$gfp(Bs), pZX9, pZX10 and pJIMcat, respectively. comX and sptA mutated promoter were amplified from the WT comX and sptA luxAB-fused promoter strain, respectively. The sarF-ST allele was amplified from pBAD-sarF-ST. The full $P_{xyl1}$-comR-spec at $tRNAs^{Ser}$ locus was amplified in one block from the strain $tRNA^{Ser}$::$P_{xyl1}$-comR-spec (Mignolet et al. Cell Rep 2018, 22:1627-1638). All the constructed plasmids were sequence-verified.

pBAD-scuR-ST. The scuR-coding sequence was PCR amplified using the rggD_NcoI SS and rggD_MunI primers. This scuR fragment was digested with NcoI/MunI and cloned into NcoI/EcoRI-digested pBAD-comR-ST (Mignolet et al. Cell Rep 2018, 22:1627-1638).

pBAD-sarF-ST. The sarF-coding sequence was PCR amplified using the rggC_NcoI SS and rggC_RI SS primers. This sarF fragment was digested with NcoI/EcoRI and cloned into NcoI/EcoRI-digested pBAD-comR-ST (Mignolet et al. Cell Rep 2018, 22:1627-1638).

Example 1: Regulon Interweaving in ComR Paralogs

Figure 1:
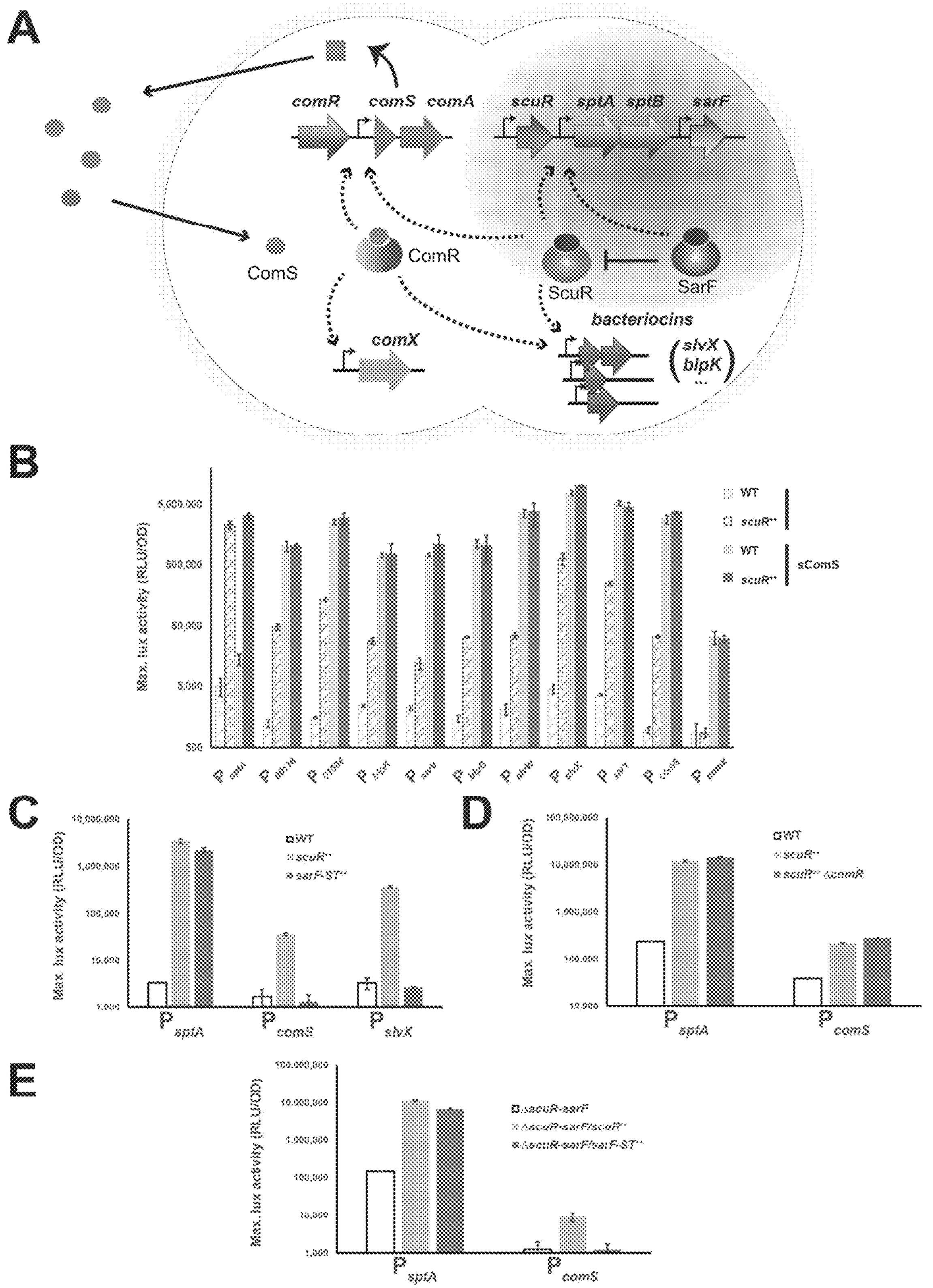
FIG. 1. Competence-Predation Dependencies of ComR Paralogs in *S. salivarius*

The bacteriocin short-circuitry imposed by ComR in the *S. salivarius* species is startling and suggests a positive selection for species-specific strategies that participate in niche adaptation. Interestingly, the *S. salivarius* HSISS4 genome encodes five RRNPP transcriptional factors, including ComR. Besides it, the two regulators ScuR (HSISS4_01166; stands for salivaricins-competence uncoupling regulator) and SarF (HSISS4_01169; ScuR-associated Rgg factor) share a high level of similarity with ComR (64 and 63%, respectively). The residues involved in HTH sequestration and homodimerization of ComR are well-conserved in both ScuR and SarF, suggesting that they could display a similar mode of activation. Moreover, the paralogous ScuR and SarF proteins are highly identical (similarity of 91%). Strikingly, residue divergences are nearly all concentrated in only 3 amino-acids stretches, one of which overlaps the α-helices 13 and 14 that form a part of the peptide recognition pocket. This indicates that the two proteins are likely to homodimerize and could accommodate specific peptides. On the chromosome, the scuR and sarF genes are located in a unique locus and separated by two genes that code for two predicted subunits of an ABC transporter, SptA and SptB (for ScuR-promoted transporter A and B, respectively) (FIG. 1A). In contrast to characterized rgg/comR loci, no small coding sequence was distinguishable upstream or downstream of scuR and sarF genes, arguing for a different genomic coding topology of the communication system.

Due to the huge conservation between ComR, ScuR and SarF, especially in the DNA binding domain, we questioned whether the two uncharacterized paralogs are capable to control competence and predation as well. Hence, we extracted mRNA of wild-type (WT) and engineered in-frame deletion mutants (ΔscuR and ΔsarF) and carried out a deep sequencing (RNAseq). With no hint about the genuine activating pheromones, we included in our high-throughput transcriptomic analyses overexpression mutants ($scuR^{++}$ and $sarF\text{-}ST^{++}$), in order to exacerbate the regulation phenotype. Indeed, a strong overproduction of ComR was reported to be sufficient for activation of its target promoters, even in absence of ComS (from endogenous production or synthetic peptide addition). Both deletion mutants did not dramatically affect the transcriptome compared to the WT strain, meaning that the function of ScuR and SarF is barely noticeable during standard growth conditions. However, the SarF loss slightly increased scuR expression, while the differential sptA and sptB mRNA level almost reached the arbitrary 5-fold induction cut-off, suggesting that SarF could be a repressor/antagonist of the ScuR-SptAB system. In contrast, the strong overexpression of scuR (28-fold) elicited a tremendous activation of the sptA-sptB operon (about 2000-fold). Furthermore, a second cluster of genes, all located inside salivaricin loci, was robustly influenced, even if with a lower magnitude of activation (ranging from 35- to 140-fold). Surprisingly, comX mRNA levels remained approximately stable in all mutants.

Altogether, these results imply that the ComR, ScuR and SarF paralogs might shape overlapping but dedicated regulatory networks.

Example 2: ScuR is an Alternative Self-Sufficient Pathway That Controls Salivaricin Production but Maintains the Competence Off In order to validate our transcript profile analyses, we performed promoter-probe assays, as previously described for ComR. We first expanded our collection of luciferase reporter strains (composed of comS, comX and bacteriocin gene promoters) to include and monitor the sptA promoter ($P_{sptA}$) and, next transformed all of them with the scuR overexpression cassette. Finally, we measured promoter activity in presence or absence of sComS (synthetic peptide) during cell growth (FIG. 1B). In agreement with our RNA-seq data, sptA and bacteriocin promoters were all markedly up in the $scuR^{++}$ strain, irrespective of the addition of sComS, and with no significant synergy. In addition, we observed no activation of the $P_{comX}$ due to ScuR accumulation, disabling ScuR as a trigger of competence state. Nonetheless, the $P_{comS}$ showed a 35-fold change in activity, suggesting that ScuR might modulate the ComR cell signaling. To complement our understanding of this bipartite system, we assessed the activity of $P_{sptA}$, $P_{comS}$ and $P_{slvX}$ in a $sarF\text{-}ST^{++}$ strain, and noticed that scuR and sarF overexpression governs $P_{sptA}$ activation amplitude in a similar range, while $P_{comS}$ and $P_{slvX}$ are irresponsive to SarF (FIG. 1C).

Considering that the effects of transcriptional regulators could be indirect, we were prompted to inactivate one Rgg by gene deletion in our reporter strains and test the residual activity of the others. We discovered that ScuR still controls both $P_{sptA}$ and $P_{comS}$ in comR (FIG. 1D) or sarF deleted strains (FIG. 1E), while SarF is sufficient to activate $P_{sptA}$ even in absence of scuR (ΔscuR-sarF/$sarF\text{-}ST^{++}$ mutant) (FIG. 1E). Finally, the sComS-mediated regulation of ComR is not crippled in absence of both ScuR and SarF (FIG. 1F), suggesting that each regulator can stand alone to fulfill its function and work in parallel.

Taken together, our results suggest that the 3 transcriptional factors have only partly redundant functions, with regulatory network specificities, presumably to ensure a broader diversity of cellular response to environment stresses. ScuR and SarF, but not ComR, control the sptAB operon, while ScuR alone has a ComR-independent extra regulatory role on bacteriocin production. Even though ScuR raises ComS production, this regulator does not act on comX promoter and is likely to disconnect the competence-predation coupling compelled by ComR.

Example 3: Randomization-Based Screen for Pheromone Identification

Typically, the major challenge to address the transduction mechanism of cell-cell communication sensor is the identification of the ligand(s) or the perceived signal(s). As inspection of the genomic neighborhood did not reveal any small encoded peptide in the vicinity of scuR-sarF locus, we decided to conduct an empirical screen to unearth peptides able to activate the ScuR-SarF system (FIG. 2A). Thence, we constructed on one side a strain harboring a translational fusion of the ScuR/SarF-specific $P_{sptA}$ to a gene conferring resistance to chloramphenicol (cat). On the other side, we amplified a DNA fragment that allows recombination at a permissive locus ($tRNA^{Ser}$) and encompasses, under xylose control, a 12 codons-long nucleotide sequence, the last 7 of which are randomized (see Experimental Procedures). We finally transformed this PCR product in the above-mentioned reporter mutant and selected clones on plates supplemented with chloramphenicol and xylose (0.1 or 1%). Note that, in order to increase the transformation rate or decrease the cytotoxicity due to concomitant bacteriocin production, we worked in comR overexpression ($P_{syl1}$-comR) or salivaricin deprived (Δslv5) background, respectively. In total, over 9 runs of screen, we collected a hundred of clones that we streaked again on selective medium with and without xylose. We sent for sequencing clones that showed a clear improvement of growth due to xylose on chloramphenicol (Table 5). As a negative control, we included in our further analyses a clone (BM1) with a xylose-independent growth. Out of the 30 positive clones, 22 harbored a non-redundant peptide/nucleotide sequence.

TABLE 5

| Fusion | Back-ground | Random peptide promoter | [xylose] | Name | Peptide sequence | SEQ ID NO | DNA sequence | SEQ ID NO |
|---|---|---|---|---|---|---|---|---|
| $P_{sptA}$-cat (lox) | $P_{xyl1}$-COMR | $P_{xyl2}$ | 1% | BH6 | MIAILAFWLILG | 26 | ATGATCGCAATCCT AGCGTTCTGGCTG ATCCTAGGTTGA | 27 |
| $P_{sptA}$-cat (lox) | $P_{xyl1}$-COMR | $P_{xyl1}$ | 0.1% | B11 | MIAILTWWLILG | 28 | ATGATCGCAATCCT AACTTGGTGGTTAA TTCTGGGATGA | 29 |
| $P_{sptA}$-cat (lox) | $P_{xyl1}$-COMR | $P_{xyl1}$ | 0.1% | B12 | MIAILPYWLGLG | 30 | ATGATCGCAATCCT ACCATACTGGTTAG GCCTAGGCTGA | 31 |
| $P_{sptA}$-cat (lox) | $P_{xyl1}$-COMR | $P_{xyl1}$ | 0.1% | B15 | MIAILPWWVSVG | 32 | ATGATCGCAATCCT ACCTTGGTGGGTAT CAGTTGGTTGA | 33 |
| $P_{sptA}$-cat (lox) | $P_{xyl1}$-COMR | $P_{xyl1}$ | 0.1% | B16 | MIAILPYWLGLG | 34 | ATGATCGCAATCCT ACCATACTGGTTAG GCCTAGGCTGA | 35 |
| $P_{sptA}$-cat (lox) | $P_{xyl1}$-COMR | $P_{xyl1}$ | 0.1% | B17 | MIAILPFWLILG | 36 | ATGATCGCAATCCT ACCCTTTTGGCTCA TATTAGGCTGA | 37 |
| $P_{sptA}$-cat (lox) | $P_{xyl1}$-COMR | $P_{xyl1}$ | 0.1% | B19 | MIAILPFWLILG | 38 | ATGATCGCAATCCT ACCCTTTTGGCTCA TATTAGGCTGA | 39 |
| $P_{sptA}$-cat (lox) | $P_{xyl1}$-COMR | $P_{xyl1}$ | 0.1% | B110 | MIAILPYWLLIG | 40 | ATGATCGCAATCCT ACCATACTGGCTTC TCATAGGTTGA | 41 |
| $P_{sptA}$-cat (lox) | $P_{xyl1}$-COMR | $P_{xyl1}$ | 0.1% | B111 | MIAILPFWLVLG | 42 | ATGATCGCAATCCT ACCTTTTTGGCTAG TCCTCGGATGA | 43 |
| $P_{sptA}$-cat (lox) | $P_{xyl1}$-COMR | $P_{xyl1}$ | 0.1% | B112 | MIAILPFWVVAG | 44 | ATGATCGCAATCCT ACCGTTCTGGGTT GTCGCGGGCTGA | 45 |
| $P_{sptA}$-cat (lox) | $P_{xyl1}$-COMR | $P_{xyl2}$ | 0.1% | BJ1 | MIAILPFWLSVG | 46 | ATGATCGCAATCCT ACCATTTTGGCTAA GCGTAGGCTGA | 47 |
| $P_{sptA}$-cat (lox) | $P_{xyl1}$-COMR | $P_{xyl1}$ | 1% | BK1 | MIAILPYWLDMG | 48 | ATGATCGCAATCCT ACCATATTGGCTTG ATATGGGATGA | 49 |
| $P_{sptA}$-cat (lox) | $P_{xyl1}$-COMR | $P_{xyl1}$ | 1% | BK2 | MIAILPYWLDMG | 50 | ATGATCGCAATCCT ACCATATTGGCTTG ATATGGGATGA | 51 |
| $P_{sptA}$-cat (lox) | $P_{xyl1}$-COMR | $P_{xyl1}$ | 1% | BK3 | MIAILWWGTMI | 52 | ATGATCGCAATCCT ATGGTGGGGCACT ATGATCTAGTGA | 53 |
| $P_{sptA}$-cat (lox) | $P_{xyl1}$-COMR | $P_{xyl1}$ | 1% | BK4 | MIAILYWATTGL | 54 | ATGATCGCAATCCT ATATTGGGCCACG ACTGGGTTATGA | 55 |
| $P_{sptA}$-cat (lox) | $P_{xyl1}$-COMR | $P_{xyl1}$ | 1% | BKS | MIAILPYWLCII | 56 | ATGATCGCAATCCT ACCCTACTGGCTCT GCATTATATGA | 57 |
| $P_{sptA}$-cat (lox) | $P_{xyl1}$-COMR | $P_{xyl1}$ | 1% | BK6 | MIAILPYWVTMG | 58 | ATGATCGCAATCCT ACCATATTGGGTCA CCATGGGTTGA | 59 |
| $P_{sptA}$-cat (lox) | $P_{xyl1}$-COMR | $P_{xyl1}$ | 1% | BK7 | MIAILPYWVVLG | 60 | ATGATCGCAATCCT ACCTTACTGGGTAG TGCTAGGGTGA | 61 |
| $P_{sptA}$-cat (lox) | $P_{xyl1}$-COMR | $P_{xyl1}$ | 1% | BK8 | MIAILPYWVTMG | 62 | ATGATCGCAATCCT ACCATATTGGGTCA CCATGGGTTGA | 63 |

TABLE 5-continued

| Fusion | Back-ground | Random peptide promoter | [xylose] | Name | Peptide sequence | SEQ ID NO | DNA sequence | SEQ ID NO |
|---|---|---|---|---|---|---|---|---|
| $P_{sptA}$-cat (lox) | $P_{xyl1}$-COMR | $P_{xyl1}$ | 1% | BK9 | MIAILPSWLVVG | 64 | ATGATCGCAATCCT ACCAAGCTGGTTA GTTGTTGGCTGA | 65 |
| $P_{sptA}$-cat (lox) | Δslv5 | $P_{xyl1}$ | 0.1% | BL1 | MIAILPHWITIG | 66 | ATGATCGCAATCCT ACCACACTGGATCA CAATAGGCTGA | 67 |
| $P_{sptA}$-cat (lox) | Δslv5 | $P_{xyl1}$ | 0.1% | BL2 | MIAILPYWLGLG | 68 | ATGATCGCAATCCT ACCATACTGGTTAG GCCTAGGCTGA | 69 |
| $P_{sptA}$-cat (lox) | Δslv5 | $P_{xyl1}$ | 0.1% | BL3 | MIAILPHWCVLG | 70 | ATGATCGCAATCCT ACCACATTGGTGC GTGCTTGGCTGA | 71 |
| $P_{sptA}$-cat (lox) | Δslv5 | $P_{xyl2}$ | 0.1% | BM1 | MIAILRPH | 72 | ATGATCGCAATCCT ACGTCCACATTAAT AGTTCCACTGA | 73 |
| $P_{sptA}$-cat (lox) | Δslv5 | $P_{xyl1}$ | 1% | BN1 | MIATLPFWLALG | 74 | ATGATCGCAACCCT ACCTTTTTGGCTTG CCCTCGGATGA | 75 |
| $P_{sptA}$-cat (lox) | Δslv5 | $P_{xyl1}$ | 1% | BN2 | MIAILTCWVCIV | 76 | ATGATCGCAATCCT AACATGTTGGGTCT GCATAGTATGA | 77 |
| $P_{sptA}$-cat (lox) | Δslv5 | $P_{xyl1}$ | 1% | BN3 | MIAILFWVELG | 78 | ATGATCGCAATCCT ATTCTGGGTGGAAT TAGGATAATGA | 79 |
| $P_{sptA}$-cat (lox) | Δslv5 | $P_{xyl1}$ | 1% | BN4 | MIAILTCWVCIV | 80 | ATGATCGCAATCCT AACATGTTGGGTCT GCATAGTATGA | 81 |
| $P_{sptA}$-cat (lox) | $P_{xyl1}$-COMR | $P_{xyl2}$ | 0.1% | BO1 | MIAILPFWCVLG | 82 | ATGATCGCAATCCT ACCCTTCTGGTGTG TCCTTGGATGA | 83 |
| $P_{sptA}$-cat (lox) | $P_{xyl1}$-COMR | $P_{xyl2}$ | 0.1% | BO2 | MIAILPFWCVLG | 84 | ATGATCGCAATCCT ACCCTTCTGGTGTG TCCTTGGATGA | 85 |
| $P_{sptA}$-cat (lox) | $P_{xyl1}$-COMR | $P_{xyl1}$ | 1% | BP1 | MIAILPFWLVLG | 86 | ATGATCGCAATCCT ACCTTTTTGGCTAG TCCTCGGATGA | 87 |

In order to discard clones with secondary mutations for which the survival phenotype was not related to the peptide nature, we amplified for each clone the full locus that encodes the small peptide and backcrossed it into WT or (Δslv5) backgrounds. We then confirmed on solid media that chloramphenicol resistance qualitatively increased upon xylose addition. We used the same PCR products to transform a strain bearing the $P_{sptA}$-luxAB report fusion and quantitatively estimate the influence of peptide production. Again, we noticed that xylose addition potentiated the promoter activity with values ranging from 5 to 100 fold, while it has no effect on BM1 (negative control) and WT strains (FIG. 2B).

We aligned the 22 unique peptide sequences to elicit common chemical properties (FIG. 2C). Strikingly, a tryptophan residue is highly conserved at position −5 from the C-terminus. On the top of this, the adjoined position (−6) is mainly occupied with an aromatic residue. Finally, the position −1 is preferentially a glycine. Positions −2, −3 and −4 are more erratic, even if we observed a tendency for hydrophobic amino acids. Given that it encodes a peptide (MIAILPFWLILG) that neatly mimics the consensus sequence (MIAILPFWLVLG), we decided to hereafter focus on clone BI7, and we disclosed that ScuR is specifically responsible for the xylose-driven phenotype. Indeed, neither comR nor sarF deletion has a dramatic effect, while ScuR loss annihilates both xylose induction and basal leaky expression (FIG. 2D).

Example 4: Exogenous Pheromones Activate the ScuR-SarF Tandem

We next checked whether we could, akin to ComS toward ComR, activate the system with synthetic peptides (FIG. 3A). We therefore selected a representative panel of peptides from our screen and ordered the synthesis of the last 8 amino acids and tested $P_{sptA}$ activation (FIG. 3B). Whatever their degree of kinship toward the consensus motif, the peptides were capable of inducing light production when supplemented to the medium. However, a weaker activation was displayed by the peptides that diverge the most from the paradigm such as sBK3, which does not harbor a C-terminus glycine, or sBK4, for which the tryptophan and glycine are shifted of one position (exacerbated effect at the non-saturating concentration of 0.01 μM). The huge variability in sequence and the similar amplitude of activation for all other peptides emphasizes that (1) the residues between the conserved tryptophan and glycine and the proline (position −7) are not essential for ScuR or SarF transactivation, while the position −6 tolerates substitutions as far as the peptide nature is aromatic. Moreover, rational mutations of the ultra-conserved tryptophan evidenced the strict requirement of the indole moiety, considering that neither alanine (sBI7$^{W\rightarrow A}$) nor phenylalanine (sBI7$^{W\rightarrow F}$) variants sustains luciferase transcription at low peptide concentration (0.001 μM, FIG. 3C). A similar strategy for the C-terminal glycine showed that its substitution by an alanine (sBI7$^{G\rightarrow A}$) decreases the $P_{sptA}$ response although to a lesser extent compare to the tryptophan (FIG. 3C). It is noteworthy that high concentration of sBI7$^{W\rightarrow F}$ and sBI7$^{G\rightarrow A}$ (but not sBI7$^{W\rightarrow A}$) can bypass the requirement of the tryptophan and glycine and activate $P_{cat}$ at a similar range than the WT sBI7 peptide (FIG. 3E), suggesting that the mutations do not totally abrogate the ScuR/SarF activation but rather modulate the kinetics of interaction.

Example 5: Selective Recognition of Targeted Promoters

To refine our view of the 2 Rgg-systems, $P_{sptA}$, $P_{comS}$ and $P_{slvX}$ were challenged with increasing amount of sBI7 at low concentration in WT, ΔscuR or ΔsarF strains (FIG. 3D). In line with our overexpression data, $P_{comS}$ and $P_{slvX}$ were totally insensitive to SarF (no activity in ΔscuR), while both ScuR and SarF can turn on $P_{sptA}$ independently of each other. Furthermore, in WT backgrounds, we observed that all promoters were responsive to less than 1 nM of peptide, with the highest amplitude for $P_{sptA}$ and the lowest for $P_{comS}$. Whereas activity of all promoters in ΔsarF were slightly up compared to the WT, supporting the notion that SarF might have a mild inhibitory effect on ScuR function. Expectedly, the induction provoked by sBI7 addition is utterly erased in a ΔscuR-SarF double mutant (FIG. 3F), however sBI7 is surprisingly able to induce the SarF-mediated $P_{sptA}$ response (FIG. 3D). This discrepancy in regard to the genome-encoded peptide results (FIG. 2D) might be due to inherent differences imposed by the screening method compared to the exogenous supplementation of a synthetic peptide (variable intracellular concentration, different peptide length, lower activation rate of SarF, . . . ). But it underlines that the peptide-binding pocket of both Rgg could accommodate a unique pheromone.

Next, we carried out in vitro mobility shift assays to assess the direct interaction between proteins and promoter probes in absence or presence of decreasing concentration of synthetic peptides. We included a $P_{comX}$ probe as a negative control. Anew, we corroborated our promoter activity data at the magnitude and protein-peptide/DNA specificity level (FIG. 4A). The ScuR regulator displayed the weakest affinity for $P_{comS}$, and the strongest one toward $P_{sptA}$, starting from 0.08 nM of sBI7 peptide and complexing the full amount of probe at maximal concentrations (presence of a doublet presumably due to a second higher order of oligomerization) (FIG. 4A). We observed similar results with unique concentration of sBI7 and decreasing concentration of ScuR on $P_{sptA}$ and $P_{slvX}$ probe (FIG. 4G). Moreover, in comparison to the sComS-bound ComR, the ScuR·sBI7 affinity for $P_{comS}$ and $P_{slvX}$ appears weaker with a less stable complex (probe smear) (FIG. 4A). Remarkably, the ScuR and SarF binding progressively and linearly increased with the amount of peptide, contrasting with ComR that showed a smaller interval between sub-activating and saturating concentrations of sComS. This suggests ScuR and SarF have a different dynamic of binding compared to ComR that might reflect the congruence between reactivity and physiological function. Finally, the ComR·sComS pair can unexpectedly bind the $P_{sptA}$ probe, indicating that the sptA promoter topology, and presumably the distance between the palindrome center and the −10 box, might be crucial to dictate the specific ScuR/SarF-driven transactivation (FIG. 4A).

The topology of ScuR, SarF or ComR responsive promoters appears extremely similar (FIGS. 4B and 4H). The architecture of every promoter includes a conserved nucleotide stretch of dyad symmetry and a T-rich spacer that separates it from the sigma-bound −10 box (exact same length in all promoters, $P_{sptA}$ apart). However, the core palindromic region of the ComR-specific $P_{comX}$ includes a mismatch, while the equivalent stretch in the ScuR- and SarF-specific $P_{sptA}$ is more extended, comprises 2 mismatches and is closer to the −10 box from one nucleotide (FIG. 4B). Considering the high degree of similitude between promoters at the primary sequence level (FIGS. 4B and 4H), we were prompted to address the nucleotide determinants that impose the protein-DNA selectivity. We therefore mutated comX and sptA promoters to sensitize them toward ScuR and ComR, respectively. In $P_{comX}$, we substituted a guanosine for an adenosine ($P_{comX}^{G\rightarrow A}$) to reconstitute the palindromic region observed in $P_{comS}$ and $P_{slvX}$ (FIG. 4B). Concerning $P_{sptA}$, we performed three kinds of mutation (FIG. 4B). We reconstituted the symmetric region with 2 substitutions ($P_{sptA}^{CT\rightarrow AC}$), we inserted a nucleoside in the T-rich stretch to redefine the same distance between palindrome center and −10 box ($P_{sptA}^{+1}$), and finally, with the mere insertion of an adenosine in the palindrome ($P_{spTA}^{+A}$), we redesigned both space and palindrome. Non-ambiguously, all these mutations impinged on selectivity at different extent, driving the engineered promoters sensitive to both pheromones (FIGS. 4C and 4D). In agreement with this, ScuR, but not SarF, is able to shift the $P_{comX}^{G\rightarrow A}$ probe (FIG. 4E). As competence entry hinders cell fitness whereas the mutation in comX promoter bolstered the ComRS-mediated activation (FIG. 4D), we suspect that evolution maintains a selective pressure to ensure an appropriate expression in time and scale of comX compatible with the bacterium life cycle.

Example 6: Pheromone-Induced ScuR Promotes Bacteriocin Production

The lower reactivity of salivaricin promoters toward ScuR (vs ComR) pheromone incited us to investigate the phenotypical output at the bacteriocin production level. Thence, we performed a standard bacteriocin test on soft overlay and showed that the scuR$^{++}$ (but not sarF-ST$^{++}$) overexpression mutant is able to produce a comA-dependent inhibitory halo in bacteriocin tests (FIG. 5A). Even if the overexpression of scuR is more potent, sBI7 induced a small halo of inhibition around the WT strain for concentration ranging from 1 nM to 1 μM (FIG. 5B). This effect is eradicated in single ΔscuR or double ΔscuR-sarF mutants, or in a strain deprived of bacteriocin genes (Δslv5), demonstrating that the toxicity is due to bacteriocins and mediated by ScuR (FIG. 5B).

Example 7: Rgg Members Requisition Predation Control in *S. salivarius*

ScuR tends to compensate for the loss/lack of a functional BlpRH system, as they usually do not co-exist in the same strain (FIG. 6A). Oddly, the direct control of competence and bacteriocin network drifts from a full TCS control in *Streptococcus pneumoniae* (ComCDE and BIpRHC) to a full Rgg regulation in *S. salivarius* (ComRS and ScuR), going through an hybrid mechanism in mutans, bovis and pyogenes streptococci groups (ComRS and BIpRHC) (FIG. 6B). Why opposing extracellular sensing vs intracellular sensing inside streptococci is a vast question. As a genuine member of the gastro-intestinal tract, *S. salivarius* is under a grueling selective pressure, competing for resources and territories in a constantly changing environment. The most tantalizing hypothesis is that a cytoplasmic receptor could be better protected from communication interferences. Indeed, quenching molecules extruded by competitors face the chemical selectivity of the semi-permeable cell membrane to penetrate the cell. A second hypothesis is that internal cues, such as starvation/lushness, might impinge on the nutritional oligopermease system (Opp) to globally modulate small peptide inward fluxes and make the cell transiently communication-less or superreactive to pheromones in particular stressful situations.

All our phenotypical and molecular data coincide to conclude that ScuR is strictly devoted for predation in contrast to competence. Although highly similar to $P_{comS}$ and $P_{slvX}$ at primary sequence level, comX promoter cannot be occupied (FIG. 4A) nor activated (FIGS. 1B and 4D) by ScuR. Inconsistently, this regulator turns on $P_{comS}$ and should somehow modulate the ComRS activity through a flicking impetus in the positive feedback loop. An obvious reason for this discrepancy might be that the ScuR-driven expression of comS (FIGS. 1B and 3D) is weaker compared to our previous observations for ComR. Therefore it is not sufficient to reach the activation threshold, but it might ensure a basal production of ComA to extrude bacteriocins. Alternatively, we suspect that promoters are not responsive to ComR and ScuR pheromone with the same timeframe. In this case, ScuR might promote ComS production in a time interval during which the comX promoter is silenced or unreactive.

Example 8: Induction of Bacteriocin Promoters, No Induction of Competence Genes Confirming the importance of the ultra-conserved tryptophane residue (see FIG. 3C), we observed similar trends for all bacteriocin gene promoters (FIG. 7), with a total inefficacy of the peptide sBI7$^{W\rightarrow A}$, and a low to high activation disability for peptides sBI7$^{W\rightarrow F}$ and sBI7$^{G\rightarrow A}$.

It was also confirmed that ScuR and SarF have no effect on the sComS-mediated competence entry (FIG. 8). Further confirming this finding, sBI7 cannot activate comX and late competence genes under direct ComX control (FIG. 9), and is ineffective to support natural transformation (Table 6).

TABLE 6

| Competence development (transformation frequency[a]) in *S. salivarius* HSISS4 derivatives | | | |
|---|---|---|---|
| Strains | — | sComS | sBI7 |
| Wild-type | ND | 1.1 (±0.08) E−03 | ND |
| ΔscuR | ND | 0.7 (±0.2) E−03 | ND |
| ΔsarF | ND | 1.5 (±0.5) E−03 | ND |

TABLE 6-continued

| Competence development (transformation frequency[a]) in *S. salivarius* HSISS4 derivatives | | | |
|---|---|---|---|
| Strains | — | sComS | sBI7 |
| $P_{32}$-scuR | ND | NA | NA |
| $P_{32}$-sarF | ND | NA | NA |

[a]calculated as the ratio of transformants (chloramphenicol-resistant CFU) to the total CFU count per 0.1 ug of linear DNA. Transformation frequencies are expressed as the arithemtic mean of three independent experiments. Geometric means ± standard deviations are provided. ND: not detected (<1.0E−08), NA: not applicable.

Example 9: C-Terminal Residues and Bacteriocin Induction Activity

To evaluate whether the synthetic pheromones could tolerate amino acid addition at the C-terminus, we tested the close-to-consensus petide LAFWDSLG (SEQ ID NO: 749) as well as the peptide LAFWDSLGLLL (SEQ ID NO: 750) that harbors a triple leucine extension at the C-terminus. Strikingly, both peptides were able to induce the sptA promoter in vivo. However, the longer peptide was much more active at 1 μM concentration than the shorter one, with an induction magnitude comparable to the peptide sBI7 (FIG. 10A). By contrast, mobility shift assay performed with the very same peptides showed that ScuR binding to $P_{sptA}$ is more intense with LAFWDSLG (SEQ ID NO: 749), while it requires extreme concentration of the peptide LAFWDSLGLLL (SEQ ID NO: 750) to get activated (FIG. 10B). This suggests that LAFWDSLGLLL (SEQ ID NO: 750) can barely bind ScuR by itself but is processed in vivo, by one or more peptidases, to liberate an active peptide, presumably LAFWDSLG (SEQ ID NO: 749). It is thus clear that the peptides can tolerate amino acids at the C-terminus and still be active in vivo.

REFERENCES

Chopin, A., Chopin, M. C., Moillo-Batt, A., and Langella, P. (1984). Two plasmid-determined restriction and modification systems in *Streptococcus lactis*. Plasmid 11, 260-263.

Fontaine, L., Dandoy, D., Boutry, C., Delplace, B., de Frahan, M. H., Fremaux, C., Horvath, P., Boyaval, P., and Hols, P. (2010). Development of a versatile procedure based on natural transformation for marker-free targeted genetic modification in *Streptococcus thermophilus*. Appl Environ Microbiol 76, 7870-7877.

Fontaine, L., Goffin, P., Dubout, H., Delplace, B., Baulard, A., Lecat-Guillet, N., Chambellon, E., Gardan, R., and Hols, P. (2013). Mechanism of competence activation by the ComRS signalling system in streptococci. Mol Microbiol 87, 1113-1132.

Haustenne, L., Bastin, G., Hols, P., and Fontaine, L. (2015). Modeling of the ComRS Signaling Pathway Reveals the Limiting Factors Controlling Competence in *Streptococcus thermophilus*. Front Microbiol 6, 1413.

Lambert, J. M., Bongers, R. S., and Kleerebezem, M. (2007). Cre-lox-based system for multiple gene deletions and selectable-marker removal in *Lactobacillus plantarum*. Appl Environ Microbiol 73, 1126-1135.

Mignolet, J., Fontaine, L., Kleerebezem, M., and Hols, P. (2016a). Complete Genome Sequence of *Streptococcus salivarius* HSISS4, a Human Commensal Bacterium Highly Prevalent in the Digestive Tract. Genome Announc 4, e01637-01615

Mignolet, J., Fontaine, L., Sass, A., Nannan, C., Mahillon, J., Coenye, T., and Hols, P. (2018). Circuitry Rewiring Directly Couples Competence to Predation in the Gut Dweller *Streptococcus salivarius*. Cell Rep 22, 1627-1638.

Mignolet, J., Holden, S., Berge, M., Panis, G., Eroglu, E., Theraulaz, L., Manley, S., and Viollier, P. H. (2016b). Functional dichotomy and distinct nanoscale assemblies of a cell cycle-controlled bipolar zinc-finger regulator. Elife 5, e18647.

Overkamp, W., Beilharz, K., Detert Oude Weme, R., Solopova, A., Karsens, H., Kovacs, A., Kok, J., Kuipers, O. P., and Veening, J. W. (2013). Benchmarking various green fluorescent protein variants in *Bacillus subtilis, Streptococcus pneumoniae*, and *Lactococcus lactis* for live cell imaging. Appl Environ Microbiol 79, 6481-6490.

Van den Bogert, B., Boekhorst, J., Herrmann, R., Smid, E. J., Zoetendal, E. G., and Kleerebezem, M. (2014). Comparative genomics analysis of *Streptococcus* isolates from the human small intestine reveals their adaptation to a highly dynamic ecosystem. PLoS One 8, e83418.

Yu, J., Sun, Z., Liu, W., Xi, X., Song, Y., Xu, H., Lv, Q., Bao, Q., Menghe, B., and Sun, T. (2015). Multilocus sequence typing of *Streptococcus thermophilus* from naturally fermented dairy foods in China and Mongolia. BMC Microbiol 15, 236.

The invention claimed is:

1. A peptide able to induce bacteriocin production in a microbial organism with a length of at least 6 residues, comprising a sequences motif selected from:

Phe-Trp-Leu-Val-Leu-Gly (SEQ ID NO: 2);

Ala-Phe-Trp-Leu-Ile-Leu-Gly (SEQ ID NO: 3); and

Pro-Phe-Trp-Leu-Ile-Leu-Gly (SEQ ID NO: 7), wherein the sequence motif is located at the C-terminus of said peptide or located so that it is followed by at most 1, 2, 3, 4 or 5 additional C-terminal residues.

2. The peptide of claim 1, wherein the sequence motif is located at the C-terminus of said peptide.

3. A polypeptide able to induce bacteriocin production in a microbial organism, comprising the peptide of claim 1, wherein the peptide can be released from the polypeptide by natural, chemical or biological peptide hydrolysis.

4. A culture medium comprising the peptide of claim 1.

5. The culture medium of claim 4, further comprising a signaling molecule and/or a quenching molecule and/or an antimicrobial peptide and/or a bacteriocin.

6. A composition for inducing bacteriocin production in a microbial organism, comprising the peptide of claim 1 and a solvent.

7. The composition of claim 6, further comprising a signaling molecule and/or a quenching molecule and/or an antimicrobial peptide and/or a bacteriocin.

8. A microbial organism genetically modified to produce, or to produce and secrete, the peptide of claim 1.

9. A peptide having a length of at least 6 residues, the peptide comprising a sequences motif selected from:

Phe-Trp-Leu-Val-Leu-Gly (SEQ ID NO: 2);
Ala-Phe-Trp-Leu-Ile-Leu-Gly (SEQ ID NO: 3); and
Pro-Phe-Trp-Leu-Ile-Leu-Gly (SEQ ID NO: 7),
wherein the sequence motif is located at the C-terminus of said peptide or is located so that it is followed by at most 1, 2, 3, 4 or 5 additional C-terminal residues.

10. The peptide of claim 9, wherein the sequence motif is located at the C-terminus of said peptide.

11. A pro-polypeptide comprising:
a peptide sequence comprising an amino acid sequence selected from:
Phe-Trp-Leu-Val-Leu-Gly (SEQ ID NO: 2);
Ala-Phe-Trp-Leu-Ile-Leu-Gly (SEQ ID NO: 3); and
Pro-Phe-Trp-Leu-Ile-Leu-Gly (SEQ ID NO: 7),
wherein the amino acid sequence is located at the C-terminus of said peptide or is located so that it is followed by at most 1, 2, 3, 4 or 5 additional C-terminal residues; and
one or more cleavage sites, wherein the one or more cleavage sites separates the peptide sequence from the rest of the pro-polypeptide.

12. The pro-polypeptide of claim 11, wherein the amino acid sequence is located at the C-terminus of said peptide sequence.

13. The pro-polypeptide of claim 11, wherein the one or more cleavage sites is one or more cleavage sites for a cleavage enzyme.

14. The polypeptide of claim 3, wherein the sequence motif is located at the C-terminus of said peptide.

* * * * *

SEQUENCE LISTING

```
<160> NUMBER OF SEQ ID NOS: 752

<210> SEQ ID NO 1
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(6)
<223> OTHER INFORMATION: Xaa can be any naturally occurring amino acid

<400> SEQUENCE: 1

Xaa Trp Xaa Xaa Xaa Xaa
1               5


<210> SEQ ID NO 2
<211> LENGTH: 6
<212> TYPE: PRT
<213> ORGANISM: Artificial Sequence
<220> FEATURE:
<223> OTHER INFORMATION: Peptide

<400> SEQUENCE: 2

Phe Trp Leu Val Leu Gly
1               5


<210> SEQ ID NO 3
<211> LENGTH: 7
<212> TYPE: PRT
<213> ORGANISM: Artificial Sequence
<220> FEATURE:
<223> OTHER INFORMATION: Peptide

<400> SEQUENCE: 3

Ala Phe Trp Leu Ile Leu Gly
1               5


<210> SEQ ID NO 4
<211> LENGTH: 7
<212> TYPE: PRT
<213> ORGANISM: Artificial Sequence
<220> FEATURE:
<223> OTHER INFORMATION: Peptide

<400> SEQUENCE: 4

Thr Trp Trp Leu Ile Leu Gly
1               5
```

<210> SEQ ID NO 5
<211> LENGTH: 7
<212> TYPE: PRT
<213> ORGANISM: Artificial Sequence
<220> FEATURE:
<223> OTHER INFORMATION: Peptide

<400> SEQUENCE: 5

Pro Tyr Trp Leu Gly Leu Gly
1               5

<210> SEQ ID NO 6
<211> LENGTH: 7
<212> TYPE: PRT
<213> ORGANISM: Artificial Sequence
<220> FEATURE:
<223> OTHER INFORMATION: Peptide

<400> SEQUENCE: 6

Pro Trp Trp Val Ser Val Gly
1               5

<210> SEQ ID NO 7
<211> LENGTH: 7
<212> TYPE: PRT
<213> ORGANISM: Artificial Sequence
<220> FEATURE:
<223> OTHER INFORMATION: Peptide

<400> SEQUENCE: 7

Pro Phe Trp Leu Ile Leu Gly
1               5

<210> SEQ ID NO 8
<211> LENGTH: 7
<212> TYPE: PRT
<213> ORGANISM: Artificial Sequence
<220> FEATURE:
<223> OTHER INFORMATION: Peptide

<400> SEQUENCE: 8

Pro Tyr Trp Leu Leu Ile Gly
1               5

<210> SEQ ID NO 9
<211> LENGTH: 7
<212> TYPE: PRT
<213> ORGANISM: Artificial Sequence
<220> FEATURE:
<223> OTHER INFORMATION: Peptide

<400> SEQUENCE: 9

Pro Phe Trp Leu Val Leu Gly
1               5

<210> SEQ ID NO 10
<211> LENGTH: 7
<212> TYPE: PRT
<213> ORGANISM: Artificial Sequence
<220> FEATURE:
<223> OTHER INFORMATION: Peptide

<400> SEQUENCE: 10

Pro Phe Trp Val Val Ala Gly
1               5

<210> SEQ ID NO 11

<211> LENGTH: 7
<212> TYPE: PRT
<213> ORGANISM: Artificial Sequence
<220> FEATURE:
<223> OTHER INFORMATION: Peptide

<400> SEQUENCE: 11

Pro Phe Trp Leu Ser Val Gly
1               5

<210> SEQ ID NO 12
<211> LENGTH: 7
<212> TYPE: PRT
<213> ORGANISM: Artificial Sequence
<220> FEATURE:
<223> OTHER INFORMATION: Peptide

<400> SEQUENCE: 12

Pro Tyr Trp Leu Asp Met Gly
1               5

<210> SEQ ID NO 13
<211> LENGTH: 7
<212> TYPE: PRT
<213> ORGANISM: Artificial Sequence
<220> FEATURE:
<223> OTHER INFORMATION: Peptide

<400> SEQUENCE: 13

Pro Tyr Trp Val Thr Met Gly
1               5

<210> SEQ ID NO 14
<211> LENGTH: 7
<212> TYPE: PRT
<213> ORGANISM: Artificial Sequence
<220> FEATURE:
<223> OTHER INFORMATION: Peptide

<400> SEQUENCE: 14

Pro Tyr Trp Val Val Leu Gly
1               5

<210> SEQ ID NO 15
<211> LENGTH: 7
<212> TYPE: PRT
<213> ORGANISM: Artificial Sequence
<220> FEATURE:
<223> OTHER INFORMATION: Peptide

<400> SEQUENCE: 15

Pro Ser Trp Leu Val Val Gly
1               5

<210> SEQ ID NO 16
<211> LENGTH: 7
<212> TYPE: PRT
<213> ORGANISM: Artificial Sequence
<220> FEATURE:
<223> OTHER INFORMATION: Peptide

<400> SEQUENCE: 16

Pro His Trp Ile Thr Ile Gly
1               5

<210> SEQ ID NO 17
<211> LENGTH: 7

<212> TYPE: PRT
<213> ORGANISM: Artificial Sequence
<220> FEATURE:
<223> OTHER INFORMATION: Peptide

<400> SEQUENCE: 17

Pro His Trp Cys Val Leu Gly
1               5

<210> SEQ ID NO 18
<211> LENGTH: 7
<212> TYPE: PRT
<213> ORGANISM: Artificial Sequence
<220> FEATURE:
<223> OTHER INFORMATION: Peptide

<400> SEQUENCE: 18

Pro Phe Trp Leu Ala Leu Gly
1               5

<210> SEQ ID NO 19
<211> LENGTH: 7
<212> TYPE: PRT
<213> ORGANISM: Artificial Sequence
<220> FEATURE:
<223> OTHER INFORMATION: Peptide

<400> SEQUENCE: 19

Pro Phe Trp Cys Val Leu Gly
1               5

<210> SEQ ID NO 20
<211> LENGTH: 6
<212> TYPE: PRT
<213> ORGANISM: Artificial Sequence
<220> FEATURE:
<223> OTHER INFORMATION: Peptide

<400> SEQUENCE: 20

Phe Trp Val Glu Leu Gly
1               5

<210> SEQ ID NO 21
<211> LENGTH: 7
<212> TYPE: PRT
<213> ORGANISM: Artificial Sequence
<220> FEATURE:
<223> OTHER INFORMATION: Peptide

<400> SEQUENCE: 21

Tyr Trp Ala Thr Thr Gly Leu
1               5

<210> SEQ ID NO 22
<211> LENGTH: 6
<212> TYPE: PRT
<213> ORGANISM: Artificial Sequence
<220> FEATURE:
<223> OTHER INFORMATION: Peptide

<400> SEQUENCE: 22

Trp Trp Gly Thr Met Ile
1               5

<210> SEQ ID NO 23
<211> LENGTH: 7
<212> TYPE: PRT

<213> ORGANISM: Artificial Sequence
<220> FEATURE:
<223> OTHER INFORMATION: Peptide

<400> SEQUENCE: 23

Pro Tyr Trp Leu Cys Ile Ile
1 5

<210> SEQ ID NO 24
<211> LENGTH: 7
<212> TYPE: PRT
<213> ORGANISM: Artificial Sequence
<220> FEATURE:
<223> OTHER INFORMATION: Peptide

<400> SEQUENCE: 24

Thr Cys Trp Val Cys Ile Val
1 5

<210> SEQ ID NO 25
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(5)
<223> OTHER INFORMATION: Xaa can be any naturally occurring amino acid

<400> SEQUENCE: 25

Xaa Trp Xaa Xaa Xaa Gly
1 5

<210> SEQ ID NO 26
<211> LENGTH: 12
<212> TYPE: PRT
<213> ORGANISM: Artificial Sequence
<220> FEATURE:
<223> OTHER INFORMATION: Peptide

<400> SEQUENCE: 26

Met Ile Ala Ile Leu Ala Phe Trp Leu Ile Leu Gly
1 5 10

<210> SEQ ID NO 27
<211> LENGTH: 39
<212> TYPE: DNA
<213> ORGANISM: Artificial Sequence
<220> FEATURE:
<223> OTHER INFORMATION: DNA

<400> SEQUENCE: 27
atgatcgcaa tcctagcgtt ctggctgatc ctaggttga 39

<210> SEQ ID NO 28
<211> LENGTH: 12
<212> TYPE: PRT
<213> ORGANISM: Artificial Sequence
<220> FEATURE:
<223> OTHER INFORMATION: Peptide

<400> SEQUENCE: 28

Met Ile Ala Ile Leu Thr Trp Trp Leu Ile Leu Gly 1 5 10

<210> SEQ ID NO 29
<211> LENGTH: 39
<212> TYPE: DNA
<213> ORGANISM: Artificial Sequence
<220> FEATURE:
<223> OTHER INFORMATION: DNA

<400> SEQUENCE: 29
atgatcgcaa tcctaacttg gtggttaatt ctgggatga 39

<210> SEQ ID NO 30
<211> LENGTH: 12
<212> TYPE: PRT
<213> ORGANISM: Artificial Sequence
<220> FEATURE:
<223> OTHER INFORMATION: Peptide

<400> SEQUENCE: 30

Met Ile Ala Ile Leu Pro Tyr Trp Leu Gly Leu Gly
1 5 10

<210> SEQ ID NO 31
<211> LENGTH: 39
<212> TYPE: DNA
<213> ORGANISM: Artificial Sequence
<220> FEATURE:
<223> OTHER INFORMATION: DNA

<400> SEQUENCE: 31
atgatcgcaa tcctaccata ctggttaggc ctaggctga 39

<210> SEQ ID NO 32
<211> LENGTH: 12
<212> TYPE: PRT
<213> ORGANISM: Artificial Sequence
<220> FEATURE:
<223> OTHER INFORMATION: Peptide

<400> SEQUENCE: 32

Met Ile Ala Ile Leu Pro Trp Trp Val Ser Val Gly
1 5 10

<210> SEQ ID NO 33
<211> LENGTH: 39
<212> TYPE: DNA
<213> ORGANISM: Artificial Sequence
<220> FEATURE:
<223> OTHER INFORMATION: DNA

<400> SEQUENCE: 33
atgatcgcaa tcctaccttg gtgggtatca gttggttga 39

<210> SEQ ID NO 34
<211> LENGTH: 12
<212> TYPE: PRT
<213> ORGANISM: Artificial Sequence
<220> FEATURE:
<223> OTHER INFORMATION: Peptide

<400> SEQUENCE: 34

Met Ile Ala Ile Leu Pro Tyr Trp Leu Gly Leu Gly
1 5 10

<210> SEQ ID NO 35

<211> LENGTH: 39
<212> TYPE: DNA
<213> ORGANISM: Artificial Sequence
<220> FEATURE:
<223> OTHER INFORMATION: DNA

<400> SEQUENCE: 35
atgatcgcaa tcctaccata ctggttaggc ctaggctga 39

<210> SEQ ID NO 36
<211> LENGTH: 12
<212> TYPE: PRT
<213> ORGANISM: Artificial Sequence
<220> FEATURE:
<223> OTHER INFORMATION: Peptide

<400> SEQUENCE: 36

Met Ile Ala Ile Leu Pro Phe Trp Leu Ile Leu Gly
1 5 10

<210> SEQ ID NO 37
<211> LENGTH: 39
<212> TYPE: DNA
<213> ORGANISM: Artificial Sequence
<220> FEATURE:
<223> OTHER INFORMATION: DNA

<400> SEQUENCE: 37
atgatcgcaa tcctaccctt ttggctcata ttaggctga 39

<210> SEQ ID NO 38
<211> LENGTH: 12
<212> TYPE: PRT
<213> ORGANISM: Artificial Sequence
<220> FEATURE:
<223> OTHER INFORMATION: Peptide

<400> SEQUENCE: 38

Met Ile Ala Ile Leu Pro Phe Trp Leu Ile Leu Gly
1 5 10

<210> SEQ ID NO 39
<211> LENGTH: 39
<212> TYPE: DNA
<213> ORGANISM: Artificial Sequence
<220> FEATURE:
<223> OTHER INFORMATION: DNA

<400> SEQUENCE: 39
atgatcgcaa tcctaccctt ttggctcata ttaggctga 39

<210> SEQ ID NO 40
<211> LENGTH: 12
<212> TYPE: PRT
<213> ORGANISM: Artificial Sequence
<220> FEATURE:
<223> OTHER INFORMATION: Peptide

<400> SEQUENCE: 40

Met Ile Ala Ile Leu Pro Tyr Trp Leu Leu Ile Gly
1 5 10

<210> SEQ ID NO 41
<211> LENGTH: 39
<212> TYPE: DNA
<213> ORGANISM: Artificial Sequence
<220> FEATURE:

<223> OTHER INFORMATION: DNA

<400> SEQUENCE: 41
atgatcgcaa tcctaccata ctggcttctc ataggttga 39

<210> SEQ ID NO 42
<211> LENGTH: 12
<212> TYPE: PRT
<213> ORGANISM: Artificial Sequence
<220> FEATURE:
<223> OTHER INFORMATION: Peptide

<400> SEQUENCE: 42

Met Ile Ala Ile Leu Pro Phe Trp Leu Val Leu Gly
1 5 10

<210> SEQ ID NO 43
<211> LENGTH: 39
<212> TYPE: DNA
<213> ORGANISM: Artificial Sequence
<220> FEATURE:
<223> OTHER INFORMATION: DNA

<400> SEQUENCE: 43
atgatcgcaa tcctaccttt ttggctagtc ctcggatga 39

<210> SEQ ID NO 44
<211> LENGTH: 12
<212> TYPE: PRT
<213> ORGANISM: Artificial Sequence
<220> FEATURE:
<223> OTHER INFORMATION: Peptide

<400> SEQUENCE: 44

Met Ile Ala Ile Leu Pro Phe Trp Val Val Ala Gly
1 5 10

<210> SEQ ID NO 45
<211> LENGTH: 39
<212> TYPE: DNA
<213> ORGANISM: Artificial Sequence
<220> FEATURE:
<223> OTHER INFORMATION: DNA

<400> SEQUENCE: 45
atgatcgcaa tcctaccgtt ctgggttgtc gcgggctga 39

<210> SEQ ID NO 46
<211> LENGTH: 12
<212> TYPE: PRT
<213> ORGANISM: Artificial Sequence
<220> FEATURE:
<223> OTHER INFORMATION: Peptide

<400> SEQUENCE: 46

Met Ile Ala Ile Leu Pro Phe Trp Leu Ser Val Gly
1 5 10

<210> SEQ ID NO 47
<211> LENGTH: 39
<212> TYPE: DNA
<213> ORGANISM: Artificial Sequence
<220> FEATURE:
<223> OTHER INFORMATION: DNA

<400> SEQUENCE: 47
atgatcgcaa tcctaccatt ttggctaagc gtaggctga 39

<210> SEQ ID NO 48
<211> LENGTH: 12
<212> TYPE: PRT
<213> ORGANISM: Artificial Sequence
<220> FEATURE:
<223> OTHER INFORMATION: Peptide

<400> SEQUENCE: 48

Met Ile Ala Ile Leu Pro Tyr Trp Leu Asp Met Gly
1 5 10

<210> SEQ ID NO 49
<211> LENGTH: 39
<212> TYPE: DNA
<213> ORGANISM: Artificial Sequence
<220> FEATURE:
<223> OTHER INFORMATION: DNA

<400> SEQUENCE: 49
atgatcgcaa tcctaccata ttggcttgat atgggatga 39

<210> SEQ ID NO 50
<211> LENGTH: 12
<212> TYPE: PRT
<213> ORGANISM: Artificial Sequence
<220> FEATURE:
<223> OTHER INFORMATION: Peptide

<400> SEQUENCE: 50

Met Ile Ala Ile Leu Pro Tyr Trp Leu Asp Met Gly
1 5 10

<210> SEQ ID NO 51
<211> LENGTH: 39
<212> TYPE: DNA
<213> ORGANISM: Artificial Sequence
<220> FEATURE:
<223> OTHER INFORMATION: DNA

<400> SEQUENCE: 51
atgatcgcaa tcctaccata ttggcttgat atgggatga 39

<210> SEQ ID NO 52
<211> LENGTH: 11
<212> TYPE: PRT
<213> ORGANISM: Artificial Sequence
<220> FEATURE:
<223> OTHER INFORMATION: Peptide

<400> SEQUENCE: 52

Met Ile Ala Ile Leu Trp Trp Gly Thr Met Ile
1 5 10

<210> SEQ ID NO 53
<211> LENGTH: 39
<212> TYPE: DNA
<213> ORGANISM: Artificial Sequence
<220> FEATURE:
<223> OTHER INFORMATION: DNA

<400> SEQUENCE: 53
atgatcgcaa tcctatggtg gggcactatg atctagtga 39

<210> SEQ ID NO 54

<211> LENGTH: 12
<212> TYPE: PRT
<213> ORGANISM: Artificial Sequence
<220> FEATURE:
<223> OTHER INFORMATION: Peptide

<400> SEQUENCE: 54

Met Ile Ala Ile Leu Tyr Trp Ala Thr Thr Gly Leu
1 5 10

<210> SEQ ID NO 55
<211> LENGTH: 39
<212> TYPE: DNA
<213> ORGANISM: Artificial Sequence
<220> FEATURE:
<223> OTHER INFORMATION: DNA

<400> SEQUENCE: 55
atgatcgcaa tcctatattg ggccacgact gggttatga 39

<210> SEQ ID NO 56
<211> LENGTH: 12
<212> TYPE: PRT
<213> ORGANISM: Artificial Sequence
<220> FEATURE:
<223> OTHER INFORMATION: Peptide

<400> SEQUENCE: 56

Met Ile Ala Ile Leu Pro Tyr Trp Leu Cys Ile Ile
1 5 10

<210> SEQ ID NO 57
<211> LENGTH: 39
<212> TYPE: DNA
<213> ORGANISM: Artificial Sequence
<220> FEATURE:
<223> OTHER INFORMATION: DNA

<400> SEQUENCE: 57
atgatcgcaa tcctacccta ctggctctgc attatatga 39

<210> SEQ ID NO 58
<211> LENGTH: 12
<212> TYPE: PRT
<213> ORGANISM: Artificial Sequence
<220> FEATURE:
<223> OTHER INFORMATION: Peptide

<400> SEQUENCE: 58

Met Ile Ala Ile Leu Pro Tyr Trp Val Thr Met Gly
1 5 10

<210> SEQ ID NO 59
<211> LENGTH: 39
<212> TYPE: DNA
<213> ORGANISM: Artificial Sequence
<220> FEATURE:
<223> OTHER INFORMATION: DNA

<400> SEQUENCE: 59
atgatcgcaa tcctaccata ttgggtcacc atgggttga 39

<210> SEQ ID NO 60
<211> LENGTH: 12
<212> TYPE: PRT
<213> ORGANISM: Artificial Sequence
<220> FEATURE:

<223> OTHER INFORMATION: Peptide

<400> SEQUENCE: 60

Met Ile Ala Ile Leu Pro Tyr Trp Val Val Leu Gly
1 5 10

<210> SEQ ID NO 61
<211> LENGTH: 39
<212> TYPE: DNA
<213> ORGANISM: Artificial Sequence
<220> FEATURE:
<223> OTHER INFORMATION: DNA

<400> SEQUENCE: 61
atgatcgcaa tcctacctta ctgggtagtg ctagggtga 39

<210> SEQ ID NO 62
<211> LENGTH: 12
<212> TYPE: PRT
<213> ORGANISM: Artificial Sequence
<220> FEATURE:
<223> OTHER INFORMATION: Peptide

<400> SEQUENCE: 62

Met Ile Ala Ile Leu Pro Tyr Trp Val Thr Met Gly
1 5 10

<210> SEQ ID NO 63
<211> LENGTH: 39
<212> TYPE: DNA
<213> ORGANISM: Artificial Sequence
<220> FEATURE:
<223> OTHER INFORMATION: DNA

<400> SEQUENCE: 63
atgatcgcaa tcctaccata ttgggtcacc atgggttga 39

<210> SEQ ID NO 64
<211> LENGTH: 12
<212> TYPE: PRT
<213> ORGANISM: Artificial Sequence
<220> FEATURE:
<223> OTHER INFORMATION: Peptide

<400> SEQUENCE: 64

Met Ile Ala Ile Leu Pro Ser Trp Leu Val Val Gly
1 5 10

<210> SEQ ID NO 65
<211> LENGTH: 39
<212> TYPE: DNA
<213> ORGANISM: Artificial Sequence
<220> FEATURE:
<223> OTHER INFORMATION: DNA

<400> SEQUENCE: 65
atgatcgcaa tcctaccaag ctggttagtt gttggctga 39

<210> SEQ ID NO 66
<211> LENGTH: 12
<212> TYPE: PRT
<213> ORGANISM: Artificial Sequence
<220> FEATURE:
<223> OTHER INFORMATION: Peptide

<400> SEQUENCE: 66

```
Met Ile Ala Ile Leu Pro His Trp Ile Thr Ile Gly
1               5                   10


<210> SEQ ID NO 67
<211> LENGTH: 39
<212> TYPE: DNA
<213> ORGANISM: Artificial Sequence
<220> FEATURE:
<223> OTHER INFORMATION: DNA

<400> SEQUENCE: 67

atgatcgcaa tcctaccaca ctggatcaca ataggctga                            39


<210> SEQ ID NO 68
<211> LENGTH: 12
<212> TYPE: PRT
<213> ORGANISM: Artificial Sequence
<220> FEATURE:
<223> OTHER INFORMATION: Peptide

<400> SEQUENCE: 68

Met Ile Ala Ile Leu Pro Tyr Trp Leu Gly Leu Gly
1               5                   10


<210> SEQ ID NO 69
<211> LENGTH: 39
<212> TYPE: DNA
<213> ORGANISM: Artificial Sequence
<220> FEATURE:
<223> OTHER INFORMATION: DNA

<400> SEQUENCE: 69

atgatcgcaa tcctaccata ctggttaggc ctaggctga                            39


<210> SEQ ID NO 70
<211> LENGTH: 12
<212> TYPE: PRT
<213> ORGANISM: Artificial Sequence
<220> FEATURE:
<223> OTHER INFORMATION: Peptide

<400> SEQUENCE: 70

Met Ile Ala Ile Leu Pro His Trp Cys Val Leu Gly
1               5                   10


<210> SEQ ID NO 71
<211> LENGTH: 39
<212> TYPE: DNA
<213> ORGANISM: Artificial Sequence
<220> FEATURE:
<223> OTHER INFORMATION: DNA

<400> SEQUENCE: 71

atgatcgcaa tcctaccaca ttggtgcgtg cttggctga                            39


<210> SEQ ID NO 72
<211> LENGTH: 8
<212> TYPE: PRT
<213> ORGANISM: Artificial Sequence
<220> FEATURE:
<223> OTHER INFORMATION: Peptide

<400> SEQUENCE: 72

Met Ile Ala Ile Leu Arg Pro His
1               5
```

<210> SEQ ID NO 73
<211> LENGTH: 39
<212> TYPE: DNA
<213> ORGANISM: Artificial Sequence
<220> FEATURE:
<223> OTHER INFORMATION: DNA

<400> SEQUENCE: 73
atgatcgcaa tcctacgtcc acattaatag ttccactga 39

<210> SEQ ID NO 74
<211> LENGTH: 12
<212> TYPE: PRT
<213> ORGANISM: Artificial Sequence
<220> FEATURE:
<223> OTHER INFORMATION: Peptide

<400> SEQUENCE: 74

Met Ile Ala Thr Leu Pro Phe Trp Leu Ala Leu Gly
1 5 10

<210> SEQ ID NO 75
<211> LENGTH: 39
<212> TYPE: DNA
<213> ORGANISM: Artificial Sequence
<220> FEATURE:
<223> OTHER INFORMATION: DNA

<400> SEQUENCE: 75
atgatcgcaa ccctaccttt ttggcttgcc ctcggatga 39

<210> SEQ ID NO 76
<211> LENGTH: 12
<212> TYPE: PRT
<213> ORGANISM: Artificial Sequence
<220> FEATURE:
<223> OTHER INFORMATION: Peptide

<400> SEQUENCE: 76

Met Ile Ala Ile Leu Thr Cys Trp Val Cys Ile Val
1 5 10

<210> SEQ ID NO 77
<211> LENGTH: 39
<212> TYPE: DNA
<213> ORGANISM: Artificial Sequence
<220> FEATURE:
<223> OTHER INFORMATION: DNA

<400> SEQUENCE: 77
atgatcgcaa tcctaacatg ttgggtctgc atagtatga 39

<210> SEQ ID NO 78
<211> LENGTH: 11
<212> TYPE: PRT
<213> ORGANISM: Artificial Sequence
<220> FEATURE:
<223> OTHER INFORMATION: Peptide

<400> SEQUENCE: 78

Met Ile Ala Ile Leu Phe Trp Val Glu Leu Gly
1 5 10

<210> SEQ ID NO 79
<211> LENGTH: 39
<212> TYPE: DNA
<213> ORGANISM: Artificial Sequence

<220> FEATURE:
<223> OTHER INFORMATION: DNA

<400> SEQUENCE: 79
atgatcgcaa tcctattctg ggtggaatta ggataatga 39

<210> SEQ ID NO 80
<211> LENGTH: 12
<212> TYPE: PRT
<213> ORGANISM: Artificial Sequence
<220> FEATURE:
<223> OTHER INFORMATION: Peptide

<400> SEQUENCE: 80

Met Ile Ala Ile Leu Thr Cys Trp Val Cys Ile Val
1 5 10

<210> SEQ ID NO 81
<211> LENGTH: 39
<212> TYPE: DNA
<213> ORGANISM: Artificial Sequence
<220> FEATURE:
<223> OTHER INFORMATION: DNA

<400> SEQUENCE: 81
atgatcgcaa tcctaacatg ttgggtctgc atagtatga 39

<210> SEQ ID NO 82
<211> LENGTH: 12
<212> TYPE: PRT
<213> ORGANISM: Artificial Sequence
<220> FEATURE:
<223> OTHER INFORMATION: Peptide

<400> SEQUENCE: 82

Met Ile Ala Ile Leu Pro Phe Trp Cys Val Leu Gly
1 5 10

<210> SEQ ID NO 83
<211> LENGTH: 39
<212> TYPE: DNA
<213> ORGANISM: Artificial Sequence
<220> FEATURE:
<223> OTHER INFORMATION: DNA

<400> SEQUENCE: 83
atgatcgcaa tcctaccctt ctggtgtgtc cttggatga 39

<210> SEQ ID NO 84
<211> LENGTH: 12
<212> TYPE: PRT
<213> ORGANISM: Artificial Sequence
<220> FEATURE:
<223> OTHER INFORMATION: Peptide

<400> SEQUENCE: 84

Met Ile Ala Ile Leu Pro Phe Trp Cys Val Leu Gly
1 5 10

<210> SEQ ID NO 85
<211> LENGTH: 39
<212> TYPE: DNA
<213> ORGANISM: Artificial Sequence
<220> FEATURE:
<223> OTHER INFORMATION: DNA

<400> SEQUENCE: 85
atgatcgcaa tcctaccctt ctggtgtgtc cttggatga 39

<210> SEQ ID NO 86
<211> LENGTH: 12
<212> TYPE: PRT
<213> ORGANISM: Artificial Sequence
<220> FEATURE:
<223> OTHER INFORMATION: Peptide

<400> SEQUENCE: 86

Met Ile Ala Ile Leu Pro Phe Trp Leu Val Leu Gly
1 5 10

<210> SEQ ID NO 87
<211> LENGTH: 39
<212> TYPE: DNA
<213> ORGANISM: Artificial Sequence
<220> FEATURE:
<223> OTHER INFORMATION: DNA

<400> SEQUENCE: 87
atgatcgcaa tcctaccttt ttggctagtc ctcggatga 39

<210> SEQ ID NO 88
<211> LENGTH: 33
<212> TYPE: DNA
<213> ORGANISM: Artificial Sequence
<220> FEATURE:
<223> OTHER INFORMATION: rggD_NcoI SS

<400> SEQUENCE: 88
aaaaaaccat ggcagaagat attaaaatca aga 33

<210> SEQ ID NO 89
<211> LENGTH: 32
<212> TYPE: DNA
<213> ORGANISM: Artificial Sequence
<220> FEATURE:
<223> OTHER INFORMATION: rggD_MunI

<400> SEQUENCE: 89
aaaaaacaat tgctttgact cgttacttgt at 32

<210> SEQ ID NO 90
<211> LENGTH: 33
<212> TYPE: DNA
<213> ORGANISM: Artificial Sequence
<220> FEATURE:
<223> OTHER INFORMATION: rggC_NcoI SS

<400> SEQUENCE: 90
aaaaaaccat ggctgaagat attaaaatcg aga 33

<210> SEQ ID NO 91
<211> LENGTH: 32
<212> TYPE: DNA
<213> ORGANISM: Artificial Sequence
<220> FEATURE:
<223> OTHER INFORMATION: rggC_RI SS

<400> SEQUENCE: 91
aaaaaagaat tcttctatat ttaaatcttt tt 32

<210> SEQ ID NO 92
<211> LENGTH: 23

<212> TYPE: DNA
<213> ORGANISM: Artificial Sequence
<220> FEATURE:
<223> OTHER INFORMATION: Uplox66

<400> SEQUENCE: 92
taaggaagat aaatcccata agg 23

<210> SEQ ID NO 93
<211> LENGTH: 23
<212> TYPE: DNA
<213> ORGANISM: Artificial Sequence
<220> FEATURE:
<223> OTHER INFORMATION: DNlox71

<400> SEQUENCE: 93
ttcacgttac taaagggaat gta 23

<210> SEQ ID NO 94
<211> LENGTH: 47
<212> TYPE: DNA
<213> ORGANISM: Artificial Sequence
<220> FEATURE:
<223> OTHER INFORMATION: lox66-ery

<400> SEQUENCE: 94
taaggaagat aaatcccata aggtacctaa taatttatct acattcc 47

<210> SEQ ID NO 95
<211> LENGTH: 44
<212> TYPE: DNA
<213> ORGANISM: Artificial Sequence
<220> FEATURE:
<223> OTHER INFORMATION: lox71-ery

<400> SEQUENCE: 95
ttcacgttac taaagggaat gtaaaatgat acaccaatca gtgc 44

<210> SEQ ID NO 96
<211> LENGTH: 20
<212> TYPE: DNA
<213> ORGANISM: Artificial Sequence
<220> FEATURE:
<223> OTHER INFORMATION: F_spec

<400> SEQUENCE: 96
taataaggcc ggccaataaa 20

<210> SEQ ID NO 97
<211> LENGTH: 20
<212> TYPE: DNA
<213> ORGANISM: Artificial Sequence
<220> FEATURE:
<223> OTHER INFORMATION: R_spec

<400> SEQUENCE: 97
ataggatgag aactcccatg 20

<210> SEQ ID NO 98
<211> LENGTH: 22
<212> TYPE: DNA
<213> ORGANISM: Artificial Sequence
<220> FEATURE:
<223> OTHER INFORMATION: UPery-oroP

<400> SEQUENCE: 98

-continued aaggttgatg ttactgctga ta 22

<210> SEQ ID NO 99
<211> LENGTH: 22
<212> TYPE: DNA
<213> ORGANISM: Artificial Sequence
<220> FEATURE:
<223> OTHER INFORMATION: DNery-oroP

<400> SEQUENCE: 99
tgctgacttg caccatatca ta 22

<210> SEQ ID NO 100
<211> LENGTH: 20
<212> TYPE: DNA
<213> ORGANISM: Artificial Sequence
<220> FEATURE:
<223> OTHER INFORMATION: UF_tRNAser

<400> SEQUENCE: 100
caagattaac catgaccttc 20

<210> SEQ ID NO 101
<211> LENGTH: 20
<212> TYPE: DNA
<213> ORGANISM: Artificial Sequence
<220> FEATURE:
<223> OTHER INFORMATION: UR_tRNAser

<400> SEQUENCE: 101
agtaattaaa aagaagatgg 20

<210> SEQ ID NO 102
<211> LENGTH: 20
<212> TYPE: DNA
<213> ORGANISM: Artificial Sequence
<220> FEATURE:
<223> OTHER INFORMATION: DF_tRNAser

<400> SEQUENCE: 102
tacctaaaaa gtgtcccttc 20

<210> SEQ ID NO 103
<211> LENGTH: 20
<212> TYPE: DNA
<213> ORGANISM: Artificial Sequence
<220> FEATURE:
<223> OTHER INFORMATION: DR2_tRNAser

<400> SEQUENCE: 103
ttggataagg tcttgacttc 20

<210> SEQ ID NO 104
<211> LENGTH: 20
<212> TYPE: DNA
<213> ORGANISM: Artificial Sequence
<220> FEATURE:
<223> OTHER INFORMATION: UF_tRNAthr

<400> SEQUENCE: 104
tgtcaaagga ttaggaaaac 20

<210> SEQ ID NO 105
<211> LENGTH: 21
<212> TYPE: DNA
<213> ORGANISM: Artificial Sequence
<220> FEATURE:
<223> OTHER INFORMATION: UR_tRNAthr

<400> SEQUENCE: 105
ttgatttata cctctcaatt t 21

<210> SEQ ID NO 106
<211> LENGTH: 21
<212> TYPE: DNA
<213> ORGANISM: Artificial Sequence
<220> FEATURE:
<223> OTHER INFORMATION: DF_tRNAthr

<400> SEQUENCE: 106
aaatcaacct ctttgaacat a 21

<210> SEQ ID NO 107
<211> LENGTH: 37
<212> TYPE: DNA
<213> ORGANISM: Artificial Sequence
<220> FEATURE:
<223> OTHER INFORMATION: DR_tRNAthr

<400> SEQUENCE: 107
aaaaaagaat tcattcatga tgagcgggtt cgtgaga 37

<210> SEQ ID NO 108
<211> LENGTH: 43
<212> TYPE: DNA
<213> ORGANISM: Artificial Sequence
<220> FEATURE:
<223> OTHER INFORMATION: F_pZX9

<400> SEQUENCE: 108
ccatcttctt tttaattact tctagattat atatgatatg atc 43

<210> SEQ ID NO 109
<211> LENGTH: 22
<212> TYPE: DNA
<213> ORGANISM: Artificial Sequence
<220> FEATURE:
<223> OTHER INFORMATION: R_pZX9_ATG

<400> SEQUENCE: 109
catatttacc tcctttgatt ta 22

<210> SEQ ID NO 110
<211> LENGTH: 22
<212> TYPE: DNA
<213> ORGANISM: Artificial Sequence
<220> FEATURE:
<223> OTHER INFORMATION: F_luxAB_ATG

<400> SEQUENCE: 110
atgaaatttg gaaacttttt gc 22

<210> SEQ ID NO 111
<211> LENGTH: 42
<212> TYPE: DNA
<213> ORGANISM: Artificial Sequence
<220> FEATURE:
<223> OTHER INFORMATION: R_cat_tRNAthr

<400> SEQUENCE: 111
tatgttcaaa gaggttgatt tcacgttact aaagggaatg ta 42

<210> SEQ ID NO 112
<211> LENGTH: 35
<212> TYPE: DNA
<213> ORGANISM: Artificial Sequence
<220> FEATURE:
<223> OTHER INFORMATION: UFcomRJIM-SS1-4

<400> SEQUENCE: 112
gcagtaccac tctatgctaa atttgccaac tttga 35

<210> SEQ ID NO 113
<211> LENGTH: 41
<212> TYPE: DNA
<213> ORGANISM: Artificial Sequence
<220> FEATURE:
<223> OTHER INFORMATION: URcomRJIM-SS1-4

<400> SEQUENCE: 113
ccttatggga tttatcttcc ttagagacac tcctttattt c 41

<210> SEQ ID NO 114
<211> LENGTH: 41
<212> TYPE: DNA
<213> ORGANISM: Artificial Sequence
<220> FEATURE:
<223> OTHER INFORMATION: DFcomRJIM-SS1-4

<400> SEQUENCE: 114
tacattccct ttagtaacgt gaaaaatggt ggtgacataa a 41

<210> SEQ ID NO 115
<211> LENGTH: 35
<212> TYPE: DNA
<213> ORGANISM: Artificial Sequence
<220> FEATURE:
<223> OTHER INFORMATION: DRcomRJIM-SS1-4

<400> SEQUENCE: 115
tgacgtgatt tcaccagtac gacgtgaact aaaga 35

<210> SEQ ID NO 116
<211> LENGTH: 20
<212> TYPE: DNA
<213> ORGANISM: Artificial Sequence
<220> FEATURE:
<223> OTHER INFORMATION: Up_comR SS1-4

<400> SEQUENCE: 116
ttgcttacag ttgctatggt 20

<210> SEQ ID NO 117
<211> LENGTH: 20
<212> TYPE: DNA
<213> ORGANISM: Artificial Sequence
<220> FEATURE:
<223> OTHER INFORMATION: Down_comR_SS1-4

<400> SEQUENCE: 117
tcatcacaat ggtcacatct 20

<210> SEQ ID NO 118
<211> LENGTH: 30
<212> TYPE: DNA
<213> ORGANISM: Artificial Sequence
<220> FEATURE:
<223> OTHER INFORMATION: UFrggC JIM

<400> SEQUENCE: 118
aaaactgcaa gtagagtcgc cgaattagaa 30

<210> SEQ ID NO 119
<211> LENGTH: 45
<212> TYPE: DNA
<213> ORGANISM: Artificial Sequence
<220> FEATURE:
<223> OTHER INFORMATION: URrggC_JIM

<400> SEQUENCE: 119
ccttatggga tttatcttcc ttaacataat tccttatgat ttaga 45

<210> SEQ ID NO 120
<211> LENGTH: 42
<212> TYPE: DNA
<213> ORGANISM: Artificial Sequence
<220> FEATURE:
<223> OTHER INFORMATION: DFrggC JIM

<400> SEQUENCE: 120
tacattccct ttagtaacgt gaagacattg atgtcctttt ga 42

<210> SEQ ID NO 121
<211> LENGTH: 30
<212> TYPE: DNA
<213> ORGANISM: Artificial Sequence
<220> FEATURE:
<223> OTHER INFORMATION: DRrggD SS

<400> SEQUENCE: 121
tagcttcatt catgtcatgt gtcgtcaaaa 30

<210> SEQ ID NO 122
<211> LENGTH: 20
<212> TYPE: DNA
<213> ORGANISM: Artificial Sequence
<220> FEATURE:
<223> OTHER INFORMATION: Up_rggC JIM

<400> SEQUENCE: 122
aaatatcgtc attgccagta 20

<210> SEQ ID NO 123
<211> LENGTH: 20
<212> TYPE: DNA
<213> ORGANISM: Artificial Sequence
<220> FEATURE:
<223> OTHER INFORMATION: Down_rggD SS

<400> SEQUENCE: 123
ctgaataagt tcagcaggtt 20

<210> SEQ ID NO 124
<211> LENGTH: 42
<212> TYPE: DNA
<213> ORGANISM: Artificial Sequence
<220> FEATURE:
<223> OTHER INFORMATION: Down_rggD SS

<400> SEQUENCE: 124
tcactttgac tcgttacttg tgattttaat atcttctgac at 42

<210> SEQ ID NO 125

-continued

<211> LENGTH: 42
<212> TYPE: DNA
<213> ORGANISM: Artificial Sequence
<220> FEATURE:
<223> OTHER INFORMATION: rggD_S4_3

<400> SEQUENCE: 125
atgtcagaag atattaaaat cacaagtaac gagtcaaagt ga 42

<210> SEQ ID NO 126
<211> LENGTH: 42
<212> TYPE: DNA
<213> ORGANISM: Artificial Sequence
<220> FEATURE:
<223> OTHER INFORMATION: rggD_S4_4

<400> SEQUENCE: 126
tatcagcagt aacatcaacc ttcatgtcat gtgtcgtcaa aa 42

<210> SEQ ID NO 127
<211> LENGTH: 42
<212> TYPE: DNA
<213> ORGANISM: Artificial Sequence
<220> FEATURE:
<223> OTHER INFORMATION: rggD_S4_5

<400> SEQUENCE: 127
tatgatatgg tgcaagtcag catcatgaag tctcctgtct at 42

<210> SEQ ID NO 128
<211> LENGTH: 20
<212> TYPE: DNA
<213> ORGANISM: Artificial Sequence
<220> FEATURE:
<223> OTHER INFORMATION: rggD_S4_6

<400> SEQUENCE: 128
ggctagtaca gtagctgtat 20

<210> SEQ ID NO 129
<211> LENGTH: 30
<212> TYPE: DNA
<213> ORGANISM: Artificial Sequence
<220> FEATURE:
<223> OTHER INFORMATION: UFrggC SS

<400> SEQUENCE: 129
ctgtttagcc ctatctttga gtttatcagt 30

<210> SEQ ID NO 130
<211> LENGTH: 42
<212> TYPE: DNA
<213> ORGANISM: Artificial Sequence
<220> FEATURE:
<223> OTHER INFORMATION: URrggD JIM

<400> SEQUENCE: 130
ccttatggga tttatcttcc ttatgtattc cccttgagtt tt 42

<210> SEQ ID NO 131
<211> LENGTH: 42
<212> TYPE: DNA
<213> ORGANISM: Artificial Sequence
<220> FEATURE:
<223> OTHER INFORMATION: DFrggD JIM

<400> SEQUENCE: 131
tacattccct ttagtaacgt gaagaaaata tatcagcaac at 42

<210> SEQ ID NO 132
<211> LENGTH: 30
<212> TYPE: DNA
<213> ORGANISM: Artificial Sequence
<220> FEATURE:
<223> OTHER INFORMATION: DRrggC SS

<400> SEQUENCE: 132
cagtggtttg acgttgtttt tgaatacggt 30

<210> SEQ ID NO 133
<211> LENGTH: 20
<212> TYPE: DNA
<213> ORGANISM: Artificial Sequence
<220> FEATURE:
<223> OTHER INFORMATION: Up_rggC SS

<400> SEQUENCE: 133
aaggtagcct aaacaactca 20

<210> SEQ ID NO 134
<211> LENGTH: 20
<212> TYPE: DNA
<213> ORGANISM: Artificial Sequence
<220> FEATURE:
<223> OTHER INFORMATION: Down_rggC SS

<400> SEQUENCE: 134
tttattggta ccaaacgcca 20

<210> SEQ ID NO 135
<211> LENGTH: 42
<212> TYPE: DNA
<213> ORGANISM: Artificial Sequence
<220> FEATURE:
<223> OTHER INFORMATION: rggC_S4_2

<400> SEQUENCE: 135
ctattctata tttaaatctt tgattttaat atcttcagac at 42

<210> SEQ ID NO 136
<211> LENGTH: 42
<212> TYPE: DNA
<213> ORGANISM: Artificial Sequence
<220> FEATURE:
<223> OTHER INFORMATION: rggC_S4_3

<400> SEQUENCE: 136
atgtctgaag atattaaaat caaagattta aatatagaat ag 42

<210> SEQ ID NO 137
<211> LENGTH: 43
<212> TYPE: DNA
<213> ORGANISM: Artificial Sequence
<220> FEATURE:
<223> OTHER INFORMATION: rggC_S4_4

<400> SEQUENCE: 137
tatcagcagt aacatcaacc ttgacgttgt ttttgaatac ggt 43

<210> SEQ ID NO 138
<211> LENGTH: 42
<212> TYPE: DNA

<213> ORGANISM: Artificial Sequence
<220> FEATURE:
<223> OTHER INFORMATION: rggC_S4_5

<400> SEQUENCE: 138
tatgatatgg tgcaagtcag caactagaca ttcctgaaga ct 42

<210> SEQ ID NO 139
<211> LENGTH: 20
<212> TYPE: DNA
<213> ORGANISM: Artificial Sequence
<220> FEATURE:
<223> OTHER INFORMATION: rggC_S4_6

<400> SEQUENCE: 139
tccgctagta ggatagcttt 20

<210> SEQ ID NO 140
<211> LENGTH: 20
<212> TYPE: DNA
<213> ORGANISM: Artificial Sequence
<220> FEATURE:
<223> OTHER INFORMATION: UF_PcomR_luxAB

<400> SEQUENCE: 140
taattgagga ggtctatgag 20

<210> SEQ ID NO 141
<211> LENGTH: 43
<212> TYPE: DNA
<213> ORGANISM: Artificial Sequence
<220> FEATURE:
<223> OTHER INFORMATION: UR_comA

<400> SEQUENCE: 141
ccttatggga tttatcttcc ttaatatgga tattttgaca tgg 43

<210> SEQ ID NO 142
<211> LENGTH: 44
<212> TYPE: DNA
<213> ORGANISM: Artificial Sequence
<220> FEATURE:
<223> OTHER INFORMATION: DF_comA

<400> SEQUENCE: 142
tacattccct ttagtaacgt gaagctaatt tcaatccatt ccag 44

<210> SEQ ID NO 143
<211> LENGTH: 20
<212> TYPE: DNA
<213> ORGANISM: Artificial Sequence
<220> FEATURE:
<223> OTHER INFORMATION: DR_comA

<400> SEQUENCE: 143
acagtactct ttatttggtg 20

<210> SEQ ID NO 144
<211> LENGTH: 39
<212> TYPE: DNA
<213> ORGANISM: Artificial Sequence
<220> FEATURE:
<223> OTHER INFORMATION: F_comR

<400> SEQUENCE: 144
ctagaggagg aatttagatg aacataaaag acagcattg 39

<210> SEQ ID NO 145
<211> LENGTH: 20
<212> TYPE: DNA
<213> ORGANISM: Artificial Sequence
<220> FEATURE:
<223> OTHER INFORMATION: Down_PcomS_JIMSS1-4

<400> SEQUENCE: 145
gacaaagtag tcaagaccgt 20

<210> SEQ ID NO 146
<211> LENGTH: 20
<212> TYPE: DNA
<213> ORGANISM: Artificial Sequence
<220> FEATURE:
<223> OTHER INFORMATION: UF_potA2

<400> SEQUENCE: 146
atactatacc tttcaatgtc 20

<210> SEQ ID NO 147
<211> LENGTH: 43
<212> TYPE: DNA
<213> ORGANISM: Artificial Sequence
<220> FEATURE:
<223> OTHER INFORMATION: UR_potA2

<400> SEQUENCE: 147
ccttatggga tttatcttcc ttaataaggt ttgtcatatc ttg 43

<210> SEQ ID NO 148
<211> LENGTH: 43
<212> TYPE: DNA
<213> ORGANISM: Artificial Sequence
<220> FEATURE:
<223> OTHER INFORMATION: DF_potA2

<400> SEQUENCE: 148
tacattccct ttagtaacgt gaaggaaaac ttaatgttta acc 43

<210> SEQ ID NO 149
<211> LENGTH: 20
<212> TYPE: DNA
<213> ORGANISM: Artificial Sequence
<220> FEATURE:
<223> OTHER INFORMATION: DR_potA2

<400> SEQUENCE: 149
actgatccct gaaagcattg 20

<210> SEQ ID NO 150
<211> LENGTH: 20
<212> TYPE: DNA
<213> ORGANISM: Artificial Sequence
<220> FEATURE:
<223> OTHER INFORMATION: Up_potA2

<400> SEQUENCE: 150
agagtatacc ttaaatgacc 20

<210> SEQ ID NO 151
<211> LENGTH: 20
<212> TYPE: DNA
<213> ORGANISM: Artificial Sequence
<220> FEATURE:

<223> OTHER INFORMATION: Down_potA2

<400> SEQUENCE: 151
gatttaaaga tttcgtgaac 20

<210> SEQ ID NO 152
<211> LENGTH: 41
<212> TYPE: DNA
<213> ORGANISM: Artificial Sequence
<220> FEATURE:
<223> OTHER INFORMATION: F_PpotA2_tRNAthr

<400> SEQUENCE: 152
aaattgagag gtataaatca atcattttgg aagcaaaata c 41

<210> SEQ ID NO 153
<211> LENGTH: 42
<212> TYPE: DNA
<213> ORGANISM: Artificial Sequence
<220> FEATURE:
<223> OTHER INFORMATION: R_PpotA2_luxAB_ATG

<400> SEQUENCE: 153
gcaaaaagtt tccaaatttc atatcttgat ttctccaatt tg 42

<210> SEQ ID NO 154
<211> LENGTH: 38
<212> TYPE: DNA
<213> ORGANISM: Artificial Sequence
<220> FEATURE:
<223> OTHER INFORMATION: F_rggD

<400> SEQUENCE: 154
ctagaggagg aatttagatg tcagaagata ttaaaatc 38

<210> SEQ ID NO 155
<211> LENGTH: 40
<212> TYPE: DNA
<213> ORGANISM: Artificial Sequence
<220> FEATURE:
<223> OTHER INFORMATION: R_rggD

<400> SEQUENCE: 155
tttattggcc ggccttatta tcactttgac tcgttacttg 40

<210> SEQ ID NO 156
<211> LENGTH: 38
<212> TYPE: DNA
<213> ORGANISM: Artificial Sequence
<220> FEATURE:
<223> OTHER INFORMATION: F_rggC

<400> SEQUENCE: 156
ctagaggagg aatttagatg tctgaagata ttaaaatc 38

<210> SEQ ID NO 157
<211> LENGTH: 38
<212> TYPE: DNA
<213> ORGANISM: Artificial Sequence
<220> FEATURE:
<223> OTHER INFORMATION: R_StrepTag

<400> SEQUENCE: 157
tttattggcc ggccttatta ctatttctcg aactgcgg 38

-continued

<210> SEQ ID NO 158
<211> LENGTH: 39
<212> TYPE: DNA
<213> ORGANISM: Artificial Sequence
<220> FEATURE:
<223> OTHER INFORMATION: F_P32-gfp+ter_spec

<400> SEQUENCE: 158
ccatcttctt tttaattact gtcctcggga tatgataag 39

<210> SEQ ID NO 159
<211> LENGTH: 20
<212> TYPE: DNA
<213> ORGANISM: Artificial Sequence
<220> FEATURE:
<223> OTHER INFORMATION: R_P32

<400> SEQUENCE: 159
catctaaatt cctcctctag 20

<210> SEQ ID NO 160
<211> LENGTH: 22
<212> TYPE: DNA
<213> ORGANISM: Artificial Sequence
<220> FEATURE:
<223> OTHER INFORMATION: F_cat_ATG

<400> SEQUENCE: 160
atgaacttta ataaaattga tt 22

<210> SEQ ID NO 161
<211> LENGTH: 39
<212> TYPE: DNA
<213> ORGANISM: Artificial Sequence
<220> FEATURE:
<223> OTHER INFORMATION: R_cat_(spec)

<400> SEQUENCE: 161
tttattggcc ggccttatta taaaagccag tcattaggc 39

<210> SEQ ID NO 162
<211> LENGTH: 42
<212> TYPE: DNA
<213> ORGANISM: Artificial Sequence
<220> FEATURE:
<223> OTHER INFORMATION: R_PpotA2_cat_ATG

<400> SEQUENCE: 162
aatcaatttt attaaagttc atatcttgat ttctccaatt tg 42

<210> SEQ ID NO 163
<211> LENGTH: 20
<212> TYPE: DNA
<213> ORGANISM: Artificial Sequence
<220> FEATURE:
<223> OTHER INFORMATION: Pxyl_seq

<400> SEQUENCE: 163
ttgtttatcc tcctctagtc 20

<210> SEQ ID NO 164
<211> LENGTH: 21
<212> TYPE: DNA
<213> ORGANISM: Artificial Sequence
<220> FEATURE:
<223> OTHER INFORMATION: spec2

<400> SEQUENCE: 164
aactcctgat ccaaacatgt a 21

<210> SEQ ID NO 165
<211> LENGTH: 40
<212> TYPE: DNA
<213> ORGANISM: Artificial Sequence
<220> FEATURE:
<223> OTHER INFORMATION: Cy3_F_PpotA2_EMSA
<220> FEATURE:
<221> NAME/KEY: misc_feature
<222> LOCATION: (1)..(1)
<223> OTHER INFORMATION: Cy3

<400> SEQUENCE: 165
taacgagtca aagtgacata gatgtccttt tgattcgtta 40

<210> SEQ ID NO 166
<211> LENGTH: 40
<212> TYPE: DNA
<213> ORGANISM: Artificial Sequence
<220> FEATURE:
<223> OTHER INFORMATION: R_PpotA2_EMSA

<400> SEQUENCE: 166
taacgaatca aaaggacatc tatgtcactt tgactcgtta 40

<210> SEQ ID NO 167
<211> LENGTH: 30
<212> TYPE: DNA
<213> ORGANISM: Artificial Sequence
<220> FEATURE:
<223> OTHER INFORMATION: Cy3_F_P01665_EMSA
<220> FEATURE:
<221> NAME/KEY: misc_feature
<222> LOCATION: (1)..(1)
<223> OTHER INFORMATION: Cy3

<400> SEQUENCE: 167
ctccatagtg acatttatgt cactattttt 30

<210> SEQ ID NO 168
<211> LENGTH: 30
<212> TYPE: DNA
<213> ORGANISM: Artificial Sequence
<220> FEATURE:
<223> OTHER INFORMATION: R_P01665_EMSA

<400> SEQUENCE: 168
aaaaatagtg acataaatgt cactatggag 30

<210> SEQ ID NO 169
<211> LENGTH: 30
<212> TYPE: DNA
<213> ORGANISM: Artificial Sequence
<220> FEATURE:
<223> OTHER INFORMATION: Cy3_F_PcomS_EMSA
<220> FEATURE:
<221> NAME/KEY: misc_feature
<222> LOCATION: (1)..(1)
<223> OTHER INFORMATION: Cy3

<400> SEQUENCE: 169
aatggtggtg acataaatgt cactactttt 30

<210> SEQ ID NO 170
<211> LENGTH: 30

<212> TYPE: DNA
<213> ORGANISM: Artificial Sequence
<220> FEATURE:
<223> OTHER INFORMATION: R_PcomS_EMSA

<400> SEQUENCE: 170
aaaagtagtg acatttatgt caccaccatt 30

<210> SEQ ID NO 171
<211> LENGTH: 30
<212> TYPE: DNA
<213> ORGANISM: Artificial Sequence
<220> FEATURE:
<223> OTHER INFORMATION: Cy3_F_PcomX_EMSA
<220> FEATURE:
<221> NAME/KEY: misc_feature
<222> LOCATION: (1)..(1)
<223> OTHER INFORMATION: Cy3

<400> SEQUENCE: 171
ttttatagtg acatatatgt cgctatttta 30

<210> SEQ ID NO 172
<211> LENGTH: 30
<212> TYPE: DNA
<213> ORGANISM: Artificial Sequence
<220> FEATURE:
<223> OTHER INFORMATION: R_PcomX_EMSA

<400> SEQUENCE: 172
taaaatagcg acatatatgt cactataaaa 30

<210> SEQ ID NO 173
<211> LENGTH: 30
<212> TYPE: DNA
<213> ORGANISM: Artificial Sequence
<220> FEATURE:
<223> OTHER INFORMATION: Cy3_F_PcomX_EMSArev
<220> FEATURE:
<221> NAME/KEY: misc_feature
<222> LOCATION: (1)..(1)
<223> OTHER INFORMATION: Cy3

<400> SEQUENCE: 173
ttttatagtg acatatatgt cactatttta 30

<210> SEQ ID NO 174
<211> LENGTH: 30
<212> TYPE: DNA
<213> ORGANISM: Artificial Sequence
<220> FEATURE:
<223> OTHER INFORMATION: R_PcomX_EMSArev

<400> SEQUENCE: 174
taaaatagtg acatatatgt cactataaaa 30

<210> SEQ ID NO 175
<211> LENGTH: 21
<212> TYPE: DNA
<213> ORGANISM: Artificial Sequence
<220> FEATURE:
<223> OTHER INFORMATION: F_PcomX_mut

<400> SEQUENCE: 175
catatatgtc actattttat t 21

<210> SEQ ID NO 176

```
<211> LENGTH: 21
<212> TYPE: DNA
<213> ORGANISM: Artificial Sequence
<220> FEATURE:
<223> OTHER INFORMATION: R_PcomX_mut

<400> SEQUENCE: 176

aataaaatag tgacatatat g                                             21

<210> SEQ ID NO 177
<211> LENGTH: 23
<212> TYPE: DNA
<213> ORGANISM: Artificial Sequence
<220> FEATURE:
<223> OTHER INFORMATION: F_PpotA2_mut2

<400> SEQUENCE: 177

acatagatgt cactttgatt cgt                                           23

<210> SEQ ID NO 178
<211> LENGTH: 23
<212> TYPE: DNA
<213> ORGANISM: Artificial Sequence
<220> FEATURE:
<223> OTHER INFORMATION: R_PpotA2_mut2

<400> SEQUENCE: 178

acgaatcaaa gtgacatcta tgt                                           23

<210> SEQ ID NO 179
<211> LENGTH: 22
<212> TYPE: DNA
<213> ORGANISM: Artificial Sequence
<220> FEATURE:
<223> OTHER INFORMATION: F_PpotA2_mut+1

<400> SEQUENCE: 179

tgattcgtta ttttttttgt tt                                            22

<210> SEQ ID NO 180
<211> LENGTH: 22
<212> TYPE: DNA
<213> ORGANISM: Artificial Sequence
<220> FEATURE:
<223> OTHER INFORMATION: R_PpotA2_mut+1

<400> SEQUENCE: 180

aaacaaaaaa aataacgaat ca                                            22

<210> SEQ ID NO 181
<211> LENGTH: 21
<212> TYPE: DNA
<213> ORGANISM: Artificial Sequence
<220> FEATURE:
<223> OTHER INFORMATION: F_PpotA2_mut+A

<400> SEQUENCE: 181

catagatgtc acttttgatt c                                             21

<210> SEQ ID NO 182
<211> LENGTH: 21
<212> TYPE: DNA
<213> ORGANISM: Artificial Sequence
<220> FEATURE:
<223> OTHER INFORMATION: R_PpotA2_mut+A

<400> SEQUENCE: 182
```

gaatcaaaag tgacatctat g 21

<210> SEQ ID NO 183
<211> LENGTH: 78
<212> TYPE: DNA
<213> ORGANISM: Artificial Sequence
<220> FEATURE:
<223> OTHER INFORMATION: F_pept_xyl
<220> FEATURE:
<221> NAME/KEY: misc_feature
<222> LOCATION: (35)..(55)
<223> OTHER INFORMATION: n may be any nucleobase

<400> SEQUENCE: 183
taaatcaaag gaggtaaata tgatcgcaat cctannnnnn nnnnnnnnnn nnnnntgata 60
ataaggccgg ccaataaa 78

<210> SEQ ID NO 184
<211> LENGTH: 12
<212> TYPE: PRT
<213> ORGANISM: Artificial Sequence
<220> FEATURE:
<223> OTHER INFORMATION: Synthetic RAP-binding peptide, RBP

<400> SEQUENCE: 184

Phe His Trp Trp Gln Thr Ser Pro Ala His Phe Ser
1 5 10

<210> SEQ ID NO 185
<211> LENGTH: 12
<212> TYPE: PRT
<213> ORGANISM: Artificial Sequence
<220> FEATURE:
<223> OTHER INFORMATION: Synthetic RAP-binding peptide, RBP

<400> SEQUENCE: 185

Trp Pro Phe Ala His Trp Pro Trp Gln Tyr Pro Arg
1 5 10

<210> SEQ ID NO 186
<211> LENGTH: 9
<212> TYPE: PRT
<213> ORGANISM: Artificial Sequence
<220> FEATURE:
<223> OTHER INFORMATION: Synthetic AgrC ligand
<220> FEATURE:
<221> NAME/KEY: misc_feature
<222> LOCATION: (5)..(5)
<223> OTHER INFORMATION: Thiolacton linkage between C5 and F9
<220> FEATURE:
<221> NAME/KEY: misc_feature
<222> LOCATION: (9)..(9)
<223> OTHER INFORMATION: Thiolacton linkage between C5 and F9

<400> SEQUENCE: 186

Gly Asp Ser Val Cys Ala Ser Tyr Phe
1 5

<210> SEQ ID NO 187
<211> LENGTH: 7
<212> TYPE: PRT
<213> ORGANISM: Artificial Sequence
<220> FEATURE:
<223> OTHER INFORMATION: Synthetic AgrC ligand
<220> FEATURE:
<221> NAME/KEY: misc_feature
<222> LOCATION: (3)..(3)
<223> OTHER INFORMATION: Thiolacton linkage between C3 and F7

<220> FEATURE:
<221> NAME/KEY: misc_feature
<222> LOCATION: (7)..(7)
<223> OTHER INFORMATION: Thiolacton linkage between C3 and F7

<400> SEQUENCE: 187

Ser Val Cys Ala Ser Tyr Phe
1               5

<210> SEQ ID NO 188
<211> LENGTH: 5
<212> TYPE: PRT
<213> ORGANISM: Artificial Sequence
<220> FEATURE:
<223> OTHER INFORMATION: Synthetic Cry1Aa ligand

<400> SEQUENCE: 188

Ser Lys Ala Asp Thr
1               5

<210> SEQ ID NO 189
<211> LENGTH: 5
<212> TYPE: PRT
<213> ORGANISM: Artificial Sequence
<220> FEATURE:
<223> OTHER INFORMATION: Synthetic Cry1Aa ligand

<400> SEQUENCE: 189

Ser Lys Pro Ala Asp
1               5

<210> SEQ ID NO 190
<211> LENGTH: 11
<212> TYPE: PRT
<213> ORGANISM: Artificial Sequence
<220> FEATURE:
<223> OTHER INFORMATION: Synthetic Fsr ligand
<220> FEATURE:
<221> NAME/KEY: misc_feature
<222> LOCATION: (3)..(3)
<223> OTHER INFORMATION: Lacton linkage between S3 and A11
<220> FEATURE:
<221> NAME/KEY: misc_feature
<222> LOCATION: (11)..(11)
<223> OTHER INFORMATION: Lacton linkage between S3 and A11

<400> SEQUENCE: 190

Gln Asn Ser Ala Ala Ala Phe Ala Ala Trp Ala
1               5                   10

<210> SEQ ID NO 191
<211> LENGTH: 11
<212> TYPE: PRT
<213> ORGANISM: Artificial Sequence
<220> FEATURE:
<223> OTHER INFORMATION: Synthetic Fsr ligand
<220> FEATURE:
<221> NAME/KEY: misc_feature
<222> LOCATION: (3)..(3)
<223> OTHER INFORMATION: Lacton linkage between S3 and A11
<220> FEATURE:
<221> NAME/KEY: misc_feature
<222> LOCATION: (11)..(11)
<223> OTHER INFORMATION: Lacton linkage between S3 and A11

<400> SEQUENCE: 191

Gln Asn Ser Ala Ala Ala Phe Gly Gln Trp Ala
1               5                   10

<210> SEQ ID NO 192
<211> LENGTH: 7
<212> TYPE: PRT
<213> ORGANISM: Artificial Sequence
<220> FEATURE:
<223> OTHER INFORMATION: Synthetic AgrC1, AgrC2
<220> FEATURE:
<221> NAME/KEY: misc_feature
<222> LOCATION: (4)..(4)
<223> OTHER INFORMATION: Thiolacton linkage between C4 and M7)
<220> FEATURE:
<221> NAME/KEY: misc_feature
<222> LOCATION: (7)..(7)
<223> OTHER INFORMATION: Thiolacton linkage between C4 and M7)

<400> SEQUENCE: 192

Tyr Ser Thr Cys Phe Ile Met
1               5

<210> SEQ ID NO 193
<211> LENGTH: 7
<212> TYPE: PRT
<213> ORGANISM: Artificial Sequence
<220> FEATURE:
<223> OTHER INFORMATION: Synthetic AgrC1, AgrC2
<220> FEATURE:
<221> NAME/KEY: misc_feature
<222> LOCATION: (3)..(3)
<223> OTHER INFORMATION: Thiolacton linkage between C3 and M7
<220> FEATURE:
<221> NAME/KEY: misc_feature
<222> LOCATION: (7)..(7)
<223> OTHER INFORMATION: Thiolacton linkage between C3 and M7

<400> SEQUENCE: 193

Ser Thr Cys Ala Phe Ile Met
1               5

<210> SEQ ID NO 194
<211> LENGTH: 30
<212> TYPE: DNA
<213> ORGANISM: Artificial Sequence
<220> FEATURE:
<223> OTHER INFORMATION: Lead promoter

<400> SEQUENCE: 194
gaaaaccttg tcaatgaaga gcgatctatg 30

<210> SEQ ID NO 195
<211> LENGTH: 30
<212> TYPE: DNA
<213> ORGANISM: Artificial Sequence
<220> FEATURE:
<223> OTHER INFORMATION: FecA promoter

<400> SEQUENCE: 195
ttctcgttcg actcatagct gaacacaaca 30

<210> SEQ ID NO 196
<211> LENGTH: 16
<212> TYPE: DNA
<213> ORGANISM: Artificial Sequence
<220> FEATURE:
<223> OTHER INFORMATION: Cu-sensitive promoter

<400> SEQUENCE: 196
atgacaaaat tgtcat 16

<210> SEQ ID NO 197

<211> LENGTH: 30
<212> TYPE: DNA
<213> ORGANISM: Artificial Sequence
<220> FEATURE:
<223> OTHER INFORMATION: Fe promoter

<400> SEQUENCE: 197
accaatgctg ggaacggcca gggcacctaa 30

<210> SEQ ID NO 198
<211> LENGTH: 30
<212> TYPE: DNA
<213> ORGANISM: Artificial Sequence
<220> FEATURE:
<223> OTHER INFORMATION: Fe and UV promoters

<400> SEQUENCE: 198
ctgaaagcgc ataccgctat ggagggggtt 30

<210> SEQ ID NO 199
<211> LENGTH: 30
<212> TYPE: DNA
<213> ORGANISM: Artificial Sequence
<220> FEATURE:
<223> OTHER INFORMATION: PrFe (PI + PII rus operon)

<400> SEQUENCE: 199
tagatatgcc tgaaagcgca taccgctatg 30

<210> SEQ ID NO 200
<211> LENGTH: 30
<212> TYPE: DNA
<213> ORGANISM: Artificial Sequence
<220> FEATURE:
<223> OTHER INFORMATION: Lux cassette right promoter

<400> SEQUENCE: 200
tgttatagtc gaatacctct ggcggtgata 30

<210> SEQ ID NO 201
<211> LENGTH: 30
<212> TYPE: DNA
<213> ORGANISM: Artificial Sequence
<220> FEATURE:
<223> OTHER INFORMATION: P(Las) TetO

<400> SEQUENCE: 201
ttttggtaca ctccctatca gtgatagaga 30

<210> SEQ ID NO 202
<211> LENGTH: 30
<212> TYPE: DNA
<213> ORGANISM: Artificial Sequence
<220> FEATURE:
<223> OTHER INFORMATION: P(Las) CIO

<400> SEQUENCE: 202
ctttttggta cactacctct ggcggtgata 30

<210> SEQ ID NO 203
<211> LENGTH: 30
<212> TYPE: DNA
<213> ORGANISM: Artificial Sequence
<220> FEATURE:
<223> OTHER INFORMATION: P(Rhl)

<400> SEQUENCE: 203
tacgcaagaa aatggtttgt tatagtcgaa 30

<210> SEQ ID NO 204
<211> LENGTH: 30
<212> TYPE: DNA
<213> ORGANISM: Artificial Sequence
<220> FEATURE:
<223> OTHER INFORMATION: Double Promoter (LuxR/HSL, positive / cI,

<400> SEQUENCE: 204
cgtgcgtgtt gataacaccg tgcgtgttga 30

<210> SEQ ID NO 205
<211> LENGTH: 30
<212> TYPE: DNA
<213> ORGANISM: Artificial Sequence
<220> FEATURE:
<223> OTHER INFORMATION: P2 promoter in agr operon from S. aureus

<400> SEQUENCE: 205
agattgtact aaatcgtata atgacagtga 30

<210> SEQ ID NO 206
<211> LENGTH: 30
<212> TYPE: DNA
<213> ORGANISM: Artificial Sequence
<220> FEATURE:
<223> OTHER INFORMATION: plux-cI hybrid promoter

<400> SEQUENCE: 206
gtgttgatgc ttttatcacc gccagtggta 30

<210> SEQ ID NO 207
<211> LENGTH: 30
<212> TYPE: DNA
<213> ORGANISM: Artificial Sequence
<220> FEATURE:
<223> OTHER INFORMATION: plux-lac hybrid promoter

<400> SEQUENCE: 207
agtgtgtgga attgtgagcg gataacaatt 30

<210> SEQ ID NO 208
<211> LENGTH: 30
<212> TYPE: DNA
<213> ORGANISM: Artificial Sequence
<220> FEATURE:
<223> OTHER INFORMATION: CinR, CinL and glucose controlled promotor

<400> SEQUENCE: 208
acatcttaaa agttttagta tcatattcgt 30

<210> SEQ ID NO 209
<211> LENGTH: 30
<212> TYPE: DNA
<213> ORGANISM: Artificial Sequence
<220> FEATURE:
<223> OTHER INFORMATION: RhIR promoter repressible by CI

<400> SEQUENCE: 209
tacgcaagaa aatggtttgt tatagtcgaa 30

<210> SEQ ID NO 210
<211> LENGTH: 30
<212> TYPE: DNA

<213> ORGANISM: Artificial Sequence
<220> FEATURE:
<223> OTHER INFORMATION: Reverse Lux Promoter

<400> SEQUENCE: 210
tcttgcgtaa acctgtacga tcctacaggt 30

<210> SEQ ID NO 211
<211> LENGTH: 30
<212> TYPE: DNA
<213> ORGANISM: Artificial Sequence
<220> FEATURE:
<223> OTHER INFORMATION: rhlI promoter

<400> SEQUENCE: 211
atcctccttt agtcttcccc ctcatgtgtg 30

<210> SEQ ID NO 212
<211> LENGTH: 30
<212> TYPE: DNA
<213> ORGANISM: Artificial Sequence
<220> FEATURE:
<223> OTHER INFORMATION: lasI promoter

<400> SEQUENCE: 212
taaaattatg aaatttgcat aaattcttca 30

<210> SEQ ID NO 213
<211> LENGTH: 30
<212> TYPE: DNA
<213> ORGANISM: Artificial Sequence
<220> FEATURE:
<223> OTHER INFORMATION: LuxR+3OC6HSL independent R0065

<400> SEQUENCE: 213
gtgttgacta ttttacctct ggcggtgata 30

<210> SEQ ID NO 214
<211> LENGTH: 30
<212> TYPE: DNA
<213> ORGANISM: Artificial Sequence
<220> FEATURE:
<223> OTHER INFORMATION: LasR/LasI Inducible & RHLR/RHLI repressible

<400> SEQUENCE: 214
gaaatctggc agtttttggt acacgaaagc 30

<210> SEQ ID NO 215
<211> LENGTH: 30
<212> TYPE: DNA
<213> ORGANISM: Artificial Sequence
<220> FEATURE:
<223> OTHER INFORMATION: pLux/cI Hybrid Promoter

<400> SEQUENCE: 215
acaccgtgcg tgttgatata gtcgaataaa 30

<210> SEQ ID NO 216
<211> LENGTH: 30
<212> TYPE: DNA
<213> ORGANISM: Artificial Sequence
<220> FEATURE:
<223> OTHER INFORMATION: pLas promoter

<400> SEQUENCE: 216
aaaattatga aatttgtata aattcttcag 30

<210> SEQ ID NO 217
<211> LENGTH: 30
<212> TYPE: DNA
<213> ORGANISM: Artificial Sequence
<220> FEATURE:
<223> OTHER INFORMATION: pLas/cI Hybrid Promoter

<400> SEQUENCE: 217
ggttcttttt ggtacctctg gcggtgataa 30

<210> SEQ ID NO 218
<211> LENGTH: 30
<212> TYPE: DNA
<213> ORGANISM: Artificial Sequence
<220> FEATURE:
<223> OTHER INFORMATION: pLas/Lux Hybrid Promoter

<400> SEQUENCE: 218
tgtaggatcg tacaggtata aattcttcag 30

<210> SEQ ID NO 219
<211> LENGTH: 30
<212> TYPE: DNA
<213> ORGANISM: Artificial Sequence
<220> FEATURE:
<223> OTHER INFORMATION: pLux

<400> SEQUENCE: 219
caagaaaatg gtttgttata gtcgaataaa 30

<210> SEQ ID NO 220
<211> LENGTH: 30
<212> TYPE: DNA
<213> ORGANISM: Artificial Sequence
<220> FEATURE:
<223> OTHER INFORMATION: pLux/Las Hybrid Promoter

<400> SEQUENCE: 220
ctatctcatt tgctagtata gtcgaataaa 30

<210> SEQ ID NO 221
<211> LENGTH: 30
<212> TYPE: DNA
<213> ORGANISM: Artificial Sequence
<220> FEATURE:
<223> OTHER INFORMATION: Hybrid promoter: HSL-LuxR activated, P22 C2

<400> SEQUENCE: 221
tagtttataa tttaagtgtt ctttaatttc 30

<210> SEQ ID NO 222
<211> LENGTH: 30
<212> TYPE: DNA
<213> ORGANISM: Artificial Sequence
<220> FEATURE:
<223> OTHER INFORMATION: PAI+LasR -> LuxI (AI)

<400> SEQUENCE: 222
caccttcggg tgggcctttc tgcgtttata 30

<210> SEQ ID NO 223
<211> LENGTH: 30
<212> TYPE: DNA
<213> ORGANISM: Artificial Sequence
<220> FEATURE:

<223> OTHER INFORMATION: PAI+LasR -> LasI & AI+LuxR --[\m]LasI

<400> SEQUENCE: 223
aataactctg atagtgctag tgtagatctc 30

<210> SEQ ID NO 224
<211> LENGTH: 30
<212> TYPE: DNA
<213> ORGANISM: Artificial Sequence
<220> FEATURE:
<223> OTHER INFORMATION: PAI+LasR -> LasI+GFP & AI+LuxR --[\m]LasI+GFP

<400> SEQUENCE: 224
caccttcggg tgggcctttc tgcgtttata 30

<210> SEQ ID NO 225
<211> LENGTH: 30
<212> TYPE: DNA
<213> ORGANISM: Artificial Sequence
<220> FEATURE:
<223> OTHER INFORMATION: Complex QS -> LuxI & LasI circuit

<400> SEQUENCE: 225
caccttcggg tgggcctttc tgcgtttata 30

<210> SEQ ID NO 226
<211> LENGTH: 30
<212> TYPE: DNA
<213> ORGANISM: Artificial Sequence
<220> FEATURE:
<223> OTHER INFORMATION: position 3 mutated promoter lux pR-3 (luxR &
HSL

<400> SEQUENCE: 226
caagaaaatg gtttgttata gtcgaataaa 30

<210> SEQ ID NO 227
<211> LENGTH: 30
<212> TYPE: DNA
<213> ORGANISM: Artificial Sequence
<220> FEATURE:
<223> OTHER INFORMATION: position 5 mutated promoter lux pR-5 (luxR &
HSL

<400> SEQUENCE: 227
caagaaaatg gtttgttata gtcgaataaa 30

<210> SEQ ID NO 228
<211> LENGTH: 30
<212> TYPE: DNA
<213> ORGANISM: Artificial Sequence
<220> FEATURE:
<223> OTHER INFORMATION: position 3&5 mutated promoter lux pR-3/5
(luxR &

<400> SEQUENCE: 228
caagaaaatg gtttgttata gtcgaataaa 30

<210> SEQ ID NO 229
<211> LENGTH: 30
<212> TYPE: DNA
<213> ORGANISM: Artificial Sequence
<220> FEATURE:
<223> OTHER INFORMATION: Promoter (HSL-mediated luxR repressor)

<400> SEQUENCE: 229
ttgacacctg taggatcgta caggtataat 30

<210> SEQ ID NO 230
<211> LENGTH: 30
<212> TYPE: DNA
<213> ORGANISM: Artificial Sequence
<220> FEATURE:
<223> OTHER INFORMATION: Promoter (luxR & HSL regulated -- lux pR)

<400> SEQUENCE: 230
caagaaaatg gtttgttata gtcgaataaa 30

<210> SEQ ID NO 231
<211> LENGTH: 30
<212> TYPE: DNA
<213> ORGANISM: Artificial Sequence
<220> FEATURE:
<223> OTHER INFORMATION: Promoter (luxR & HSL regulated -- lux pL)

<400> SEQUENCE: 231
cacgcaaaac ttgcgacaaa caataggtaa 30

<210> SEQ ID NO 232
<211> LENGTH: 30
<212> TYPE: DNA
<213> ORGANISM: Artificial Sequence
<220> FEATURE:
<223> OTHER INFORMATION: Promoter (RhlR & C4-HSL regulated)

<400> SEQUENCE: 232
gttagctttc gaattggcta aaaagtgttc 30

<210> SEQ ID NO 233
<211> LENGTH: 30
<212> TYPE: DNA
<213> ORGANISM: Artificial Sequence
<220> FEATURE:
<223> OTHER INFORMATION: Promoter (cinR and HSL regulated)

<400> SEQUENCE: 233
ccattctgct ttccacgaac ttgaaaacgc 30

<210> SEQ ID NO 234
<211> LENGTH: 30
<212> TYPE: DNA
<213> ORGANISM: Artificial Sequence
<220> FEATURE:
<223> OTHER INFORMATION: Promoter (LasR & PAI regulated)

<400> SEQUENCE: 234
ggccgcgggt tctttttggt acacgaaagc 30

<210> SEQ ID NO 235
<211> LENGTH: 30
<212> TYPE: DNA
<213> ORGANISM: Artificial Sequence
<220> FEATURE:
<223> OTHER INFORMATION: Promoter, Standard (luxR and HSL regulated --
lux

<400> SEQUENCE: 235
aagaaaatgg tttgttgata ctcgaataaa 30

<210> SEQ ID NO 236
<211> LENGTH: 5
<212> TYPE: PRT

<213> ORGANISM: Artificial sequence
<220> FEATURE:
<223> OTHER INFORMATION: N-terminal motif of class IIa bacteriocins
<220> FEATURE:
<221> NAME/KEY: misc_feature
<222> LOCATION: (3)..(3)
<223> OTHER INFORMATION: Xaa may be any amino acid

<400> SEQUENCE: 236

Tyr Gly Xaa Gly Val
1 5

<210> SEQ ID NO 237
<211> LENGTH: 5
<212> TYPE: PRT
<213> ORGANISM: Artificial sequence
<220> FEATURE:
<223> OTHER INFORMATION: Motif of some class IIb bacteriocins
<220> FEATURE:
<221> NAME/KEY: misc_feature
<222> LOCATION: (2)..(4)
<223> OTHER INFORMATION: Xaa may be any amino acid

<400> SEQUENCE: 237

Gly Xaa Xaa Xaa Gly
1 5

<210> SEQ ID NO 238
<211> LENGTH: 135
<212> TYPE: PRT
<213> ORGANISM: Artificial sequence
<220> FEATURE:
<223> OTHER INFORMATION: Hybrid bacteriocin Ent35-MccV

<400> SEQUENCE: 238

Gly Lys Tyr Tyr Gly Asn Gly Val Ser Cys Asn Lys Lys Gly Cys Ser
1 5 10 15

Val Asp Trp Gly Arg Ala Ile Gly Ile Ile Gly Asn Asn Ser Ala Ala
20 25 30

Asn Leu Ala Thr Gly Gly Ala Ala Gly Trp Lys Ser Gly Gly Gly Ala
35 40 45

Ser Gly Arg Asp Ile Ala Met Ala Ile Gly Thr Leu Ser Gly Gln Phe
50 55 60

Val Ala Gly Gly Ile Gly Ala Ala Ala Gly Gly Val Ala Gly Gly Ala
65 70 75 80

Ile Tyr Asp Tyr Ala Ser Thr His Lys Pro Asn Pro Ala Met Ser Pro
85 90 95

Ser Gly Leu Gly Gly Thr Ile Lys Gln Lys Pro Glu Gly Ile Pro Ser
100 105 110

Glu Ala Trp Asn Tyr Ala Ala Gly Arg Leu Cys Asn Trp Ser Pro Asn
115 120 125

Asn Leu Ser Asp Val Cys Leu
130 135

<210> SEQ ID NO 239
<211> LENGTH: 46
<212> TYPE: PRT
<213> ORGANISM: Lactobacillus acidophilus

<400> SEQUENCE: 239

Met Ile Ser Ser His Gln Lys Thr Leu Thr Asp Lys Glu Leu Ala Leu
1 5 10 15

Ile Ser Gly Gly Lys Thr His Tyr Pro Thr Asn Ala Trp Lys Ser Leu 20 25 30

Trp Lys Gly Phe Trp Glu Ser Leu Arg Tyr Thr Asp Gly Phe
35 40 45

<210> SEQ ID NO 240
<211> LENGTH: 141
<212> TYPE: DNA
<213> ORGANISM: Lactobacillus acidophilus

<400> SEQUENCE: 240
atgatttcat ctcatcaaaa aacgttaact gataaagaat tagcattaat ttctgggggg 60
aaaacgcact acccgactaa tgcatggaaa agtctttgga aaggtttctg ggaaagcctt 120
cgttatactg acggttttta g 141

<210> SEQ ID NO 241
<211> LENGTH: 81
<212> TYPE: PRT
<213> ORGANISM: Lactobacillus acidophilus

<400> SEQUENCE: 241

Met Ile Ser Met Ile Ser Ser His Gln Lys Thr Leu Thr Asp Lys Glu
1 5 10 15

Leu Ala Leu Ile Ser Gly Gly Lys Thr Tyr Tyr Gly Thr Asn Gly Val
20 25 30

His Cys Thr Lys Lys Ser Leu Trp Gly Lys Val Arg Leu Lys Asn Val
35 40 45

Ile Pro Gly Thr Leu Cys Arg Lys Gln Ser Leu Pro Ile Lys Gln Asp
50 55 60

Leu Lys Ile Leu Leu Gly Trp Ala Thr Gly Ala Phe Gly Lys Thr Phe
65 70 75 80

His

<210> SEQ ID NO 242
<211> LENGTH: 246
<212> TYPE: DNA
<213> ORGANISM: Lactobacillus acidophilus

<400> SEQUENCE: 242
atgatttcaa tgatttcatc tcatcaaaaa acgttaactg ataaagaatt agcattaatt 60
tctgggggga aaacgtacta tggtactaat ggtgtgcatt gtactaaaaa gagtctttgg 120
ggtaaagtac gcttaaaaaa cgtgattcct ggaactcttt gtcgtaagca atcgttgccg 180
atcaaacagg atttaaaaat tttactgggc tgggctacag gtgcttttgg caagacattt 240
cattaa 246

<210> SEQ ID NO 243
<211> LENGTH: 60
<212> TYPE: PRT
<213> ORGANISM: Lactobacillus acidophilus

<400> SEQUENCE: 243

Met Asp Lys Lys Thr Lys Ile Leu Phe Glu Val Leu Tyr Ile Ile Cys
1 5 10 15

Ile Ile Gly Pro Gln Phe Ile Leu Phe Val Thr Ala Lys Asn Asn Met
20 25 30

Tyr Gln Leu Val Gly Ser Phe Val Gly Ile Val Trp Phe Ser Tyr Ile
35 40 45

-continued

```
Phe Trp Tyr Ile Phe Phe Lys Gln His Lys Lys Met
    50                  55                  60


<210> SEQ ID NO 244
<211> LENGTH: 183
<212> TYPE: DNA
<213> ORGANISM: Lactobacillus acidophilus

<400> SEQUENCE: 244

atggataaga aaacaaaaat attatttgaa gtattataca tcatctgtat aataggccct      60

caatttatat tatttgtgac tgcaaaaaac aatatgtatc agttggtggg ttcgtttgtt     120

ggaatagtat ggttttcgta tattttttgg tatatttttt tcaaacaaca taaaaaaatg     180

tag                                                                   183


<210> SEQ ID NO 245
<211> LENGTH: 65
<212> TYPE: PRT
<213> ORGANISM: Lactobacillus gasseri

<400> SEQUENCE: 245

Met Ala Leu Lys Thr Leu Glu Lys His Glu Leu Arg Asn Val Met Gly
1               5                   10                  15

Gly Asn Lys Trp Gly Asn Ala Val Ile Gly Ala Ala Thr Gly Ala Thr
            20                  25                  30

Arg Gly Val Ser Trp Cys Arg Gly Phe Gly Pro Trp Gly Met Thr Ala
        35                  40                  45

Cys Ala Leu Gly Gly Ala Ala Ile Gly Gly Tyr Leu Gly Tyr Lys Ser
    50                  55                  60

Asn
65


<210> SEQ ID NO 246
<211> LENGTH: 198
<212> TYPE: DNA
<213> ORGANISM: Lactobacillus gasseri

<400> SEQUENCE: 246

atggctttaa aaacattaga aaaacatgaa ttaagaaatg taatgggtgg aaacaagtgg      60

gggaatgctg taataggagc tgctacggga gctactcgcg gagtaagttg gtgcagagga     120

ttcggaccat ggggaatgac tgcctgtgcg ttaggaggtg ctgcaattgg aggatatctg     180

ggatataaga gtaattaa                                                   198


<210> SEQ ID NO 247
<211> LENGTH: 51
<212> TYPE: PRT
<213> ORGANISM: Staphylococcus aureus

<400> SEQUENCE: 247

Met Ser Trp Leu Asn Phe Leu Lys Tyr Ile Ala Lys Tyr Gly Lys Lys
1               5                   10                  15

Ala Val Ser Ala Ala Trp Lys Tyr Lys Gly Lys Val Leu Glu Trp Leu
            20                  25                  30

Asn Val Gly Pro Thr Leu Glu Trp Val Trp Gln Lys Leu Lys Lys Ile
        35                  40                  45

Ala Gly Leu
    50
```

<210> SEQ ID NO 248
<211> LENGTH: 156
<212> TYPE: DNA
<213> ORGANISM: Staphylococcus aureus

<400> SEQUENCE: 248
atgagttggt taaatttttt aaaatacatc gctaaatatg gcaaaaaagc ggtatctgct 60
gcttggaagt acaaaggtaa agtattagaa tggcttaatg ttggtcctac tcttgaatgg 120
gtatggcaaa aattaaagaa aattgctgga ttataa 156

<210> SEQ ID NO 249
<211> LENGTH: 61
<212> TYPE: PRT
<213> ORGANISM: Enterococcus avium

<400> SEQUENCE: 249

Met Thr Arg Ser Lys Lys Leu Asn Leu Arg Glu Met Lys Asn Val Val
1 5 10 15

Gly Gly Thr Tyr Tyr Gly Asn Gly Val Ser Cys Asn Lys Lys Gly Cys
20 25 30

Ser Val Asp Trp Gly Lys Ala Ile Ser Ile Ile Gly Asn Asn Ser Ala
35 40 45

Ala Asn Leu Ala Thr Gly Gly Ala Ala Gly Trp Lys Ser
50 55 60

<210> SEQ ID NO 250
<211> LENGTH: 186
<212> TYPE: DNA
<213> ORGANISM: Enterococcus avium

<400> SEQUENCE: 250
atgacaagat caaaaaaatt aaatttacgc gaaatgaaga atgttgttgg tggtacctac 60
tatggaaatg gtgtatcttg taacaagaaa ggctgttcag ttgactgggg caaagccatc 120
agtattatag gaaataattc cgcagcaaac ttagcaactg gtggtgctgc tggttggaag 180
tcataa 186

<210> SEQ ID NO 251
<211> LENGTH: 67
<212> TYPE: PRT
<213> ORGANISM: Enterococcus faecalis

<400> SEQUENCE: 251

Met Lys Lys Lys Leu Val Ile Cys Gly Ile Ile Gly Ile Gly Phe Thr
1 5 10 15

Ala Leu Gly Thr Asn Val Glu Ala Ala Thr Tyr Tyr Gly Asn Gly Leu
20 25 30

Tyr Cys Asn Lys Gln Lys Cys Trp Val Asp Trp Asn Lys Ala Ser Arg
35 40 45

Glu Ile Gly Lys Ile Ile Val Asn Gly Trp Val Gln His Gly Pro Trp
50 55 60

Ala Pro Arg
65

<210> SEQ ID NO 252
<211> LENGTH: 204
<212> TYPE: DNA
<213> ORGANISM: Enterococcus faecalis

<400> SEQUENCE: 252
atgaaaaaga aattagttat ttgtggcatt attgggattg gttttacagc attaggaaca 60
aatgtagaag ctgctacgta ttacggaaat ggtttatatt gtaataagca aaaatgttgg 120
gtagactgga ataaagcttc aagggaaatt ggaaaaatta ttgttaatgg ttgggtacaa 180
catggccctt gggctcctag atag 204

<210> SEQ ID NO 253
<211> LENGTH: 51
<212> TYPE: PRT
<213> ORGANISM: Lactococcus lactis

<400> SEQUENCE: 253

Met Lys Glu Gln Asn Ser Phe Asn Leu Leu Gln Glu Val Thr Glu Ser
1 5 10 15

Glu Leu Asp Leu Ile Leu Gly Ala Lys Gly Gly Ser Gly Val Ile His
20 25 30

Thr Ile Ser His Glu Val Ile Tyr Asn Ser Trp Asn Phe Val Phe Thr
35 40 45

Cys Cys Ser
50

<210> SEQ ID NO 254
<211> LENGTH: 156
<212> TYPE: DNA
<213> ORGANISM: Lactococcus lactis

<400> SEQUENCE: 254
atgaaagaac aaaactcttt taatcttctt caagaagtga cagaaagtga attggacctt 60
attttaggtg caaaaggcgg cagtggagtt attcatacaa tttctcatga agtaatatat 120
aatagctgga actttgtatt tacttgctgc tcttaa 156

<210> SEQ ID NO 255
<211> LENGTH: 74
<212> TYPE: PRT
<213> ORGANISM: Enterococcus faecium

<400> SEQUENCE: 255

Met Lys Lys Lys Val Leu Lys His Cys Val Ile Leu Gly Ile Leu Gly
1 5 10 15

Thr Cys Leu Ala Gly Ile Gly Thr Gly Ile Lys Val Asp Ala Ala Thr
20 25 30

Tyr Tyr Gly Asn Gly Leu Tyr Cys Asn Lys Glu Lys Cys Trp Val Asp
35 40 45

Trp Asn Gln Ala Lys Gly Glu Ile Gly Lys Ile Ile Val Asn Gly Trp
50 55 60

Val Asn His Gly Pro Trp Ala Pro Arg Arg
65 70

<210> SEQ ID NO 256
<211> LENGTH: 225
<212> TYPE: DNA
<213> ORGANISM: Enterococcus faecium

<400> SEQUENCE: 256
atgaaaaaga aagtattaaa acattgtgtt attctaggaa tattaggaac ttgtctagct 60
ggcatcggta caggaataaa agttgatgca gctacttact atggaaatgg tctttattgt 120
aacaaagaaa aatgttgggt agattggaat caagctaaag gagaaattgg aaaaattatt 180
gttaatggtt gggttaatca tggtccatgg gcacctagaa ggtag 225

<210> SEQ ID NO 257
<211> LENGTH: 50
<212> TYPE: PRT
<213> ORGANISM: Clostridium botulinum

<400> SEQUENCE: 257

Met Gln Lys Pro Glu Ile Ile Ser Ala Asp Leu Gly Leu Cys Ala Val
1 5 10 15

Asn Glu Phe Val Ala Leu Ala Ala Ile Pro Gly Gly Ala Ala Thr Phe
20 25 30

Ala Val Cys Gln Met Pro Asn Leu Asp Glu Ile Val Ser Asn Ala Ala
35 40 45

Tyr Val
50

<210> SEQ ID NO 258
<211> LENGTH: 153
<212> TYPE: DNA
<213> ORGANISM: Clostridium botulinum

<400> SEQUENCE: 258
atgcaaaaac cagaaattat tagtgctgat ttagggcttt gtgcagttaa tgaatttgta 60
gctcttgctg ccattcctgg tggtgctgct acatttgcag tatgccaaat gccaaacttg 120
gatgagattg ttagtaatgc agcatatgtt taa 153

<210> SEQ ID NO 259
<211> LENGTH: 58
<212> TYPE: PRT
<213> ORGANISM: Streptococcus equinus

<400> SEQUENCE: 259

Met Met Asn Ala Thr Glu Asn Gln Ile Phe Val Glu Thr Val Ser Asp
1 5 10 15

Gln Glu Leu Glu Met Leu Ile Gly Gly Ala Asp Arg Gly Trp Ile Lys
20 25 30

Thr Leu Thr Lys Asp Cys Pro Asn Val Ile Ser Ser Ile Cys Ala Gly
35 40 45

Thr Ile Ile Thr Ala Cys Lys Asn Cys Ala
50 55

<210> SEQ ID NO 260
<211> LENGTH: 177
<212> TYPE: DNA
<213> ORGANISM: Streptococcus equinus

<400> SEQUENCE: 260
atgatgaatg ctactgaaaa ccaaattttt gttgagactg tgagtgacca agaattagaa 60
atgttaattg gtggtgcaga tcgtggatgg attaagactt taacaaaaga ttgtccaaat 120
gtaatttctt caatttgtgc aggtacaatt attacagctt gtaaaaattg tgcttaa 177

<210> SEQ ID NO 261
<211> LENGTH: 77
<212> TYPE: PRT
<213> ORGANISM: Brochothrix campestris

<400> SEQUENCE: 261

-continued

```
Met His Lys Val Lys Lys Leu Asn Asn Gln Glu Leu Gln Gln Ile Val
1               5                   10                  15

Gly Gly Tyr Ser Ser Lys Asp Cys Leu Lys Asp Ile Gly Lys Gly Ile
            20                  25                  30

Gly Ala Gly Thr Val Ala Gly Ala Ala Gly Gly Gly Leu Ala Ala Gly
        35                  40                  45

Leu Gly Ala Ile Pro Gly Ala Phe Val Gly Ala His Phe Gly Val Ile
    50                  55                  60

Gly Gly Ser Ala Ala Cys Ile Gly Gly Leu Leu Gly Asn
65                  70                  75


<210> SEQ ID NO 262
<211> LENGTH: 234
<212> TYPE: DNA
<213> ORGANISM: Brochothrix campestris

<400> SEQUENCE: 262

atgcacaagg taaaaaaatt aaacaatcaa gagttacaac agatcgtggg aggttacagt      60

tcaaaagatt gtctaaaaga tattggtaaa ggaattggtg ctggtacagt agctggggca     120

gccggcggtg gcctagctgc aggattaggt gctatcccag gagcattcgt tggagcacat     180

tttggagtaa tcggcggatc tgccgcatgc attggtggat tattaggtaa ctag           234


<210> SEQ ID NO 263
<211> LENGTH: 80
<212> TYPE: PRT
<213> ORGANISM: Butyrivibrio fibrisolvens

<400> SEQUENCE: 263

Met Ser Lys Lys Gln Ile Met Ser Asn Cys Ile Ser Ile Ala Leu Leu
1               5                   10                  15

Ile Ala Leu Ile Pro Asn Ile Tyr Phe Ile Ala Asp Lys Met Gly Ile
            20                  25                  30

Gln Leu Ala Pro Ala Trp Tyr Gln Asp Ile Val Asn Trp Val Ser Ala
        35                  40                  45

Gly Gly Thr Leu Thr Thr Gly Phe Ala Ile Ile Val Gly Val Thr Val
    50                  55                  60

Pro Ala Trp Ile Ala Glu Ala Ala Ala Ala Phe Gly Ile Ala Ser Ala
65                  70                  75                  80


<210> SEQ ID NO 264
<211> LENGTH: 243
<212> TYPE: DNA
<213> ORGANISM: Butyrivibrio fibrisolvens

<400> SEQUENCE: 264

atgagtaaaa aacaaattat gagtaactgt atatcaattg cattattaat agcactaatt      60

cctaatatct attttattgc agataaaatg ggaattcagt tagcacctgc ttggtatcaa     120

gatattgtga attgggtatc tgctggtgga acacttacta ctggttttgc gattattgta     180

ggagttacag taccggcatg gatagcagaa gcagctgcag cttttggtat agcttcagca     240

tga                                                                    243


<210> SEQ ID NO 265
<211> LENGTH: 48
<212> TYPE: PRT
<213> ORGANISM: Butyrivibrio fibrisolvens

<400> SEQUENCE: 265
```

-continued

```
Met Asn Lys Glu Leu Asn Ala Leu Thr Asn Pro Ile Asp Glu Lys Glu
1               5                   10                  15

Leu Glu Gln Ile Leu Gly Gly Gly Asn Gly Val Ile Lys Thr Ile Ser
            20                  25                  30

His Glu Cys His Met Asn Thr Trp Gln Phe Ile Phe Thr Cys Cys Ser
        35                  40                  45


<210> SEQ ID NO 266
<211> LENGTH: 147
<212> TYPE: DNA
<213> ORGANISM: Butyrivibrio fibrisolvens

<400> SEQUENCE: 266

atgaacaaag aacttaatgc acttacaaat cctattgacg agaaggagct tgagcagatc      60

ctcggtggtg gcaatggtgt catcaagaca atcagccacg agtgccacat gaacacatgg     120

cagttcattt tcacatgttg ctcttaa                                         147


<210> SEQ ID NO 267
<211> LENGTH: 66
<212> TYPE: PRT
<213> ORGANISM: Carnobacterium maltaromaticum

<400> SEQUENCE: 267

Met Asn Ser Val Lys Glu Leu Asn Val Lys Glu Met Lys Gln Leu His
1               5                   10                  15

Gly Gly Val Asn Tyr Gly Asn Gly Val Ser Cys Ser Lys Thr Lys Cys
            20                  25                  30

Ser Val Asn Trp Gly Gln Ala Phe Gln Glu Arg Tyr Thr Ala Gly Ile
        35                  40                  45

Asn Ser Phe Val Ser Gly Val Ala Ser Gly Ala Gly Ser Ile Gly Arg
    50                  55                  60

Arg Pro
65


<210> SEQ ID NO 268
<211> LENGTH: 201
<212> TYPE: DNA
<213> ORGANISM: Carnobacterium maltaromaticum

<400> SEQUENCE: 268

atgaatagcg taaaagaatt aaacgtgaaa gaaatgaaac aattacacgg tggagtaaat      60

tatggtaatg gtgtttcttg cagtaaaaca aaatgttcag ttaactgggg acaagccttt     120

caagaaagat acacagctgg aattaactca tttgtaagtg gagtcgcttc tggggcagga     180

tccattggta ggagaccgta a                                               201


<210> SEQ ID NO 269
<211> LENGTH: 61
<212> TYPE: PRT
<213> ORGANISM: Carnobacterium maltaromaticum

<400> SEQUENCE: 269

Met Lys Ser Val Lys Glu Leu Asn Lys Lys Glu Met Gln Gln Ile Asn
1               5                   10                  15

Gly Gly Ala Ile Ser Tyr Gly Asn Gly Val Tyr Cys Asn Lys Glu Lys
            20                  25                  30

Cys Trp Val Asn Lys Ala Glu Asn Lys Gln Ala Ile Thr Gly Ile Val
        35                  40                  45
```

```
Ile Gly Gly Trp Ala Ser Ser Leu Ala Gly Met Gly His
    50                  55                  60
```

<210> SEQ ID NO 270
<211> LENGTH: 186
<212> TYPE: DNA
<213> ORGANISM: Carnobacterium maltaromaticum

<400> SEQUENCE: 270

```
atgaaaagcg ttaaagaact aaataaaaaa gaaatgcaac aaattaatgg tggagctatc      60

tcttatggca atggtgttta ttgtaacaaa gagaaatgtt gggtaaacaa ggcagaaaac     120

aaacaagcta ttactggaat agttatcggt ggatgggctt ctagtttagc aggaatggga     180

cattaa                                                                186
```

<210> SEQ ID NO 271
<211> LENGTH: 71
<212> TYPE: PRT
<213> ORGANISM: Carnobacterium maltaromaticum

<400> SEQUENCE: 271

```
Met Asn Asn Val Lys Glu Leu Ser Ile Lys Glu Met Gln Gln Val Thr
1               5                   10                  15

Gly Gly Asp Gln Met Ser Asp Gly Val Asn Tyr Gly Lys Gly Ser Ser
            20                  25                  30

Leu Ser Lys Gly Gly Ala Lys Cys Gly Leu Gly Ile Val Gly Gly Leu
        35                  40                  45

Ala Thr Ile Pro Ser Gly Pro Leu Gly Trp Leu Ala Gly Ala Ala Gly
    50                  55                  60

Val Ile Asn Ser Cys Met Lys
65                  70
```

<210> SEQ ID NO 272
<211> LENGTH: 216
<212> TYPE: DNA
<213> ORGANISM: Carnobacterium maltaromaticum

<400> SEQUENCE: 272

```
atgaataatg taaaagagtt aagtattaaa gaaatgcaac aagttactgg tggagaccaa      60

atgtcagatg gtgtaaatta tggaaaaggc tctagcttat caaaaggtgg tgccaaatgt     120

ggtttaggga tcgtcggcgg attagctact atcccttcag gtcctttagg ctggttagcc     180

ggagcagcag gtgtaattaa tagctgtatg aaataa                               216
```

<210> SEQ ID NO 273
<211> LENGTH: 64
<212> TYPE: PRT
<213> ORGANISM: Carnobacterium maltaromaticum

<400> SEQUENCE: 273

```
Met Leu Tyr Glu Leu Val Ala Tyr Gly Ile Ala Gln Gly Thr Ala Glu
1               5                   10                  15

Lys Val Val Ser Leu Ile Asn Ala Gly Leu Thr Val Gly Ser Ile Ile
            20                  25                  30

Ser Ile Leu Gly Gly Val Thr Val Gly Leu Ser Gly Val Phe Thr Ala
        35                  40                  45

Val Lys Ala Ala Ile Ala Lys Gln Gly Ile Lys Lys Ala Ile Gln Leu
    50                  55                  60
```

<210> SEQ ID NO 274
<211> LENGTH: 195
<212> TYPE: DNA
<213> ORGANISM: Carnobacterium maltaromaticum

<400> SEQUENCE: 274
atgttatatg aattagttgc atatggtatc gcacaaggta cagctgaaaa ggttgtaagt 60
ctaattaacg caggtttaac agtagggtct attatttcaa ttttgggtgg ggtcacagtc 120
ggtttatcag gtgtcttcac agcagttaaa gcagcaattg ctaaacaagg aataaaaaaa 180
gcaattcaat tataa 195

<210> SEQ ID NO 275
<211> LENGTH: 836
<212> TYPE: PRT
<213> ORGANISM: Pectobacterium carotovorum subsp. carotovorum

<400> SEQUENCE: 275

Met Ile Lys Tyr Arg Leu Tyr Ala Pro Asn Asp Gly Asp Thr Met Thr
1 5 10 15

Val Ser Gly Gly Gly Gly Trp Val Ser Asn Asp Asp Arg Lys Gly Gly
20 25 30

Asn Asp Arg Asp Asn Gly Lys Gly Gly Ser Ala Val Asp Phe Ser Lys
35 40 45

Asn Pro Glu Lys Gln Ala Ile Val Asn Pro Tyr Leu Ala Ile Ala Ile
50 55 60

Pro Met Pro Val Tyr Pro Leu Tyr Gly Lys Leu Gly Phe Thr Ile Asn
65 70 75 80

Thr Thr Ala Ile Glu Thr Glu Leu Ala Asn Val Arg Ala Ala Ile Asn
85 90 95

Thr Lys Leu Ala Thr Leu Ser Ala Val Ile Gly Arg Ser Leu Pro Val
100 105 110

Val Gly Arg Val Phe Gly Val Thr Ala Ala Gly Met Trp Pro Ser Ser
115 120 125

Thr Ala Pro Ser Ser Leu Asp Ser Ile Tyr Asn Gln Ala His Gln Gln
130 135 140

Ala Leu Ala Gln Leu Ala Ala Gln Gln Gly Val Leu Asn Lys Gly Tyr
145 150 155 160

Asn Val Thr Ala Met Pro Ala Gly Phe Val Ser Ser Leu Pro Val Ser
165 170 175

Glu Ile Lys Ser Leu Pro Thr Ala Pro Ala Ser Leu Leu Ala Gln Ser
180 185 190

Val Ile Asn Thr Glu Leu Ser Gln Arg Gln Leu Ala Leu Thr Gln Pro
195 200 205

Thr Thr Asn Ala Pro Val Ala Asn Ile Pro Val Val Lys Ala Glu Lys
210 215 220

Thr Ala Met Pro Gly Val Tyr Ser Ala Lys Ile Ile Ala Gly Glu Pro
225 230 235 240

Ala Phe Gln Ile Lys Val Asp Asn Thr Lys Pro Ala Leu Ala Gln Asn
245 250 255

Pro Pro Lys Val Lys Asp Asp Ile Gln Val Ser Ser Phe Leu Ser Ser
260 265 270

Pro Val Ala Asp Thr His His Ala Phe Ile Asp Phe Gly Ser Asp His
275 280 285

Glu Pro Val Tyr Val Ser Leu Ser Lys Ile Val Thr Ala Glu Glu Glu

```
    290                 295                 300

Lys Lys Gln Val Glu Glu Ala Lys Arg Arg Glu Gln Glu Trp Leu Leu
305                 310                 315                 320

Arg His Pro Ile Thr Ala Ala Glu Arg Lys Leu Thr Glu Ile Arg Gln
                325                 330                 335

Val Ile Ser Phe Ala Gln Gln Leu Lys Glu Ser Ser Val Ala Thr Ile
            340                 345                 350

Ser Glu Lys Thr Lys Thr Val Ala Val Tyr Gln Glu Gln Val Asn Thr
        355                 360                 365

Ala Ala Lys Asn Arg Asp Asn Phe Tyr Asn Gln Asn Arg Gly Leu Leu
    370                 375                 380

Ser Ala Gly Ile Thr Gly Gly Pro Gly Tyr Pro Ile Tyr Leu Ala Leu
385                 390                 395                 400

Trp Gln Thr Met Asn Asn Phe His Gln Ala Tyr Phe Arg Ala Asn Asn
                405                 410                 415

Ala Leu Glu Gln Glu Ser His Val Leu Asn Leu Ala Arg Ser Asp Leu
            420                 425                 430

Ala Lys Ala Glu Gln Leu Leu Ala Glu Asn Asn Arg Leu Gln Val Glu
        435                 440                 445

Thr Glu Arg Thr Leu Ala Glu Glu Lys Glu Ile Lys Arg Asn Arg Val
    450                 455                 460

Asn Val Ser Thr Phe Gly Thr Val Gln Thr Gln Leu Ser Lys Leu Leu
465                 470                 475                 480

Ser Asp Phe Tyr Ala Val Thr Ser Leu Ser Gln Ser Val Pro Ser Gly
                485                 490                 495

Ala Leu Ala Ser Phe Ser Tyr Asn Pro Gln Gly Met Ile Gly Ser Gly
            500                 505                 510

Lys Ile Val Gly Lys Asp Val Asp Val Leu Phe Ser Ile Pro Val Lys
        515                 520                 525

Asp Ile Pro Gly Tyr Lys Ser Pro Ile Asn Leu Asp Asp Leu Ala Lys
    530                 535                 540

Lys Asn Gly Ser Leu Asp Leu Pro Ile Arg Leu Ala Phe Ser Asp Glu
545                 550                 555                 560

Asn Gly Glu Arg Val Leu Arg Ala Phe Lys Ala Asp Ser Leu Arg Ile
                565                 570                 575

Pro Ser Ser Val Arg Gly Val Ala Gly Ser Tyr Asp Lys Asn Thr Gly
            580                 585                 590

Ile Phe Ser Ala Glu Ile Asp Gly Val Ser Ser Arg Leu Val Leu Glu
        595                 600                 605

Asn Pro Ala Phe Pro Pro Thr Gly Asn Val Gly Asn Thr Gly Asn Thr
    610                 615                 620

Ala Pro Asp Tyr Lys Ala Leu Leu Asn Thr Gly Val Asp Val Lys Pro
625                 630                 635                 640

Val Asp Lys Ile Thr Val Thr Val Thr Pro Val Ala Asp Pro Val Asp
                645                 650                 655

Ile Asp Asp Tyr Ile Ile Trp Leu Pro Thr Ala Ser Gly Ser Gly Val
            660                 665                 670

Glu Pro Ile Tyr Val Val Phe Asn Ser Asn Pro Tyr Gly Gly Thr Glu
        675                 680                 685

Lys Gly Lys Tyr Ser Lys Arg Tyr Tyr Asn Pro Asp Lys Ala Gly Gly
    690                 695                 700

Pro Ile Leu Glu Leu Asp Trp Lys Asn Val Lys Ile Asp His Ala Gly
705                 710                 715                 720
```

```
Val Asp Asn Val Lys Leu His Thr Gly Arg Phe Lys Ala Ser Val Glu
                725                 730                 735

Asn Lys Val Met Ile Glu Arg Leu Glu Asn Ile Leu Asn Gly Gln Ile
            740                 745                 750

Thr Ala Thr Asp Thr Asp Lys Arg Phe Tyr Thr His Glu Leu Arg Glu
        755                 760                 765

Leu Asn Arg Tyr Arg Asn Leu Gly Ile Lys Asp Gly Glu Val Pro Ser
    770                 775                 780

Ser Ile Gln Glu Glu Ser Ala Val Trp Asn Asp Thr His Thr Ala Thr
785                 790                 795                 800

Leu Glu Asp Tyr Lys Ile Asn Glu Lys Glu Gln Pro Leu Tyr Thr Asp
                805                 810                 815

Ala Ala Leu Gln Ala Ala Tyr Glu Gln Glu Leu Lys Asp Ala Leu Gly
            820                 825                 830

Gly Lys His Gly
        835


<210> SEQ ID NO 276
<211> LENGTH: 2511
<212> TYPE: DNA
<213> ORGANISM: Pectobacterium carotovorum subsp. carotovorum

<400> SEQUENCE: 276

atgattaaat accgtttata tgctccaaat gatggagaca ccatgacagt gagtggtggt     60

ggtggttggg tttcaaacga tgatcgcaaa ggtggtaatg acagggacaa tggcaaaggt    120

ggttctgccg ttgattttag taaaaatcca gaaaagcagg ctatcgttaa tccctatttg    180

gcaatcgcga taccgatgcc ggtctaccct ctttatggaa agctagggtt cacaataaat    240

acgacggcaa ttgagactga actcgcaaat gtcagagcag caattaacac taaacttgca    300

acactcagtg cagtgattgg cagatcactt ccggtcgttg ggcgggtatt tggtgttact    360

gccgccggaa tgtggccttc tagtaccgct cccagtagtc tcgattctat atacaatcaa    420

gcacatcagc aggctttagc ccagttagct gctcaacagg gagtattaaa taaagggtat    480

aacgttacag caatgcctgc aggtttcgtc agcagtttgc ctgttagtga aatcaaatca    540

ttgccaacag ctcccgccag tttactggca caaagtgtga ttaataccga actttcccag    600

cgtcaactgg ctcttactca gcccacgacg aatgcaccag tcgcgaatat tcccgtagtt    660

aaagcagaga aaacagcaat gccaggtgtg tattcagcga aaattattgc tggtgagcct    720

gcattccaaa tcaaggtcga taataccaaa cctgctttgg cacagaatcc gccgaaagta    780

aaagatgata ttcaggtatc ttctttcctt tcctcgccag tagctgatac gcaccatgca    840

tttattgatt ttggcagcga tcatgaaccg gtatacgtgt ctctttcaaa gatcgtgaca    900

gccgaggagg agaaaaaaca ggttgaagag gccaagcgcc gtgagcagga gtggttgttg    960

cgtcatccaa ttacagctgc ggagcgaaaa ttaactgaaa tccgccaagt gatctctttt   1020

gctcaacagc taaaagaaag ctctgtcgca accatttcag aaaaaactaa aactgttgcg   1080

gtttaccaag aacaggtgaa taccgctgca aaaaatcgcg acaattttta taatcaaaat   1140

agaggtctgt taagtgcggg tataactggg ggaccgggat atcctattta tcttgcttta   1200

tggcaaacga tgaataactt tcatcaggct tatttcagag caaataatgc attggaacaa   1260

gagagtcatg ttctgaacct ggctcgttct gatctggcta aggctgagca attgcttgct   1320

gagaataatc gacttcaggt tgaaacggag cgaacgcttg ccgaagaaaa agagataaaa   1380
```

cgcaacaggg ttaatgtatc aacatttggc acagtgcaaa ctcaacttag taaattgctg 1440
tcagattttt atgctgttac atcactttcc caaagtgttc cttcgggggc attagcctct 1500
ttttcatata atccacaagg gatgattggc agcggtaaga ttgttgggaa ggatgtcgat 1560
gttttatttt ccatcccagt aaaagatatt ccgggatata aatctcctat taacttggac 1620
gatttagcca agaaaaatgg aagtctggat cttcccattc gtctggcatt ttctgatgag 1680
aatggagaaa gggttcttcg ggcattcaaa gcggatagtc tgcgaatccc ttcgagtgtc 1740
agaggtgtag cgggcagtta tgacaaaaat acgggtattt ttagtgcaga aattgatggt 1800
gtttcatctc gccttgtact ggaaaaccca gcgtttcctc cgaccggaaa tgtcggtaat 1860
acgggtaata ctgcacctga ctataaagca ttactgaata ctggtgttga tgttaaacct 1920
gttgataaaa tcacagttac ggtaacacca gttgctgatc cagtggatat tgatgactat 1980
ataatctggt tgccaactgc gtctggttct ggcgtggaac ccatttatgt cgtgtttaac 2040
agtaatccgt atggtgggac ggaaaaagga aaatatagca aacgttatta taatccagat 2100
aaggcaggcg gtccgatctt ggagctggat tggaaaaacg ttaagattga ccatgcaggt 2160
gtggacaatg ttaaattaca cacagggcgt ttcaaagcgt cggttgaaaa caaagtgatg 2220
attgaacgtt tggaaaacat actgaatggt caaatcacgg ccacggatac tgacaagcga 2280
ttctatacgc atgaattaag agagttaaac cgctacagaa atttaggcat caaagacggt 2340
gaagtgccta gtagcattca agaagaaagc gctgtttgga acgacacaca cacagcgacg 2400
cttgaagact acaaaattaa tgagaaagag caaccgttgt acactgatgc tgctttgcag 2460
gcagcctacg aacaggaact caaagacgca ttaggaggga aacatggcta a 2511

<210> SEQ ID NO 277
<211> LENGTH: 74
<212> TYPE: PRT
<213> ORGANISM: Bacillus cereus

<400> SEQUENCE: 277

Met Glu Asn Leu Gln Met Leu Thr Glu Glu Glu Leu Met Glu Ile Glu
1 5 10 15

Gly Gly Gly Trp Trp Asn Ser Trp Gly Lys Cys Val Ala Gly Thr Ile
20 25 30

Gly Gly Ala Gly Thr Gly Gly Leu Gly Gly Ala Ala Ala Gly Ser Ala
35 40 45

Val Pro Val Ile Gly Thr Gly Ile Gly Gly Ala Ile Gly Gly Val Ser
50 55 60

Gly Gly Leu Thr Gly Ala Ala Thr Phe Cys
65 70

<210> SEQ ID NO 278
<211> LENGTH: 225
<212> TYPE: DNA
<213> ORGANISM: Bacillus cereus

<400> SEQUENCE: 278
atggaaaact tacaaatgtt aactgaagaa gaattaatgg aaattgaagg tggaggctgg 60
tggaatagct ggggtaaatg tgttgctgga actatcggtg gagctggaac tggtggttta 120
ggtggagctg ctgcaggttc agctgttccg gttattggta ctggtattgg tggcgctatt 180
ggtggagtta gcggtggcct tacaggtgca gctacttttt gctaa 225

<210> SEQ ID NO 279

<211> LENGTH: 78
<212> TYPE: PRT
<213> ORGANISM: Streptoverticillium griseoverticillatum

<400> SEQUENCE: 279

Met Thr Ala Ser Ile Leu Gln Gln Ser Val Val Asp Ala Asp Phe Arg
1               5                   10                  15

Ala Ala Leu Leu Glu Asn Pro Ala Ala Phe Gly Ala Ser Ala Ala Ala
            20                  25                  30

Leu Pro Thr Pro Val Glu Ala Gln Asp Gln Ala Ser Leu Asp Phe Trp
        35                  40                  45

Thr Lys Asp Ile Ala Ala Thr Glu Ala Phe Ala Cys Arg Gln Ser Cys
    50                  55                  60

Ser Phe Gly Pro Phe Thr Phe Val Cys Asp Gly Asn Thr Lys
65                  70                  75

<210> SEQ ID NO 280
<211> LENGTH: 237
<212> TYPE: DNA
<213> ORGANISM: Streptoverticillium griseoverticillatum

<400> SEQUENCE: 280
atgaccgctt ccattcttca gcagtccgtc gtggacgccg acttccgcgc ggcgctgctt     60
gagaaccccg ccgccttcgg cgcttccgcc gcggccctgc ccacgcccgt cgaggcccag    120
gaccaggcgt cccttgactt ctggaccaag gacatcgccg ccacggaagc cttcgcctgc    180
cgccagagct gcagcttcgg cccgttcacc ttcgtgtgcg acggcaacac caagtaa       237

<210> SEQ ID NO 281
<211> LENGTH: 76
<212> TYPE: PRT
<213> ORGANISM: Geobacillus kaustophilus

<400> SEQUENCE: 281

Met Ser Leu Leu Ala Leu Val Ala Gly Thr Leu Gly Val Ser Gln Ser
1               5                   10                  15

Ile Ala Thr Thr Val Val Ser Ile Val Leu Thr Gly Ser Thr Leu Ile
            20                  25                  30

Ser Ile Ile Leu Gly Ile Thr Ala Ile Leu Ser Gly Gly Val Asp Ala
        35                  40                  45

Ile Leu Glu Ile Gly Trp Ser Ala Phe Val Ala Thr Val Lys Lys Ile
    50                  55                  60

Val Ala Glu Arg Gly Lys Ala Ala Ala Ile Ala Trp
65                  70                  75

<210> SEQ ID NO 282
<211> LENGTH: 231
<212> TYPE: DNA
<213> ORGANISM: Geobacillus kaustophilus

<400> SEQUENCE: 282
atgagtttgc tggcgcttgt tgccgggacg ctcggcgtgt cacagtcaat cgcgacgacg     60
gttgtttcga ttgtgttgac cggctccact ctcatttcta ttattcttgg gatcaccgct    120
attttgtcag gtggagtcga cgccattttg gaaattgggt ggtcagcttt tgtcgcgacg    180
gtgaaaaaaa tagtggcgga acgaggaaaa gcggcagcga ttgcatggta a             231

<210> SEQ ID NO 283
<211> LENGTH: 309

<212> TYPE: PRT
<213> ORGANISM: Clostridium tyrobutyricum

<400> SEQUENCE: 283

Met Arg Lys Val Phe Leu Arg Ser Ile Ile Ser Thr Leu Val Met Cys
1 5 10 15

Ala Phe Val Ser Ser Ser Phe Ser Val Asn Ala Asp Glu Ser Lys Pro
20 25 30

Asn Asp Glu Lys Ile Ile Asn Asn Ile Glu Asn Val Thr Thr Thr Lys
35 40 45

Asp Ile Val Lys Ser Asn Lys Asn Asn Ile Val Tyr Leu Asp Glu Gly
50 55 60

Val Met Ser Ile Pro Leu Ser Gly Arg Lys Pro Ile Ala Ile Lys Asp
65 70 75 80

Asp Asn Asn Lys Glu Asp Leu Thr Val Thr Leu Pro Ile Lys Asn Thr
85 90 95

Gly Asp Ile Ser Lys Ile Ser Ser Asn Gly Thr Ile Leu Tyr Lys Asn
100 105 110

Asn Ser Ser Asn Ser Ser Asn Ile Ala Leu Gln Pro Lys Asn Asp Gly
115 120 125

Phe Lys Ala Leu Ile Asn Ile Asn Asp Lys Leu Ala Asn Lys Glu Tyr
130 135 140

Glu Phe Thr Phe Asn Leu Pro Lys Asn Ser Lys Leu Ile Ser Ala Ala
145 150 155 160

Thr Tyr Leu Gly Lys Glu Tyr Asp Thr Lys Glu Val Phe Val Val Asp
165 170 175

Lys Asn Asn Ile Ile Thr Ser Ile Ile Ser Pro Ala Trp Ala Lys Asp
180 185 190

Ala Asn Gly His Asn Val Ser Thr Tyr Tyr Lys Ile Val Ser Asn Asn
195 200 205

Lys Leu Val Gln Val Val Glu Phe Thr Glu Asn Thr Ala Phe Pro Val
210 215 220

Val Ala Asp Pro Asn Trp Thr Lys Ile Gly Lys Cys Ala Gly Ser Ile
225 230 235 240

Ala Trp Ala Ile Gly Ser Gly Leu Phe Gly Gly Ala Lys Leu Ile Lys
245 250 255

Ile Lys Lys Tyr Ile Ala Glu Leu Gly Gly Leu Gln Lys Ala Ala Lys
260 265 270

Leu Leu Val Gly Ala Thr Thr Trp Glu Glu Lys Leu His Ala Gly Gly
275 280 285

Tyr Ala Leu Ile Asn Leu Ala Ala Glu Leu Thr Gly Val Ala Gly Ile
290 295 300

Gln Ala Asn Cys Phe
305

<210> SEQ ID NO 284
<211> LENGTH: 930
<212> TYPE: DNA
<213> ORGANISM: Clostridium tyrobutyricum

<400> SEQUENCE: 284
ttgagaaaag tatttttaag atcaataatt tcaacattag ttatgtgtgc atttgtttca 60
agcagctttt cagtaaatgc ggatgaaagc aaaccaaatg atgaaaaaat aattaataac 120
atagaaaacg ttactactac taaagatatt gtaaaaagta ataaaaataa tattgtatat 180

```
ttagatgaag gtgtaatgag tattccattg tctgggagaa aacccattgc tattaaagat    240

gataataata aagaagattt aactgttaca ttacctatta agaatactgg agatatatct    300

aaaattagta gtaatggtac tattctgtat aaaaataata gtagtaattc atctaatata    360

gctttacaac ctaaaaatga tggatttaag gctttaataa atattaatga taagttagct    420

aataaagaat atgaatttac atttaattta cccaaaaaca gtaaattaat tagtgctgcc    480

acatatttgg gtaaagaata tgatacaaaa gaagtatttg tagtagacaa aaataatata    540

attacgagta ttattagtcc agcttgggct aaagatgcaa atggacataa tgtttctact    600

tattataaga tagtatcgaa taataaatta gtacaagttg ttgaattcac agaaaatact    660

gcattcccgg tggtagctga tcctaattgg actaaaattg ggaaatgcgc tgggtcaata    720

gcatgggcta taggttctgg ccttttggt ggagcaaagc taattaaaat aaaaaaatat     780

atagcagagc ttggaggact tcaaaaagca gctaaattat tagttggtgc aaccacttgg    840

gaagaaaaat tacacgcagg cggttatgca ttaattaact tagctgctga gctaacaggt    900

gtagcaggta tacaagcaaa ttgtttttaa                                     930
```

<210> SEQ ID NO 285
<211> LENGTH: 62
<212> TYPE: PRT
<213> ORGANISM: Bacillus coagulans

<400> SEQUENCE: 285

```
Met Lys Lys Ile Glu Lys Leu Thr Glu Lys Glu Met Ala Asn Ile Ile
1               5                   10                  15

Gly Gly Lys Tyr Tyr Gly Asn Gly Val Thr Cys Gly Lys His Ser Cys
            20                  25                  30

Ser Val Asp Trp Gly Lys Ala Thr Thr Cys Ile Ile Asn Asn Gly Ala
        35                  40                  45

Met Ala Trp Ala Thr Gly Gly His Gln Gly Thr His Lys Cys
    50                  55                  60
```

<210> SEQ ID NO 286
<211> LENGTH: 189
<212> TYPE: DNA
<213> ORGANISM: Bacillus coagulans

<400> SEQUENCE: 286

```
atgaaaaaaa ttgaaaaatt aactgaaaaa gaaatggcca atatcattgg tggtaaatac     60

tacggtaatg gggttacttg tggcaaacat tcctgctctg ttgactgggg taaggctacc    120

acctgcataa tcaataatgg agctatggca tgggctactg gtggacatca aggtactcat    180

aaatgctag                                                            189
```

<210> SEQ ID NO 287
<211> LENGTH: 490
<212> TYPE: PRT
<213> ORGANISM: Escherichia coli

<400> SEQUENCE: 287

```
Met Asp Lys Val Thr Asp Asn Ser Pro Asp Val Glu Ser Thr Glu Ser
1               5                   10                  15

Thr Glu Gly Ser Phe Pro Thr Val Gly Val Asp Thr Gly Asp Thr Ile
            20                  25                  30

Thr Ala Thr Leu Ala Thr Gly Thr Glu Asn Val Gly Gly Gly Gly Gly
        35                  40                  45
```

-continued

```
Ala Phe Gly Gly Ala Ser Glu Ser Ser Ala Ala Ile His Ala Thr Ala
    50                  55                  60

Lys Trp Ser Thr Ala Gln Leu Lys Lys His Gln Ala Glu Gln Ala Ala
65                  70                  75                  80

Arg Ala Ala Ala Ala Glu Ala Ala Leu Ala Lys Ala Lys Ser Gln Arg
                85                  90                  95

Asp Ala Leu Thr Gln Arg Leu Lys Asp Ile Val Asn Asp Ala Leu Arg
            100                 105                 110

Ala Asn Ala Ala Arg Ser Pro Ser Val Thr Asp Leu Ala His Ala Asn
        115                 120                 125

Asn Met Ala Met Gln Ala Glu Ala Glu Arg Leu Arg Leu Ala Lys Ala
    130                 135                 140

Glu Gln Lys Ala Arg Glu Glu Ala Glu Ala Ala Glu Lys Ala Leu Arg
145                 150                 155                 160

Glu Ala Glu Arg Gln Arg Asp Glu Ile Ala Arg Gln Gln Ala Glu Thr
                165                 170                 175

Ala His Leu Leu Ala Met Ala Glu Ala Ala Glu Ala Glu Lys Asn Arg
            180                 185                 190

Gln Asp Ser Leu Asp Glu Glu His Arg Ala Val Glu Val Ala Glu Lys
        195                 200                 205

Lys Leu Ala Glu Ala Lys Ala Glu Leu Ala Lys Ala Glu Ser Asp Val
    210                 215                 220

Gln Ser Lys Gln Ala Ile Val Ser Arg Val Ala Gly Glu Leu Glu Asn
225                 230                 235                 240

Ala Gln Lys Ser Val Asp Val Lys Val Thr Gly Phe Pro Gly Trp Arg
                245                 250                 255

Asp Val Gln Lys Lys Leu Glu Arg Gln Leu Gln Asp Lys Lys Asn Glu
            260                 265                 270

Tyr Ser Ser Val Thr Asn Ala Leu Asn Ser Ala Val Ser Ile Arg Asp
        275                 280                 285

Ala Lys Lys Thr Glu Val Gln Asn Ala Glu Ile Lys Leu Lys Glu Ala
    290                 295                 300

Lys Asp Ala Leu Glu Lys Ser Gln Val Lys Asp Ser Val Asp Thr Met
305                 310                 315                 320

Val Gly Phe Tyr Gln Tyr Ile Thr Glu Gln Tyr Gly Glu Lys Tyr Ser
                325                 330                 335

Arg Ile Ala Gln Asp Leu Ala Glu Lys Ala Lys Gly Ser Lys Phe Asn
            340                 345                 350

Ser Val Asp Glu Ala Leu Ala Ala Phe Glu Lys Tyr Lys Asn Val Leu
        355                 360                 365

Asp Lys Lys Phe Ser Lys Val Asp Arg Asp Asp Ile Phe Asn Ala Leu
    370                 375                 380

Glu Ser Ile Thr Tyr Asp Glu Trp Ala Lys His Leu Glu Lys Ile Ser
385                 390                 395                 400

Arg Ala Leu Lys Val Thr Gly Tyr Leu Ser Phe Gly Tyr Asp Val Trp
                405                 410                 415

Asp Gly Thr Leu Lys Gly Leu Lys Thr Gly Asp Trp Lys Pro Leu Phe
            420                 425                 430

Val Thr Leu Glu Lys Ser Ala Val Asp Phe Gly Val Ala Lys Ile Val
        435                 440                 445

Ala Leu Met Phe Ser Phe Ile Val Gly Ala Pro Leu Gly Phe Trp Gly
    450                 455                 460

Ile Ala Ile Ile Thr Gly Ile Val Ser Ser Tyr Ile Gly Asp Asp Glu
```

```
465                 470                 475                 480

Leu Asn Lys Leu Asn Glu Leu Leu Gly Ile
                485                 490
```

<210> SEQ ID NO 288
<211> LENGTH: 1473
<212> TYPE: DNA
<213> ORGANISM: Escherichia coli

<400> SEQUENCE: 288

```
atggataaag tcactgataa ttctccagat gtggagagca cagaatctac tgaggggtca      60

ttcccaactg ttggggttga tactggcgat acgattacag cgacgcttgc aactggaact     120

gaaaatgttg gtggaggcgg tggagcattt ggtggggcca gtgaaagttc tgctgcgata     180

catgcaaccg ctaaatggtc taccgcgcag ttgaaaaaac atcaggctga acaggctgcc     240

cgtgctgctg cggctgaggc agcattggca aaagcgaaat ctcagcgtga tgccctgact     300

caacgtctca aggatattgt taatgacgct ttacgtgcta atgccgctcg tagtccatca     360

gtaactgacc ttgctcatgc caataatatg gcaatgcagg cagaggctga gcgtttgcgc     420

cttgcgaagg cagagcaaaa agcccgtgaa gaagctgaag cagcagaaaa agcgctccgg     480

gaagcagaac gccaacgtga tgagattgcc cgccaacagg ctgaaaccgc gcatttgtta     540

gcaatggcgg aggcagcaga ggctgagaaa aatcgacagg attctcttga tgaagagcat     600

cgggctgtgg aagtggcaga gaagaagctg gctgaggcta aagctgaact ggcgaaggcc     660

gaaagcgatg tacagagtaa gcaagcgatt gtttccagag ttgcagggga gcttgaaaac     720

gctcaaaaaa gtgttgatgt gaaggttacc ggatttcctg gatggcgtga tgttcagaaa     780

aaactggaga gacaattgca ggataagaag aatgaatatt cgtcagtgac gaatgctctt     840

aattctgctg ttagcattag agatgctaaa aaaacagaag ttcagaatgc tgagataaaa     900

ttaaaagaag ctaaggatgc tcttgagaag agtcaggtaa aagactctgt tgatactatg     960

gttgggtttt atcaatatat aaccgaacaa tatggggaaa aatattccag aatagctcag    1020

gatttagctg aaaaggcgaa gggtagtaaa tttaatagtg ttgatgaagc acttgctgca    1080

tttgaaaagt ataaaaatgt actggataag aaattcagta aggttgatag ggatgatatt    1140

tttaatgctt tagagtctat tacttatgat gagtgggcca agcatctaga aaagatctct    1200

agggctctta aggttactgg atatttgtct ttcgggtatg atgtatggga tggtacccta    1260

aagggattaa aaacaggaga ctggaagcct ttatttgtca ctctggagaa gagcgcggta    1320

gatttcggcg tggcaaaaat tgtggcatta atgtttagtt ttattgttgg tgcgcctctt    1380

ggcttctggg gaattgcaat tatcacaggt attgtttctt cttacatagg ggatgatgag    1440

ttgaacaagc ttaatgaatt actaggtatt taa                                 1473
```

<210> SEQ ID NO 289
<211> LENGTH: 522
<212> TYPE: PRT
<213> ORGANISM: Escherichia coli

<400> SEQUENCE: 289

```
Met Glu Thr Ala Val Ala Tyr Tyr Lys Asp Gly Val Pro Tyr Asp Asp
1               5                   10                  15

Lys Gly Gln Val Ile Ile Thr Leu Leu Asn Gly Thr Pro Asp Gly Ser
            20                  25                  30

Gly Ser Gly Gly Gly Gly Gly Lys Gly Gly Ser Lys Ser Glu Ser Ser
        35                  40                  45
```

-continued

```
Ala Ala Ile His Ala Thr Ala Lys Trp Ser Thr Ala Gln Leu Lys Lys
    50                  55                  60

Thr Gln Ala Glu Gln Ala Ala Arg Ala Lys Ala Ala Ala Glu Ala Gln
65                  70                  75                  80

Ala Lys Ala Lys Ala Asn Arg Asp Ala Leu Thr Gln Arg Leu Lys Asp
                85                  90                  95

Ile Val Asn Glu Ala Leu Arg His Asn Ala Ser Arg Thr Pro Ser Ala
            100                 105                 110

Thr Glu Leu Ala His Ala Asn Asn Ala Ala Met Gln Ala Glu Asp Glu
        115                 120                 125

Arg Leu Arg Leu Ala Lys Ala Glu Glu Lys Ala Arg Lys Glu Ala Glu
    130                 135                 140

Ala Ala Glu Lys Ala Phe Gln Glu Ala Glu Gln Arg Arg Lys Glu Ile
145                 150                 155                 160

Glu Arg Glu Lys Ala Glu Thr Glu Arg Gln Leu Lys Leu Ala Glu Ala
                165                 170                 175

Glu Glu Lys Arg Leu Ala Ala Leu Ser Glu Glu Ala Lys Ala Val Glu
            180                 185                 190

Ile Ala Gln Lys Lys Leu Ser Ala Ala Gln Ser Glu Val Val Lys Met
        195                 200                 205

Asp Gly Glu Ile Lys Thr Leu Asn Ser Arg Leu Ser Ser Ser Ile His
    210                 215                 220

Ala Arg Asp Ala Glu Met Lys Thr Leu Ala Gly Lys Arg Asn Glu Leu
225                 230                 235                 240

Ala Gln Ala Ser Ala Lys Tyr Lys Glu Leu Asp Glu Leu Val Lys Lys
                245                 250                 255

Leu Ser Pro Arg Ala Asn Asp Pro Leu Gln Asn Arg Pro Phe Phe Glu
            260                 265                 270

Ala Thr Arg Arg Arg Val Gly Ala Gly Lys Ile Arg Glu Glu Lys Gln
        275                 280                 285

Lys Gln Val Thr Ala Ser Glu Thr Arg Ile Asn Arg Ile Asn Ala Asp
    290                 295                 300

Ile Thr Gln Ile Gln Lys Ala Ile Ser Gln Val Ser Asn Asn Arg Asn
305                 310                 315                 320

Ala Gly Ile Ala Arg Val His Glu Ala Glu Glu Asn Leu Lys Lys Ala
                325                 330                 335

Gln Asn Asn Leu Leu Asn Ser Gln Ile Lys Asp Ala Val Asp Ala Thr
            340                 345                 350

Val Ser Phe Tyr Gln Thr Leu Thr Glu Lys Tyr Gly Glu Lys Tyr Ser
        355                 360                 365

Lys Met Ala Gln Glu Leu Ala Asp Lys Ser Lys Gly Lys Lys Ile Gly
    370                 375                 380

Asn Val Asn Glu Ala Leu Ala Ala Phe Glu Lys Tyr Lys Asp Val Leu
385                 390                 395                 400

Asn Lys Lys Phe Ser Lys Ala Asp Arg Asp Ala Ile Phe Asn Ala Leu
                405                 410                 415

Ala Ser Val Lys Tyr Asp Asp Trp Ala Lys His Leu Asp Gln Phe Ala
            420                 425                 430

Lys Tyr Leu Lys Ile Thr Gly His Val Ser Phe Gly Tyr Asp Val Val
        435                 440                 445

Ser Asp Ile Leu Lys Ile Lys Asp Thr Gly Asp Trp Lys Pro Leu Phe
    450                 455                 460
```

```
Leu Thr Leu Glu Lys Lys Ala Ala Asp Ala Gly Val Ser Tyr Val Val
465                 470                 475                 480

Ala Leu Leu Phe Ser Leu Leu Ala Gly Thr Thr Leu Gly Ile Trp Gly
                485                 490                 495

Ile Ala Ile Val Thr Gly Ile Leu Cys Ser Tyr Ile Asp Lys Asn Lys
            500                 505                 510

Leu Asn Thr Ile Asn Glu Val Leu Gly Ile
        515                 520


<210> SEQ ID NO 290
<211> LENGTH: 1569
<212> TYPE: DNA
<213> ORGANISM: Escherichia coli

<400> SEQUENCE: 290

atggaaaccg cggtagcgta ctataaagat ggtgttcctt atgatgataa gggacaggta     60

attattactc ttttgaatgg tactcctgac gggagtggct ctggcggcgg aggtggaaaa    120

ggaggcagta aaagtgaaag ttctgcagct attcatgcaa ctgctaaatg gtctactgct    180

caattaaaga aaacacaggc agagcaggct gcccgggcaa aagctgcagc ggaagcacag    240

gcgaaagcaa aggcaaacag ggatgcgctg actcagcgcc tgaaggatat cgtgaatgag    300

gctcttcgtc acaatgcctc acgtacgcct tcagcaacag agcttgctca tgctaataat    360

gcagctatgc aggcggaaga cgagcgtttg cgccttgcga aagcagaaga aaaagcccgt    420

aaagaagcgg aagcagcaga aaaggctttt caggaagcag aacaacgacg taaagagatt    480

gaacgggaga aggctgaaac agaacgccag ttgaaactgg ctgaagctga agagaaacga    540

ctggctgcat tgagtgaaga agctaaagct gttgagatcg cccaaaaaaa actttctgct    600

gcacaatctg aagtggtgaa aatggatgga gagattaaga ctctcaattc tcgtttaagc    660

tccagtatcc atgcccgtga tgcagaaatg aaaacgctcg ctggaaaacg aaatgaactg    720

gctcaggcat ccgctaaata taaagaactg gatgagctgg tcaaaaaact atcaccaaga    780

gccaatgatc cgcttcagaa ccgtcctttt tttgaagcaa ccagacgacg ggttggggcc    840

ggtaagatta gagaagaaaa acaaaaacag gtaacagcat cagaaacacg tattaaccgg    900

ataaatgctg atataactca gatccagaag gctatttctc aggtcagtaa taatcgtaat    960

gccggtatcg ctcgtgttca tgaagctgaa gaaaatttga aaaaagcaca gaataatctc   1020

cttaattcac agattaagga tgctgttgat gcaacagtta gcttttatca aacgctgact   1080

gaaaaatatg gtgaaaaata ttcgaaaatg gcacaggaac ttgctgataa gtctaaaggt   1140

aagaaaatcg gcaatgtgaa tgaagctctc gctgcttttg aaaaatacaa ggatgtttta   1200

aataagaaat tcagcaaagc cgatcgtgat gctattttta atgcgttggc atcggtgaag   1260

tatgatgact gggctaaaca tttagatcag tttgccaagt acttgaagat tacggggcat   1320

gtttcttttg gatatgatgt ggtatctgat atcctaaaaa ttaaggatac aggtgactgg   1380

aagccactat ttcttacatt agagaagaaa gctgcagatg caggggtgag ttatgttgtt   1440

gctttacttt ttagcttgct tgctggaact acattaggta tttggggtat tgctattgtt   1500

acaggaattc tatgctccta tattgataag aataaactta atactataaa tgaggtgtta   1560

gggatttaa                                                            1569


<210> SEQ ID NO 291
<211> LENGTH: 626
<212> TYPE: PRT
<213> ORGANISM: Escherichia coli
```

<400> SEQUENCE: 291

Met Ser Asp Pro Val Arg Ile Thr Asn Pro Gly Ala Glu Ser Leu Gly
1               5                   10                  15

Tyr Asp Ser Asp Gly His Glu Ile Met Ala Val Asp Ile Tyr Val Asn
            20                  25                  30

Pro Pro Arg Val Asp Val Phe His Gly Thr Pro Pro Ala Trp Ser Ser
        35                  40                  45

Phe Gly Asn Lys Thr Ile Trp Gly Gly Asn Glu Trp Val Asp Asp Ser
    50                  55                  60

Pro Thr Arg Ser Asp Ile Glu Lys Arg Asp Lys Glu Ile Thr Ala Tyr
65                  70                  75                  80

Lys Asn Thr Leu Ser Ala Gln Gln Lys Glu Asn Glu Asn Lys Arg Thr
                85                  90                  95

Glu Ala Gly Lys Arg Leu Ser Ala Ala Ile Ala Ala Arg Glu Lys Asp
            100                 105                 110

Glu Asn Thr Leu Lys Thr Leu Arg Ala Gly Asn Ala Asp Ala Ala Asp
        115                 120                 125

Ile Thr Arg Gln Glu Phe Arg Leu Leu Gln Ala Glu Leu Arg Glu Tyr
    130                 135                 140

Gly Phe Arg Thr Glu Ile Ala Gly Tyr Asp Ala Leu Arg Leu His Thr
145                 150                 155                 160

Glu Ser Arg Met Leu Phe Ala Asp Ala Asp Ser Leu Arg Ile Ser Pro
                165                 170                 175

Arg Glu Ala Arg Ser Leu Ile Glu Gln Ala Glu Lys Arg Gln Lys Asp
            180                 185                 190

Ala Gln Asn Ala Asp Lys Lys Ala Ala Asp Met Leu Ala Glu Tyr Glu
        195                 200                 205

Arg Arg Lys Gly Ile Leu Asp Thr Arg Leu Ser Glu Leu Glu Lys Asn
    210                 215                 220

Gly Gly Ala Ala Leu Ala Val Leu Asp Ala Gln Gln Ala Arg Leu Leu
225                 230                 235                 240

Gly Gln Gln Thr Arg Asn Asp Arg Ala Ile Ser Glu Ala Arg Asn Lys
                245                 250                 255

Leu Ser Ser Val Thr Glu Ser Leu Asn Thr Ala Arg Asn Ala Leu Thr
            260                 265                 270

Arg Ala Glu Gln Gln Leu Thr Gln Gln Lys Asn Thr Pro Asp Gly Lys
        275                 280                 285

Thr Ile Val Ser Pro Glu Lys Phe Pro Gly Arg Ser Ser Thr Asn His
    290                 295                 300

Ser Ile Val Val Ser Gly Asp Pro Arg Phe Ala Gly Thr Ile Lys Ile
305                 310                 315                 320

Thr Thr Ser Ala Val Ile Asp Asn Arg Ala Asn Leu Asn Tyr Leu Leu
                325                 330                 335

Ser His Ser Gly Leu Asp Tyr Lys Arg Asn Ile Leu Asn Asp Arg Asn
            340                 345                 350

Pro Val Val Thr Glu Asp Val Glu Gly Asp Lys Lys Ile Tyr Asn Ala
        355                 360                 365

Glu Val Ala Glu Trp Asp Lys Leu Arg Gln Arg Leu Leu Asp Ala Arg
    370                 375                 380

Asn Lys Ile Thr Ser Ala Glu Ser Ala Val Asn Ser Ala Arg Asn Asn
385                 390                 395                 400

Leu Ser Ala Arg Thr Asn Glu Gln Lys His Ala Asn Asp Ala Leu Asn

```
                405                 410                 415

Ala Leu Leu Lys Glu Lys Glu Asn Ile Arg Asn Gln Leu Ser Gly Ile
            420                 425                 430

Asn Gln Lys Ile Ala Glu Glu Lys Arg Lys Gln Asp Glu Leu Lys Ala
        435                 440                 445

Thr Lys Asp Ala Ile Asn Phe Thr Thr Glu Phe Leu Lys Ser Val Ser
    450                 455                 460

Glu Lys Tyr Gly Ala Lys Ala Glu Gln Leu Ala Arg Glu Met Ala Gly
465                 470                 475                 480

Gln Ala Lys Gly Lys Lys Ile Arg Asn Val Glu Glu Ala Leu Lys Thr
                485                 490                 495

Tyr Glu Lys Tyr Arg Ala Asp Ile Asn Lys Lys Ile Asn Ala Lys Asp
            500                 505                 510

Arg Ala Ala Ile Ala Ala Ala Leu Glu Ser Val Lys Leu Ser Asp Ile
        515                 520                 525

Ser Ser Asn Leu Asn Arg Phe Ser Arg Gly Leu Gly Tyr Ala Gly Lys
    530                 535                 540

Phe Thr Ser Leu Ala Asp Trp Ile Thr Glu Phe Gly Lys Ala Val Arg
545                 550                 555                 560

Thr Glu Asn Trp Arg Pro Leu Phe Val Lys Thr Glu Thr Ile Ile Ala
                565                 570                 575

Gly Asn Ala Ala Thr Ala Leu Val Ala Leu Val Phe Ser Ile Leu Thr
            580                 585                 590

Gly Ser Ala Leu Gly Ile Ile Gly Tyr Gly Leu Leu Met Ala Val Thr
        595                 600                 605

Gly Ala Leu Ile Asp Glu Ser Leu Val Glu Lys Ala Asn Lys Phe Trp
    610                 615                 620

Gly Ile
625
```

<210> SEQ ID NO 292
<211> LENGTH: 1881
<212> TYPE: DNA
<213> ORGANISM: Escherichia coli

<400> SEQUENCE: 292

```
atgtctgacc ctgtacgtat tacaaatccc ggtgcagaat cgctggggta tgattcagat     60

ggccatgaaa ttatggccgt tgatatttat gtaaaccctc cacgtgtcga tgtctttcat    120

ggtaccccgc ctgcatggag ttccttcggg aacaaaacca tctggggcgg aaacgagtgg    180

gttgatgatt ccccaacccg aagtgatatc gaaaaaaggg acaaggaaat cacagcgtac    240

aaaaacacgc tcagcgcgca gcagaaagag aatgagaata agcgtactga agccggaaaa    300

cgcctctctg cggcgattgc tgcaagggaa aaagatgaaa acacactgaa aacactccgt    360

gccggaaacg cagatgccgc tgatattaca cgacaggagt tcagactcct gcaggcagag    420

ctgagagaat acggattccg tactgaaatc gccggatatg acgccctccg gctgcataca    480

gagagccgga tgctgtttgc tgatgctgat tctcttcgta tatctccccg ggaggccagg    540

tcgttaatcg aacaggctga aaaacggcag aaggatgcgc agaacgcaga caagaaggcc    600

gctgatatgc ttgctgaata cgagcgcaga aaaggtattc tggacacccg gttgtcagag    660

ctggaaaaaa atggcggggc agcccttgcc gttcttgatg cacaacaggc ccgtctgctc    720

gggcagcaga cacggaatga cagggccatt tcagaggccc ggaataaact cagttcagtg    780

acggaatcgc ttaacacggc ccgtaatgca ttaaccagag ctgaacaaca gctgacgcaa    840
```

```
cagaaaaaca cgcctgacgg caaaacgata gtttcccctg aaaaattccc ggggcgttca    900

tcaacaaatg attctattgt tgtgagcggt gatccgagat ttgccggtac gataaaaatc    960

acaaccagcg cagtcatcga taaccgtgca aacctgaatt atcttctgag ccattccggt   1020

ctggactata aacgcaatat tctgaatgac cggaatccgg tggtgacaga ggatgtggaa   1080

ggtgacaaga aaatttataa tgctgaagtt gctgaatggg ataagttacg gcaaagattg   1140

cttgatgcca gaaataaaat cacctctgct gaatctgcgg taaattcggc gagaaataac   1200

ctcagtgcca gaacaaatga gcaaaagcat gcaaatgacg ctcttaatgc cctgttgaag   1260

gaaaaagaga atatccgtaa ccagctttcc ggcatcaatc agaagatagc ggaagagaaa   1320

agaaaacagg atgaactgaa ggcaacgaaa gacgcaatta atttcacaac agagttcctg   1380

aaatcagttt cagaaaaata tggtgcaaaa gctgagcagt tagccagaga gatggccggg   1440

caggctaaag ggaagaaaat acgtaatgtt gaagaggcat taaaaacgta tgaaaagtac   1500

cgggctgaca ttaacaaaaa aattaatgca aaagatcgtg cagcgattgc cgcagccctt   1560

gagtctgtga agctgtctga tatatcgtct aatctgaaca gattcagtcg gggactggga   1620

tatgcaggaa aatttacaag tcttgctgac tggatcactg agtttggtaa ggctgtccgg   1680

acagagaact ggcgtcctct tttgttaaa acagaaacca tcatagcagg caatgccgca    1740

acggctcttg tggcactggt cttcagtatt cttaccggaa gcgctttagg cattatcggg   1800

tatggtttac tgatggctgt caccggtgcg ctgattgatg aatcgcttgt ggaaaaagcg   1860

aataagttct ggggtattta a                                              1881
```

<210> SEQ ID NO 293
<211> LENGTH: 626
<212> TYPE: PRT
<213> ORGANISM: Escherichia coli

<400> SEQUENCE: 293

```
Met Ser Asp Pro Val Arg Ile Thr Asn Pro Gly Ala Glu Ser Leu Gly
1               5                   10                  15

Tyr Asp Ser Asp Gly His Glu Ile Met Ala Val Asp Ile Tyr Val Asn
            20                  25                  30

Pro Pro Arg Val Asp Val Phe His Gly Thr Pro Pro Ala Trp Ser Ser
        35                  40                  45

Phe Gly Asn Lys Thr Ile Trp Gly Gly Asn Glu Trp Val Asp Asp Ser
    50                  55                  60

Pro Thr Arg Ser Asp Ile Glu Lys Arg Asp Lys Glu Ile Thr Ala Tyr
65                  70                  75                  80

Lys Asn Thr Leu Ser Ala Gln Gln Lys Glu Asn Glu Asn Lys Arg Thr
                85                  90                  95

Glu Ala Gly Lys Arg Leu Ser Ala Ala Ile Ala Ala Arg Glu Lys Asp
            100                 105                 110

Glu Asn Thr Leu Lys Thr Leu Arg Ala Gly Asn Ala Asp Ala Ala Asp
        115                 120                 125

Ile Thr Arg Gln Glu Phe Arg Leu Leu Gln Ala Glu Leu Arg Glu Tyr
    130                 135                 140

Gly Phe Arg Thr Glu Ile Ala Gly Tyr Asp Ala Leu Arg Leu His Thr
145                 150                 155                 160

Glu Ser Arg Met Leu Phe Ala Asp Ala Asp Ser Leu Arg Ile Ser Pro
                165                 170                 175

Arg Glu Ala Arg Ser Leu Ile Glu Gln Ala Glu Lys Arg Gln Lys Asp
```

-continued

```
            180                 185                 190

Ala Gln Asn Ala Asp Lys Lys Ala Ala Asp Met Leu Ala Glu Tyr Glu
        195                 200                 205

Arg Arg Lys Gly Ile Leu Asp Thr Arg Leu Ser Glu Leu Glu Lys Asn
    210                 215                 220

Gly Gly Ala Ala Leu Ala Val Leu Asp Ala Gln Gln Ala Arg Leu Leu
225                 230                 235                 240

Gly Gln Gln Thr Arg Asn Asp Arg Ala Ile Ser Glu Ala Arg Asn Lys
                245                 250                 255

Leu Ser Ser Val Thr Glu Ser Leu Lys Thr Ala Arg Asn Ala Leu Thr
            260                 265                 270

Arg Ala Glu Gln Gln Leu Thr Gln Gln Lys Asn Thr Pro Asp Gly Lys
        275                 280                 285

Thr Ile Val Ser Pro Glu Lys Phe Pro Gly Arg Ser Ser Thr Asn His
    290                 295                 300

Ser Ile Val Val Ser Gly Asp Pro Arg Phe Ala Gly Thr Ile Lys Ile
305                 310                 315                 320

Thr Thr Ser Ala Val Ile Asp Asn Arg Ala Asn Leu Asn Tyr Leu Leu
                325                 330                 335

Thr His Ser Gly Leu Asp Tyr Lys Arg Asn Ile Leu Asn Asp Arg Asn
            340                 345                 350

Pro Val Val Thr Glu Asp Val Glu Gly Asp Lys Lys Ile Tyr Asn Ala
        355                 360                 365

Glu Val Ala Glu Trp Asp Lys Leu Arg Gln Arg Leu Leu Asp Ala Arg
    370                 375                 380

Asn Lys Ile Thr Ser Ala Glu Ser Ala Ile Asn Ser Ala Arg Asn Asn
385                 390                 395                 400

Val Ser Ala Arg Thr Asn Glu Gln Lys His Ala Asn Asp Ala Leu Asn
                405                 410                 415

Ala Leu Leu Lys Glu Lys Glu Asn Ile Arg Ser Gln Leu Ala Asp Ile
            420                 425                 430

Asn Gln Lys Ile Ala Glu Glu Lys Arg Lys Arg Asp Glu Ile Asn Met
        435                 440                 445

Val Lys Asp Ala Ile Lys Leu Thr Ser Asp Phe Tyr Arg Thr Ile Tyr
    450                 455                 460

Asp Glu Phe Gly Lys Gln Ala Ser Glu Leu Ala Lys Glu Leu Ala Ser
465                 470                 475                 480

Val Ser Gln Gly Lys Gln Ile Lys Ser Val Asp Asp Ala Leu Asn Ala
                485                 490                 495

Phe Asp Lys Phe Arg Asn Asn Leu Asn Lys Lys Tyr Asn Ile Gln Asp
            500                 505                 510

Arg Met Ala Ile Ser Lys Ala Leu Glu Ala Ile Asn Gln Val His Met
        515                 520                 525

Ala Glu Asn Phe Lys Leu Phe Ser Lys Ala Phe Gly Phe Thr Gly Lys
    530                 535                 540

Val Ile Glu Arg Tyr Asp Val Ala Val Glu Leu Gln Lys Ala Val Lys
545                 550                 555                 560

Thr Asp Asn Trp Arg Pro Phe Phe Val Lys Leu Glu Ser Leu Ala Ala
                565                 570                 575

Gly Arg Ala Ala Ser Ala Val Thr Ala Trp Ala Phe Ser Val Met Leu
            580                 585                 590

Gly Thr Pro Val Gly Ile Leu Gly Phe Ala Ile Ile Met Ala Ala Val
        595                 600                 605
```

Ser Ala Leu Val Asn Asp Lys Phe Ile Glu Gln Val Asn Lys Leu Ile
    610                 615                 620

Gly Ile
625

<210> SEQ ID NO 294
<211> LENGTH: 1881
<212> TYPE: DNA
<213> ORGANISM: Escherichia coli

<400> SEQUENCE: 294
atgtctgacc ctgtacgtat tacaaatccc ggtgcagaat cgctgggata tgattcagat 60
ggccatgaaa ttatggccgt tgatatttat gtaaaccctc cacgtgtcga tgtctttcat 120
ggtaccccgc ctgcatggag ttccttcggg aacaaaacca tctggggtgg aaacgagtgg 180
gtcgatgatt ccccaacccg aagtgatatc gaaaaaaggg acaaggaaat cacagcgtac 240
aaaaacacgc tcagcgcgca gcagaaagag aatgagaata agcgtactga agctggaaaa 300
cgcctttctg cggcaattgc tgcaagggaa aaagatgaaa acacactgaa aacactccgt 360
gccggaaacg cagatgccgc tgatattaca cgacaggagt tcagactcct gcaggcagag 420
ctgagagaat acggattccg tactgaaatc gccggatatg atgccctccg gctgcataca 480
gagagccgga tgctgtttgc tgatgctgat tctcttcgta tatctccccg cgaggccagg 540
tcgttaatcg aacaggctga aaaacggcag aaggatgcgc agaacgcaga caagaaggcc 600
gctgatatgc ttgctgaata cgagcgcaga aaaggtattc tggacacgcg gttgtcagag 660
ctggaaaaaa atggcggggc agcccttgcc gttcttgatg cacaacaggc ccgtctgctc 720
gggcagcaga cacggaatga cagggccatt tcagaggccc ggaataaact cagttcggtg 780
acggaatcgc ttaagacggc ccgtaatgca ttaaccagag ctgaacaaca gctgacgcaa 840
cagaaaaaca cgcctgacgg caaaacgata gtttcccctg aaaaattccc ggggcgttca 900
tcaacaaatc attctattgt tgtgagtggt gatccgaggt ttgccggtac gataaaaatc 960
acaaccagcg cggtcatcga taaccgtgca aacctgaatt atcttctgac ccattccggt 1020
ctggactata aacgcaatat tctgaatgac cggaatccgg tggtgacaga ggatgtggaa 1080
ggtgacaaga aaatttataa tgctgaagtt gctgaatggg ataagttacg gcaacgattg 1140
cttgatgcca gaaataaaat cacctctgct gaatctgcga taaattcggc gagaaataac 1200
gtcagtgcca gaacaaatga acaaaagcat gcaaatgacg ctcttaatgc cctgttgaag 1260
gaaaaagaga atatccgtag ccagcttgct gacatcaatc agaaaatagc tgaagagaaa 1320
agaaaaaggg atgaaataaa tatggtaaag gatgccataa aactcacctc tgatttctac 1380
agaacgatat atgatgagtt cggtaaacaa gcatccgaac ttgctaagga gctggcttct 1440
gtatctcaag ggaaacagat taagagtgtg gatgatgcac tgaacgcttt tgataaattc 1500
cgtaataatc tgaacaagaa atataacata caagatcgca tggccatttc taaagccctg 1560
gaagctatta atcaggtcca tatggcggag aattttaagc tgttcagtaa ggcatttggt 1620
tttaccggaa aagttattga acgttatgat gttgctgtgg agttacaaaa ggctgtaaaa 1680
acggacaact ggcgtccatt ttttgtaaaa cttgaatcac tggcagcagg aagagctgct 1740
tcagcagtta cagcatgggc gttttccgtc atgctgggaa cccctgtagg tattctgggt 1800
tttgcaatta ttatggcggc tgtgagtgcg cttgttaatg ataagtttat tgagcaggtc 1860
aataaactta ttggtatctg a 1881

<210> SEQ ID NO 295
<211> LENGTH: 271
<212> TYPE: PRT
<213> ORGANISM: Escherichia coli

<400> SEQUENCE: 295

```
Met Glu Thr Leu Thr Val His Ala Pro Ser Pro Ser Thr Asn Leu Pro
1               5                   10                  15

Ser Tyr Gly Asn Gly Ala Phe Ser Leu Ser Ala Pro His Val Pro Gly
            20                  25                  30

Ala Gly Pro Leu Leu Val Gln Val Val Tyr Ser Phe Phe Gln Ser Pro
        35                  40                  45

Asn Met Cys Leu Gln Ala Leu Thr Gln Leu Glu Asp Tyr Ile Lys Lys
    50                  55                  60

His Gly Ala Ser Asn Pro Leu Thr Leu Gln Ile Ile Ser Thr Asn Ile
65                  70                  75                  80

Gly Tyr Phe Cys Asn Ala Asp Arg Asn Leu Val Leu His Pro Gly Ile
                85                  90                  95

Ser Val Tyr Asp Ala Tyr His Phe Ala Lys Pro Ala Pro Ser Gln Tyr
            100                 105                 110

Asp Tyr Arg Ser Met Asn Met Lys Gln Met Ser Gly Asn Val Thr Thr
        115                 120                 125

Pro Ile Val Ala Leu Ala His Tyr Leu Trp Gly Asn Gly Ala Glu Arg
    130                 135                 140

Ser Val Asn Ile Ala Asn Ile Gly Leu Lys Ile Ser Pro Met Lys Ile
145                 150                 155                 160

Asn Gln Ile Lys Asp Ile Ile Lys Ser Gly Val Val Gly Thr Phe Pro
                165                 170                 175

Val Ser Thr Lys Phe Thr His Ala Thr Gly Asp Tyr Asn Val Ile Thr
            180                 185                 190

Gly Ala Tyr Leu Gly Asn Ile Thr Leu Lys Thr Glu Gly Thr Leu Thr
        195                 200                 205

Ile Ser Ala Asn Gly Ser Trp Thr Tyr Asn Gly Val Val Arg Ser Tyr
    210                 215                 220

Asp Asp Lys Tyr Asp Phe Asn Ala Ser Thr His Arg Gly Ile Ile Gly
225                 230                 235                 240

Glu Ser Leu Thr Arg Leu Gly Ala Met Phe Ser Gly Lys Glu Tyr Gln
                245                 250                 255

Ile Leu Leu Pro Gly Glu Ile His Ile Lys Glu Ser Gly Lys Arg
            260                 265                 270
```

<210> SEQ ID NO 296
<211> LENGTH: 816
<212> TYPE: DNA
<213> ORGANISM: Escherichia coli

<400> SEQUENCE: 296

```
atggaaacct taactgttca tgcaccatca ccatcaacta acttaccaag ttatggcaat     60

ggtgcatttt ctctttcagc accacatgtg cctggtgctg gccctctttt agtccaggtt    120

gtttatagtt ttttccagag tccaaacatg tgtcttcagg ctttaactca acttgaggat    180

tacatcaaaa aacatggggc cagcaaccct ctcacattgc agatcatatc gacaaatatt    240

ggttacttct gtaacgccga ccgaaatctg gttcttcacc ctggaataag cgtttatgac    300

gcttaccact tcgcaaaacc agcgccaagt caatatgact atcgctcaat gaatatgaaa    360
```

-continued

```
caaatgagcg gtaatgtcac tacaccaatt gtggcgcttg ctcactattt atggggtaat    420

ggcgctgaaa ggagcgttaa tatcgccaac attggtctta aaatttcccc tatgaaaatt    480

aatcagataa aagacattat aaaatctggt gtagtaggca cattccctgt ttctacaaag    540

ttcacacatg ccactggtga ttataatgtt attaccggtg catatcttgg taatatcaca    600

ctgaaaacag aaggtacttt aactatctct gccaatggct cctggactta caatggcgtt    660

gttcgttcat atgatgataa atacgatttt aacgccagca ctcaccgtgg cattatcgga    720

gagtcgctca caaggctcgg ggcgatgttt tctggtaaag agtaccagat actgcttcct    780

ggtgaaattc acattaaaga aagtggtaag cgataa                              816


<210> SEQ ID NO 297
<211> LENGTH: 387
<212> TYPE: PRT
<213> ORGANISM: Escherichia coli

<400> SEQUENCE: 297

Met Gly Ser Asn Gly Ala Asp Asn Ala His Asn Asn Ala Phe Gly Gly
1               5                   10                  15

Gly Lys Asn Pro Gly Ile Gly Asn Thr Ser Gly Ala Gly Ser Asn Gly
            20                  25                  30

Ser Ala Ser Ser Asn Arg Gly Asn Ser Asn Gly Trp Ser Trp Ser Asn
        35                  40                  45

Lys Pro His Lys Asn Asp Gly Phe His Ser Asp Gly Ser Tyr His Ile
    50                  55                  60

Thr Phe His Gly Asp Asn Asn Ser Lys Pro Lys Pro Gly Gly Asn Ser
65                  70                  75                  80

Gly Asn Arg Gly Asn Asn Gly Asp Gly Ala Ser Ala Lys Val Gly Glu
                85                  90                  95

Ile Thr Ile Thr Pro Asp Asn Ser Lys Pro Gly Arg Tyr Ile Ser Ser
            100                 105                 110

Asn Pro Glu Tyr Ser Leu Leu Ala Lys Leu Ile Asp Ala Glu Ser Ile
        115                 120                 125

Lys Gly Thr Glu Val Tyr Thr Phe His Thr Arg Lys Gly Gln Tyr Val
    130                 135                 140

Lys Val Thr Val Pro Asp Ser Asn Ile Asp Lys Met Arg Val Asp Tyr
145                 150                 155                 160

Val Asn Trp Lys Gly Pro Lys Tyr Asn Asn Lys Leu Val Lys Arg Phe
                165                 170                 175

Val Ser Gln Phe Leu Leu Phe Arg Lys Glu Glu Lys Glu Lys Asn Glu
            180                 185                 190

Lys Glu Ala Leu Leu Lys Ala Ser Glu Leu Val Ser Gly Met Gly Asp
        195                 200                 205

Lys Leu Gly Glu Tyr Leu Gly Val Lys Tyr Lys Asn Val Ala Lys Glu
    210                 215                 220

Val Ala Asn Asp Ile Lys Asn Phe His Gly Arg Asn Ile Arg Ser Tyr
225                 230                 235                 240

Asn Glu Ala Met Ala Ser Leu Asn Lys Val Leu Ala Asn Pro Lys Met
                245                 250                 255

Lys Val Asn Lys Ser Asp Lys Asp Ala Ile Val Asn Ala Trp Lys Gln
            260                 265                 270

Val Asn Ala Lys Asp Met Ala Asn Lys Ile Gly Asn Leu Gly Lys Ala
        275                 280                 285

Phe Lys Val Ala Asp Leu Ala Ile Lys Val Glu Lys Ile Arg Glu Lys
```

290 295 300

Ser Ile Glu Gly Tyr Asn Thr Gly Asn Trp Gly Pro Leu Leu Leu Glu
305 310 315 320

Val Glu Ser Trp Ile Ile Gly Gly Val Val Ala Gly Val Ala Ile Ser
325 330 335

Leu Phe Gly Ala Val Leu Ser Phe Leu Pro Ile Ser Gly Leu Ala Val
340 345 350

Thr Ala Leu Gly Val Ile Gly Ile Met Thr Ile Ser Tyr Leu Ser Ser
355 360 365

Phe Ile Asp Ala Asn Arg Val Ser Asn Ile Asn Asn Ile Ile Ser Ser
370 375 380

Val Ile Arg
385

<210> SEQ ID NO 298
<211> LENGTH: 1171
<212> TYPE: DNA
<213> ORGANISM: Escherichia coli

<400> SEQUENCE: 298
atgggtagta atggcgcaga taatgcacat aacaatgctt ttggtggagg gaaaaatccg 60
ggcattggta ataccagtgg cgcaggaagt aatggtagtg catcaagtaa ccgaggaaat 120
tccaatggat ggtcatggag taataagcct cataaaaatg atggcttcca cagtgatggt 180
tcttaccata ttacatttca tggggacaat aattcaaagc ctaaacctgg agggaatagt 240
ggaaatcgag gtaataacgg tgatggagcg agtgctaagg ttggagagat aacaatcaca 300
cctgacaact cgaaaccagg tcgttatatt tcgtcaaatc ctgaatattc attgttggca 360
aaattaattg atgcggaatc aattaaaggt acagaggtat atacttttca caccagaaaa 420
ggtcagtatg ttaaggttac tgttccagat agtaatattg ataaaatgag agttgattat 480
gtgaactgga agggaccgaa atataacaat aaacttgtga agaggtttgt gagccagttt 540
ttattattta ggaaggaaga aaaagaaaaa aatgaaaaag aagccttgct aaaggctagt 600
gaacttgtgt ctggtatggg ggataagctt ggcgagtatc ttggagtaaa atataaaaat 660
gtagctaagg aagttgccaa tgatattaaa aacttccatg gtcgtaatat tcgtagctat 720
aatgaagcaa tggcttcact taataaagtg ttagcaaatc caaagatgaa agtaaacaaa 780
tctgataagg atgccattgt gaatgcctgg aaacaggtta atgctaagga catggctaat 840
aagattggta atcttggcaa ggcatttaag gttgctgatt tagctataaa ggttgagaaa 900
attagggaaa aaagcattga gggatacaat actggcaact ggggacctct cctgttggag 960
gttgaatcat ggatcattgg tggcgttgtt gctggagttg ctattagttt attcggggct 1020
gtgttgagtt ttctcccaat ctctggactt gcagttactg cgttgggggt aataggaata 1080
atgacgatta gttacttgtc atctttcata gatgcaaatc gagtttcgaa tataaataac 1140
attatatcta gtgttattcg agcaaatcga g 1171

<210> SEQ ID NO 299
<211> LENGTH: 103
<212> TYPE: PRT
<213> ORGANISM: Escherichia coli

<400> SEQUENCE: 299

Met Arg Thr Leu Thr Leu Asn Glu Leu Asp Ser Val Ser Gly Gly Ala
1 5 10 15

-continued

```
Ser Gly Arg Asp Ile Ala Met Ala Ile Gly Thr Leu Ser Gly Gln Phe
            20                  25                  30

Val Ala Gly Gly Ile Gly Ala Ala Ala Gly Gly Val Ala Gly Gly Ala
        35                  40                  45

Ile Tyr Asp Tyr Ala Ser Thr His Lys Pro Asn Pro Ala Met Ser Pro
    50                  55                  60

Ser Gly Leu Gly Gly Thr Ile Lys Gln Lys Pro Glu Gly Ile Pro Ser
65                  70                  75                  80

Glu Ala Trp Asn Tyr Ala Ala Gly Arg Leu Cys Asn Trp Ser Pro Asn
                85                  90                  95

Asn Leu Ser Asp Val Cys Leu
            100


<210> SEQ ID NO 300
<211> LENGTH: 312
<212> TYPE: DNA
<213> ORGANISM: Escherichia coli

<400> SEQUENCE: 300

atgagaactc tgactctaaa tgaattagat tctgtttctg gtggtgcttc agggcgtgat      60

attgcgatgg ctataggaac actatccgga caatttgttg caggaggaat tggagcagct     120

gctgggggtg tggctggagg tgcaatatat gactatgcat ccactcacaa acctaatcct     180

gcaatgtctc catccggttt aggaggaaca attaagcaaa aacccgaagg gataccttca     240

gaagcatgga actatgctgc gggaagattg tgtaattgga gtccaaataa tcttagtgat     300

gtttgtttat aa                                                         312


<210> SEQ ID NO 301
<211> LENGTH: 58
<212> TYPE: PRT
<213> ORGANISM: Enterococcus columbae

<400> SEQUENCE: 301

Met Met Asn Ala Thr Glu Asn Gln Ile Phe Val Glu Thr Val Ser Asp
1               5                   10                  15

Gln Glu Leu Glu Met Leu Ile Gly Gly Ala Gly Arg Gly Trp Ile Lys
            20                  25                  30

Thr Leu Thr Lys Asp Cys Pro Asn Val Ile Ser Ser Ile Cys Ala Gly
        35                  40                  45

Thr Ile Ile Thr Ala Cys Lys Asn Cys Ala
    50                  55


<210> SEQ ID NO 302
<211> LENGTH: 177
<212> TYPE: DNA
<213> ORGANISM: Enterococcus columbae

<400> SEQUENCE: 302

atgatgaatg ctactgaaaa ccaaattttt gttgagactg tgagtgacca agaattagaa      60

atgttaattg gtggtgcagg tcgtggatgg attaagactt taacaaaaga ttgtccaaat     120

gtgatttctt caatttgtgc aggtacaatt attacagctt gtaaaaattg tgcttaa        177


<210> SEQ ID NO 303
<211> LENGTH: 59
<212> TYPE: PRT
<213> ORGANISM: Lactobacillus curvatus

<400> SEQUENCE: 303
```

```
Met Asn Asn Val Lys Glu Leu Ser Met Thr Glu Leu Gln Thr Ile Thr
1               5                   10                  15

Gly Gly Ala Arg Ser Tyr Gly Asn Gly Val Tyr Cys Asn Asn Lys Lys
            20                  25                  30

Cys Trp Val Asn Arg Gly Glu Ala Thr Gln Ser Ile Ile Gly Gly Met
        35                  40                  45

Ile Ser Gly Trp Ala Ser Gly Leu Ala Gly Met
    50                  55


<210> SEQ ID NO 304
<211> LENGTH: 180
<212> TYPE: DNA
<213> ORGANISM: Lactobacillus curvatus

<400> SEQUENCE: 304

atgaataatg taaaagaatt aagtatgaca gaattacaaa caattaccgg cggtgctaga      60

tcatatggca acggtgttta ctgtaataat aaaaaatgtt gggtaaatcg gggtgaagca     120

acgcaaagta ttattggtgg tatgattagc ggctgggcta gtggtttagc tggaatgtaa     180


<210> SEQ ID NO 305
<211> LENGTH: 64
<212> TYPE: PRT
<213> ORGANISM: Streptomyces sp.

<400> SEQUENCE: 305

Met Arg Ser Glu Met Thr Leu Thr Ser Thr Asn Ser Ala Glu Ala Leu
1               5                   10                  15

Ala Ala Gln Asp Phe Ala Asn Thr Val Leu Ser Ala Ala Ala Pro Gly
            20                  25                  30

Phe His Ala Asp Cys Glu Thr Pro Ala Met Ala Thr Pro Ala Thr Pro
        35                  40                  45

Thr Val Ala Gln Phe Val Ile Gln Gly Ser Thr Ile Cys Leu Val Cys
    50                  55                  60


<210> SEQ ID NO 306
<211> LENGTH: 195
<212> TYPE: DNA
<213> ORGANISM: Streptomyces sp.

<400> SEQUENCE: 306

gtgcgatctg agatgactct tacgagcacg aattccgctg aggctctggc ggcgcaggac      60

tttgcgaaca ccgttctcag cgcggcggcc ccgggcttcc acgcggactg cgagacgccg     120

gccatggcca ccccggccac gccgaccgtc gcccagttcg tgatccaggg cagcacgatc     180

tgcctggtct gctga                                                      195


<210> SEQ ID NO 307
<211> LENGTH: 65
<212> TYPE: PRT
<213> ORGANISM: Bacillus halodurans

<400> SEQUENCE: 307

Met Val Asn Ser Lys Asp Leu Arg Asn Pro Glu Phe Arg Lys Ala Gln
1               5                   10                  15

Gly Leu Gln Phe Val Asp Glu Val Asn Glu Lys Glu Leu Ser Ser Leu
            20                  25                  30

Ala Gly Ser Gly Asp Val His Ala Gln Thr Thr Trp Pro Cys Ala Thr
        35                  40                  45
```

Val Gly Val Ser Val Ala Leu Cys Pro Thr Thr Lys Cys Thr Ser Gln
    50                  55                  60

Cys
65

<210> SEQ ID NO 308
<211> LENGTH: 198
<212> TYPE: DNA
<213> ORGANISM: Bacillus halodurans

<400> SEQUENCE: 308
atggtaaatt caaaagattt gcgtaatcct gaattccgca aagcccaagg tctacaattc      60
gttgacgagg tgaacgagaa ggaactttcg tctctagctg gttcaggaga tgtgcatgca     120
caaacaactt ggccttgcgc tacagttggt gtctccgtag ccttgtgccc aactacaaag     180
tgtacaagcc agtgctaa                                                   198

<210> SEQ ID NO 309
<211> LENGTH: 66
<212> TYPE: PRT
<213> ORGANISM: Carnobacterium divergens

<400> SEQUENCE: 309

Met Lys Asn Leu Lys Glu Gly Ser Tyr Thr Ala Val Asn Thr Asp Glu
1               5                   10                  15

Leu Lys Ser Ile Asn Gly Gly Thr Lys Tyr Tyr Gly Asn Gly Val Tyr
            20                  25                  30

Cys Asn Ser Lys Lys Cys Trp Val Asp Trp Gly Gln Ala Ser Gly Cys
        35                  40                  45

Ile Gly Gln Thr Val Val Gly Gly Trp Leu Gly Gly Ala Ile Pro Gly
    50                  55                  60

Lys Cys
65

<210> SEQ ID NO 310
<211> LENGTH: 201
<212> TYPE: DNA
<213> ORGANISM: Carnobacterium divergens

<400> SEQUENCE: 310
atgaaaaact taaaagaagg ttcatacact gctgttaata ctgatgaatt aaaaagtatc      60
aatggtggaa caaaatatta tgggaatggc gtttattgca attctaaaaa atgttgggta     120
gattggggac aagcttcagg ttgtatcggt caaactgttg ttggcggatg gctaggcgga     180
gctataccag gtaaatgcta a                                               201

<210> SEQ ID NO 311
<211> LENGTH: 63
<212> TYPE: PRT
<213> ORGANISM: Carnobacterium divergens

<400> SEQUENCE: 311

Met Ile Lys Arg Glu Lys Asn Arg Thr Ile Ser Ser Leu Gly Tyr Glu
1               5                   10                  15

Glu Ile Ser Asn His Lys Leu Gln Glu Ile Gln Gly Gly Lys Gly Ile
            20                  25                  30

Leu Gly Lys Leu Gly Val Val Gln Ala Gly Val Asp Phe Val Ser Gly
        35                  40                  45

```
Val Trp Ala Gly Ile Lys Gln Ser Ala Lys Asp His Pro Asn Ala
    50                  55                  60


<210> SEQ ID NO 312
<211> LENGTH: 192
<212> TYPE: DNA
<213> ORGANISM: Carnobacterium divergens

<400> SEQUENCE: 312

atgattaaaa gagaaaagaa cagaacaatt tcttcccttg gttatgaaga aatttctaat      60

cataaattgc aagaaataca aggtggaaaa ggaattcttg gtaaactagg agtagtacag     120

gcaggagtgg attttgtatc aggagtgtgg gctggaataa aacagtctgc caaagatcat     180

cctaatgcgt aa                                                         192


<210> SEQ ID NO 313
<211> LENGTH: 75
<212> TYPE: PRT
<213> ORGANISM: Carnobacterium divergens

<400> SEQUENCE: 313

Met Lys Lys Gln Ile Leu Lys Gly Leu Val Ile Val Val Cys Leu Ser
1               5                   10                  15

Gly Ala Thr Phe Phe Ser Thr Pro Gln Gln Ala Ser Ala Ala Ala Pro
            20                  25                  30

Lys Ile Thr Gln Lys Gln Lys Asn Cys Val Asn Gly Gln Leu Gly Gly
        35                  40                  45

Met Leu Ala Gly Ala Leu Gly Gly Pro Gly Gly Val Val Leu Gly Gly
    50                  55                  60

Ile Gly Gly Ala Ile Ala Gly Gly Cys Phe Asn
65                  70                  75


<210> SEQ ID NO 314
<211> LENGTH: 228
<212> TYPE: DNA
<213> ORGANISM: Carnobacterium divergens

<400> SEQUENCE: 314

atgaaaaaac aaattttaaa agggttggtt atagttgttt gtttatctgg ggcaacattt      60

ttctcaacac cacaacaagc ttctgctgct gcaccgaaaa ttactcaaaa acaaaaaaat     120

tgtgttaatg gacaattagg tggaatgctt gctggagctt tgggtggacc tggcggagtt     180

gtgttaggtg gtataggtgg tgcaatagca ggaggttgtt ttaattaa                  228


<210> SEQ ID NO 315
<211> LENGTH: 72
<212> TYPE: PRT
<213> ORGANISM: Enterococcus durans

<400> SEQUENCE: 315

Met Gln Thr Ile Lys Glu Leu Asn Thr Met Glu Leu Gln Glu Ile Ile
1               5                   10                  15

Gly Gly Glu Asn Asp His Arg Met Pro Tyr Glu Leu Asn Arg Pro Asn
            20                  25                  30

Asn Leu Ser Lys Gly Gly Ala Lys Cys Ala Ala Gly Ile Leu Gly Ala
        35                  40                  45

Gly Leu Gly Ala Val Gly Gly Gly Pro Gly Gly Phe Ile Ser Ala Gly
    50                  55                  60

Ile Ser Ala Val Leu Gly Cys Met
```

65 70

<210> SEQ ID NO 316
<211> LENGTH: 219
<212> TYPE: DNA
<213> ORGANISM: Enterococcus durans

<400> SEQUENCE: 316
atgcaaacga tcaaagaatt gaacacgatg gaattacaag aaataattgg aggtgaaaat 60
gaccatcgga tgccttacga attgaaccgt ccaaataatt tatccaaagg tggggctaag 120
tgtgctgctg gaatacttgg cgctggacta ggcgcagtag gcggtggacc tggcggattt 180
attagtgccg gaatcagtgc tgttcttggt tgtatgtaa 219

<210> SEQ ID NO 317
<211> LENGTH: 72
<212> TYPE: PRT
<213> ORGANISM: Enterococcus durans

<400> SEQUENCE: 317

Met Gln Thr Ile Lys Glu Leu Asn Thr Met Glu Leu Gln Lys Ile Ile
1 5 10 15

Gly Gly Glu Asn Asp His Arg Met Pro Tyr Glu Leu Asn Arg Pro Asn
20 25 30

Asn Leu Ser Lys Gly Gly Ala Lys Cys Ala Ala Gly Ile Leu Gly Ala
35 40 45

Gly Leu Gly Ala Val Gly Gly Gly Pro Gly Gly Phe Ile Ser Ala Gly
50 55 60

Ile Ser Ala Val Leu Gly Cys Met
65 70

<210> SEQ ID NO 318
<211> LENGTH: 219
<212> TYPE: DNA
<213> ORGANISM: Enterococcus durans

<400> SEQUENCE: 318
atgcaaacga tcaaagaatt gaacacgatg gaattacaaa aaataattgg aggtgaaaat 60
gaccatcgga tgccttacga attgaaccgt ccaaataatt tatccaaagg tggagctaag 120
tgcgctgccg gaatacttgg tgctggatta ggcgcagtag gcggtggacc tggcggattt 180
attagtgccg gaatcagtgc tgttcttggt tgtatgtaa 219

<210> SEQ ID NO 319
<211> LENGTH: 220
<212> TYPE: PRT
<213> ORGANISM: Streptococcus dysgalactiae subsp. equisimilis

<400> SEQUENCE: 319

Met Lys Lys Leu Lys Arg Leu Val Ile Ser Leu Val Thr Ser Leu Leu
1 5 10 15

Val Ile Ser Ser Thr Val Pro Ala Leu Val Tyr Ala Asn Glu Thr Asn
20 25 30

Asn Phe Ala Glu Thr Gln Lys Glu Ile Thr Thr Asn Ser Glu Ala Thr
35 40 45

Leu Thr Asn Glu Asp Tyr Thr Lys Leu Thr Ser Glu Val Lys Thr Ile
50 55 60

Tyr Thr Asn Leu Ile Gln Tyr Asp Gln Thr Lys Asn Lys Phe Tyr Val
65 70 75 80

Asp Glu Asp Lys Thr Glu Gln Tyr Tyr Asn Tyr Asp Asp Glu Ser Ile
85 90 95

Lys Gly Val Tyr Leu Met Lys Asp Ser Leu Asn Asp Glu Leu Asn Asn
100 105 110

Asn Asn Ser Ser Asn Tyr Ser Glu Ile Ile Asn Gln Lys Ile Ser Glu
115 120 125

Ile Asp Tyr Val Leu Gln Gly Asn Asp Ile Asn Asn Leu Ile Pro Ser
130 135 140

Asn Thr Arg Val Lys Arg Ser Ala Asp Phe Ser Trp Ile Gln Arg Cys
145 150 155 160

Leu Glu Glu Ala Trp Gly Tyr Ala Ile Ser Leu Val Thr Leu Lys Gly
165 170 175

Ile Ile Asn Leu Phe Lys Ala Gly Lys Phe Glu Ala Ala Ala Ala Lys
180 185 190

Leu Ala Ser Ala Thr Ala Gly Arg Ile Ala Gly Met Ala Ala Leu Phe
195 200 205

Ala Phe Val Ala Thr Cys Gly Ala Thr Thr Val Ser
210 215 220

<210> SEQ ID NO 320
<211> LENGTH: 663
<212> TYPE: DNA
<213> ORGANISM: Streptococcus dysgalactiae subsp. equisimilis

<400> SEQUENCE: 320
atgaaaaaat taaaacgtct tgttatctct cttgttactt cattactagt aatttcaagt 60
acagttccag cacttgttta cgctaatgaa acaaataact ttgcagaaac tcaaaaagaa 120
attacaacaa attcagaagc aacattaacc aatgaagact acactaaatt aacttccgaa 180
gtaaaaacaa tttatacaaa tctgattcaa tacgaccaaa caaaaaacaa attttacgtc 240
gatgaagaca aaactgaaca atattataac tacgatgatg aaagtataaa aggggtttat 300
ctcatgaaag atagtttgaa cgatgagtta aacaataata actcttcaaa ctattctgaa 360
ataattaatc aaaaaatctc tgaaattgac tatgtccttc aaggaaacga tataaataat 420
ttaattccta gcaataccag agtaaaaaga tcagcagatt tttcttggat tcaaagatgt 480
ctagaagaag catggggata tgctattagt ctagttactc taaaaggaat aatcaatcta 540
tttaaagcag gaaaatttga agctgctgct gctaaattag cttctgctac agcaggtaga 600
atcgctggaa tggctgcctt atttgctttc gtagcaactt gcggtgcgac aactgtatca 660
taa 663

<210> SEQ ID NO 321
<211> LENGTH: 57
<212> TYPE: PRT
<213> ORGANISM: Enterococcus faecalis

<400> SEQUENCE: 321

Met Lys Gln Tyr Lys Val Leu Asn Glu Lys Glu Met Lys Lys Pro Ile
1 5 10 15

Gly Gly Glu Ser Val Phe Ser Lys Ile Gly Asn Ala Val Gly Pro Ala
20 25 30

Ala Tyr Trp Ile Leu Lys Gly Leu Gly Asn Met Ser Asp Val Asn Gln
35 40 45

Ala Asp Arg Ile Asn Arg Lys Lys His
50 55

<210> SEQ ID NO 322
<211> LENGTH: 174
<212> TYPE: DNA
<213> ORGANISM: Enterococcus faecalis

<400> SEQUENCE: 322
atgaagcaat ataaagtatt gaatgaaaaa gaaatgaaaa aacctattgg gggagagtcg 60
gtttttagta aaataggtaa tgctgtaggt ccagctgctt attggatttt aaaaggatta 120
ggtaatatga gtgatgtaaa ccaagctgat agaattaata gaaagaaaca ttaa 174

<210> SEQ ID NO 323
<211> LENGTH: 44
<212> TYPE: PRT
<213> ORGANISM: Enterococcus faecalis

<400> SEQUENCE: 323

Met Gly Ala Ile Ala Lys Leu Val Ala Lys Phe Gly Trp Pro Ile Val
1 5 10 15

Lys Lys Tyr Tyr Lys Gln Ile Met Gln Phe Ile Gly Glu Gly Trp Ala
20 25 30

Ile Asn Lys Ile Ile Asp Trp Ile Lys Lys His Ile
35 40

<210> SEQ ID NO 324
<211> LENGTH: 135
<212> TYPE: DNA
<213> ORGANISM: Enterococcus faecalis

<400> SEQUENCE: 324
atgggagcaa tcgcaaaatt agtagcaaag tttggatggc caattgttaa aaagtattac 60
aaacaaatta tgcaatttat tggagaagga tgggcaatta acaaaattat tgattggatc 120
aaaaaacata tttaa 135

<210> SEQ ID NO 325
<211> LENGTH: 43
<212> TYPE: PRT
<213> ORGANISM: Enterococcus faecalis

<400> SEQUENCE: 325

Met Gly Ala Ile Ala Lys Leu Val Ala Lys Phe Gly Trp Pro Phe Ile
1 5 10 15

Lys Lys Phe Tyr Lys Gln Ile Met Gln Phe Ile Gly Gln Gly Trp Thr
20 25 30

Ile Asp Gln Ile Glu Lys Trp Leu Lys Arg His
35 40

<210> SEQ ID NO 326
<211> LENGTH: 132
<212> TYPE: DNA
<213> ORGANISM: Enterococcus faecalis

<400> SEQUENCE: 326
atgggagcaa tcgcaaaatt agtagcaaag tttggatggc catttattaa aaaattctac 60
aaacaaatta tgcagtttat cggacaagga tggacaatag atcaaattga aaaatggtta 120
aaaagacatt ga 132

<210> SEQ ID NO 327

<211> LENGTH: 74
<212> TYPE: PRT
<213> ORGANISM: Enterococcus faecalis

<400> SEQUENCE: 327

Met Leu Asn Lys Lys Leu Leu Glu Asn Gly Val Val Asn Ala Val Thr
1 5 10 15

Ile Asp Glu Leu Asp Ala Gln Phe Gly Gly Met Ser Lys Arg Asp Cys
20 25 30

Asn Leu Met Lys Ala Cys Cys Ala Gly Gln Ala Val Thr Tyr Ala Ile
35 40 45

His Ser Leu Leu Asn Arg Leu Gly Gly Asp Ser Ser Asp Pro Ala Gly
50 55 60

Cys Asn Asp Ile Val Arg Lys Tyr Cys Lys
65 70

<210> SEQ ID NO 328
<211> LENGTH: 225
<212> TYPE: DNA
<213> ORGANISM: Enterococcus faecalis

<400> SEQUENCE: 328
atgttaaata aaaaattatt agaaaatggt gtagtaaatg ctgtaacaat tgatgaactt 60
gatgctcaat ttggtggaat gagcaaacgt gattgtaact tgatgaaggc gtgttgtgct 120
ggacaagcag taacatatgc tattcatagt cttttaaatc gattaggtgg agactctagt 180
gatccagctg gttgtaatga tattgtaaga aaatattgta aataa 225

<210> SEQ ID NO 329
<211> LENGTH: 65
<212> TYPE: PRT
<213> ORGANISM: Enterococcus faecium

<400> SEQUENCE: 329

Met Lys His Leu Lys Ile Leu Ser Ile Lys Glu Thr Gln Leu Ile Tyr
1 5 10 15

Gly Gly Thr Thr His Ser Gly Lys Tyr Tyr Gly Asn Gly Val Tyr Cys
20 25 30

Thr Lys Asn Lys Cys Thr Val Asp Trp Ala Lys Ala Thr Thr Cys Ile
35 40 45

Ala Gly Met Ser Ile Gly Gly Phe Leu Gly Gly Ala Ile Pro Gly Lys
50 55 60

Cys
65

<210> SEQ ID NO 330
<211> LENGTH: 195
<212> TYPE: DNA
<213> ORGANISM: Enterococcus faecium

<400> SEQUENCE: 330
atgaaacatt taaaaatttt gtctattaaa gagacacaac ttatctatgg gggtaccact 60
catagtggaa aatattatgg aaatggagtg tattgcacta aaaataaatg tacggtcgat 120
tgggccaagg caactacttg tattgcagga atgtctatag gtggtttttt aggtggagca 180
attccaggga agtgc 195

<210> SEQ ID NO 331
<211> LENGTH: 105

<212> TYPE: PRT
<213> ORGANISM: Enterococcus faecalis

<400> SEQUENCE: 331

Met Val Lys Glu Asn Lys Phe Ser Lys Ile Phe Ile Leu Met Ala Leu
1               5                   10                  15

Ser Phe Leu Gly Leu Ala Leu Phe Ser Ala Ser Leu Gln Phe Leu Pro
            20                  25                  30

Ile Ala His Met Ala Lys Glu Phe Gly Ile Pro Ala Ala Val Ala Gly
        35                  40                  45

Thr Val Leu Asn Val Val Glu Ala Gly Gly Trp Val Thr Thr Ile Val
    50                  55                  60

Ser Ile Leu Thr Ala Val Gly Ser Gly Gly Leu Ser Leu Leu Ala Ala
65                  70                  75                  80

Ala Gly Arg Glu Ser Ile Lys Ala Tyr Leu Lys Lys Glu Ile Lys Lys
                85                  90                  95

Lys Gly Lys Arg Ala Val Ile Ala Trp
            100                 105

<210> SEQ ID NO 332
<211> LENGTH: 318
<212> TYPE: DNA
<213> ORGANISM: Enterococcus faecalis

<400> SEQUENCE: 332
atggttaaag aaaataaatt ttctaagatt tttattttaa tggctttgag ttttttgggg 60
ttagccttgt ttagtgcaag tcttcagttt ttgcccattg cacatatggc taaagagttc 120
ggtataccag cagcagttgc aggaactgtg cttaatgtag ttgaagctgg tggatgggtc 180
actactattg tatcaattct tactgctgta ggtagcggag gtctttcttt actcgctgca 240
gcaggaagag agtcaattaa agcatacctt aagaaagaaa ttaagaaaaa aggaaaaaga 300
gcagttattg cttggtaa 318

<210> SEQ ID NO 333
<211> LENGTH: 71
<212> TYPE: PRT
<213> ORGANISM: Enterococcus faecium

<400> SEQUENCE: 333

Met Gln Asn Val Lys Glu Leu Ser Thr Lys Glu Met Lys Gln Ile Ile
1               5                   10                  15

Gly Gly Glu Asn Asp His Arg Met Pro Asn Glu Leu Asn Arg Pro Asn
            20                  25                  30

Asn Leu Ser Lys Gly Gly Ala Lys Cys Gly Ala Ala Ile Ala Gly Gly
        35                  40                  45

Leu Phe Gly Ile Pro Lys Gly Pro Leu Ala Trp Ala Ala Gly Leu Ala
    50                  55                  60

Asn Val Tyr Ser Lys Cys Asn
65                  70

<210> SEQ ID NO 334
<211> LENGTH: 216
<212> TYPE: DNA
<213> ORGANISM: Enterococcus faecium

<400> SEQUENCE: 334
atgcaaaatg taaaagaatt aagtacgaaa gagatgaaac aaattatcgg tggagaaaat 60

-continued

```
gatcacagaa tgcctaatga gttaaataga cctaacaact tatctaaagg tggagcaaaa    120

tgtggtgctg caattgctgg gggattattt ggaatcccaa aaggaccact agcatgggct    180

gctgggttag caaatgtata ctctaaatgc aactaa                              216


<210> SEQ ID NO 335
<211> LENGTH: 58
<212> TYPE: PRT
<213> ORGANISM: Enterococcus mundtii

<400> SEQUENCE: 335

Met Lys Lys Leu Thr Ser Lys Glu Met Ala Gln Val Val Gly Gly Lys
1               5                   10                  15

Tyr Tyr Gly Asn Gly Val Ser Cys Asn Lys Lys Gly Cys Ser Val Asp
            20                  25                  30

Trp Gly Lys Ala Ile Gly Ile Ile Gly Asn Asn Ser Ala Ala Asn Leu
        35                  40                  45

Ala Thr Gly Gly Ala Ala Gly Trp Lys Ser
    50                  55


<210> SEQ ID NO 336
<211> LENGTH: 177
<212> TYPE: DNA
<213> ORGANISM: Enterococcus mundtii

<400> SEQUENCE: 336

ttgaagaaat taacatcaaa agaaatggca caagtagtag gtggaaaata ctacggtaat     60

ggagtctcat gtaataaaaa agggtgcagt gttgattggg gaaaagctat tggcattatt    120

ggaaataatt ctgctgcgaa tttagctact ggtggagcag ctggttggaa aagttaa       177


<210> SEQ ID NO 337
<211> LENGTH: 44
<212> TYPE: PRT
<213> ORGANISM: Enterococcus faecalis

<400> SEQUENCE: 337

Met Leu Ala Lys Ile Lys Ala Met Ile Lys Lys Phe Pro Asn Pro Tyr
1               5                   10                  15

Thr Leu Ala Ala Lys Leu Thr Thr Tyr Glu Ile Asn Trp Tyr Lys Gln
            20                  25                  30

Gln Tyr Gly Arg Tyr Pro Trp Glu Arg Pro Val Ala
        35                  40


<210> SEQ ID NO 338
<211> LENGTH: 135
<212> TYPE: DNA
<213> ORGANISM: Enterococcus faecalis

<400> SEQUENCE: 338

atgttagcaa aaattaaagc gatgattaag aagtttccga acccttatac tttagcagct     60

aagctaacga cttacgaaat taattggtat aaacaacaat acggtcgtta tccttgggag    120

cgccctgtag cataa                                                     135


<210> SEQ ID NO 339
<211> LENGTH: 71
<212> TYPE: PRT
<213> ORGANISM: Enterococcus faecium

<400> SEQUENCE: 339
```

```
Met Arg Lys Lys Leu Phe Ser Leu Ala Leu Ile Gly Ile Phe Gly Leu
1               5                   10                  15

Val Val Thr Asn Phe Gly Thr Lys Val Asp Ala Ala Thr Arg Ser Tyr
            20                  25                  30

Gly Asn Gly Val Tyr Cys Asn Asn Ser Lys Cys Trp Val Asn Trp Gly
        35                  40                  45

Glu Ala Lys Glu Asn Ile Ala Gly Ile Val Ile Ser Gly Trp Ala Ser
    50                  55                  60

Gly Leu Ala Gly Met Gly His
65                  70


<210> SEQ ID NO 340
<211> LENGTH: 216
<212> TYPE: DNA
<213> ORGANISM: Enterococcus faecium

<400> SEQUENCE: 340

atgagaaaaa aattatttag tttagctctt attggaatat ttgggttagt tgtgacaaat      60

tttggtacaa aagttgatgc agctacgcgt tcatatggta atggtgttta ttgtaataat     120

agtaaatgct gggttaactg gggagaagct aaagagaata ttgcaggaat cgttattagt     180

ggctgggctt ctggtttggc aggtatggga cattaa                               216


<210> SEQ ID NO 341
<211> LENGTH: 34
<212> TYPE: PRT
<213> ORGANISM: Enterococcus faecium

<400> SEQUENCE: 341

Met Asn Phe Leu Lys Asn Gly Ile Ala Lys Trp Met Thr Gly Ala Glu
1               5                   10                  15

Leu Gln Ala Tyr Lys Lys Lys Tyr Gly Cys Leu Pro Trp Glu Lys Ile
            20                  25                  30

Ser Cys


<210> SEQ ID NO 342
<211> LENGTH: 105
<212> TYPE: DNA
<213> ORGANISM: Enterococcus faecium

<400> SEQUENCE: 342

atgaattttc ttaaaaatgg tatcgcaaaa tggatgaccg gtgctgaatt gcaagcgtat      60

aaaaagaaat atggatgctt gccatgggaa aaaatttctt gttaa                     105


<210> SEQ ID NO 343
<211> LENGTH: 76
<212> TYPE: PRT
<213> ORGANISM: Enterococcus faecalis

<400> SEQUENCE: 343

Met Lys Lys Lys Leu Val Lys Gly Leu Val Ile Cys Gly Met Ile Gly
1               5                   10                  15

Ile Gly Phe Thr Ala Leu Gly Thr Asn Val Glu Ala Ala Thr Tyr Tyr
            20                  25                  30

Gly Asn Gly Val Tyr Cys Asn Lys Gln Lys Cys Trp Val Asp Trp Ser
        35                  40                  45

Arg Ala Arg Ser Glu Ile Ile Asp Arg Gly Val Lys Ala Tyr Val Asn
    50                  55                  60
```

```
Gly Phe Thr Lys Val Leu Gly Gly Ile Gly Gly Arg
65                  70                  75


<210> SEQ ID NO 344
<211> LENGTH: 231
<212> TYPE: DNA
<213> ORGANISM: Enterococcus faecalis

<400> SEQUENCE: 344

atgaaaaaga aattagttaa aggcttagtt atttgtggca tgattgggat tggttttaca      60

gcattaggaa caaatgtaga agccgccacg tattacggaa atggtgtcta ttgcaataag     120

caaaaatgtt gggtagattg gagtagagca cgttctgaaa ttatagacag aggcgtaaaa     180

gcatacgtca atggatttac gaaagtgtta ggtggtatag gtggaagata a              231


<210> SEQ ID NO 345
<211> LENGTH: 60
<212> TYPE: PRT
<213> ORGANISM: Enterococcus faecalis

<400> SEQUENCE: 345

Met Lys Lys Glu Glu Leu Val Gly Met Ala Lys Glu Asp Phe Leu Asn
1               5                   10                  15

Val Ile Cys Glu Asn Asp Asn Lys Leu Glu Asn Ser Gly Ala Lys Cys
            20                  25                  30

Pro Trp Trp Asn Leu Ser Cys His Leu Gly Asn Asp Gly Lys Ile Cys
        35                  40                  45

Thr Tyr Ser His Glu Cys Thr Ala Gly Cys Asn Ala
    50                  55                  60


<210> SEQ ID NO 346
<211> LENGTH: 183
<212> TYPE: DNA
<213> ORGANISM: Enterococcus faecalis

<400> SEQUENCE: 346

atgaaaaaag aagaattagt aggaatggct aaggaagact tttaaatgt tatttgtgaa       60

aatgacaaca aactagaaaa tagtggagca aaatgtcctt ggtggaatct ttcttgtcat     120

ttaggcaatg atggtaaaat ttgcacttat tcacatgaat gtaccgcagg ttgtaatgca     180

taa                                                                   183


<210> SEQ ID NO 347
<211> LENGTH: 61
<212> TYPE: PRT
<213> ORGANISM: Enterococcus faecalis

<400> SEQUENCE: 347

Met Thr Glu Leu Asn Lys Arg Leu Gln Leu Lys Arg Asp Val Ser Thr
1               5                   10                  15

Glu Asn Ser Leu Lys Lys Ile Ser Asn Thr Asp Glu Thr His Gly Gly
            20                  25                  30

Val Thr Thr Ser Ile Pro Cys Thr Val Met Val Ser Ala Ala Val Cys
        35                  40                  45

Pro Thr Leu Val Cys Ser Asn Lys Cys Gly Gly Arg Gly
    50                  55                  60


<210> SEQ ID NO 348
<211> LENGTH: 186
<212> TYPE: DNA
```

<213> ORGANISM: Enterococcus faecalis

<400> SEQUENCE: 348
atgactgaac ttaacaaaag attacaatta aaaagagatg tttcaacaga aaatagtttg 60
aaaaaaattt ctaatactga tgaaacacat gggggagtta ctacatcaat tccatgtaca 120
gtaatggtta gtgcggcagt atgtcctacc cttgtttgct cgaataaatg tggcggtaga 180
ggctag 186

<210> SEQ ID NO 349
<211> LENGTH: 58
<212> TYPE: PRT
<213> ORGANISM: Enterococcus faecium

<400> SEQUENCE: 349

Met Gln Asn Val Lys Glu Val Ser Val Lys Glu Met Lys Gln Ile Ile
1 5 10 15

Gly Gly Ser Asn Asp Ser Leu Trp Tyr Gly Val Gly Gln Phe Met Gly
20 25 30

Lys Gln Ala Asn Cys Ile Thr Asn His Pro Val Lys His Met Ile Ile
35 40 45

Pro Gly Tyr Cys Leu Ser Lys Ile Leu Gly
50 55

<210> SEQ ID NO 350
<211> LENGTH: 177
<212> TYPE: DNA
<213> ORGANISM: Enterococcus faecium

<400> SEQUENCE: 350
atgcaaaatg taaaagaagt ttctgtaaaa gagatgaaac aaattatcgg tggttctaat 60
gatagtcttt ggtatggtgt aggacaattt atgggtaaac aagcaaactg tataacaaac 120
catcctgtta aacacatgat aattcctgga tattgtttat cgaaaatttt agggtaa 177

<210> SEQ ID NO 351
<211> LENGTH: 55
<212> TYPE: PRT
<213> ORGANISM: Enterococcus faecium

<400> SEQUENCE: 351

Met Lys Lys Tyr Asn Glu Leu Ser Lys Lys Glu Leu Leu Gln Ile Gln
1 5 10 15

Gly Gly Ile Ala Pro Ile Ile Val Ala Gly Leu Gly Tyr Leu Val Lys
20 25 30

Asp Ala Trp Asp His Ser Asp Gln Ile Ile Ser Gly Phe Lys Lys Gly
35 40 45

Trp Asn Gly Gly Arg Arg Lys
50 55

<210> SEQ ID NO 352
<211> LENGTH: 168
<212> TYPE: DNA
<213> ORGANISM: Enterococcus faecium

<400> SEQUENCE: 352
atgaaaaaat ataatgagtt atctaaaaaa gaacttctac agattcaagg aggaatagca 60
cctattatag ttgctggcct tggctattta gtaaaagatg catgggatca ctcagatcaa 120
ataatctcag gatttaaaaa aggttggaat ggtggacgta gaaaataa 168

<210> SEQ ID NO 353
<211> LENGTH: 343
<212> TYPE: PRT
<213> ORGANISM: Enterococcus faecalis

<400> SEQUENCE: 353

```
Met Lys Asn Ile Leu Leu Ser Ile Leu Gly Val Leu Ser Ile Val Val
1               5                   10                  15

Ser Leu Ala Phe Ser Ser Tyr Ser Val Asn Ala Ala Ser Asn Glu Trp
            20                  25                  30

Ser Trp Pro Leu Gly Lys Pro Tyr Ala Gly Arg Tyr Glu Glu Gly Gln
        35                  40                  45

Gln Phe Gly Asn Thr Ala Phe Asn Arg Gly Gly Thr Tyr Phe His Asp
    50                  55                  60

Gly Phe Asp Phe Gly Ser Ala Ile Tyr Gly Asn Gly Ser Val Tyr Ala
65                  70                  75                  80

Val His Asp Gly Lys Ile Leu Tyr Ala Gly Trp Asp Pro Val Gly Gly
                85                  90                  95

Gly Ser Leu Gly Ala Phe Ile Val Leu Gln Ala Gly Asn Thr Asn Val
            100                 105                 110

Ile Tyr Gln Glu Phe Ser Arg Asn Val Gly Asp Ile Lys Val Ser Thr
        115                 120                 125

Gly Gln Thr Val Lys Lys Gly Gln Leu Ile Gly Lys Phe Thr Ser Ser
    130                 135                 140

His Leu His Leu Gly Met Thr Lys Lys Glu Trp Arg Ser Ala His Ser
145                 150                 155                 160

Ser Trp Asn Lys Asp Asp Gly Thr Trp Phe Asn Pro Ile Pro Ile Leu
                165                 170                 175

Gln Gly Gly Ser Thr Pro Thr Pro Pro Asn Pro Gly Pro Lys Asn Phe
            180                 185                 190

Thr Thr Asn Val Arg Tyr Gly Leu Arg Val Leu Gly Gly Ser Trp Leu
        195                 200                 205

Pro Glu Val Thr Asn Phe Asn Asn Thr Asn Asp Gly Phe Ala Gly Tyr
    210                 215                 220

Pro Asn Arg Gln His Asp Met Leu Tyr Ile Lys Val Asp Lys Gly Gln
225                 230                 235                 240

Met Lys Tyr Arg Val His Thr Ala Gln Ser Gly Trp Leu Pro Trp Val
                245                 250                 255

Ser Lys Gly Asp Lys Ser Asp Thr Val Asn Gly Ala Ala Gly Met Pro
            260                 265                 270

Gly Gln Ala Ile Asp Gly Val Gln Leu Asn Tyr Ile Thr Pro Lys Gly
        275                 280                 285

Glu Lys Leu Ser Gln Ala Tyr Tyr Arg Ser Gln Thr Thr Lys Arg Ser
    290                 295                 300

Gly Trp Leu Lys Val Ser Ala Asp Asn Gly Ser Ile Pro Gly Leu Asp
305                 310                 315                 320

Ser Tyr Ala Gly Ile Phe Gly Glu Pro Leu Asp Arg Leu Gln Ile Gly
                325                 330                 335

Ile Ser Gln Ser Asn Pro Phe
            340
```

<210> SEQ ID NO 354
<211> LENGTH: 1032
<212> TYPE: DNA

<213> ORGANISM: Enterococcus faecalis

<400> SEQUENCE: 354

```
atgaaaaata ttttactttc tattctaggg gtattatcta tcgttgtttc tttggcgttt     60
tcttcttatt ctgtcaacgc agcttctaat gagtggtcgt ggccactggg caaaccatat    120
gcgggaagat atgaagaagg acaacaattc gggaacactg catttaaccg aggaggtact    180
tatttccatg atgggtttga ctttggttct gctatttatg gaaatggcag tgtgtatgct    240
gtgcatgatg gtaaaatttt atatgctggt tgggatcctg taggtggagg ctcattaggt    300
gcatttattg tactacaagc gggaaacaca aatgtgattt atcaagaatt tagccgaaat    360
gttggagata ttaaagttag cactggacaa actgttaaaa aaggacagct gataggaaag    420
tttacttcta gtcatttaca tttaggaatg acaaaaaaag aatggcgttc tgctcattct    480
tcttggaata aagatgatgg cacttggttt aacccaattc ctatacttca aggaggatct    540
acgcctacgc ctccaaatcc aggaccaaaa aatttcacaa caaatgttcg ttacggattg    600
cgggtcctcg gaggttcatg gttaccagaa gtaaccaact ttaacaatac caatgatggt    660
ttcgcaggtt accctaatcg tcaacatgat atgctttata taaaggtaga taaagggcaa    720
atgaaatatc gtgttcacac ggctcaaagt ggatggttgc cttgggtaag taaaggggat    780
aagagcgata cagtaaatgg agcggcaggt atgcctggac aagcaattga tggtgttcag    840
ctaaactata taactcctaa gggagaaaaa ttatcacagg cttactatcg ttcacaaact    900
acgaaacgat caggctggtt aaaagtaagt gcagataatg gttctattcc tggactagac    960
agttatgcag gaatctttgg agaaccgttg gatcgcttgc aaataggtat ttcacagtca   1020
aatccatttt aa                                                       1032
```

<210> SEQ ID NO 355
<211> LENGTH: 56
<212> TYPE: PRT
<213> ORGANISM: Staphylococcus epidermidis

<400> SEQUENCE: 355

```
Met Glu Asn Lys Lys Asp Leu Phe Asp Leu Glu Ile Lys Lys Asp Asn
1               5                   10                  15

Met Glu Asn Asn Asn Glu Leu Glu Ala Gln Ser Leu Gly Pro Ala Ile
            20                  25                  30

Lys Ala Thr Arg Gln Val Cys Pro Lys Ala Thr Arg Phe Val Thr Val
        35                  40                  45

Ser Cys Lys Lys Ser Asp Cys Gln
    50                  55
```

<210> SEQ ID NO 356
<211> LENGTH: 171
<212> TYPE: DNA
<213> ORGANISM: Staphylococcus epidermidis

<400> SEQUENCE: 356

```
atggaaaaca aaaaagattt atttgattta gaaatcaaaa aagataatat ggaaaataat     60
aatgaattag aagctcaatc tcttggtcct gcaattaagg caactagaca ggtatgtcct    120
aaagcaacac gttttgttac agtttcttgt aaaaaaagtg attgtcaata g             171
```

<210> SEQ ID NO 357
<211> LENGTH: 51
<212> TYPE: PRT
<213> ORGANISM: Staphylococcus epidermidis

<400> SEQUENCE: 357

Met Ala Ala Phe Met Lys Leu Ile Gln Phe Leu Ala Thr Lys Gly Gln
1               5                   10                  15

Lys Tyr Val Ser Leu Ala Trp Lys His Lys Gly Thr Ile Leu Lys Trp
            20                  25                  30

Ile Asn Ala Gly Gln Ser Phe Glu Trp Ile Tyr Lys Gln Ile Lys Lys
        35                  40                  45

Leu Trp Ala
    50

<210> SEQ ID NO 358
<211> LENGTH: 156
<212> TYPE: DNA
<213> ORGANISM: Staphylococcus epidermidis

<400> SEQUENCE: 358
atggcagcat ttatgaagtt aattcagttc ttagcaacta aaggtcaaaa gtatgtttca     60
cttgcatgga aacataaagg tactatttta aaatggatta acgccggtca aagttttgaa    120
tggatttata aacaaatcaa aaaattatgg gcataa                              156

<210> SEQ ID NO 359
<211> LENGTH: 52
<212> TYPE: PRT
<213> ORGANISM: Staphylococcus epidermidis

<400> SEQUENCE: 359

Met Glu Ala Val Lys Glu Lys Asn Asp Leu Phe Asn Leu Asp Val Lys
1               5                   10                  15

Val Asn Ala Lys Glu Ser Asn Asp Ser Gly Ala Glu Pro Arg Ile Ala
            20                  25                  30

Ser Lys Phe Ile Cys Thr Pro Gly Cys Ala Lys Thr Gly Ser Phe Asn
        35                  40                  45

Ser Tyr Cys Cys
    50

<210> SEQ ID NO 360
<211> LENGTH: 159
<212> TYPE: DNA
<213> ORGANISM: Staphylococcus epidermidis

<400> SEQUENCE: 360
atggaagcag taaaagaaaa aaatgatctt tttaatcttg atgttaaagt taatgcaaaa     60
gaatctaacg attcaggagc tgaaccaaga attgctagta aatttatatg tactcctgga    120
tgtgcaaaaa caggtagttt taacagttat tgttgttaa                           159

<210> SEQ ID NO 361
<211> LENGTH: 55
<212> TYPE: PRT
<213> ORGANISM: Staphylococcus epidermidis

<400> SEQUENCE: 361

Met Asn Asn Ser Leu Phe Asp Leu Asn Leu Asn Lys Gly Val Glu Thr
1               5                   10                  15

Gln Lys Ser Asp Leu Ser Pro Gln Ser Ala Ser Val Leu Lys Thr Ser
            20                  25                  30

Ile Lys Val Ser Lys Lys Tyr Cys Lys Gly Val Thr Leu Thr Cys Gly
        35                  40                  45

```
Cys Asn Ile Thr Gly Gly Lys
    50                  55


<210> SEQ ID NO 362
<211> LENGTH: 168
<212> TYPE: DNA
<213> ORGANISM: Staphylococcus epidermidis

<400> SEQUENCE: 362

atgaataact cattattcga tttaaaccta aacaaaggtg tagaaactca aaagagtgat      60

ttaagtccgc aatctgctag tgtcttgaag acttctatta aagtatctaa aaaatattgt     120

aaaggtgtta ctttaacatg cggttgcaat attactggtg gtaaataa                 168


<210> SEQ ID NO 363
<211> LENGTH: 52
<212> TYPE: PRT
<213> ORGANISM: Staphylococcus gallinarum

<400> SEQUENCE: 363

Met Glu Ala Val Lys Glu Lys Asn Glu Leu Phe Asp Leu Asp Val Lys
1               5                   10                  15

Val Asn Ala Lys Glu Ser Asn Asp Ser Gly Ala Glu Pro Arg Ile Ala
            20                  25                  30

Ser Lys Phe Leu Cys Thr Pro Gly Cys Ala Lys Thr Gly Ser Phe Asn
        35                  40                  45

Ser Tyr Cys Cys
    50


<210> SEQ ID NO 364
<211> LENGTH: 159
<212> TYPE: DNA
<213> ORGANISM: Staphylococcus gallinarum

<400> SEQUENCE: 364

atggaagcag taaaagagaa aaatgaactt tttgatcttg acgttaaagt aaatgcaaaa      60

gagtctaatg attcaggcgc agaaccacga attgctagta aatttttatg tactcctgga     120

tgtgccaaaa caggtagctt caatagctac tgttgttaa                          159


<210> SEQ ID NO 365
<211> LENGTH: 63
<212> TYPE: PRT
<213> ORGANISM: Lactococcus garvieae

<400> SEQUENCE: 365

Met Glu Asn Asn Asn Tyr Thr Val Leu Ser Asp Glu Glu Leu Gln Lys
1               5                   10                  15

Ile Asp Gly Gly Ile Gly Gly Ala Leu Gly Asn Ala Leu Asn Gly Leu
            20                  25                  30

Gly Thr Trp Ala Asn Met Met Asn Gly Gly Gly Phe Val Asn Gln Trp
        35                  40                  45

Gln Val Tyr Ala Asn Lys Gly Lys Ile Asn Gln Tyr Arg Pro Tyr
    50                  55                  60


<210> SEQ ID NO 366
<211> LENGTH: 192
<212> TYPE: DNA
<213> ORGANISM: Lactococcus garvieae

<400> SEQUENCE: 366
```

atggaaaaca acaattacac agtactttca gatgaagaac tacaaaaaat tgatggtgga 60
atcggcgggg ctcttggtaa tgctctcaac ggattaggta cctgggcaaa catgatgaac 120
ggtggaggat ttgttaatca gtggcaagtt tatgctaata aaggaaaaat aaatcaatac 180
cgtccgtatt aa 192

<210> SEQ ID NO 367
<211> LENGTH: 63
<212> TYPE: PRT
<213> ORGANISM: Lactococcus garvieae

<400> SEQUENCE: 367

Met Phe Asp Leu Val Ala Thr Gly Met Ala Ala Gly Val Ala Lys Thr
1 5 10 15

Ile Val Asn Ala Val Ser Ala Gly Met Asp Ile Ala Thr Ala Leu Ser
20 25 30

Leu Phe Ser Gly Ala Phe Thr Ala Ala Gly Gly Ile Met Ala Leu Ile
35 40 45

Lys Lys Tyr Ala Gln Lys Lys Leu Trp Lys Gln Leu Ile Ala Ala
50 55 60

<210> SEQ ID NO 368
<211> LENGTH: 192
<212> TYPE: DNA
<213> ORGANISM: Lactococcus garvieae

<400> SEQUENCE: 368
atgtttgatt tagtcgcgac tggaatggct gcaggtgtag caaaaactat tgttaatgcc 60
gttagtgctg gtatggatat tgccactgct ttatcattgt tctcaggagc ttttactgca 120
gctgggggaa ttatggcact cattaaaaaa tatgctcaaa agaaattatg gaaacagctt 180
attgctgcat aa 192

<210> SEQ ID NO 369
<211> LENGTH: 91
<212> TYPE: PRT
<213> ORGANISM: Lactobacillus gasseri

<400> SEQUENCE: 369

Met Val Thr Lys Tyr Gly Arg Asn Leu Gly Leu Asn Lys Val Glu Leu
1 5 10 15

Phe Ala Ile Trp Ala Val Leu Val Val Ala Leu Leu Leu Thr Thr Ala
20 25 30

Asn Ile Tyr Trp Ile Ala Asp Gln Phe Gly Ile His Leu Ala Thr Gly
35 40 45

Thr Ala Arg Lys Leu Leu Asp Ala Met Ala Ser Gly Ala Ser Leu Gly
50 55 60

Thr Ala Phe Ala Ala Ile Leu Gly Val Thr Leu Pro Ala Trp Ala Leu
65 70 75 80

Ala Ala Ala Gly Ala Leu Gly Ala Thr Ala Ala
85 90

<210> SEQ ID NO 370
<211> LENGTH: 276
<212> TYPE: DNA
<213> ORGANISM: Lactobacillus gasseri

<400> SEQUENCE: 370

```
atggttacta agtacggacg taatttaggt ttgaacaagg tagagttgtt tgcaatttgg      60

gcggttttag tagttgctct tttattgacc acagcgaaca tttattggat tgctgatcaa     120

ttcgggattc atttagcgac tggaacagcc cgtaagttat tagatgcaat ggcttctggt     180

gcctcattgg gaactgcctt tgctgctatt ttgggcgtga cattacctgc atgggctttg     240

gcagctgcag gagcattggg agcgactgca gcctag                               276


<210> SEQ ID NO 371
<211> LENGTH: 75
<212> TYPE: PRT
<213> ORGANISM: Lactobacillus gasseri

<400> SEQUENCE: 371

Met Lys Asn Phe Asn Thr Leu Ser Phe Glu Thr Leu Ala Asn Ile Val
1               5                   10                  15

Gly Gly Arg Asn Asn Trp Ala Ala Asn Ile Gly Gly Val Gly Gly Ala
            20                  25                  30

Thr Val Ala Gly Trp Ala Leu Gly Asn Ala Val Cys Gly Pro Ala Cys
        35                  40                  45

Gly Phe Val Gly Ala His Tyr Val Pro Ile Ala Trp Ala Gly Val Thr
    50                  55                  60

Ala Ala Thr Gly Gly Phe Gly Lys Ile Arg Lys
65                  70                  75


<210> SEQ ID NO 372
<211> LENGTH: 228
<212> TYPE: DNA
<213> ORGANISM: Lactobacillus gasseri

<400> SEQUENCE: 372

atgaaaaatt ttaatacatt atcatttgaa acattggcta acatagttgg tgggagaaat      60

aattgggctg ctaatatagg tggagtaggt ggagcgacag tcgctggatg ggctcttgga     120

aatgcagttt gcggtcctgc ttgtggcttt gttggagcac actatgttcc aatagcatgg     180

gctggcgtaa cggcagctac tggtggattc ggaaagataa gaaagtag                  228


<210> SEQ ID NO 373
<211> LENGTH: 64
<212> TYPE: PRT
<213> ORGANISM: Lactobacillus plantarum

<400> SEQUENCE: 373

Met Ser Lys Leu Val Lys Thr Leu Thr Ile Ser Glu Ile Ser Lys Ala
1               5                   10                  15

Gln Asn Asn Gly Gly Lys Pro Ala Trp Cys Trp Tyr Thr Leu Ala Met
            20                  25                  30

Cys Gly Ala Gly Tyr Asp Ser Gly Thr Cys Asp Tyr Met Tyr Ser His
        35                  40                  45

Cys Phe Gly Ile Lys His His Ser Ser Gly Ser Ser Ser Tyr His Cys
    50                  55                  60


<210> SEQ ID NO 374
<211> LENGTH: 195
<212> TYPE: DNA
<213> ORGANISM: Lactobacillus plantarum

<400> SEQUENCE: 374

atgagtaaat tggttaagac acttactata agtgaaattt ctaaggctca aaacaacggt      60
```

```
ggaaaacctg catggtgttg gtatacttta gcaatgtgtg gtgctggtta tgattcggga    120

acctgtgatt atatgtattc gcattgtttt ggtataaagc atcatagtag tggtagtagc    180

agttatcatt gttag                                                     195


<210> SEQ ID NO 375
<211> LENGTH: 359
<212> TYPE: PRT
<213> ORGANISM: Haloferax mediterranei

<400> SEQUENCE: 375

Met Ser Lys Asp Arg Asp Gly Arg Arg Thr Ser Arg Arg Gly Thr Leu
1               5                   10                  15

Lys Lys Ile Gly Gly Phe Ser Leu Gly Ala Leu Ser Phe Gly Ala Val
            20                  25                  30

Gly Arg Thr Gln Ala Ala Thr Gly Ser Ser Val Thr Thr Ala Asp Ile
        35                  40                  45

Ala Pro Pro Gly Pro Asn Gly Asp Pro Lys Ser Val Gln Ile Asp Asp
    50                  55                  60

Lys Tyr Thr Gly Ala Glu Met Tyr Gly Glu Gly Asp Phe Arg Val Gly
65                  70                  75                  80

Leu Gly Thr Asp Leu Thr Met Tyr Pro Pro Val Tyr Arg Glu Ser Leu
                85                  90                  95

Gly Asn Gly Ser Gly Gly Trp Glu Phe Asp Phe Thr Val Cys Gly Ser
            100                 105                 110

Thr Ala Cys Arg Phe Val Asp Ser Asn Gly Asp Val Lys Glu Asp Asp
        115                 120                 125

Lys Ala Lys Glu Met Trp Trp Gln Glu Ile Asn Phe Asn Asp Ile Asn
    130                 135                 140

Gln Asp Leu Tyr Ser Arg Asn Asp Ser Asp Trp Val Gly Ser Thr Pro
145                 150                 155                 160

Ala Asp Thr Gln Pro Glu Phe Asp Tyr Thr Glu Phe Ala Leu Ala Arg
                165                 170                 175

Asp Gly Val Thr Leu Ala Leu Thr Ala Leu Asn Pro Ala Met Gly Ser
            180                 185                 190

Leu Ala Leu Gly Ala Thr Tyr Phe Leu Ser Asp Met Val Asn Trp Ile
        195                 200                 205

Ala Ser Gln His Glu Asp Asp Ser Ser Leu Lys Arg Lys Trp Asp Tyr
    210                 215                 220

Asp Gly Leu Ser Gly Pro Leu Tyr Ala Asp Ser Ser Thr Tyr Leu Leu
225                 230                 235                 240

Ala Arg Asp Glu Met Thr Ser Asn Ser Tyr Glu Ser Phe Thr Ile Asp
                245                 250                 255

Asn Ile Ala Val Ala Phe Pro Glu Phe Pro Val Arg Thr Lys Tyr Tyr
            260                 265                 270

Val Thr Phe Thr Ala Pro Asp Asp Pro Ser Thr Gln Ser Ile Ser Thr
        275                 280                 285

Leu Glu Glu Glu Gly Ile Tyr Arg Val Pro Ala Thr Glu Val Ala Ala
    290                 295                 300

Ala Arg Pro Pro Gly Ser Arg Arg Ser Lys Ser Ala Ala Asp Glu Met
305                 310                 315                 320

Val Tyr Val Ala Asp Pro Lys Lys Phe Ile Glu Val Glu Pro Val Lys
                325                 330                 335

Asn Pro Ser Ile Pro Asp Arg Ile Tyr Glu Glu Ile Glu Gln Lys Lys
            340                 345                 350
```

Lys Gln Arg Ser Arg Lys Gln
355

<210> SEQ ID NO 376
<211> LENGTH: 1080
<212> TYPE: DNA
<213> ORGANISM: Haloferax mediterranei

<400> SEQUENCE: 376
atgtcgaaag acagagatgg gagaaggaca agtcggcgag gcacgttaaa gaaaatcggc 60
ggtttcagtc tcggagcgct tagtttcggg gcagtcggac gaactcaagc ggcgaccggc 120
tcatcggtta cgaccgctga tatcgcacct cccggaccga acggagaccc gaagagtgtt 180
cagatagatg ataaatacac cggagccgag atgtacggcg agggtgactt cagagtcggt 240
ctcggaactg acctgacgat gtatccgccc gtgtaccgtg agagtcttgg aaatggaagc 300
gggggttggg aattcgactt caccgtttgt gggtccactg cctgtcgatt tgtggacagt 360
aacggtgacg tcaaagagga cgacaaggcg aaagaaatgt ggtggcagga aattaacttc 420
aacgacataa atcaggattt atacagtcgg aacgattccg actgggtcgg gtcgacccct 480
gccgataccc aaccggagtt cgattacacc gactttgcgc tcgctcggga cggagtgacg 540
ctcgctctca cggcactcaa ccccgcaatg gggagtcttg cactcggtgc cacgtacttc 600
ctcagcgaca tggtgaactg gattgcgagc cagcacgaag acgacagttc gctcaagaga 660
aaatgggatt acgacgggct aagtgggccg ttgtacgccg attcgtcgac gtacctactg 720
gcacgcgacg agatgacttc gaactcgtac gaatcattca cgatcgataa catcgccgtt 780
gccttcccag agttccccgt ccggaccaag tactacgtca cattcactgc gccggatgac 840
ccgtcaacgc agtcgatatc tacgctcgaa gaggagggaa tctaccgagt gcccgctacg 900
gaagtggctg cggccagacc accggggtcc cgacgttcca aatcggcagc cgacgagatg 960
gtgtacgttg ccgatccgaa gaagttcata gaggtcgagc cggtgaagaa cccaagtatc 1020
ccggaccgaa tctacgagga gatagagcaa aaaaagaaac aacggagtag gaaacagtag 1080

<210> SEQ ID NO 377
<211> LENGTH: 311
<212> TYPE: PRT
<213> ORGANISM: Haloarchaeon S8a

<400> SEQUENCE: 377

Met Ser Asp Lys Asp Ser Ile Asn Arg Arg Asn Val Leu Arg Lys Ile
1 5 10 15

Gly Gly Ile Gly Val Ala Ser Ala Val Gly Phe Ser Gly Leu Ala Ser
20 25 30

Gly Glu Ser Leu Ser Asp Asp Glu Lys Gln Asp Val Ile Asp Thr Ile
35 40 45

Tyr Lys Ser Gln Arg Val Glu Gln Ile Lys Lys Lys Phe Gly Gly Val
50 55 60

Asn Ile Glu Pro Lys Lys Val Gln Ser Val Thr Thr Asn Gln Ser Gly
65 70 75 80

Asp Leu Val Thr Ala Lys Leu Ser Val Ser Asp Gly Asp Leu Val Tyr
85 90 95

Ser Ser Val Lys Asp Thr Thr Val Ile Val Gln Phe Asp Arg Ser Ala
100 105 110

Ser Glu Ile Gly Glu Ser Trp Pro Lys Asn Thr Glu Ala Phe Ile Lys
115 120 125

-continued

Ser Thr Ser Ser Gly Val Asp Leu Leu Arg Thr Ala Thr Asp Glu Glu
    130                 135                 140

Ile Lys Asp Val Thr Glu Gly Val Asn Thr Ser Glu Ile Glu Ser Ala
145                 150                 155                 160

Asp Ala Val Asn Ile Phe Ile Asp Pro Glu Ser Gln Thr Tyr Tyr Met
                165                 170                 175

Glu Lys Tyr Asp Phe Asn Asn Lys Val Leu Glu Met Phe Glu Leu Ala
            180                 185                 190

Thr Gly Gly Thr Ser Ser Gly Lys Ile Ser Pro Thr Arg Glu Asp Gln
        195                 200                 205

Asn His Glu Tyr Asn Val Arg Glu His Lys Val Phe Asn Ser Glu Lys
    210                 215                 220

Gln Asn Ile Gln Leu Gln Ser Asp Cys Asn Ile Asn Ser Asn Thr Ala
225                 230                 235                 240

Ala Asp Val Ile Leu Cys Phe Asn Gln Val Gly Ser Cys Ala Leu Cys
                245                 250                 255

Ser Pro Thr Leu Val Gly Gly Pro Val Pro Thr Val Ala Cys Leu Leu
            260                 265                 270

Val Val Cys Phe Gly Thr Pro Asn Ala Val Ser Ala Ile Leu Glu Glu
        275                 280                 285

Val Asp Asn Ser Cys Phe Asn Leu Ile Lys Asp Val Ile Ser Cys Trp
    290                 295                 300

Asp Glu Trp Thr Ser Phe Trp
305                 310

<210> SEQ ID NO 378
<211> LENGTH: 936
<212> TYPE: DNA
<213> ORGANISM: Haloarchaeon S8a

<400> SEQUENCE: 378
atgtcggata aagacagcat taacagaaga aatgtattaa gaaaaattgg cggtatcggt 60
gtggcttcag ctgtcggatt ttctggtttg gcaagcgggg aaagtcttag cgatgatgag 120
aaacaagatg ttattgacac aatttacaaa tcacaaagag ttgaacagat aaagaaaaag 180
ttcggaggag tgaatattga gccgaaaaag gttcaatctg taacgaccaa tcagagcgga 240
gatcttgtta cggcgaagct gtcggttagt gatggggatt tggtatattc gagtgtcaaa 300
gatacaactg taatagttca gttcgataga tcggcttctg aaattggtga aagttggccc 360
aagaatactg aggcattcat caaatcgacg tcctctgggg tcgatcttct acgtacagca 420
actgatgaag aaataaagga cgttactgag ggagtcaaca catctgaaat tgaatctgcg 480
gatgctgtta acatatttat tgatcctgaa tcacagacat actatatgga gaaatatgac 540
tttaataata aggtacttga gatgtttgaa ttagcgacag gtgggacaag tagtggtaaa 600
atctccccca cacgtgaaga ccagaatcac gaatataatg ttagggaaca taaagtattt 660
aactcagaaa aacagaatat acaacttcag agtgactgta atataaacag taacaccgct 720
gctgatgtta ttctatgctt caaccaggtt ggttcttgtg cactctgctc cccgacttta 780
gtcggaggtc cagtccctac agttgcatgt ctcttagtcg tctgtttcgg cactccaaat 840
gctgtgtccg cgatacttga agaagtcgat aattcttgct ttaacttgat caaggatgta 900
atttcgtgtt gggatgaatg gactagcttc tggtga 936

<210> SEQ ID NO 379

<211> LENGTH: 333
<212> TYPE: PRT
<213> ORGANISM: Lactobacillus helveticus

<400> SEQUENCE: 379

```
Met Lys His Leu Asn Glu Thr Thr Asn Val Arg Ile Leu Ser Gln Phe
1               5                   10                  15

Asp Met Asp Thr Gly Tyr Gln Ala Val Val Gln Lys Gly Asn Val Gly
            20                  25                  30

Ser Lys Tyr Val Tyr Gly Leu Gln Leu Arg Lys Gly Ala Thr Thr Ile
        35                  40                  45

Leu Arg Gly Tyr Arg Gly Ser Lys Ile Asn Asn Pro Ile Leu Glu Leu
    50                  55                  60

Ser Gly Gln Ala Gly Gly His Thr Gln Thr Trp Glu Phe Ala Gly Asp
65                  70                  75                  80

Arg Lys Asp Ile Asn Gly Glu Glu Arg Ala Gly Gln Trp Phe Ile Gly
                85                  90                  95

Val Lys Pro Ser Lys Ile Glu Gly Ser Lys Ile Ile Trp Ala Lys Gln
            100                 105                 110

Ile Ala Arg Val Asp Leu Arg Asn Gln Met Gly Pro His Tyr Ser Asn
        115                 120                 125

Thr Asp Phe Pro Arg Leu Ser Tyr Leu Asn Arg Ala Gly Ser Asn Pro
    130                 135                 140

Phe Ala Gly Asn Lys Met Thr His Ala Glu Ala Ala Val Ser Pro Asp
145                 150                 155                 160

Tyr Thr Lys Phe Leu Ile Ala Thr Val Glu Asn Asn Cys Ile Gly His
                165                 170                 175

Phe Thr Ile Tyr Asn Leu Asp Thr Ile Asn Glu Lys Leu Asp Glu Lys
            180                 185                 190

Gly Asn Ser Glu Asp Val Asn Leu Glu Thr Val Lys Tyr Glu Asp Ser
        195                 200                 205

Phe Ile Ile Asp Asn Leu Tyr Gly Asp Asp Asn Asn Ser Ile Val Asn
    210                 215                 220

Ser Ile Gln Gly Tyr Asp Leu Asp Asn Asp Gly Asn Ile Tyr Ile Ser
225                 230                 235                 240

Ser Gln Lys Ala Pro Asp Phe Asp Gly Ser Tyr Tyr Ala His His Lys
                245                 250                 255

Gln Ile Val Lys Ile Pro Tyr Tyr Ala Arg Ser Lys Glu Ser Glu Asp
            260                 265                 270

Gln Trp Arg Ala Val Asn Leu Ser Glu Phe Gly Gly Leu Asp Ile Pro
        275                 280                 285

Gly Lys His Ser Glu Val Glu Ser Ile Gln Ile Ile Gly Glu Asn His
    290                 295                 300

Cys Tyr Leu Thr Val Ala Tyr His Ser Lys Asn Lys Ala Gly Glu Asn
305                 310                 315                 320

Lys Thr Thr Leu Asn Glu Ile Tyr Glu Leu Ser Trp Asn
                325                 330
```

<210> SEQ ID NO 380
<211> LENGTH: 1002
<212> TYPE: DNA
<213> ORGANISM: Lactobacillus helveticus

<400> SEQUENCE: 380

```
atgaagcatt taaatgaaac aactaatgtt agaattttaa gtcaatttga tatggatact      60
```

```
ggctatcaag cagtagttca aaaaggcaat gtaggttcaa aatatgtata tggattacaa    120

cttcgcaaag gtgctactac tatcttgcgt ggttaccgtg gaagtaaaat taataaccct    180

attcttgaat tatctggtca agcaggtggt cacacacaga catgggaatt tgctggtgat    240

cgtaaagaca ttaatggtga agaaagagca ggtcaatggt ttataggtgt taaaccatcg    300

aaaattgaag gaagcaaaat tatttgggca aagcaaattg caagagttga tcttagaaat    360

caaatgggac ctcattattc aaatactgac tttcctcgat tatcctactt gaatcgcgcc    420

ggttctaatc catttgctgg taataagatg acgcatgccg aagccgcagt atcacctgat    480

tatactaagt ttttaattgc tactgttgaa aataactgta ttggtcattt tactatatac    540

aatttagata caattaatga aaaacttgat gaaaagggaa atagtgaaga tgttaatctc    600

gaaactgtta aatacgaaga tagttttatc attgataatt tatatggtga tgataataat    660

tctattgtaa attcaattca agggtatgat ttggataatg atggaaatat ttatatttcc    720

agtcaaaaag cgccagattt tgatggctct tattatgcac atcataagca gattgttaag    780

attccatatt atgctcggtc taaagaaagc gaagaccaat ggagagctgt aaatttaagc    840

gaattcggtg gcttggatat tccaggtaaa catagtgaag ttgaaagcat ccaaattatt    900

ggtgagaatc attgttactt aactgttgca tatcattcta aaaataaagc gggtgaaaat    960

aaaactactt tgaatgagat ttatgaatta tcttggaatt ag                      1002
```

<210> SEQ ID NO 381
<211> LENGTH: 74
<212> TYPE: PRT
<213> ORGANISM: Enterococcus hirae

<400> SEQUENCE: 381

```
Met Lys Lys Lys Val Leu Lys His Cys Val Ile Leu Gly Ile Leu Gly
1               5                   10                  15

Thr Cys Leu Ala Gly Ile Gly Thr Gly Ile Lys Val Asp Ala Ala Thr
            20                  25                  30

Tyr Tyr Gly Asn Gly Leu Tyr Cys Asn Lys Glu Lys Cys Trp Val Asp
        35                  40                  45

Trp Asn Gln Ala Lys Gly Glu Ile Gly Lys Ile Ile Val Asn Gly Trp
    50                  55                  60

Val Asn His Gly Pro Trp Ala Pro Arg Arg
65                  70
```

<210> SEQ ID NO 382
<211> LENGTH: 225
<212> TYPE: DNA
<213> ORGANISM: Enterococcus hirae

<400> SEQUENCE: 382

```
atgaaaaaga aagtattaaa acattgtgtt attctaggaa tattaggaac ttgtctagct     60

ggcatcggta caggaataaa agttgatgca gctacttact atggaaatgg tctttattgt    120

aacaaagaaa aatgttgggt agattggaat caagctaaag gagaaattgg aaaaattatt    180

gttaatggtt gggttaatca tggtccatgg gcacctagaa ggtag                    225
```

<210> SEQ ID NO 383
<211> LENGTH: 75
<212> TYPE: PRT
<213> ORGANISM: Lactobacillus johnsonii

<400> SEQUENCE: 383

-continued

```
Met Lys Gln Phe Asn Tyr Leu Ser His Lys Asp Leu Ala Val Val Val
1               5                   10                  15

Gly Gly Arg Asn Asn Trp Gln Thr Asn Val Gly Gly Ala Val Gly Ser
            20                  25                  30

Ala Met Ile Gly Ala Thr Val Gly Gly Thr Ile Cys Gly Pro Ala Cys
        35                  40                  45

Ala Val Ala Gly Ala His Tyr Leu Pro Ile Leu Trp Thr Ala Val Thr
    50                  55                  60

Ala Ala Thr Gly Gly Phe Gly Lys Ile Arg Lys
65                  70                  75
```

<210> SEQ ID NO 384
<211> LENGTH: 228
<212> TYPE: DNA
<213> ORGANISM: Lactobacillus johnsonii

<400> SEQUENCE: 384

```
atgaaacaat ttaattattt atcacataaa gatttagcag tcgttgttgg tggaagaaat     60

aattggcaaa caaatgtggg aggagcagtg ggatcagcta tgattggggc tacagttggt    120

ggtacaattt gtggacctgc atgtgctgta gctggtgccc attatcttcc tattttatgg    180

acagcggtta cagctgcaac aggtggtttt ggcaagataa gaaagtag                 228
```

<210> SEQ ID NO 385
<211> LENGTH: 62
<212> TYPE: PRT
<213> ORGANISM: Lactobacillus johnsonii

<400> SEQUENCE: 385

```
Met Lys Leu Asn Asp Lys Glu Leu Ser Lys Ile Val Gly Gly Asn Arg
1               5                   10                  15

Trp Gly Asp Thr Val Leu Ser Ala Ala Ser Gly Ala Gly Thr Gly Ile
            20                  25                  30

Lys Ala Cys Lys Ser Phe Gly Pro Trp Gly Met Ala Ile Cys Gly Val
        35                  40                  45

Gly Gly Ala Ala Ile Gly Gly Tyr Phe Gly Tyr Thr His Asn
    50                  55                  60
```

<210> SEQ ID NO 386
<211> LENGTH: 189
<212> TYPE: DNA
<213> ORGANISM: Lactobacillus johnsonii

<400> SEQUENCE: 386

```
atgaaattaa atgacaaaga attatcaaag attgttggtg gaaatcgatg gggagatact     60

gttttatcag ctgctagtgg cgcaggaact ggtattaaag catgtaaaag ttttggccca    120

tggggaatgg caatttgtgg tgtaggaggt gcagcaatag gaggttattt tggctatact    180

cataattaa                                                            189
```

<210> SEQ ID NO 387
<211> LENGTH: 59
<212> TYPE: PRT
<213> ORGANISM: Lactococcus lactis subsp. lactis

<400> SEQUENCE: 387

```
Met Asn Lys Asn Glu Ile Glu Thr Gln Pro Val Thr Trp Leu Glu Glu
1               5                   10                  15

Val Ser Asp Gln Asn Phe Asp Glu Asp Val Phe Gly Ala Cys Ser Thr
```

```
            20                  25                  30

Asn Thr Phe Ser Leu Ser Asp Tyr Trp Gly Asn Asn Gly Ala Trp Cys
        35                  40                  45

Thr Leu Thr His Glu Cys Met Ala Trp Cys Lys
    50                  55


<210> SEQ ID NO 388
<211> LENGTH: 180
<212> TYPE: DNA
<213> ORGANISM: Lactococcus lactis subsp. lactis

<400> SEQUENCE: 388

atgaacaaaa atgaaattga aacacaacca gttacatggt tggaagaagt atctgatcaa      60

aattttgatg aagatgtatt tggtgcgtgt agtactaaca cattctcgct cagtgattac     120

tggggaaata acggggcttg gtgtacactc actcatgaat gtatggcttg gtgtaaataa     180


<210> SEQ ID NO 389
<211> LENGTH: 65
<212> TYPE: PRT
<213> ORGANISM: Lactococcus lactis subsp. lactis

<400> SEQUENCE: 389

Met Lys Glu Lys Asn Met Lys Lys Asn Asp Thr Ile Glu Leu Gln Leu
1               5                   10                  15

Gly Lys Tyr Leu Glu Asp Asp Met Ile Glu Leu Ala Glu Gly Asp Glu
            20                  25                  30

Ser His Gly Gly Thr Thr Pro Ala Thr Pro Ala Ile Ser Ile Leu Ser
        35                  40                  45

Ala Tyr Ile Ser Thr Asn Thr Cys Pro Thr Thr Lys Cys Thr Arg Ala
    50                  55                  60

Cys
65


<210> SEQ ID NO 390
<211> LENGTH: 198
<212> TYPE: DNA
<213> ORGANISM: Lactococcus lactis subsp. lactis

<400> SEQUENCE: 390

atgaaagaaa aaaatatgaa aaagaatgac actattgaat tacaattggg aaaatacctt      60

gaagatgata tgattgaatt agctgaaggg gatgagtctc atggaggaac aacaccagca     120

actcctgcaa tctctattct cagtgcatat attagtacca atacttgtcc aacaacaaaa     180

tgtacacgtg cttgttaa                                                   198


<210> SEQ ID NO 391
<211> LENGTH: 51
<212> TYPE: PRT
<213> ORGANISM: Lactococcus lactis subsp. lactis

<400> SEQUENCE: 391

Met Lys Glu Gln Asn Ser Phe Asn Leu Leu Gln Glu Val Thr Glu Ser
1               5                   10                  15

Glu Leu Asp Leu Ile Leu Gly Ala Lys Gly Gly Ser Gly Val Ile His
            20                  25                  30

Thr Ile Ser His Glu Cys Asn Met Asn Ser Trp Gln Phe Val Phe Thr
        35                  40                  45

Cys Cys Ser
```

50

<210> SEQ ID NO 392
<211> LENGTH: 156
<212> TYPE: DNA
<213> ORGANISM: Lactococcus lactis subsp. lactis

<400> SEQUENCE: 392
atgaaagaac aaaactcttt taatcttctt caagaagtga cagaaagtga attggacctt 60
attttaggtg caaaaggcgg cagtggagtt attcatacaa tttctcatga atgtaatatg 120
aatagctggc aatttgtatt tacttgctgc tcttaa 156

<210> SEQ ID NO 393
<211> LENGTH: 53
<212> TYPE: PRT
<213> ORGANISM: Lactococcus lactis

<400> SEQUENCE: 393

Met Ala Gly Phe Leu Lys Val Val Gln Leu Leu Ala Lys Tyr Gly Ser
1 5 10 15

Lys Ala Val Gln Trp Ala Trp Ala Asn Lys Gly Lys Ile Leu Asp Trp
20 25 30

Leu Asn Ala Gly Gln Ala Ile Asp Trp Val Val Ser Lys Ile Lys Gln
35 40 45

Ile Leu Gly Ile Lys
50

<210> SEQ ID NO 394
<211> LENGTH: 162
<212> TYPE: DNA
<213> ORGANISM: Lactococcus lactis

<400> SEQUENCE: 394
atggcagggt ttttaaaagt agttcaatta ctagctaaat atggttctaa agctgtacaa 60
tgggcttggg caaacaaggg taagatttta gattggctta atgcaggtca ggctattgat 120
tgggtagttt cgaaaattaa gcaaatttta ggtattaagt aa 162

<210> SEQ ID NO 395
<211> LENGTH: 53
<212> TYPE: PRT
<213> ORGANISM: Lactococcus lactis

<400> SEQUENCE: 395

Met Ala Gly Phe Leu Lys Val Val Gln Ile Leu Ala Lys Tyr Gly Ser
1 5 10 15

Lys Ala Val Gln Trp Ala Trp Ala Asn Lys Gly Lys Ile Leu Asp Trp
20 25 30

Ile Asn Ala Gly Gln Ala Ile Asp Trp Val Val Glu Lys Ile Lys Gln
35 40 45

Ile Leu Gly Ile Lys
50

<210> SEQ ID NO 396
<211> LENGTH: 162
<212> TYPE: DNA
<213> ORGANISM: Lactococcus lactis

<400> SEQUENCE: 396
atggcagggt ttttaaaagt agtccaaatt ttggctaagt atggttctaa agccgtacaa 60
tgggcatggg caaataaagg aaaaatctta gattggatta atgcaggtca agctattgac 120
tgggtagttg aaaagattaa gcaaattttg ggtattaaat aa 162

<210> SEQ ID NO 397
<211> LENGTH: 65
<212> TYPE: PRT
<213> ORGANISM: Lactobacillus amylovorus

<400> SEQUENCE: 397

Met Lys Gln Leu Asn Ser Glu Gln Leu Gln Asn Ile Ile Gly Gly Asn
1 5 10 15

Arg Trp Thr Asn Ala Tyr Ser Ala Ala Leu Gly Cys Ala Val Pro Gly
20 25 30

Val Lys Tyr Gly Lys Lys Leu Gly Gly Val Trp Gly Ala Val Ile Gly
35 40 45

Gly Val Gly Gly Ala Ala Val Cys Gly Leu Ala Gly Tyr Val Arg Lys
50 55 60

Gly
65

<210> SEQ ID NO 398
<211> LENGTH: 198
<212> TYPE: DNA
<213> ORGANISM: Lactobacillus amylovorus

<400> SEQUENCE: 398
atgaaacaat tgaattcaga acaattacaa aatattatcg gtggaaatag atggactaat 60
gcatacagcg cagctttggg atgcgctgtc cctggagtta aatatggaaa aaaacttggt 120
ggcgtatggg gtgctgtaat tggtggcgta ggcggtgcag cagtctgtgg cttggcgggt 180
tatgttcgta aaggctaa 198

<210> SEQ ID NO 399
<211> LENGTH: 68
<212> TYPE: PRT
<213> ORGANISM: Lactobacillus sakei L45

<400> SEQUENCE: 399

Met Lys Thr Glu Lys Lys Val Leu Asp Glu Leu Ser Leu His Ala Ser
1 5 10 15

Ala Lys Met Gly Ala Arg Asp Val Glu Ser Ser Met Asn Ala Asp Ser
20 25 30

Thr Pro Val Leu Ala Ser Val Ala Val Ser Met Glu Leu Leu Pro Thr
35 40 45

Ala Ser Val Leu Tyr Ser Asp Val Ala Gly Cys Phe Lys Tyr Ser Ala
50 55 60

Lys His His Cys
65

<210> SEQ ID NO 400
<211> LENGTH: 207
<212> TYPE: DNA
<213> ORGANISM: Lactobacillus sakei L45

<400> SEQUENCE: 400
atgaaaacag aaaaaaaggt tttagatgaa ctgagcttac acgcttctgc aaaaatggga 60
gcacgtgatg ttgaatccag catgaatgca gactcaacac cagttttagc atcagtcgct 120
gtatccatgg aattattgcc aactgcgtct gttctttatt cggatgttgc aggttgcttc 180
aaatattctg caaaacatca ttgttag 207

<210> SEQ ID NO 401
<211> LENGTH: 91
<212> TYPE: PRT
<213> ORGANISM: Lactococcus lactis subsp. lactis

<400> SEQUENCE: 401

Met Lys Thr Lys Ser Leu Val Leu Ala Leu Ser Ala Val Thr Leu Phe
1 5 10 15

Ser Ala Gly Gly Ile Val Ala Gln Ala Glu Gly Thr Trp Gln His Gly
20 25 30

Tyr Gly Val Ser Ser Ala Tyr Ser Asn Tyr His His Gly Ser Lys Thr
35 40 45

His Ser Ala Thr Val Val Asn Asn Asn Thr Gly Arg Gln Gly Lys Asp
50 55 60

Thr Gln Arg Ala Gly Val Trp Ala Lys Ala Thr Val Gly Arg Asn Leu
65 70 75 80

Thr Glu Lys Ala Ser Phe Tyr Tyr Asn Phe Trp
85 90

<210> SEQ ID NO 402
<211> LENGTH: 276
<212> TYPE: DNA
<213> ORGANISM: Lactococcus lactis subsp. lactis

<400> SEQUENCE: 402
atgaaaacca agtctctcgt attggcatta tctgcggtta cgttattctc tgccggagga 60
attgtagctc aagctgaagg aacatggcaa catggatatg gtgttagttc ggcatattca 120
aattatcatc atggtagcaa aactcattca gccacagttg taaataataa tactggccga 180
caaggtaagg atacacaacg tgccggtgtt tgggcaaaag ctactgttgg acgtaactta 240
actgaaaaag cttcatttta ttataacttt tggtaa 276

<210> SEQ ID NO 403
<211> LENGTH: 75
<212> TYPE: PRT
<213> ORGANISM: Lactococcus lactis subsp. cremoris

<400> SEQUENCE: 403

Met Lys Asn Gln Leu Asn Phe Asn Ile Val Ser Asp Glu Glu Leu Ser
1 5 10 15

Glu Ala Asn Gly Gly Lys Leu Thr Phe Ile Gln Ser Thr Ala Ala Gly
20 25 30

Asp Leu Tyr Tyr Asn Thr Asn Thr His Lys Tyr Val Tyr Gln Gln Thr
35 40 45

Gln Asn Ala Phe Gly Ala Ala Ala Asn Thr Ile Val Asn Gly Trp Met
50 55 60

Gly Gly Ala Ala Gly Gly Phe Gly Leu His His
65 70 75

<210> SEQ ID NO 404
<211> LENGTH: 228
<212> TYPE: DNA
<213> ORGANISM: Lactococcus lactis subsp. cremoris

<400> SEQUENCE: 404
atgaaaaatc aattaaattt taatattgtt tcagatgaag aactttcaga agctaacgga 60
ggaaaattaa catttattca atcgacagcg gctggagatt tatattacaa tactaataca 120
cacaaatatg tttaccaaca aactcaaaac gcttttgggg ctgctgctaa taccattgtt 180
aatggatgga tgggtggcgc tgctggaggt ttcgggttgc accattga 228

<210> SEQ ID NO 405
<211> LENGTH: 68
<212> TYPE: PRT
<213> ORGANISM: Lactococcus lactis subsp. cremoris

<400> SEQUENCE: 405

Met Lys Asn Gln Leu Asn Phe Asn Ile Val Ser Asp Glu Glu Leu Ala
1 5 10 15

Glu Val Asn Gly Gly Ser Leu Gln Tyr Val Met Ser Ala Gly Pro Tyr
20 25 30

Thr Trp Tyr Lys Asp Thr Arg Thr Gly Lys Thr Ile Cys Lys Gln Thr
35 40 45

Ile Asp Thr Ala Ser Tyr Thr Phe Gly Val Met Ala Glu Gly Trp Gly
50 55 60

Lys Thr Phe His
65

<210> SEQ ID NO 406
<211> LENGTH: 207
<212> TYPE: DNA
<213> ORGANISM: Lactococcus lactis subsp. cremoris

<400> SEQUENCE: 406
atgaaaaatc aattaaattt taatattgtt tctgatgaag aacttgcaga agttaatgga 60
ggaagcttgc agtatgttat gagtgctgga ccatatactt ggtataaaga tactagaaca 120
ggaaaaacaa tatgtaaaca gacaattgac acagcaagtt atacatttgg tgtaatggca 180
gaaggatggg gaaaaacatt ccactaa 207

<210> SEQ ID NO 407
<211> LENGTH: 63
<212> TYPE: PRT
<213> ORGANISM: Lactococcus sp. QU 12

<400> SEQUENCE: 407

Met Lys Leu Ile Asp His Leu Gly Ala Pro Arg Trp Ala Val Asp Thr
1 5 10 15

Ile Leu Gly Ala Ile Ala Val Gly Asn Leu Ala Ser Trp Val Leu Ala
20 25 30

Leu Val Pro Gly Pro Gly Trp Ala Val Lys Ala Gly Leu Ala Thr Ala
35 40 45

Ala Ala Ile Val Lys His Gln Gly Lys Ala Ala Ala Ala Ala Trp
50 55 60

<210> SEQ ID NO 408
<211> LENGTH: 192
<212> TYPE: DNA
<213> ORGANISM: Lactococcus sp. QU 12

<400> SEQUENCE: 408
atgaaattaa ttgatcattt aggtgctcca agatgggccg ttgatactat tttaggtgca 60
atcgcagttg ggaacttagc aagttgggtt ctagcgcttg tccctggtcc agggtgggca 120
gtaaaagctg gtttagcaac tgctgctgcc atcgttaaac atcaaggtaa agctgccgct 180
gctgcttggt aa 192

<210> SEQ ID NO 409
<211> LENGTH: 50
<212> TYPE: PRT
<213> ORGANISM: Brevibacillus sp. GI-9

<400> SEQUENCE: 409

Met Ala Cys Gln Cys Pro Asp Ala Ile Ser Gly Trp Thr His Thr Asp
1 5 10 15

Tyr Gln Cys His Gly Leu Glu Asn Lys Met Tyr Arg His Val Tyr Ala
20 25 30

Ile Cys Met Asn Gly Thr Gln Val Tyr Cys Arg Thr Glu Trp Gly Ser
35 40 45

Ser Cys
50

<210> SEQ ID NO 410
<211> LENGTH: 153
<212> TYPE: DNA
<213> ORGANISM: Brevibacillus sp. GI-9

<400> SEQUENCE: 410
atggcttgcc aatgtccaga tgcgatctca ggttggacgc atacagatta ccagtgtcac 60
ggtttggaga ataaaatgta tagacatgtt tatgcaattt gcatgaacgg tactcaagta 120
tattgcagaa cagagtgggg tagcagctgc tag 153

<210> SEQ ID NO 411
<211> LENGTH: 57
<212> TYPE: PRT
<213> ORGANISM: Leuconostoc pseudomesenteroides

<400> SEQUENCE: 411

Met Asn Lys Glu Tyr Asn Ser Ile Ser Asn Phe Lys Lys Ile Thr Asn
1 5 10 15

Lys Asp Leu Gln Asn Ile Asn Gly Gly Phe Ile Gly Arg Ala Ile Gly
20 25 30

Asp Phe Val Tyr Phe Gly Ala Lys Gly Leu Arg Glu Ser Gly Lys Leu
35 40 45

Leu Asn Tyr Tyr Tyr Lys His Lys His
50 55

<210> SEQ ID NO 412
<211> LENGTH: 174
<212> TYPE: DNA
<213> ORGANISM: Leuconostoc pseudomesenteroides

<400> SEQUENCE: 412
atgaataaag aatataatag cattagcaat tttaaaaaaa ttactaataa agacttgcaa 60
aacataaatg gtggatttat tggtagggca ataggtgact ttgtgtactt tggagcgaag 120
ggactaagag aatctggtaa actacttaat tattactata agcataagca ttga 174

<210> SEQ ID NO 413
<211> LENGTH: 53
<212> TYPE: PRT
<213> ORGANISM: Leuconostoc pseudomesenteroides

<400> SEQUENCE: 413

```
Met Lys Asn Gln Leu Met Ser Phe Glu Val Ile Ser Glu Lys Glu Leu
1               5                   10                  15

Ser Thr Val Gln Gly Gly Lys Gly Leu Gly Lys Leu Ile Gly Ile Asp
            20                  25                  30

Trp Leu Leu Gly Gln Ala Lys Asp Ala Val Lys Gln Tyr Lys Lys Asp
        35                  40                  45

Tyr Lys Arg Trp His
    50


<210> SEQ ID NO 414
<211> LENGTH: 162
<212> TYPE: DNA
<213> ORGANISM: Leuconostoc pseudomesenteroides

<400> SEQUENCE: 414

atgaaaaatc agttaatgtc tttcgaagtg atatcagaaa aagaattgtc cacggtacaa      60

ggtggcaaag gcttaggtaa actcatagga attgattggc ttttgggtca agctaaggac     120

gctgttaaac agtacaagaa ggattacaaa cgttggcact aa                        162


<210> SEQ ID NO 415
<211> LENGTH: 61
<212> TYPE: PRT
<213> ORGANISM: Leuconostoc gelidum

<400> SEQUENCE: 415

Met Met Asn Met Lys Pro Thr Glu Ser Tyr Glu Gln Leu Asp Asn Ser
1               5                   10                  15

Ala Leu Glu Gln Val Val Gly Gly Lys Tyr Tyr Gly Asn Gly Val His
            20                  25                  30

Cys Thr Lys Ser Gly Cys Ser Val Asn Trp Gly Glu Ala Phe Ser Ala
        35                  40                  45

Gly Val His Arg Leu Ala Asn Gly Gly Asn Gly Phe Trp
    50                  55                  60


<210> SEQ ID NO 416
<211> LENGTH: 186
<212> TYPE: DNA
<213> ORGANISM: Leuconostoc gelidum

<400> SEQUENCE: 416

atgatgaaca tgaaacctac ggaaagctat gagcaattgg ataatagtgc tctcgaacaa      60

gtcgtaggag gtaagtatta tggtaacgga gttcattgca caaaaagtgg ttgttctgta     120

aactggggag aagccttttc agctggagta catcgtttag caaatggtgg aaatggtttc     180

tggtaa                                                                186


<210> SEQ ID NO 417
<211> LENGTH: 61
<212> TYPE: PRT
<213> ORGANISM: Leuconostoc carnosum

<400> SEQUENCE: 417

Met Asn Asn Met Lys Ser Ala Asp Asn Tyr Gln Gln Leu Asp Asn Asn
1               5                   10                  15

Ala Leu Glu Gln Val Val Gly Gly Lys Tyr Tyr Gly Asn Gly Val His
            20                  25                  30

Cys Thr Lys Ser Gly Cys Ser Val Asn Trp Gly Glu Ala Phe Ser Ala
        35                  40                  45
```

```
Gly Val His Arg Leu Ala Asn Gly Gly Asn Gly Phe Trp
    50                  55                  60


<210> SEQ ID NO 418
<211> LENGTH: 186
<212> TYPE: DNA
<213> ORGANISM: Leuconostoc carnosum

<400> SEQUENCE: 418

atgaataaca tgaaatctgc ggataattat cagcaattgg ataataatgc tctcgaacaa      60

gtcgtaggag gtaagtatta tggtaacgga gttcattgca caaaaagtgg ttgttctgta     120

aactggggag aagccttttc agctggagta catcgtttag caaatggtgg aaatggtttc     180

tggtaa                                                                186


<210> SEQ ID NO 419
<211> LENGTH: 63
<212> TYPE: PRT
<213> ORGANISM: Leuconostoc mesenteroides

<400> SEQUENCE: 419

Met Phe Leu Val Asn Gln Leu Gly Ile Ser Lys Ser Leu Ala Asn Thr
1               5                   10                  15

Ile Leu Gly Ala Ile Ala Val Gly Asn Leu Ala Ser Trp Leu Leu Ala
            20                  25                  30

Leu Val Pro Gly Pro Gly Trp Ala Thr Lys Ala Ala Leu Ala Thr Ala
        35                  40                  45

Glu Thr Ile Val Lys His Glu Gly Lys Ala Ala Ala Ile Ala Trp
    50                  55                  60


<210> SEQ ID NO 420
<211> LENGTH: 192
<212> TYPE: DNA
<213> ORGANISM: Leuconostoc mesenteroides

<400> SEQUENCE: 420

atgttcttgg taaatcagtt agggatttca aaatcgttag ctaatactat tcttggtgca      60

attgctgttg gtaatttggc cagttggtta ttagctttgg ttcctggtcc gggttgggca     120

acaaaagcag cacttgcgac agctgaaaca attgtgaagc atgaaggaaa agcagctgct     180

attgcgtggt aa                                                         192


<210> SEQ ID NO 421
<211> LENGTH: 74
<212> TYPE: PRT
<213> ORGANISM: Bacillus licheniformis

<400> SEQUENCE: 421

Met Ser Lys Lys Glu Met Ile Leu Ser Trp Lys Asn Pro Met Tyr Arg
1               5                   10                  15

Thr Glu Ser Ser Tyr His Pro Ala Gly Asn Ile Leu Lys Glu Leu Gln
            20                  25                  30

Glu Glu Glu Gln His Ser Ile Ala Gly Gly Thr Ile Thr Leu Ser Thr
        35                  40                  45

Cys Ala Ile Leu Ser Lys Pro Leu Gly Asn Asn Gly Tyr Leu Cys Thr
    50                  55                  60

Val Thr Lys Glu Cys Met Pro Ser Cys Asn
65                  70
```

<210> SEQ ID NO 422
<211> LENGTH: 225
<212> TYPE: DNA
<213> ORGANISM: Bacillus licheniformis

<400> SEQUENCE: 422
atgtcaaaaa aggaaatgat tctttcatgg aaaaatccta tgtatcgcac tgaatcttct 60
tatcatccag cagggaacat ccttaaagaa ctccaggaag aggaacagca cagcatcgcc 120
ggaggcacaa tcacgctcag cacttgtgcc atcttgagca agccgttagg aaataacgga 180
tacctgtgta cagtgacaaa agaatgcatg ccaagctgta actaa 225

<210> SEQ ID NO 423
<211> LENGTH: 266
<212> TYPE: PRT
<213> ORGANISM: Brevibacterium linens

<400> SEQUENCE: 423

Met Asn Asn Leu Tyr Arg Glu Leu Ala Pro Ile Pro Gly Pro Ala Trp
1 5 10 15

Ala Glu Ile Glu Glu Glu Ala Arg Arg Thr Phe Lys Arg Asn Ile Ala
20 25 30

Gly Arg Arg Ile Val Asp Val Ala Gly Pro Thr Gly Phe Glu Thr Ser
35 40 45

Ala Val Thr Thr Gly His Ile Arg Asp Val Gln Ser Glu Thr Ser Gly
50 55 60

Leu Gln Val Lys Gln Arg Ile Val Gln Glu Tyr Ile Glu Leu Arg Thr
65 70 75 80

Pro Phe Thr Val Thr Arg Gln Ala Ile Asp Asp Val Ala Arg Gly Ser
85 90 95

Gly Asp Ser Asp Trp Gln Pro Val Lys Asp Ala Ala Thr Thr Ile Ala
100 105 110

Met Ala Glu Asp Arg Ala Ile Leu His Gly Leu Asp Ala Ala Gly Ile
115 120 125

Gly Gly Ile Val Pro Gly Ser Ser Asn Ala Ala Val Ala Ile Pro Asp
130 135 140

Ala Val Glu Asp Phe Ala Asp Ala Val Ala Gln Ala Leu Ser Val Leu
145 150 155 160

Arg Thr Val Gly Val Asp Gly Pro Tyr Ser Leu Leu Leu Ser Ser Ala
165 170 175

Glu Tyr Thr Lys Val Ser Glu Ser Thr Asp His Gly Tyr Pro Ile Arg
180 185 190

Glu His Leu Ser Arg Gln Leu Gly Ala Gly Glu Ile Ile Trp Ala Pro
195 200 205

Ala Leu Glu Gly Ala Leu Leu Val Ser Thr Arg Gly Gly Asp Tyr Glu
210 215 220

Leu His Leu Gly Gln Asp Leu Ser Ile Gly Tyr Tyr Ser His Asp Ser
225 230 235 240

Glu Thr Val Glu Leu Tyr Leu Gln Glu Thr Phe Gly Phe Leu Ala Leu
245 250 255

Thr Asp Glu Ser Ser Val Pro Leu Ser Leu
260 265

<210> SEQ ID NO 424
<211> LENGTH: 801
<212> TYPE: DNA

<213> ORGANISM: Brevibacterium linens

<400> SEQUENCE: 424
gtgaataacc tctatcgcga gcttgccccc atccccggcc cggcctgggc ggagatcgag 60
gaggaggctc gacggacatt caaacgcaat atcgccggcc gccggatcgt cgatgtcgca 120
gggcccacgg gcttcgagac ctccgcggtg accactggcc acatccgaga cgtccagtcg 180
gagacgagcg gactgcaggt taagcagcgc atcgtgcagg aatacatcga gctgcggacc 240
ccattcaccg tgactcggca ggccatcgat gacgtggccc gcgggtccgg tgactcggac 300
tggcagcccg tcaaggatgc ggccacgacg atcgcgatgg ctgaagatcg ggccattctc 360
cacgggctcg atgcggccgg gatcggcgga atcgttcccg gcagctcgaa tgccgcagtg 420
gccatccccg acgccgtcga ggacttcgcg gacgccgtcg cccaggcgct gagtgtgctg 480
cgcacggtgg gagtcgacgg gccctacagc ctgttgctct cctccgcgga gtacaccaag 540
gtctccgagt ccaccgacca cggctacccg atccgcgagc acctctcccg gcagctcggc 600
gccggagaga tcatctgggc gcccgcgctc gaaggggcgc tgctcgtctc cacgcgcggg 660
ggtgactacg agctccacct cggccaggac ctgtcgatcg gttactacag ccacgacagc 720
gagaccgtcg aactctatct gcaggagacc ttcggattcc tcgcgctgac cgacgaatcc 780
agtgtgcctt tgagcctctg a 801

<210> SEQ ID NO 425
<211> LENGTH: 71
<212> TYPE: PRT
<213> ORGANISM: Listeria innocua

<400> SEQUENCE: 425

Met Lys Lys Ala Ala Leu Lys Phe Ile Ile Val Ile Ala Ile Leu Gly
1 5 10 15

Phe Ser Phe Ser Phe Phe Ser Ile Gln Ser Glu Ala Lys Ser Tyr Gly
20 25 30

Asn Gly Val Gln Cys Asn Lys Lys Lys Cys Trp Val Asp Trp Gly Ser
35 40 45

Ala Ile Ser Thr Ile Gly Asn Asn Ser Ala Ala Asn Trp Ala Thr Gly
50 55 60

Gly Ala Ala Gly Trp Lys Ser
65 70

<210> SEQ ID NO 426
<211> LENGTH: 216
<212> TYPE: DNA
<213> ORGANISM: Listeria innocua

<400> SEQUENCE: 426
ttgaagaagg cagcgttaaa atttattatt gttattgcta ttctaggttt cagtttttct 60
ttctttagca tacaatctga agctaaatct tatggaaatg gagttcagtg taataagaaa 120
aaatgttggg tagattgggg tagtgctata agtactattg gaaataattc tgcagcgaat 180
tgggctacag gtggagcagc tggttggaaa agctga 216

<210> SEQ ID NO 427
<211> LENGTH: 68
<212> TYPE: PRT
<213> ORGANISM: Bacillus sp.

<400> SEQUENCE: 427

-continued

```
Met Ser Gln Glu Ala Ile Ile Arg Ser Trp Lys Asp Pro Phe Ser Arg
1               5                   10                  15

Glu Asn Ser Thr Gln Asn Pro Ala Gly Asn Pro Phe Ser Glu Leu Lys
            20                  25                  30

Glu Ala Gln Met Asp Lys Leu Val Gly Ala Gly Asp Met Glu Ala Ala
        35                  40                  45

Cys Thr Phe Thr Leu Pro Gly Gly Gly Gly Val Cys Thr Leu Thr Ser
    50                  55                  60

Glu Cys Ile Cys
65
```

<210> SEQ ID NO 428
<211> LENGTH: 207
<212> TYPE: DNA
<213> ORGANISM: Bacillus sp.

<400> SEQUENCE: 428

```
atgagtcaag aagctatcat tcgttcatgg aaagatcctt tttcccgtga aaattctaca     60

caaaatccag ctggtaaccc attcagtgag ctgaaagaag cacaaatgga taagttagta    120

ggtgcgggag acatggaagc agcatgtact tttacattgc ctggtggcgg cggtgtttgt    180

actctaactt ctgaatgtat ttgttaa                                        207
```

<210> SEQ ID NO 429
<211> LENGTH: 61
<212> TYPE: PRT
<213> ORGANISM: Leuconostoc mesenteroides

<400> SEQUENCE: 429

```
Met Thr Asn Met Lys Ser Val Glu Ala Tyr Gln Gln Leu Asp Asn Gln
1               5                   10                  15

Asn Leu Lys Lys Val Val Gly Gly Lys Tyr Tyr Gly Asn Gly Val His
            20                  25                  30

Cys Thr Lys Ser Gly Cys Ser Val Asn Trp Gly Glu Ala Ala Ser Ala
        35                  40                  45

Gly Ile His Arg Leu Ala Asn Gly Gly Asn Gly Phe Trp
    50                  55                  60
```

<210> SEQ ID NO 430
<211> LENGTH: 186
<212> TYPE: DNA
<213> ORGANISM: Leuconostoc mesenteroides

<400> SEQUENCE: 430

```
atgacgaata tgaagtctgt ggaagcatat cagcaattag ataaccagaa tctcaagaaa     60

gttgttggtg gaaagtatta tgggaatggt gttcactgta caaaaagtgg atgctctgtt    120

aactggggag aagctgcctc agctggcata catcgtttgg ccaatggtgg aaatggattt    180

tggtaa                                                               186
```

<210> SEQ ID NO 431
<211> LENGTH: 68
<212> TYPE: PRT
<213> ORGANISM: Clavibacter michiganensis subsp. michiganensis

<400> SEQUENCE: 431

```
Met Asn Asp Ile Leu Glu Thr Glu Thr Pro Val Met Val Ser Pro Arg
1               5                   10                  15

Trp Asp Met Leu Leu Asp Ala Gly Glu Asp Thr Ser Pro Ser Val Gln
```

```
            20                  25                  30

Thr Gln Ile Asp Ala Glu Phe Arg Arg Val Val Ser Pro Tyr Met Ser
        35                  40                  45

Ser Ser Gly Trp Leu Cys Thr Leu Thr Ile Glu Cys Gly Thr Ile Ile
    50                  55                  60

Cys Ala Cys Arg
65


<210> SEQ ID NO 432
<211> LENGTH: 207
<212> TYPE: DNA
<213> ORGANISM: Clavibacter michiganensis subsp. michiganensis

<400> SEQUENCE: 432

atgaacgaca tcctcgagac ggagaccccc gtcatggtca gcccccggtg ggacatgctg      60

ctcgacgcgg gcgaggacac cagcccgtcc gtccagaccc agatcgacgc ggagttccgt     120

cgcgtcgtga gcccgtacat gtccagcagc ggctggctct gcacgctcac catcgaatgt     180

ggcaccatca tctgcgcgtg tcgctga                                         207


<210> SEQ ID NO 433
<211> LENGTH: 69
<212> TYPE: PRT
<213> ORGANISM: Escherichia coli

<400> SEQUENCE: 433

Met Glu Leu Lys Ala Ser Glu Phe Gly Val Val Leu Ser Val Asp Ala
1               5                   10                  15

Leu Lys Leu Ser Arg Gln Ser Pro Leu Gly Val Gly Ile Gly Gly Gly
            20                  25                  30

Gly Gly Gly Gly Gly Gly Gly Ser Cys Gly Gly Gln Gly Gly Gly Cys
        35                  40                  45

Gly Gly Cys Ser Asn Gly Cys Ser Gly Gly Asn Gly Gly Ser Gly Gly
    50                  55                  60

Ser Gly Ser His Ile
65


<210> SEQ ID NO 434
<211> LENGTH: 207
<212> TYPE: DNA
<213> ORGANISM: Escherichia coli

<400> SEQUENCE: 434

atggaattaa aagcgagtga atttggtgta gttttgtccg ttgatgctct taaattatca      60

cgccagtctc cattaggtgt tggcattggt ggtggtggcg gcggcggcgg cggcggtagc     120

tgcggtggtc aaggtggcgg ttgtggtggt tgcagcaacg gttgtagtgg tggaaacggt     180

ggcagcggcg gaagtggttc acatatc                                         207


<210> SEQ ID NO 435
<211> LENGTH: 7
<212> TYPE: PRT
<213> ORGANISM: Escherichia coli

<400> SEQUENCE: 435

Met Arg Thr Gly Asn Ala Asn
1               5


<210> SEQ ID NO 436
```

<211> LENGTH: 24
<212> TYPE: DNA
<213> ORGANISM: Escherichia coli

<400> SEQUENCE: 436
atgcgtactg gtaatgcaaa ctaa 24

<210> SEQ ID NO 437
<211> LENGTH: 99
<212> TYPE: PRT
<213> ORGANISM: Klebsiella pneumoniae

<400> SEQUENCE: 437

Met Arg Glu Ile Ser Gln Lys Asp Leu Asn Leu Ala Phe Gly Ala Gly
1 5 10 15

Glu Thr Asp Pro Asn Thr Gln Leu Leu Asn Asp Leu Gly Asn Asn Met
20 25 30

Ala Trp Gly Ala Ala Leu Gly Ala Pro Gly Gly Leu Gly Ser Ala Ala
35 40 45

Leu Gly Ala Ala Gly Gly Ala Leu Gln Thr Val Gly Gln Gly Leu Ile
50 55 60

Asp His Gly Pro Val Asn Val Pro Ile Pro Val Leu Ile Gly Pro Ser
65 70 75 80

Trp Asn Gly Ser Gly Ser Gly Tyr Asn Ser Ala Thr Ser Ser Ser Gly
85 90 95

Ser Gly Ser

<210> SEQ ID NO 438
<211> LENGTH: 300
<212> TYPE: DNA
<213> ORGANISM: Klebsiella pneumoniae

<400> SEQUENCE: 438
atgagagaaa ttagtcaaaa ggacttaaat cttgcttttg gtgcaggaga gaccgatcca 60
aatactcaac ttctaaacga ccttggaaat aatatggcat ggggtgctgc tcttggcgct 120
cctggcggat taggatcagc agctttgggg gccgcgggag gtgcattaca aactgtaggg 180
caaggattaa ttgaccatgg tcctgtaaat gtccccatcc ctgtactcat cgggccaagc 240
tggaatggta gcggtagtgg ttataacagc gcaacatcca gttccggtag tggtagttaa 300

<210> SEQ ID NO 439
<211> LENGTH: 75
<212> TYPE: PRT
<213> ORGANISM: Escherichia coli

<400> SEQUENCE: 439

Met Arg Glu Ile Thr Glu Ser Gln Leu Arg Tyr Ile Ser Gly Ala Gly
1 5 10 15

Gly Ala Pro Ala Thr Ser Ala Asn Ala Ala Gly Ala Ala Ala Ile Val
20 25 30

Gly Ala Leu Ala Gly Ile Pro Gly Gly Pro Leu Gly Val Val Val Gly
35 40 45

Ala Val Ser Ala Gly Leu Thr Thr Ala Ile Gly Ser Thr Val Gly Ser
50 55 60

Gly Ser Ala Ser Ser Ser Ala Gly Gly Gly Ser
65 70 75

<210> SEQ ID NO 440

<211> LENGTH: 228
<212> TYPE: DNA
<213> ORGANISM: Escherichia coli

<400> SEQUENCE: 440
atgcgagaaa taacagaatc acagttaaga tatatttccg gggcgggagg tgcgccagcg 60
acttcagcta atgccgcagg tgctgcagct attgttggag ctctcgccgg aatacctggt 120
ggtccacttg gggttgtagt tggagccgta tctgccggtt tgacaacagc aattggctcg 180
accgtgggaa gtggtagtgc cagttcttct gctggtggcg gtagctaa 228

<210> SEQ ID NO 441
<211> LENGTH: 58
<212> TYPE: PRT
<213> ORGANISM: Escherichia coli

<400> SEQUENCE: 441

Met Ile Lys His Phe His Phe Asn Lys Leu Ser Ser Gly Lys Lys Asn
1 5 10 15

Asn Val Pro Ser Pro Ala Lys Gly Val Ile Gln Ile Lys Lys Ser Ala
20 25 30

Ser Gln Leu Thr Lys Gly Gly Ala Gly His Val Pro Glu Tyr Phe Val
35 40 45

Gly Ile Gly Thr Pro Ile Ser Phe Tyr Gly
50 55

<210> SEQ ID NO 442
<211> LENGTH: 177
<212> TYPE: DNA
<213> ORGANISM: Escherichia coli

<400> SEQUENCE: 442
atgattaagc attttcattt taataaactg tcttctggta aaaaaaataa tgttccatct 60
cctgcaaagg gggttataca aataaaaaaa tcagcatcgc aactcacaaa aggtggtgca 120
ggacatgtgc ctgagtattt tgtggggatt ggtacaccta tatctttcta tggctga 177

<210> SEQ ID NO 443
<211> LENGTH: 90
<212> TYPE: PRT
<213> ORGANISM: Escherichia coli

<400> SEQUENCE: 443

Met Tyr Met Arg Glu Leu Asp Arg Glu Glu Leu Asn Cys Val Gly Gly
1 5 10 15

Ala Gly Asp Pro Leu Ala Asp Pro Asn Ser Gln Ile Val Arg Gln Ile
20 25 30

Met Ser Asn Ala Ala Trp Gly Pro Pro Leu Val Pro Glu Arg Phe Arg
35 40 45

Gly Met Ala Val Gly Ala Ala Gly Gly Val Thr Gln Thr Val Leu Gln
50 55 60

Gly Ala Ala Ala His Met Pro Val Asn Val Pro Ile Pro Lys Val Pro
65 70 75 80

Met Gly Pro Ser Trp Asn Gly Ser Lys Gly
85 90

<210> SEQ ID NO 444
<211> LENGTH: 273
<212> TYPE: DNA
<213> ORGANISM: Escherichia coli

<400> SEQUENCE: 444
atgtatatga gagagttaga tagagaggaa ttaaattgcg ttggtggggc tggagatccg 60
cttgcagatc ctaattccca aattgtaaga cagataatgt ctaatgcggc atggggcccg 120
cctttggtgc cagagcggtt taggggaatg gctgttggag ccgcaggtgg ggttacgcag 180
acagttcttc aaggagcagc agctcatatg ccggttaatg tccctatacc taaagttccg 240
atgggaccct catggaacgg aagtaaagga taa 273

<210> SEQ ID NO 445
<211> LENGTH: 50
<212> TYPE: PRT
<213> ORGANISM: Enterococcus mundtii

<400> SEQUENCE: 445

Met Ser Gln Val Val Gly Gly Lys Tyr Tyr Gly Asn Gly Val Ser Cys
1 5 10 15

Asn Lys Lys Gly Cys Ser Val Asp Trp Gly Lys Ala Ile Gly Ile Ile
20 25 30

Gly Asn Asn Ser Ala Ala Asn Leu Ala Thr Gly Gly Ala Ala Gly Trp
35 40 45

Lys Ser
50

<210> SEQ ID NO 446
<211> LENGTH: 153
<212> TYPE: DNA
<213> ORGANISM: Enterococcus mundtii

<400> SEQUENCE: 446
atgtcacagg tagtaggtgg aaaatactac ggtaatggag tctcatgtaa taaaaaaggg 60
tgcagtgttg attggggaaa agcgattggc attattggaa ataattctgc tgcgaattta 120
gctactggtg gagcagctgg ttggaaaagt taa 153

<210> SEQ ID NO 447
<211> LENGTH: 58
<212> TYPE: PRT
<213> ORGANISM: Enterococcus mundtii

<400> SEQUENCE: 447

Met Lys Lys Leu Thr Ser Lys Glu Met Ala Gln Val Val Gly Gly Lys
1 5 10 15

Tyr Tyr Gly Asn Gly Leu Ser Cys Asn Lys Lys Gly Cys Ser Val Asp
20 25 30

Trp Gly Lys Ala Ile Gly Ile Ile Gly Asn Asn Ser Ala Ala Asn Leu
35 40 45

Ala Thr Gly Gly Ala Ala Gly Trp Lys Ser
50 55

<210> SEQ ID NO 448
<211> LENGTH: 177
<212> TYPE: DNA
<213> ORGANISM: Enterococcus mundtii

<400> SEQUENCE: 448
ttgaagaaat taacatcaaa agaaatggca caagtagtag gtgggaaata ctacggtaat 60
ggattatcat gtaataaaaa agggtgcagt gttgattggg gaaaagctat tggcattatt 120
ggaaataatt ctgctgcgaa tttagctact ggtggagcag ctggttggaa aagttaa 177

<210> SEQ ID NO 449
<211> LENGTH: 63
<212> TYPE: PRT
<213> ORGANISM: Streptococcus mutans

<400> SEQUENCE: 449

Met Ser Asn Thr Gln Leu Leu Glu Val Leu Gly Thr Glu Thr Phe Asp
1 5 10 15

Val Gln Glu Asp Leu Phe Ala Phe Asp Thr Thr Asp Thr Thr Ile Val
20 25 30

Ala Ser Asn Asp Asp Pro Asp Thr Arg Phe Lys Ser Trp Ser Leu Cys
35 40 45

Thr Pro Gly Cys Ala Arg Thr Gly Ser Phe Asn Ser Tyr Cys Cys
50 55 60

<210> SEQ ID NO 450
<211> LENGTH: 192
<212> TYPE: DNA
<213> ORGANISM: Streptococcus mutans

<400> SEQUENCE: 450
atgtcaaaca cacaattatt agaagtcctt ggtactgaaa cttttgatgt tcaagaagat 60
ctctttgctt ttgatacaac agatactact attgtggcaa gcaacgacga tccagatact 120
cgtttcaaaa gttggagcct ttgtacgcct ggttgtgcaa ggacaggtag tttcaatagt 180
tactgttgct ga 192

<210> SEQ ID NO 451
<211> LENGTH: 53
<212> TYPE: PRT
<213> ORGANISM: Streptococcus mutans

<400> SEQUENCE: 451

Met Asn Lys Leu Asn Ser Asn Ala Val Val Ser Leu Asn Glu Val Ser
1 5 10 15

Asp Ser Glu Leu Asp Thr Ile Leu Gly Gly Asn Arg Trp Trp Gln Gly
20 25 30

Val Val Pro Thr Val Ser Tyr Glu Cys Arg Met Asn Ser Trp Gln His
35 40 45

Val Phe Thr Cys Cys
50

<210> SEQ ID NO 452
<211> LENGTH: 162
<212> TYPE: DNA
<213> ORGANISM: Streptococcus mutans

<400> SEQUENCE: 452
atgaacaagt taaacagtaa cgcagtagtt tctttgaatg aagtttcaga ttctgaattg 60
gatactattt tgggtggtaa tcgttggtgg caaggtgttg tgccaacggt ctcatatgag 120
tgtcgcatga attcatggca acatgttttc acttgctgtt aa 162

<210> SEQ ID NO 453
<211> LENGTH: 57
<212> TYPE: PRT
<213> ORGANISM: Lactococcus lactis subsp. lactis

<400> SEQUENCE: 453

```
Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
        35                  40                  45

Cys His Cys Ser Ile His Val Ser Lys
    50                  55


<210> SEQ ID NO 454
<211> LENGTH: 174
<212> TYPE: DNA
<213> ORGANISM: Lactococcus lactis subsp. lactis

<400> SEQUENCE: 454

atgagtacaa aagattttaa cttggatttg gtatctgttt cgaagaaaga ttcaggtgca      60

tcaccacgca ttacaagtat ttcgctatgt acacccggtt gtaaaacagg agctctgatg     120

ggttgtaaca tgaaaacagc aacttgtcat tgtagtattc acgtaagcaa ataa           174


<210> SEQ ID NO 455
<211> LENGTH: 57
<212> TYPE: PRT
<213> ORGANISM: Lactococcus lactis

<400> SEQUENCE: 455

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
        35                  40                  45

Cys Asn Cys Ser Val His Val Ser Lys
    50                  55


<210> SEQ ID NO 456
<211> LENGTH: 171
<212> TYPE: DNA
<213> ORGANISM: Lactococcus lactis

<400> SEQUENCE: 456

atgagtacaa aagatttcaa cttggatttg gtatctgttt cgaagaaaga ttcaggtgca      60

tcaccacgca ttacaagtat ttcgctatgt acacccggtt gtaaaacagg agctctgatg     120

ggttgtaaca tgaaaacagc aacttgtaat tgtagcgttc acgtaagcaa a              171


<210> SEQ ID NO 457
<211> LENGTH: 57
<212> TYPE: PRT
<213> ORGANISM: Lactococcus lactis

<400> SEQUENCE: 457

Met Ser Thr Lys Asp Phe Asn Leu Asp Leu Val Ser Val Ser Lys Thr
1               5                   10                  15

Asp Ser Gly Ala Ser Thr Arg Ile Thr Ser Ile Ser Leu Cys Thr Pro
            20                  25                  30

Gly Cys Lys Thr Gly Val Leu Met Gly Cys Asn Leu Lys Thr Ala Thr
        35                  40                  45

Cys Asn Cys Ser Val His Val Ser Lys
```

50 55

<210> SEQ ID NO 458
<211> LENGTH: 174
<212> TYPE: DNA
<213> ORGANISM: Lactococcus lactis

<400> SEQUENCE: 458
atgagtacaa aagatttcaa cttagatttg gtatctgttt caaaaacaga ttctggcgct 60
tcaacacgta ttaccagcat ttcgctttgt acaccaggtt gtaaaacagg tgttctgatg 120
ggatgtaacc tgaaaacagc aacttgtaat tgtagcgttc acgtaagcaa ataa 174

<210> SEQ ID NO 459
<211> LENGTH: 55
<212> TYPE: PRT
<213> ORGANISM: Streptococcus uberis

<400> SEQUENCE: 459

Met Asn Asn Glu Asp Phe Asn Leu Asp Leu Ile Lys Ile Ser Lys Glu
1 5 10 15

Asn Asn Ser Gly Ala Ser Pro Arg Ile Thr Ser Lys Ser Leu Cys Thr
20 25 30

Pro Gly Cys Lys Thr Gly Ile Leu Met Thr Cys Pro Leu Lys Thr Ala
35 40 45

Thr Cys Gly Cys His Phe Gly
50 55

<210> SEQ ID NO 460
<211> LENGTH: 168
<212> TYPE: DNA
<213> ORGANISM: Streptococcus uberis

<400> SEQUENCE: 460
atgaacaatg aagattttaa tttggatctc atcaaaatct caaaggaaaa caactcagga 60
gcttcacctc gaataactag taaatcatta tgtactcctg gatgtaagac gggtattttg 120
atgacttgtc cactaaaaac tgcaacctgt ggttgtcatt ttggataa 168

<210> SEQ ID NO 461
<211> LENGTH: 57
<212> TYPE: PRT
<213> ORGANISM: Lactococcus lactis subsp. lactis

<400> SEQUENCE: 461

Met Ser Thr Lys Asp Phe Asn Leu Asp Leu Val Ser Val Ser Lys Lys
1 5 10 15

Asp Ser Gly Ala Ser Pro Arg Ile Thr Ser Ile Ser Leu Cys Thr Pro
20 25 30

Gly Cys Lys Thr Gly Ala Leu Met Gly Cys Asn Met Lys Thr Ala Thr
35 40 45

Cys Asn Cys Ser Ile His Val Ser Lys
50 55

<210> SEQ ID NO 462
<211> LENGTH: 174
<212> TYPE: DNA
<213> ORGANISM: Lactococcus lactis subsp. lactis

<400> SEQUENCE: 462
atgagtacaa aagattttaa cttggatttg gtatctgttt cgaagaaaga ttcaggtgca 60
tcaccacgca ttacaagtat ttcgctatgt acacccggtt gtaaaacagg agctctgatg 120
ggttgtaaca tgaaaacagc aacttgtaat tgtagtattc acgtaagcaa ataa 174

<210> SEQ ID NO 463
<211> LENGTH: 57
<212> TYPE: PRT
<213> ORGANISM: Staphylococcus warneri

<400> SEQUENCE: 463

Met Glu Asn Ser Lys Val Met Lys Asp Ile Glu Val Ala Asn Leu Leu
1 5 10 15

Glu Glu Val Gln Glu Asp Glu Leu Asn Glu Val Leu Gly Ala Lys Lys
20 25 30

Lys Ser Gly Val Ile Pro Thr Val Ser His Asp Cys His Met Asn Ser
35 40 45

Phe Gln Phe Val Phe Thr Cys Cys Ser
50 55

<210> SEQ ID NO 464
<211> LENGTH: 174
<212> TYPE: DNA
<213> ORGANISM: Staphylococcus warneri

<400> SEQUENCE: 464
atggaaaatt ctaaagttat gaaggacatt gaagtagcaa atttattaga agaggttcaa 60
gaagatgaat tgaatgaagt cttaggagct aagaaaaagt caggagtaat cccaactgtg 120
tcacacgatt gccatatgaa ttctttccaa tttgtattta cttgttgttc ataa 174

<210> SEQ ID NO 465
<211> LENGTH: 58
<212> TYPE: PRT
<213> ORGANISM: Paenibacillus polymyxa

<400> SEQUENCE: 465

Met Ala Glu Asn Leu Phe Asp Leu Asp Ile Gln Val Asn Lys Ser Gln
1 5 10 15

Gly Ser Val Glu Pro Gln Val Leu Ser Ile Val Ala Cys Ser Ser Gly
20 25 30

Cys Gly Ser Gly Lys Thr Ala Ala Ser Cys Val Glu Thr Cys Gly Asn
35 40 45

Arg Cys Phe Thr Asn Val Gly Ser Leu Cys
50 55

<210> SEQ ID NO 466
<211> LENGTH: 177
<212> TYPE: DNA
<213> ORGANISM: Paenibacillus polymyxa

<400> SEQUENCE: 466
atggctgaaa acttatttga tctggacatt caagtaaaca aatctcaagg ttctgtagag 60
cctcaggttc tgagcattgt tgcatgttct agcggatgtg gtagcggtaa aacagctgcc 120
agttgtgttg aaacttgtgg caaccggtgc tttactaacg ttggttcact ctgctaa 177

<210> SEQ ID NO 467
<211> LENGTH: 62
<212> TYPE: PRT
<213> ORGANISM: Pediococcus acidilactici

<400> SEQUENCE: 467

Met Lys Lys Ile Glu Lys Leu Thr Glu Lys Glu Met Ala Asn Ile Ile
1               5                   10                  15

Gly Gly Lys Tyr Tyr Gly Asn Gly Val Thr Cys Gly Lys His Ser Cys
            20                  25                  30

Ser Val Asp Trp Gly Lys Ala Thr Thr Cys Ile Ile Asn Asn Gly Ala
        35                  40                  45

Met Ala Trp Ala Thr Gly Gly His Gln Gly Asn His Lys Cys
    50                  55                  60

<210> SEQ ID NO 468
<211> LENGTH: 189
<212> TYPE: DNA
<213> ORGANISM: Pediococcus acidilactici

<400> SEQUENCE: 468
atgaaaaaaa ttgaaaaatt aactgaaaaa gaaatggcca atatcattgg tggtaaatac     60
tacggtaatg gggttacttg tggcaaacat tcctgctctg ttgactgggg taaggctacc    120
acttgcataa tcaataatgg agctatggca tgggctactg gtggacatca aggtaatcat    180
aaatgctag                                                            189

<210> SEQ ID NO 469
<211> LENGTH: 60
<212> TYPE: PRT
<213> ORGANISM: Pediococcus pentosaceus

<400> SEQUENCE: 469

Met Thr Glu Ile Lys Val Leu Asn Asp Lys Glu Leu Lys Asn Val Val
1               5                   10                  15

Gly Gly Lys Tyr Tyr Gly Asn Gly Val His Cys Gly Lys Lys Thr Cys
            20                  25                  30

Tyr Val Asp Trp Gly Gln Ala Thr Ala Ser Ile Gly Lys Ile Ile Val
        35                  40                  45

Asn Gly Trp Thr Gln His Gly Pro Trp Ala His Arg
    50                  55                  60

<210> SEQ ID NO 470
<211> LENGTH: 183
<212> TYPE: DNA
<213> ORGANISM: Pediococcus pentosaceus

<400> SEQUENCE: 470
atgactgaaa ttaaagtact aaacgataag gaactaaaaa atgtcgtagg aggaaagtat     60
tacggtaacg gagtgcattg tggtaaaaag acttgctatg tggactgggg acaagctaca    120
gctagcattg gaaaaattat agtgaacgga tggacacaac acgggccttg ggcacataga    180
taa                                                                  183

<210> SEQ ID NO 471
<211> LENGTH: 60
<212> TYPE: PRT
<213> ORGANISM: Staphylococcus epidermidis

<400> SEQUENCE: 471

Met Lys Asn Asn Lys Asn Leu Phe Asp Leu Glu Ile Lys Lys Glu Thr
1               5                   10                  15

Ser Gln Asn Thr Asp Glu Leu Glu Pro Gln Thr Ala Gly Pro Ala Ile
            20                  25                  30

Arg Ala Ser Val Lys Gln Cys Gln Lys Thr Leu Lys Ala Thr Arg Leu
35 40 45

Phe Thr Val Ser Cys Lys Gly Lys Asn Gly Cys Lys
50 55 60

<210> SEQ ID NO 472
<211> LENGTH: 183
<212> TYPE: DNA
<213> ORGANISM: Staphylococcus epidermidis

<400> SEQUENCE: 472
atgaaaaata acaaaaattt atttgattta gaaattaaaa aagaaacaag tcaaaacact 60
gatgaacttg aacctcaaac tgctggacca gcgattagag cttctgtgaa acaatgtcag 120
aaaactttga aagctacgcg tttatttaca gtgtcttgca aaggaaaaaa cggatgtaaa 180
tag 183

<210> SEQ ID NO 473
<211> LENGTH: 62
<212> TYPE: PRT
<213> ORGANISM: Carnobacterium maltaromaticum

<400> SEQUENCE: 473

Met Lys Thr Val Lys Glu Leu Ser Val Lys Glu Met Gln Leu Thr Thr
1 5 10 15

Gly Gly Lys Tyr Tyr Gly Asn Gly Val Ser Cys Asn Lys Asn Gly Cys
20 25 30

Thr Val Asp Trp Ser Lys Ala Ile Gly Ile Ile Gly Asn Asn Ala Ala
35 40 45

Ala Asn Leu Thr Thr Gly Gly Ala Ala Gly Trp Asn Lys Gly
50 55 60

<210> SEQ ID NO 474
<211> LENGTH: 189
<212> TYPE: DNA
<213> ORGANISM: Carnobacterium maltaromaticum

<400> SEQUENCE: 474
atgaaaactg ttaaagaact tagcgttaaa gaaatgcaac taactacagg aggtaagtat 60
tacggaaatg gcgtttcctg taataaaaat ggttgtactg tagattggag caaagctatt 120
gggattatag gaaacaatgc agcagcaaat ttgactacag gtggagccgc tggttggaac 180
aaaggataa 189

<210> SEQ ID NO 475
<211> LENGTH: 69
<212> TYPE: PRT
<213> ORGANISM: Lactobacillus plantarum
<220> FEATURE:
<221> NAME/KEY: misc_feature
<222> LOCATION: (40)..(40)
<223> OTHER INFORMATION: Xaa = any amino acid

<400> SEQUENCE: 475

Met Tyr Lys Glu Leu Thr Val Asp Glu Leu Ala Leu Ile Asp Gly Gly
1 5 10 15

Lys Lys Lys Lys Lys Lys Val Ala Cys Thr Trp Gly Asn Ala Ala Thr
20 25 30

Ala Ala Ala Ser Gly Ala Val Xaa Gly Ile Leu Gly Gly Pro Thr Gly
35 40 45

Ala Leu Ala Gly Ala Ile Trp Gly Val Ser Gln Cys Ala Ser Asn Asn
    50                  55                  60

Leu His Gly Met His
65

<210> SEQ ID NO 476
<211> LENGTH: 210
<212> TYPE: DNA
<213> ORGANISM: Lactobacillus plantarum
<220> FEATURE:
<221> NAME/KEY: misc_feature
<222> LOCATION: (119)..(119)
<223> OTHER INFORMATION: n = a, c, t or g

<400> SEQUENCE: 476
atgtataaag aattaacagt tgatgaatta gcattgattg atggaggaaa aaagaagaag 60
aaaaaagtag cttgtacttg gggaaatgca gcaacagccg ctgcttctgg tgcagttang 120
ggtattcttg gtgggcctac tggtgcactg gctggagcta tctggggcgt ttcacaatgc 180
gcgtctaaca acttacacgg catgcactaa 210

<210> SEQ ID NO 477
<211> LENGTH: 56
<212> TYPE: PRT
<213> ORGANISM: Lactobacillus plantarum

<400> SEQUENCE: 477

Met Met Lys Lys Ile Glu Lys Leu Thr Glu Lys Glu Met Ala Asn Ile
1               5                   10                  15

Ile Gly Gly Lys Tyr Tyr Gly Asn Gly Val Thr Cys Gly Lys His Ser
            20                  25                  30

Cys Ser Val Asn Trp Gly Gln Ala Phe Ser Cys Ser Val Ser His Leu
        35                  40                  45

Ala Asn Phe Gly His Gly Lys Cys
    50                  55

<210> SEQ ID NO 478
<211> LENGTH: 171
<212> TYPE: DNA
<213> ORGANISM: Lactobacillus plantarum

<400> SEQUENCE: 478
atgatgaaaa aaattgaaaa attaactgaa aaagaaatgg ccaatatcat tggtggtaaa 60
tactatggta atggggttac ttgtggtaaa cattcctgct ctgttaactg ggccaagca 120 ttttcttgta gtgtgtcaca tttagctaac ttcggtcatg gaaagtgcta a 171

<210> SEQ ID NO 479
<211> LENGTH: 64
<212> TYPE: PRT
<213> ORGANISM: Lactobacillus plantarum

<400> SEQUENCE: 479

Met Ser Lys Leu Val Lys Thr Leu Thr Val Asp Glu Ile Ser Lys Ile
1               5                   10                  15

Gln Thr Asn Gly Gly Lys Pro Ala Trp Cys Trp Tyr Thr Leu Ala Met
            20                  25                  30

Cys Gly Ala Gly Tyr Asp Ser Gly Thr Cys Asp Tyr Met Tyr Ser His
        35                  40                  45

Cys Phe Gly Val Lys His Ser Ser Gly Gly Gly Gly Ser Tyr His Cys 50 55 60

<210> SEQ ID NO 480
<211> LENGTH: 195
<212> TYPE: DNA
<213> ORGANISM: Lactobacillus plantarum

<400> SEQUENCE: 480
atgagtaaac tagttaaaac attaactgtc gatgaaatct ctaagattca aaccaatggt 60
ggaaaacctg catggtgttg gtacacattg gcaatgtgcg gtgctggtta tgattcaggc 120
acttgtgatt atatgtattc acactgcttt ggtgtaaaac actctagcgg tggtggcggt 180
agctaccatt gttag 195

<210> SEQ ID NO 481
<211> LENGTH: 56
<212> TYPE: PRT
<213> ORGANISM: Lactobacillus plantarum

<400> SEQUENCE: 481

Met Leu Gln Phe Glu Lys Leu Gln Tyr Ser Arg Leu Pro Gln Lys Lys
1 5 10 15

Leu Ala Lys Ile Ser Gly Gly Phe Asn Arg Gly Gly Tyr Asn Phe Gly
20 25 30

Lys Ser Val Arg His Val Val Asp Ala Ile Gly Ser Val Ala Gly Ile
35 40 45

Arg Gly Ile Leu Lys Ser Ile Arg
50 55

<210> SEQ ID NO 482
<211> LENGTH: 171
<212> TYPE: DNA
<213> ORGANISM: Lactobacillus plantarum

<400> SEQUENCE: 482
atgctacagt ttgagaaatt acaatattcc aggttgccgc aaaaaaagct tgccaaaata 60
tctggtggtt ttaatcgggg cggttataac tttggtaaaa gtgttcgaca tgttgttgat 120
gcaattggtt cagttgcagg cattcgtggt attttgaaaa gtattcgtta a 171

<210> SEQ ID NO 483
<211> LENGTH: 52
<212> TYPE: PRT
<213> ORGANISM: Lactobacillus plantarum

<400> SEQUENCE: 483

Met Lys Lys Phe Leu Val Leu Arg Asp Arg Glu Leu Asn Ala Ile Ser
1 5 10 15

Gly Gly Val Phe His Ala Tyr Ser Ala Arg Gly Val Arg Asn Asn Tyr
20 25 30

Lys Ser Ala Val Gly Pro Ala Asp Trp Val Ile Ser Ala Val Arg Gly
35 40 45

Phe Ile His Gly
50

<210> SEQ ID NO 484
<211> LENGTH: 159
<212> TYPE: DNA
<213> ORGANISM: Lactobacillus plantarum

<400> SEQUENCE: 484
atgaaaaaat ttctagtttt gcgtgaccgt gaattaaatg ctatttcagg tggcgttttc 60
catgcctata gcgcgcgtgg cgttcggaat aattataaaa gtgctgttgg gcctgccgat 120
tgggtcatta gcgctgtccg aggattcatc cacggatag 159

<210> SEQ ID NO 485
<211> LENGTH: 55
<212> TYPE: PRT
<213> ORGANISM: Lactobacillus plantarum

<400> SEQUENCE: 485

Met Thr Val Asn Lys Met Ile Lys Asp Leu Asp Val Val Asp Ala Phe
1 5 10 15

Ala Pro Ile Ser Asn Asn Lys Leu Asn Gly Val Val Gly Gly Gly Ala
20 25 30

Trp Lys Asn Phe Trp Ser Ser Leu Arg Lys Gly Phe Tyr Asp Gly Glu
35 40 45

Ala Gly Arg Ala Ile Arg Arg
50 55

<210> SEQ ID NO 486
<211> LENGTH: 168
<212> TYPE: DNA
<213> ORGANISM: Lactobacillus plantarum

<400> SEQUENCE: 486
atgactgtga acaaaatgat taaggatttg gatgtagtag atgcatttgc acctatttct 60
aataataagt tgaacggggt tgttggggga ggcgcttgga aaaatttctg gtctagttta 120
agaaaaggat tttatgatgg cgaagctggc agagcaatcc gtcgttaa 168

<210> SEQ ID NO 487
<211> LENGTH: 57
<212> TYPE: PRT
<213> ORGANISM: Lactobacillus plantarum

<400> SEQUENCE: 487

Met Lys Ile Lys Leu Thr Val Leu Asn Glu Phe Glu Glu Leu Thr Ala
1 5 10 15

Asp Ala Glu Lys Asn Ile Ser Gly Gly Arg Arg Ser Arg Lys Asn Gly
20 25 30

Ile Gly Tyr Ala Ile Gly Tyr Ala Phe Gly Ala Val Glu Arg Ala Val
35 40 45

Leu Gly Gly Ser Arg Asp Tyr Asn Lys
50 55

<210> SEQ ID NO 488
<211> LENGTH: 174
<212> TYPE: DNA
<213> ORGANISM: Lactobacillus plantarum

<400> SEQUENCE: 488
atgaaaatta aattaactgt tttaaatgaa tttgaagaat taactgctga cgctgaaaag 60
aatatttctg gtggccgtcg gagtcgtaaa aatggaattg gatacgctat tggttatgcg 120
tttggcgcgg ttgaacgggc cgtgcttggt ggttcaaggg attataataa gtga 174

<210> SEQ ID NO 489
<211> LENGTH: 47
<212> TYPE: PRT

<213> ORGANISM: Lactobacillus plantarum

<400> SEQUENCE: 489

Met Asp Lys Phe Glu Lys Ile Ser Thr Ser Asn Leu Glu Lys Ile Ser
1 5 10 15

Gly Gly Asp Leu Thr Thr Lys Leu Trp Ser Ser Trp Gly Tyr Tyr Leu
20 25 30

Gly Lys Lys Ala Arg Trp Asn Leu Lys His Pro Tyr Val Gln Phe
35 40 45

<210> SEQ ID NO 490
<211> LENGTH: 141
<212> TYPE: DNA
<213> ORGANISM: Lactobacillus plantarum

<400> SEQUENCE: 490
atggataaat ttgaaaaaat tagtacatct aacctagaaa agatctctgg cggtgattta 60
acaaccaagt tatggagctc ttggggatat tatcttggca agaaagcacg ttggaattta 120
aagcacccat atgttcaatt t 141

<210> SEQ ID NO 491
<211> LENGTH: 55
<212> TYPE: PRT
<213> ORGANISM: Lactobacillus plantarum

<400> SEQUENCE: 491

Met Asn Asn Leu Asn Lys Phe Ser Thr Leu Gly Lys Ser Ser Leu Ser
1 5 10 15

Gln Ile Glu Gly Gly Ser Val Pro Thr Ser Val Tyr Thr Leu Gly Ile
20 25 30

Lys Ile Leu Trp Ser Ala Tyr Lys His Arg Lys Thr Ile Glu Lys Ser
35 40 45

Phe Asn Lys Gly Phe Tyr His
50 55

<210> SEQ ID NO 492
<211> LENGTH: 168
<212> TYPE: DNA
<213> ORGANISM: Lactobacillus plantarum

<400> SEQUENCE: 492
atgaataact tgaataaatt ttctactcta ggcaagagta gcttgtctca aattgagggc 60
ggatcagtcc caacttcagt atatacgctt ggaattaaaa ttctatggtc tgcgtataag 120
catcgcaaaa cgattgaaaa aagttttaat aaaggctttt atcattaa 168

<210> SEQ ID NO 493
<211> LENGTH: 55
<212> TYPE: PRT
<213> ORGANISM: Lactobacillus plantarum

<400> SEQUENCE: 493

Met Asn Asn Ala Leu Ser Phe Glu Gln Gln Phe Thr Asp Phe Ser Thr
1 5 10 15

Leu Ser Asp Ser Glu Leu Glu Ser Val Glu Gly Gly Arg Asn Lys Leu
20 25 30

Ala Tyr Asn Met Gly His Tyr Ala Gly Lys Ala Thr Ile Phe Gly Leu
35 40 45

Ala Ala Trp Ala Leu Leu Ala 50 55

<210> SEQ ID NO 494
<211> LENGTH: 168
<212> TYPE: DNA
<213> ORGANISM: Lactobacillus plantarum

<400> SEQUENCE: 494
atgaataacg cattaagttt tgaacaacaa tttacagact tcagcacctt atcggactct 60
gaattagaat ccgttgaggg tggccgaaat aagcttgcat ataatatggg gcattacgct 120
ggtaaggcaa ccatttttgg acttgcagca tgggcactcc ttgcatga 168

<210> SEQ ID NO 495
<211> LENGTH: 47
<212> TYPE: PRT
<213> ORGANISM: Lactobacillus plantarum

<400> SEQUENCE: 495

Met Asp Lys Ile Ile Lys Phe Gln Gly Ile Ser Asp Asp Gln Leu Asn
1 5 10 15

Ala Val Ile Gly Gly Lys Lys Lys Lys Gln Ser Trp Tyr Ala Ala Ala
20 25 30

Gly Asp Ala Ile Val Ser Phe Gly Glu Gly Phe Leu Asn Ala Trp
35 40 45

<210> SEQ ID NO 496
<211> LENGTH: 144
<212> TYPE: DNA
<213> ORGANISM: Lactobacillus plantarum

<400> SEQUENCE: 496
atggataaga ttattaagtt tcaagggatt tctgatgatc aattaaatgc tgttatcggt 60
gggaaaaaga aaaaacaatc ttggtacgca gcagctggtg atgcaatcgt tagttttggt 120
gaaggatttt taaatgcttg gtaa 144

<210> SEQ ID NO 497
<211> LENGTH: 59
<212> TYPE: PRT
<213> ORGANISM: Lactobacillus plantarum

<400> SEQUENCE: 497

Met Lys Ile Ser Lys Ile Glu Ala Gln Ala Arg Lys Asp Phe Phe Lys
1 5 10 15

Lys Ile Asp Thr Asn Ser Asn Leu Leu Asn Val Asn Gly Ala Lys Cys
20 25 30

Lys Trp Trp Asn Ile Ser Cys Asp Leu Gly Asn Asn Gly His Val Cys
35 40 45

Thr Leu Ser His Glu Cys Gln Val Ser Cys Asn
50 55

<210> SEQ ID NO 498
<211> LENGTH: 180
<212> TYPE: DNA
<213> ORGANISM: Lactobacillus plantarum

<400> SEQUENCE: 498
atgaaaattt ctaagattga agctcaggct cgtaaagatt tttttaaaaa aatcgatact 60
aactcgaact tattaaatgt aaatggtgcc aaatgcaagt ggtggaatat ttcgtgtgat 120

```
ttaggaaata atggccatgt ttgtaccttg tcacatgaat gccaagtatc ttgtaactaa    180


<210> SEQ ID NO 499
<211> LENGTH: 67
<212> TYPE: PRT
<213> ORGANISM: Lactobacillus plantarum

<400> SEQUENCE: 499

Met Thr Lys Thr Ser Arg Arg Lys Asn Ala Ile Ala Asn Tyr Leu Glu
1               5                   10                  15

Pro Val Asp Glu Lys Ser Ile Asn Glu Ser Phe Gly Ala Gly Asp Pro
            20                  25                  30

Glu Ala Arg Ser Gly Ile Pro Cys Thr Ile Gly Ala Ala Val Ala Ala
        35                  40                  45

Ser Ile Ala Val Cys Pro Thr Thr Lys Cys Ser Lys Arg Cys Gly Lys
    50                  55                  60

Arg Lys Lys
65


<210> SEQ ID NO 500
<211> LENGTH: 204
<212> TYPE: DNA
<213> ORGANISM: Lactobacillus plantarum

<400> SEQUENCE: 500

atgactaaaa ctagtcgtcg taagaatgct attgctaatt atttagaacc agtcgacgaa     60

aaaagtatta atgaatcttt tggggctggg gatccggaag caagatccgg aattccatgt    120

acaatcggcg cagctgtcgc agcatcaatt gcagtttgtc caactactaa gtgtagtaaa    180

cgttgtggca agcgtaagaa ataa                                            204


<210> SEQ ID NO 501
<211> LENGTH: 48
<212> TYPE: PRT
<213> ORGANISM: Lactobacillus plantarum

<400> SEQUENCE: 501

Met Lys Ile Gln Ile Lys Gly Met Lys Gln Leu Ser Asn Lys Glu Met
1               5                   10                  15

Gln Lys Ile Val Gly Gly Lys Ser Ser Ala Tyr Ser Leu Gln Met Gly
            20                  25                  30

Ala Thr Ala Ile Lys Gln Val Lys Lys Leu Phe Lys Lys Trp Gly Trp
        35                  40                  45


<210> SEQ ID NO 502
<211> LENGTH: 147
<212> TYPE: DNA
<213> ORGANISM: Lactobacillus plantarum

<400> SEQUENCE: 502

atgaaaattc aaattaaagg tatgaagcaa cttagtaata aggaaatgca aaaaatagta     60

ggtggaaaga gtagtgcgta ttctttgcag atgggggcaa ctgcaattaa acaggtaaag    120

aaactgttta aaaaatgggg atggtaa                                         147


<210> SEQ ID NO 503
<211> LENGTH: 207
<212> TYPE: PRT
<213> ORGANISM: Propionibacterium jensenii

<400> SEQUENCE: 503
```

```
Met Asn Lys Thr His Lys Met Ala Thr Leu Val Ile Ala Ala Ile Leu
1               5                   10                  15

Ala Ala Gly Met Thr Ala Pro Thr Ala Tyr Ala Asp Ser Pro Gly Asn
            20                  25                  30

Thr Arg Ile Thr Ala Ser Glu Gln Ser Val Leu Thr Gln Ile Leu Gly
        35                  40                  45

His Lys Pro Thr Gln Thr Glu Tyr Asn Arg Tyr Val Glu Thr Tyr Gly
    50                  55                  60

Ser Val Pro Thr Glu Ala Asp Ile Asn Ala Tyr Ile Glu Ala Ser Glu
65                  70                  75                  80

Ser Glu Gly Ser Ser Ser Gln Thr Ala Ala His Asp Asp Ser Thr Ser
                85                  90                  95

Pro Gly Thr Ser Thr Glu Ile Tyr Thr Gln Ala Ala Pro Ala Arg Phe
            100                 105                 110

Ser Met Phe Phe Leu Ser Gly Thr Trp Ile Thr Arg Ser Gly Val Val
        115                 120                 125

Ser Leu Ser Leu Lys Pro Arg Lys Gly Gly Ile Gly Asn Glu Gly Asp
    130                 135                 140

Glu Arg Thr Trp Lys Thr Val Tyr Asp Lys Phe His Asn Ala Gly Gln
145                 150                 155                 160

Trp Thr Arg Tyr Lys Asn Asn Gly Val Asp Ala Ser Met Lys Lys Gln
                165                 170                 175

Tyr Met Cys His Phe Lys Tyr Gly Met Val Lys Thr Pro Trp Asn Leu
            180                 185                 190

Glu Pro His Lys Lys Ala Ala Asp Val Ser Pro Val Lys Cys Asn
        195                 200                 205
```

<210> SEQ ID NO 504
<211> LENGTH: 624
<212> TYPE: DNA
<213> ORGANISM: Propionibacterium jensenii

<400> SEQUENCE: 504

```
atgaacaaaa cacacaaaat ggcgacgctg gtaattgccg cgatcttggc cgccggaatg      60

accgcaccaa ctgcctatgc agattctcct ggaaacacca gaattacagc cagcgagcaa     120

agcgtcctta cccagatact cggccacaaa cctacacaaa ctgaatataa ccgatacgtt     180

gagacttacg gaagcgtacc gaccgaagca gacatcaacg catatataga agcgtctgaa     240

tctgagggat catcaagtca aacggctgct cacgatgact cgacatcacc cggcacgagt     300

accgaaatct acacgcaggc agcccctgcc aggttctcaa tgtttttcct gtccggaact     360

tggatcacta ggagtggtgt agtatcgctc tccttgaagc caaggaaggg tggtattggc     420

aacgaggggg acgagcgtac ctggaagact gtatacgaca aattccataa cgctgggcaa     480

tggacacgat acaagaacaa cggcgtagac gccagcatga aaaagcagta catgtgccac     540

ttcaagtacg ggatggtgaa gacgccatgg aatctggagc cccacaagaa ggctgcagac     600

gtcagtccag tcaagtgcaa ctag                                            624
```

<210> SEQ ID NO 505
<211> LENGTH: 96
<212> TYPE: PRT
<213> ORGANISM: Propionibacterium thoenii

<400> SEQUENCE: 505

```
Met Lys Lys Thr Leu Leu Arg Ser Gly Thr Ile Ala Leu Ala Thr Ala
```

```
1               5                   10                  15

Ala Ala Phe Gly Ala Ser Leu Ala Ala Ala Pro Ser Ala Met Ala Val
            20                  25                  30

Pro Gly Gly Cys Thr Tyr Thr Arg Ser Asn Arg Asp Val Ile Gly Thr
        35                  40                  45

Cys Lys Thr Gly Ser Gly Gln Phe Arg Ile Arg Leu Asp Cys Asn Asn
    50                  55                  60

Ala Pro Asp Lys Thr Ser Val Trp Ala Lys Pro Lys Val Met Val Ser
65                  70                  75                  80

Val His Cys Leu Val Gly Gln Pro Arg Ser Ile Ser Phe Glu Thr Lys
                85                  90                  95


<210> SEQ ID NO 506
<211> LENGTH: 291
<212> TYPE: DNA
<213> ORGANISM: Propionibacterium thoenii

<400> SEQUENCE: 506

atgaagaaga ccctcctgcg aagtggaacg atcgcactgg cgaccgcggc tgcatttggc      60

gcatcattgg cagccgcccc atctgccatg gccgttcctg gtggttgcac gtacacaaga     120

agcaatcgcg acgtcatcgg tacctgcaag actggaagcg gccagttccg aatccgactt     180

gactgcaaca acgctccaga caaaacttca gtctgggcca agcccaaggt aatggtgtcg     240

gttcactgtc ttgttggtca accgaggtcc atctcgttcg agaccaagtg a              291


<210> SEQ ID NO 507
<211> LENGTH: 255
<212> TYPE: PRT
<213> ORGANISM: Propionibacterium freudenreichii subsp freudenreii

<400> SEQUENCE: 507

Met Asn Thr Lys Ala Val Asn Leu Lys Ser Glu Asn Thr Thr Lys Leu
1               5                   10                  15

Val Ser Tyr Leu Thr Glu Asn Gln Leu Asp Glu Phe Ile Arg Arg Ile
            20                  25                  30

Arg Ile Asp Gly Ala Leu Val Glu Glu Val Ser Gln Asn Ala Lys Gln
        35                  40                  45

Ala Leu Asp Asn Thr Gly Leu Asn Gly Trp Ile Asn Thr Asp Cys Asp
    50                  55                  60

Glu Gly Leu Leu Ser Asp Phe Ile Ser Lys Ile Ala Ser Ala Arg Trp
65                  70                  75                  80

Ile Pro Leu Ala Glu Ser Ile Arg Pro Ala Val Thr Asp Arg Asp Lys
                85                  90                  95

Tyr Arg Val Ser Cys Trp Phe Tyr Gln Gly Met Asn Ile Ala Ile Tyr
            100                 105                 110

Ala Asn Ile Gly Gly Val Ala Asn Ile Ile Gly Tyr Thr Glu Ala Ala
        115                 120                 125

Val Ala Thr Leu Leu Gly Ala Val Val Ala Val Ala Pro Val Val Pro
    130                 135                 140

Gly Thr Pro Thr Pro Pro Lys Asp Lys Ser Ser Gln Tyr Lys Glu Val
145                 150                 155                 160

Pro Leu Ala Val Arg Leu Ser Glu Thr Tyr His Glu Glu Gly Val Arg
                165                 170                 175

Gly Leu Phe Asp Glu Leu Asn Tyr Ser Glu Ser Arg Met Ile Ser Thr
            180                 185                 190
```

```
Leu Arg Arg Ala Ser Thr Asp Gly Val Leu Ile Asn Ser Trp Asn Asp
        195                 200                 205

Gly Gln Asp Thr Ile Leu Leu Lys Lys Tyr Asn Phe Gln Asp Leu Gln
    210                 215                 220

Leu Thr Val Arg Ser Arg Ile Val Gly Asn Gln Thr Ile Ile Glu Glu
225                 230                 235                 240

Cys Lys Ile Thr Asp Gly Arg Lys Thr Leu Ser Asp Glu Thr Val
                245                 250                 255


<210> SEQ ID NO 508
<211> LENGTH: 768
<212> TYPE: DNA
<213> ORGANISM: Propionibacterium freudenreichii subsp freudenreii

<400> SEQUENCE: 508

atgaatacca aagctgtaaa tctgaagtca gaaaacacga ctaagttggt gagctacctt      60

acggaaaatc aattggatga gtttattaga aggattcgca ttgatggcgc tcttgtggaa     120

gaggtcagtc aaaatgctaa gcaggcctta gataatactg ggctcaatgg ctggataaat     180

actgattgcg atgaaggcct tctctctgat ttcatttcaa agatagcaag tgctagatgg     240

attccattag ctgagtcaat tcgacctgcg gtgactgaca gggataagta tcgagtaagt     300

tgctggttct accaggggat gaatatagca atttacgcaa atatcggtgg cgtggccaat     360

attatcggct atacggaggc cgcagtcgca acactccttg gtgcagttgt ggcggtagct     420

cctgtggtcc ctggaactcc aacccctcca aaggacaaga gttcgcaata taaggaggtt     480

cccccttgccg ttcgtctttc cgaaacatac cacgaagagg gagtacgagg tctattcgac     540

gagctgaact actccgagag ccgtatgatc tctactctaa ggcgagcatc aaccgatgga     600

gtcctaatta attcttggaa cgatgggcag gatacaattc tgcttaagaa gtacaatttc     660

caagacttgc aactgactgt caggagccgc attgttggga atcaaacaat aattgaagaa     720

tgcaaaatca ctgatggtag aaaaactctt tcagacgaga ctgtgtag                  768


<210> SEQ ID NO 509
<211> LENGTH: 618
<212> TYPE: PRT
<213> ORGANISM: Pseudomonas aeruginosa

<400> SEQUENCE: 509

Met Ala Arg Pro Ile Ala Asp Leu Ile His Phe Asn Ser Thr Thr Val
1               5                   10                  15

Thr Ala Ser Gly Asp Val Tyr Tyr Gly Pro Gly Gly Gly Thr Gly Ile
            20                  25                  30

Gly Pro Ile Ala Arg Pro Ile Glu His Gly Leu Asp Ser Ser Thr Glu
        35                  40                  45

Asn Gly Trp Gln Glu Phe Glu Ser Tyr Ala Asp Val Gly Val Asp Pro
    50                  55                  60

Arg Arg Tyr Val Pro Leu Gln Val Lys Glu Lys Arg Arg Glu Ile Glu
65                  70                  75                  80

Leu Gln Phe Arg Asp Ala Glu Lys Lys Leu Glu Ala Ser Val Gln Ala
                85                  90                  95

Glu Leu Asp Lys Ala Asp Ala Ala Leu Gly Pro Ala Lys Asn Leu Ala
            100                 105                 110

Pro Leu Asp Val Ile Asn Arg Ser Leu Thr Ile Val Gly Asn Ala Leu
        115                 120                 125

Gln Gln Lys Asn Gln Lys Leu Leu Leu Asn Gln Lys Lys Ile Thr Ser
```

```
    130                 135                 140

Leu Gly Ala Lys Asn Phe Leu Thr Arg Thr Ala Glu Glu Ile Gly Glu
145                 150                 155                 160

Gln Ala Val Arg Glu Gly Asn Ile Asn Gly Pro Glu Ala Tyr Met Arg
                165                 170                 175

Phe Leu Asp Arg Glu Met Glu Gly Leu Thr Ala Ala Tyr Asn Val Lys
            180                 185                 190

Leu Phe Thr Glu Ala Ile Ser Ser Leu Gln Ile Arg Met Asn Thr Leu
        195                 200                 205

Thr Ala Ala Lys Ala Ser Ile Glu Ala Ala Ala Ala Asn Lys Ala Arg
    210                 215                 220

Glu Gln Ala Ala Ala Glu Ala Lys Arg Lys Ala Glu Glu Gln Ala Arg
225                 230                 235                 240

Gln Gln Ala Ala Ile Arg Ala Ala Asn Thr Tyr Ala Met Pro Ala Asn
                245                 250                 255

Gly Ser Val Val Ala Thr Ala Ala Gly Arg Gly Leu Ile Gln Val Ala
            260                 265                 270

Gln Gly Ala Ala Ser Leu Ala Gln Ala Ile Ser Asp Ala Ile Ala Val
        275                 280                 285

Leu Gly Arg Val Leu Ala Ser Ala Pro Ser Val Met Ala Val Gly Phe
    290                 295                 300

Ala Ser Leu Thr Tyr Ser Ser Arg Thr Ala Glu Gln Trp Gln Asp Gln
305                 310                 315                 320

Thr Pro Asp Ser Val Arg Tyr Ala Leu Gly Met Asp Ala Ala Lys Leu
                325                 330                 335

Gly Leu Pro Pro Ser Val Asn Leu Asn Ala Val Ala Lys Ala Ser Gly
            340                 345                 350

Thr Val Asp Leu Pro Met Arg Leu Thr Asn Glu Ala Arg Gly Asn Thr
        355                 360                 365

Thr Thr Leu Ser Val Val Ser Thr Asp Gly Val Ser Val Pro Lys Ala
    370                 375                 380

Val Pro Val Arg Met Ala Ala Tyr Asn Ala Thr Thr Gly Leu Tyr Glu
385                 390                 395                 400

Val Thr Val Pro Ser Thr Thr Ala Glu Ala Pro Pro Leu Ile Leu Thr
                405                 410                 415

Trp Thr Pro Ala Ser Pro Pro Gly Asn Gln Asn Pro Ser Ser Thr Thr
            420                 425                 430

Pro Val Val Pro Lys Pro Val Pro Val Tyr Glu Gly Ala Thr Leu Thr
        435                 440                 445

Pro Val Lys Ala Thr Pro Glu Thr Tyr Pro Gly Val Ile Thr Leu Pro
    450                 455                 460

Glu Asp Leu Ile Ile Gly Phe Pro Ala Asp Ser Gly Ile Lys Pro Ile
465                 470                 475                 480

Tyr Val Met Phe Arg Asp Pro Arg Asp Val Pro Gly Ala Ala Thr Gly
                485                 490                 495

Lys Gly Gln Pro Val Ser Gly Asn Trp Leu Gly Ala Ala Ser Gln Gly
            500                 505                 510

Glu Gly Ala Pro Ile Pro Ser Gln Ile Ala Asp Lys Leu Arg Gly Lys
        515                 520                 525

Thr Phe Lys Asn Trp Arg Asp Phe Arg Glu Gln Phe Trp Ile Ala Val
    530                 535                 540

Ala Asn Asp Pro Glu Leu Ser Lys Gln Phe Asn Pro Gly Ser Leu Ala
545                 550                 555                 560
```

-continued

Val Met Arg Asp Gly Gly Ala Pro Tyr Val Arg Glu Ser Glu Gln Ala
565 570 575

Gly Gly Arg Ile Lys Ile Glu Ile His His Lys Val Arg Val Ala Asp
580 585 590

Gly Gly Gly Val Tyr Asn Met Gly Asn Leu Val Ala Val Thr Pro Lys
595 600 605

Arg His Ile Glu Ile His Lys Gly Gly Lys
610 615

<210> SEQ ID NO 510
<211> LENGTH: 1857
<212> TYPE: DNA
<213> ORGANISM: Pseudomonas aeruginosa

<400> SEQUENCE: 510
atggcacgac ccattgctga ccttatccac ttcaactcta caactgtcac ggcaagcgga 60
gacgtttatt acggccctgg gggaggtacc ggcattggcc ccattgccag acctatagag 120
cacggcttgg attcgtccac tgaaaatggc tggcaagagt ttgaaagtta tgctgatgtg 180
ggcgttgacc ccagacgcta tgttcctctt caggttaaag aaaaacgcag ggagatcgag 240
cttcagttcc gagatgccga gaaaaaactt gaggcgtcgg tacaagccga gctggataag 300
gctgatgccg ctcttggtcc ggcaaagaat cttgcaccat tggacgtcat caaccgcagt 360
ctgaccatcg ttggaaacgc cctccagcaa aagaatcaaa aactactgct gaatcagaag 420
aagattacca gcctgggtgc aaagaatttc cttacccgta cggcggaaga gatcggtgaa 480
caagcggtgc gagaaggcaa tattaacggg cctgaagcct atatgcgctt cctcgacagg 540
gaaatggaag gtctcacggc agcttataac gtaaaactct tcaccgaagc gatcagtagt 600
ctccagatcc gcatgaatac gttgaccgcc gccaaagcaa gtattgaggc ggccgcagca 660
aacaaggcgc gtgaacaagc agcggctgag gccaaacgca aagccgaaga gcaggcccgc 720
cagcaagcgg cgataagagc tgccaatacc tatgccatgc cggccaatgg cagcgttgtc 780
gccaccgccg caggccgggg tctgatccag gtcgcacaag gcgccgcatc ccttgctcaa 840
gcgatctccg atgcgattgc cgtcctgggc cgggtcctgg cttcagcacc ctcggtgatg 900
gccgtgggct ttgccagtct gacctactcc tcccggactg ccgagcaatg gcaggaccaa 960
acgcccgata gcgttcgtta cgccctgggc atggatgccg ctaaattggg gcttccccca 1020
agcgtaaacc tgaacgcggt tgcaaaagcc agcggtaccg tcgatctgcc gatgcgcctg 1080
accaacgagg cacgaggcaa cacgacgacc ctttcggtgg tcagcaccga tggtgtgagc 1140
gttccgaaag ccgttccggt ccggatggcg gcctacaatg ccacgacagg cctgtacgag 1200
gttacggttc cctctacgac cgcagaagcg ccgccactga tcctgacctg gacgccggcg 1260
agtcctccag gaaaccagaa cccttcgagt accactccgg tcgtaccgaa gccggtgccg 1320
gtatatgagg gagcgaccct tacaccggtg aaggctaccc cggaaaccta tcctggggtg 1380
attacactac cggaagacct gatcatcggc ttcccggccg actcggggat caagccgatc 1440
tatgtgatgt tcagggatcc gcgggatgta cctggtgctg cgactggcaa gggacagccc 1500
gtcagcggta attggctcgg cgccgcctct caaggtgagg gggctccaat tccaagccag 1560
attgcggata aactacgtgg taagacattc aaaaactggc gggactttcg ggaacaattc 1620
tggatagctg tggctaatga tcctgagtta agtaaacagt ttaatcctgg tagtttagct 1680
gtaatgagag atggaggggc tccttatgtc agagagtcag aacaggctgg cgggagaata 1740

```
aagatcgaaa tccaccacaa ggttcgagta gcagatggag gcggcgttta caatatgggg   1800

aaccttgttg cagtaacgcc aaaacgtcat atagaaatcc acaagggagg gaagtga      1857


<210> SEQ ID NO 511
<211> LENGTH: 689
<212> TYPE: PRT
<213> ORGANISM: Pseudomonas aeruginosa

<400> SEQUENCE: 511

Met Ala Val Asn Asp Tyr Glu Pro Gly Ser Met Val Ile Thr His Val
1               5                   10                  15

Gln Gly Gly Gly Arg Asp Ile Ile Gln Tyr Ile Pro Ala Arg Ser Ser
            20                  25                  30

Tyr Gly Thr Pro Pro Phe Val Pro Pro Gly Pro Ser Pro Tyr Val Gly
        35                  40                  45

Thr Gly Met Gln Glu Tyr Arg Lys Leu Arg Ser Thr Leu Asp Lys Ser
    50                  55                  60

His Ser Glu Leu Lys Lys Asn Leu Lys Asn Glu Thr Leu Lys Glu Val
65                  70                  75                  80

Asp Glu Leu Lys Ser Glu Ala Gly Leu Pro Gly Lys Ala Val Ser Ala
                85                  90                  95

Asn Asp Ile Arg Asp Glu Lys Ser Ile Val Asp Ala Leu Met Asp Ala
            100                 105                 110

Lys Ala Lys Ser Leu Lys Ala Ile Glu Asp Arg Pro Ala Asn Leu Tyr
        115                 120                 125

Thr Ala Ser Asp Phe Pro Gln Lys Ser Glu Ser Met Tyr Gln Ser Gln
    130                 135                 140

Leu Leu Ala Ser Arg Lys Phe Tyr Gly Glu Phe Leu Asp Arg His Met
145                 150                 155                 160

Ser Glu Leu Ala Lys Ala Tyr Ser Ala Asp Ile Tyr Lys Ala Gln Ile
                165                 170                 175

Ala Ile Leu Lys Gln Thr Ser Gln Glu Leu Glu Asn Lys Ala Arg Ser
            180                 185                 190

Leu Glu Ala Glu Ala Gln Arg Ala Ala Ala Glu Val Glu Ala Asp Tyr
        195                 200                 205

Lys Ala Arg Lys Ala Asn Val Glu Lys Lys Val Gln Ser Glu Leu Asp
    210                 215                 220

Gln Ala Gly Asn Ala Leu Pro Gln Leu Thr Asn Pro Thr Pro Glu Gln
225                 230                 235                 240

Trp Leu Glu Arg Ala Thr Gln Leu Val Thr Gln Ala Ile Ala Asn Lys
                245                 250                 255

Lys Lys Leu Gln Thr Ala Asn Asn Ala Leu Ile Ala Lys Ala Pro Asn
            260                 265                 270

Ala Leu Glu Lys Gln Lys Ala Thr Tyr Asn Ala Asp Leu Leu Val Asp
        275                 280                 285

Glu Ile Ala Ser Leu Gln Ala Arg Leu Asp Lys Leu Asn Ala Glu Thr
    290                 295                 300

Ala Arg Arg Lys Glu Ile Ala Arg Gln Ala Ala Ile Arg Ala Ala Asn
305                 310                 315                 320

Thr Tyr Ala Met Pro Ala Asn Gly Ser Val Val Ala Thr Ala Ala Gly
                325                 330                 335

Arg Gly Leu Ile Gln Val Ala Gln Gly Ala Ala Ser Leu Ala Gln Ala
            340                 345                 350

Ile Ser Asp Ala Ile Ala Val Leu Gly Arg Val Leu Ala Ser Ala Pro
```

```
        355                 360                 365

Ser Val Met Ala Val Gly Phe Ala Ser Leu Thr Tyr Ser Ser Arg Thr
    370                 375                 380

Ala Glu Gln Trp Gln Asp Gln Thr Pro Asp Ser Val Arg Tyr Ala Leu
385                 390                 395                 400

Gly Met Asp Ala Ala Lys Leu Gly Leu Pro Pro Ser Val Asn Leu Asn
                405                 410                 415

Ala Val Ala Lys Ala Ser Gly Thr Val Asp Leu Pro Met Arg Leu Thr
            420                 425                 430

Asn Glu Ala Arg Gly Asn Thr Thr Thr Leu Ser Val Val Ser Thr Asp
        435                 440                 445

Gly Val Ser Val Pro Lys Ala Val Pro Val Arg Met Ala Ala Tyr Asn
    450                 455                 460

Ala Thr Thr Gly Leu Tyr Glu Val Thr Val Pro Ser Thr Thr Ala Glu
465                 470                 475                 480

Ala Pro Pro Leu Ile Leu Thr Trp Thr Pro Ala Ser Pro Pro Gly Asn
                485                 490                 495

Gln Asn Pro Ser Ser Thr Thr Pro Val Val Pro Lys Pro Val Pro Val
            500                 505                 510

Tyr Glu Gly Ala Thr Leu Thr Pro Val Lys Ala Thr Pro Glu Thr Tyr
        515                 520                 525

Pro Gly Val Ile Thr Leu Pro Glu Asp Leu Ile Ile Gly Phe Pro Ala
    530                 535                 540

Asp Ser Gly Ile Lys Pro Ile Tyr Val Met Phe Arg Asp Pro Arg Asp
545                 550                 555                 560

Val Pro Gly Ala Ala Thr Gly Lys Gly Gln Pro Val Ser Gly Asn Trp
                565                 570                 575

Leu Gly Ala Ala Ser Gln Gly Glu Gly Ala Pro Ile Pro Ser Gln Ile
            580                 585                 590

Ala Asp Lys Leu Arg Gly Lys Thr Phe Lys Asn Trp Arg Asp Phe Arg
        595                 600                 605

Glu Gln Phe Trp Ile Ala Val Ala Asn Asp Pro Glu Leu Ser Lys Gln
    610                 615                 620

Phe Asn Pro Gly Ser Leu Ala Val Met Arg Asp Gly Gly Ala Pro Tyr
625                 630                 635                 640

Val Arg Glu Ser Glu Gln Ala Gly Gly Arg Ile Lys Ile Glu Ile His
                645                 650                 655

His Lys Val Arg Ile Ala Asp Gly Gly Gly Val Tyr Asn Met Gly Asn
            660                 665                 670

Leu Val Ala Val Thr Pro Lys Arg His Ile Glu Ile His Lys Gly Gly
        675                 680                 685

Lys
```

<210> SEQ ID NO 512
<211> LENGTH: 2070
<212> TYPE: DNA
<213> ORGANISM: Pseudomonas aeruginosa

<400> SEQUENCE: 512

```
atggctgtca atgattacga acctggttcg atggttatta cacatgtgca gggtggtggg      60

cgtgacataa tccagtatat tcctgctcga tcaagctacg gtactccacc atttgtccca     120

ccaggaccaa gtccgtatgt cggtactgga atgcaggagt acaggaagct aagaagtacg     180

cttgataagt cccattcaga actcaagaaa aacctgaaaa atgaaaccct gaaggaggtt     240
```

-continued

```
gatgaactca agagtgaagc ggggttgcca ggtaaagcgg tcagtgccaa tgacatccgc    300
gatgaaaaga gtatcgttga tgcactcatg gatgccaaag caaaatcgct aaaggccatt    360
gaggatcgcc cggccaatct ttatacggct tcagactttc ctcagaagtc agagtcgatg    420
taccagagtc agttgctggc cagccgaaaa ttctatggag agttcctgga tcgccatatg    480
agtgagctgg ccaaagcgta cagcgccgat atctataagg cgcaaatcgc tatcttgaaa    540
caaacgtctc aagagctgga gaataaagcc cggtcattgg aagcagaagc ccagcgagcc    600
gctgctgagg tggaggcgga ctacaaggcc aggaaggcaa atgtcgagaa aaaagtgcag    660
tccgagcttg accaggctgg gaatgctttg cctcaactga ccaatccaac gccagagcag    720
tggcttgaac gcgctactca actggttacg caggcgatcg ccaataagaa gaaattgcag    780
actgcaaaca atgccttgat tgccaaggca cccaatgcac tggagaaaca aaaggcaacc    840
tacaacgccg atctcctagt ggatgaaatc gccagcctgc aagcacggct ggacaagctg    900
aacgccgaaa cggcaaggcg caaggaaatc gctcgtcaag cggcgatcag ggctgccaat    960
acttatgcca tgccagccaa tggcagcgtt gtcgccaccg ccgcaggccg ggtctgatc    1020
caggtcgcac aaggcgccgc atcccttgct caagcgatct ccgatgcgat tgccgtcctg   1080
ggccgggtcc tggcttcagc accctcggtg atggccgtgg gctttgccag tctgacctac   1140
tcctcccgga ctgccgagca atggcaggac caaacgcccg atagcgttcg ttacgccctg   1200
ggcatggatg ccgctaaatt ggggcttccc ccaagcgtaa acctgaacgc ggttgcaaaa   1260
gccagcggta ccgtcgatct gccgatgcgc ctgaccaacg aggcacgagg caacacgacg   1320
accctttcgg tggtcagcac cgatggtgtg agcgttccga aagccgttcc ggtccggatg   1380
gcggcctaca atgccacgac aggcctgtac gaggttacgg ttccctctac gaccgcagaa   1440
gcgccgccac tgatcctgac ctggacgccg gcgagtcctc caggaaacca gaacccttcg   1500
agtaccactc cggtcgtacc gaagccggtg ccggtatatg agggagcgac ccttacaccg   1560
gtgaaggcta ccccggaaac ctatcctggg gtgattacac taccggaaga cctgatcatc   1620
ggcttcccgg ccgactcggg gatcaagccg atctatgtga tgttcaggga tccgcgggat   1680
gtacctggtg ctgcgactgg caagggacag cccgtcagcg gtaattggct cggcgccgcc   1740
tctcaaggtg agggggctcc aattccaagc cagattgcgg ataaactacg tggtaagaca   1800
ttcaaaaact ggcgggactt tcgggaacaa ttctggatag ctgtggctaa tgatcctgag   1860
ttaagtaaac agtttaatcc tggtagttta gctgtaatga gagatggagg ggctccttat   1920
gtcagagagt cagaacaggc tggcgggaga ataaagatcg aaatccacca caaggttcga   1980
atagcagatg gaggcggcgt ttacaatatg gggaaccttg ttgcagtaac gccaaaacgt   2040
catatagaaa tccacaaggg agggaagtga                                    2070
```

<210> SEQ ID NO 513
<211> LENGTH: 47
<212> TYPE: PRT
<213> ORGANISM: Ruminococcus gnavus

<400> SEQUENCE: 513

```
Met Arg Asn Asp Val Leu Thr Leu Thr Asn Pro Met Glu Glu Lys Glu
1               5                   10                  15

Leu Glu Gln Ile Leu Gly Gly Gly Asn Gly Val Leu Lys Thr Ile Ser
            20                  25                  30

His Glu Cys Asn Met Asn Thr Trp Gln Phe Leu Phe Thr Cys Cys
        35                  40                  45
```

<210> SEQ ID NO 514
<211> LENGTH: 144
<212> TYPE: DNA
<213> ORGANISM: Ruminococcus gnavus

<400> SEQUENCE: 514
atgagaaatg acgtattaac attaacaaac ccaatggaag agaacgaact ggagcagatc 60
ttaggtggtg gcaatggtgt gttaaaaacg attagccacg aatgcaatat gaacacatgg 120
cagttcctgt ttacttgttg ctaa 144

<210> SEQ ID NO 515
<211> LENGTH: 55
<212> TYPE: PRT
<213> ORGANISM: Lactobacillus sakei

<400> SEQUENCE: 515

Met Lys Asn Ala Lys Ser Leu Thr Ile Gln Glu Met Lys Ser Ile Thr
1 5 10 15

Gly Gly Lys Tyr Tyr Gly Asn Gly Val Ser Cys Asn Ser His Gly Cys
20 25 30

Ser Val Asn Trp Gly Gln Ala Trp Thr Cys Gly Val Asn His Leu Ala
35 40 45

Asn Gly Gly His Gly Val Cys
50 55

<210> SEQ ID NO 516
<211> LENGTH: 168
<212> TYPE: DNA
<213> ORGANISM: Lactobacillus sakei

<400> SEQUENCE: 516
atgaaaaacg caaaaagcct aacaattcaa gaaatgaaat ctattacagg tggtaaatac 60
tatggtaatg gcgttagctg taactctcac ggctgttcag taaattgggg gcaagcatgg 120
acttgtggag taaaccatct agctaatggc ggtcatggag tttgttaa 168

<210> SEQ ID NO 517
<211> LENGTH: 59
<212> TYPE: PRT
<213> ORGANISM: Lactobacillus sakei

<400> SEQUENCE: 517

Met Asn Asn Val Lys Glu Leu Ser Met Thr Glu Leu Gln Thr Ile Thr
1 5 10 15

Gly Gly Ala Arg Ser Tyr Gly Asn Gly Val Tyr Cys Asn Asn Lys Lys
20 25 30

Cys Trp Val Asn Arg Gly Glu Ala Thr Gln Ser Ile Ile Gly Gly Met
35 40 45

Ile Ser Gly Trp Ala Ser Gly Leu Ala Gly Met
50 55

<210> SEQ ID NO 518
<211> LENGTH: 180
<212> TYPE: DNA
<213> ORGANISM: Lactobacillus sakei

<400> SEQUENCE: 518
atgaataatg taaaagaatt aagtatgaca gaattacaaa caattaccgg cggtgctaga 60
tcatatggca acggtgttta ctgtaataat aaaaaatgtt gggtaaatcg gggtgaagca 120
acgcaaagta ttattggtgg tatgattagc ggctgggcta gtggtttagc tggaatgtaa 180

<210> SEQ ID NO 519
<211> LENGTH: 61
<212> TYPE: PRT
<213> ORGANISM: Lactobacillus sakei

<400> SEQUENCE: 519

Met Glu Lys Phe Ile Glu Leu Ser Leu Lys Glu Val Thr Ala Ile Thr
1 5 10 15

Gly Gly Lys Tyr Tyr Gly Asn Gly Val His Cys Gly Lys His Ser Cys
20 25 30

Thr Val Asp Trp Gly Thr Ala Ile Gly Asn Ile Gly Asn Asn Ala Ala
35 40 45

Ala Asn Trp Ala Thr Gly Gly Asn Ala Gly Trp Asn Lys
50 55 60

<210> SEQ ID NO 520
<211> LENGTH: 186
<212> TYPE: DNA
<213> ORGANISM: Lactobacillus sakei

<400> SEQUENCE: 520
atggaaaagt ttattgaatt atctttaaaa gaagtaacag caattacagg tggaaaatat 60
tatggtaacg gtgtacactg tggaaaacat tcatgtaccg tagactgggg aacagctatt 120
ggaaatatcg gaaataatgc agctgcaaac tgggccacag gcggaaacgc tggctggaat 180
aaataa 186

<210> SEQ ID NO 521
<211> LENGTH: 56
<212> TYPE: PRT
<213> ORGANISM: Streptococcus salivarius

<400> SEQUENCE: 521

Met Lys Ser Thr Asn Asn Gln Ser Ile Ala Glu Ile Ala Ala Val Asn
1 5 10 15

Ser Leu Gln Glu Val Ser Met Glu Glu Leu Asp Gln Ile Ile Gly Ala
20 25 30

Gly Asn Gly Val Val Leu Thr Leu Thr His Glu Cys Asn Leu Ala Thr
35 40 45

Trp Thr Lys Lys Leu Lys Cys Cys
50 55

<210> SEQ ID NO 522
<211> LENGTH: 171
<212> TYPE: DNA
<213> ORGANISM: Streptococcus salivarius

<400> SEQUENCE: 522
atgaaatcaa caaataatca aagtatcgca gaaattgcag cagtaaactc actacaagaa 60
gtaagtatgg aggaactaga ccaaattatt ggtgccggaa acggagtggt tcttactctt 120
actcatgaat gtaacctagc aacttggaca aaaaaactaa aatgttgcta a 171

<210> SEQ ID NO 523
<211> LENGTH: 51
<212> TYPE: PRT
<213> ORGANISM: Streptococcus pyogenes serotype M28

<400> SEQUENCE: 523

Met Ser Phe Met Lys Asn Ser Lys Asp Ile Leu Thr Asn Ala Ile Glu
1               5                   10                  15

Glu Val Ser Glu Lys Glu Leu Met Glu Val Ala Gly Gly Lys Lys Gly
            20                  25                  30

Ser Gly Trp Phe Ala Thr Ile Thr Asp Asp Cys Pro Asn Ser Val Phe
        35                  40                  45

Val Cys Cys
    50

<210> SEQ ID NO 524
<211> LENGTH: 156
<212> TYPE: DNA
<213> ORGANISM: Streptococcus pyogenes serotype M28

<400> SEQUENCE: 524
atgagtttta tgaaaaattc aaaggatatt ttgactaatg ctatcgaaga agtttctgaa      60
aaagaactta tggaagtagc tggtggtaaa aaaggttccg gttggtttgc aactattact     120
gatgactgtc cgaactcagt attcgtttgt tgttaa                               156

<210> SEQ ID NO 525
<211> LENGTH: 48
<212> TYPE: PRT
<213> ORGANISM: Streptococcus salivarius

<400> SEQUENCE: 525

Met Lys Asn Ser Lys Asp Val Leu Asn Asn Ala Ile Glu Glu Val Ser
1               5                   10                  15

Glu Lys Glu Leu Met Glu Val Ala Gly Gly Lys Lys Gly Pro Gly Trp
            20                  25                  30

Ile Ala Thr Ile Thr Asp Asp Cys Pro Asn Ser Ile Phe Val Cys Cys
        35                  40                  45

<210> SEQ ID NO 526
<211> LENGTH: 147
<212> TYPE: DNA
<213> ORGANISM: Streptococcus salivarius

<400> SEQUENCE: 526
atgaaaaact caaaagatgt tttgaacaat gctatcgaag aggtttctga aaaagaactt      60
atggaagtag ctggtggtaa aaaaggtcca ggttggattg caactattac tgatgactgt     120
ccaaactcaa tattcgtttg ttgttaa                                          147

<210> SEQ ID NO 527
<211> LENGTH: 48
<212> TYPE: PRT
<213> ORGANISM: Streptococcus salivarius

<400> SEQUENCE: 527

Met Lys Asn Ser Lys Asp Ile Leu Asn Asn Ala Ile Glu Glu Val Ser
1               5                   10                  15

Glu Lys Glu Leu Met Glu Val Ala Gly Gly Lys Arg Gly Ser Gly Trp
            20                  25                  30

Ile Ala Thr Ile Thr Asp Asp Cys Pro Asn Ser Val Phe Val Cys Cys
        35                  40                  45

<210> SEQ ID NO 528

<211> LENGTH: 147
<212> TYPE: DNA
<213> ORGANISM: Streptococcus salivarius

<400> SEQUENCE: 528
atgaaaaact caaaagatat tttgaacaat gctatcgaag aagtttctga aaaagaactt 60
atggaagtag ctggtggtaa aagaggttca ggttggattg caactattac tgatgactgt 120
ccaaactcag tattcgtttg ttgttaa 147

<210> SEQ ID NO 529
<211> LENGTH: 62
<212> TYPE: PRT
<213> ORGANISM: Staphylococcus aureus

<400> SEQUENCE: 529

Met Lys Ser Ser Phe Leu Glu Lys Asp Ile Glu Glu Gln Val Thr Trp
1 5 10 15

Phe Glu Glu Val Ser Glu Gln Glu Phe Asp Asp Asp Ile Phe Gly Ala
20 25 30

Cys Ser Thr Asn Thr Phe Ser Leu Ser Asp Tyr Trp Gly Asn Lys Gly
35 40 45

Asn Trp Cys Thr Ala Thr His Glu Cys Met Ser Trp Cys Lys
50 55 60

<210> SEQ ID NO 530
<211> LENGTH: 189
<212> TYPE: DNA
<213> ORGANISM: Staphylococcus aureus

<400> SEQUENCE: 530
atgaaaagtt cttttttaga aaaagatata gaagaacaag tgacatggtt cgaggaagtt 60
tcagaacaag aatttgacga tgatattttt ggagcttgta gtacaaacac tttttctttg 120
agtgactatt ggggtaataa aggaaattgg tgtactgcta ctcacgaatg tatgtcttgg 180
tgtaaataa 189

<210> SEQ ID NO 531
<211> LENGTH: 67
<212> TYPE: PRT
<213> ORGANISM: Staphylococcus aureus

<400> SEQUENCE: 531

Met Lys Asn Glu Leu Gly Lys Phe Leu Glu Glu Asn Glu Leu Glu Leu
1 5 10 15

Gly Lys Phe Ser Glu Ser Asp Met Leu Glu Ile Thr Asp Asp Glu Val
20 25 30

Tyr Ala Ala Gly Thr Pro Leu Ala Leu Leu Gly Gly Ala Ala Thr Gly
35 40 45

Val Ile Gly Tyr Ile Ser Asn Gln Thr Cys Pro Thr Thr Ala Cys Thr
50 55 60

Arg Ala Cys
65

<210> SEQ ID NO 532
<211> LENGTH: 204
<212> TYPE: DNA
<213> ORGANISM: Staphylococcus aureus

<400> SEQUENCE: 532

```
atgaaaaatg aattaggtaa gtttttagaa gaaaacgaat tagagttagg taaattttca      60

gaatcagaca tgctagaaat tactgatgat gaagtatatg cagctggaac acctttagcc     120

ttattgggtg gagctgccac cggggtgata ggttatattt ctaaccaaac atgtccaaca     180

actgcttgta cacgcgcttg ctag                                            204


<210> SEQ ID NO 533
<211> LENGTH: 46
<212> TYPE: PRT
<213> ORGANISM: Streptococcus pyogenes

<400> SEQUENCE: 533

Met Asn Asn Thr Ile Lys Asp Phe Asp Leu Asp Leu Lys Thr Asn Lys
1               5                   10                  15

Lys Asp Thr Ala Thr Pro Tyr Val Gly Ser Arg Tyr Leu Cys Thr Pro
            20                  25                  30

Gly Ser Cys Trp Lys Leu Val Cys Phe Thr Thr Thr Val Lys
        35                  40                  45


<210> SEQ ID NO 534
<211> LENGTH: 141
<212> TYPE: DNA
<213> ORGANISM: Streptococcus pyogenes

<400> SEQUENCE: 534

atgaataaca caattaaaga ctttgatctc gatttgaaaa caaataaaaa agacactgct      60

acaccttatg ttggtagccg ttacctatgt acccctggtt cttgttggaa attagtttgc     120

tttacaacaa ctgttaaata a                                               141


<210> SEQ ID NO 535
<211> LENGTH: 51
<212> TYPE: PRT
<213> ORGANISM: Streptococcus pyogenes

<400> SEQUENCE: 535

Met Glu Lys Asn Asn Glu Val Ile Asn Ser Ile Gln Glu Val Ser Leu
1               5                   10                  15

Glu Glu Leu Asp Gln Ile Ile Gly Ala Gly Lys Asn Gly Val Phe Lys
            20                  25                  30

Thr Ile Ser His Glu Cys His Leu Asn Thr Trp Ala Phe Leu Ala Thr
        35                  40                  45

Cys Cys Ser
    50


<210> SEQ ID NO 536
<211> LENGTH: 156
<212> TYPE: DNA
<213> ORGANISM: Streptococcus pyogenes

<400> SEQUENCE: 536

atggaaaaaa ataatgaagt aatcaactct attcaagaag ttagtcttga agaactcgat      60

caaattatcg gtgctggaaa aaatggtgtg tttaaaacaa tttctcatga gtgtcatttg     120

aatacatggg cattccttgc tacttgttgt tcataa                               156


<210> SEQ ID NO 537
<211> LENGTH: 51
<212> TYPE: PRT
<213> ORGANISM: Streptococcus pyogenes serotype M49
```

<400> SEQUENCE: 537

Met Thr Lys Glu His Glu Ile Ile Asn Ser Ile Gln Glu Val Ser Leu
1 5 10 15

Glu Glu Leu Asp Gln Ile Ile Gly Ala Gly Lys Asn Gly Val Phe Lys
20 25 30

Thr Ile Ser His Glu Cys His Leu Asn Thr Trp Ala Phe Leu Ala Thr
35 40 45

Cys Cys Ser
50

<210> SEQ ID NO 538
<211> LENGTH: 156
<212> TYPE: DNA
<213> ORGANISM: Streptococcus pyogenes serotype M49

<400> SEQUENCE: 538
atggaaaaaa ataatgaagt aatcaactct attcaagaag ttagtcttga agaactcgat 60
caaattatcg gtgctggaaa aaatggtgtg tttaaaacaa tttctcatga gtgtcatttg 120
aatacatggg cattccttgc tacttgttgc tcataa 156

<210> SEQ ID NO 539
<211> LENGTH: 56
<212> TYPE: PRT
<213> ORGANISM: Bacillus subtilis

<400> SEQUENCE: 539

Met Glu Lys Leu Phe Lys Glu Val Lys Leu Glu Glu Leu Glu Asn Gln
1 5 10 15

Lys Gly Ser Gly Leu Gly Lys Ala Gln Cys Ala Ala Leu Trp Leu Gln
20 25 30

Cys Ala Ser Gly Gly Thr Ile Gly Cys Gly Gly Gly Ala Val Ala Cys
35 40 45

Gln Asn Tyr Arg Gln Phe Cys Arg
50 55

<210> SEQ ID NO 540
<211> LENGTH: 171
<212> TYPE: DNA
<213> ORGANISM: Bacillus subtilis

<400> SEQUENCE: 540
atggaaaagc tatttaaaga agttaaacta gaggaactcg aaaaccaaaa aggtagtgga 60
ttaggaaaag ctcagtgtgc tgcgttgtgg ctacaatgtg ctagtggcgg tacaattggt 120
tgtggtggcg gagctgttgc ttgtcaaaac tatcgtcaat tctgcagata a 171

<210> SEQ ID NO 541
<211> LENGTH: 56
<212> TYPE: PRT
<213> ORGANISM: Bacillus subtilis

<400> SEQUENCE: 541

Met Ser Lys Phe Asp Asp Phe Asp Leu Asp Val Val Lys Val Ser Lys
1 5 10 15

Gln Asp Ser Lys Ile Thr Pro Gln Trp Lys Ser Glu Ser Leu Cys Thr
20 25 30

Pro Gly Cys Val Thr Gly Ala Leu Gln Thr Cys Phe Leu Gln Thr Leu
35 40 45

Thr Cys Asn Cys Lys Ile Ser Lys
    50                  55

<210> SEQ ID NO 542
<211> LENGTH: 171
<212> TYPE: DNA
<213> ORGANISM: Bacillus subtilis

<400> SEQUENCE: 542
atgtcaaagt tcgatgattt cgatttggat gttgtgaaag tctctaaaca agactcaaaa 60
atcactccgc aatggaaaag tgaatcactt tgtacaccag gatgtgtaac tggtgcattg 120
caaacttgct tccttcaaac actaacttgt aactgcaaaa tctctaaata a 171

<210> SEQ ID NO 543
<211> LENGTH: 50
<212> TYPE: PRT
<213> ORGANISM: Bacillus subtilis

<400> SEQUENCE: 543

Met Lys Leu Pro Val Gln Gln Val Tyr Ser Val Tyr Gly Gly Lys Asp
1               5                   10                  15

Leu Pro Lys Gly His Ser His Ser Thr Met Pro Phe Leu Ser Lys Leu
            20                  25                  30

Gln Phe Leu Thr Lys Ile Tyr Leu Leu Asp Ile His Thr Gln Pro Phe
        35                  40                  45

Phe Ile
    50

<210> SEQ ID NO 544
<211> LENGTH: 153
<212> TYPE: DNA
<213> ORGANISM: Bacillus subtilis

<400> SEQUENCE: 544
ttgaaattgc cggtgcaaca ggtctattcg gtctatgggg gtaaggatct cccaaaaggg 60
catagtcatt ctactatgcc ctttttaagt aaattacaat ttttaactaa aatctacctc 120
ttggatatac atacacaacc gtttttcatt tga 153

<210> SEQ ID NO 545
<211> LENGTH: 43
<212> TYPE: PRT
<213> ORGANISM: Bacillus subtilis

<400> SEQUENCE: 545

Met Lys Lys Ala Val Ile Val Glu Asn Lys Gly Cys Ala Thr Cys Ser
1               5                   10                  15

Ile Gly Ala Ala Cys Leu Val Asp Gly Pro Ile Pro Asp Phe Glu Ile
            20                  25                  30

Ala Gly Ala Thr Gly Leu Phe Gly Leu Trp Gly
        35                  40

<210> SEQ ID NO 546
<211> LENGTH: 132
<212> TYPE: DNA
<213> ORGANISM: Bacillus subtilis

<400> SEQUENCE: 546
atgaaaaaag ctgtcattgt agaaaacaaa ggttgtgcaa catgctcgat cggagccgct 60
tgtctagtgg acggtcctat ccctgatttt gaaattgccg gtgcaacagg tctattcggt 120
ctatgggggt aa 132

<210> SEQ ID NO 547
<211> LENGTH: 58
<212> TYPE: PRT
<213> ORGANISM: Streptococcus thermophilus

<400> SEQUENCE: 547

Met Met Asn Ala Thr Glu Asn Gln Ile Phe Val Glu Thr Val Ser Asp
1 5 10 15

Gln Glu Leu Glu Met Leu Ile Gly Gly Ala Asp Arg Gly Trp Ile Lys
20 25 30

Thr Leu Thr Lys Asp Cys Pro Asn Val Ile Ser Ser Ile Cys Ala Gly
35 40 45

Thr Ile Ile Thr Ala Cys Lys Asn Cys Ala
50 55

<210> SEQ ID NO 548
<211> LENGTH: 177
<212> TYPE: DNA
<213> ORGANISM: Streptococcus thermophilus

<400> SEQUENCE: 548
atgatgaatg ctactgaaaa ccaaattttt gttgagactg tgagtgacca agaattagaa 60
atgttaattg gtggtgcaga tcgtggatgg attaagactt taacaaaaga ttgtccaaat 120
gtaatttctt caatttgtgc aggtacaatt attacagcct gtaaaaattg tgcttaa 177

<210> SEQ ID NO 549
<211> LENGTH: 64
<212> TYPE: PRT
<213> ORGANISM: Streptococcus thermophilus

<400> SEQUENCE: 549

Met Lys Gln Tyr Asn Gly Phe Glu Val Leu His Glu Leu Asp Leu Ala
1 5 10 15

Asn Val Thr Gly Gly Gln Ile Asn Trp Gly Ser Val Val Gly His Cys
20 25 30

Ile Gly Gly Ala Ile Ile Gly Gly Ala Phe Ser Gly Gly Ala Ala Ala
35 40 45

Gly Val Gly Cys Leu Val Gly Ser Gly Lys Ala Ile Ile Asn Gly Leu
50 55 60

<210> SEQ ID NO 550
<211> LENGTH: 195
<212> TYPE: DNA
<213> ORGANISM: Streptococcus thermophilus

<400> SEQUENCE: 550
atgaagcagt ataatggttt tgaggttcta catgaacttg acttagcaaa tgtaactggc 60
ggtcaaatta attggggatc agttgtagga cactgtatag gtggagctat tatcggaggt 120
gcattttcag gaggtgcagc ggctggagta ggatgccttg ttgggagcgg aaaggcaatc 180
ataaatggat tataa 195

<210> SEQ ID NO 551
<211> LENGTH: 85
<212> TYPE: PRT
<213> ORGANISM: Streptococcus thermophilus

<400> SEQUENCE: 551

Met Asn Thr Ile Thr Ile Cys Lys Phe Asp Val Leu Asp Ala Glu Leu
1               5                   10                  15

Leu Ser Thr Val Glu Gly Gly Tyr Ser Gly Lys Asp Cys Leu Lys Asp
            20                  25                  30

Met Gly Gly Tyr Ala Leu Ala Gly Ala Gly Ser Gly Ala Leu Trp Gly
        35                  40                  45

Ala Pro Ala Gly Gly Val Gly Ala Leu Pro Gly Ala Phe Val Gly Ala
    50                  55                  60

His Val Gly Ala Ile Ala Gly Gly Phe Ala Cys Met Gly Gly Met Ile
65                  70                  75                  80

Gly Asn Lys Phe Asn
                85

<210> SEQ ID NO 552
<211> LENGTH: 258
<212> TYPE: DNA
<213> ORGANISM: Streptococcus thermophilus

<400> SEQUENCE: 552
atgaatacaa taactatttg taaatttgat gttttagatg ctgaacttct ttcgacagtt     60
gagggtggat actctggtaa ggattgttta aaagacatgg gaggatatgc attggcagga    120
gctggaagtg gagctctgtg gggagctcca gcaggaggtg ttggagcact tccaggtgca    180
tttgtcggag ctcatgttgg ggcaattgca ggaggctttg catgtatggg tggaatgatt    240
ggtaataagt ttaactaa                                                  258

<210> SEQ ID NO 553
<211> LENGTH: 52
<212> TYPE: PRT
<213> ORGANISM: Bacillus cereus

<400> SEQUENCE: 553

Met Ser Glu Ile Lys Lys Ala Leu Asn Thr Leu Glu Ile Glu Asp Phe
1               5                   10                  15

Asp Ala Ile Glu Met Val Asp Val Asp Ala Met Pro Glu Asn Glu Ala
            20                  25                  30

Leu Glu Ile Met Gly Ala Ser Cys Thr Thr Cys Val Cys Thr Cys Ser
        35                  40                  45

Cys Cys Thr Thr
    50

<210> SEQ ID NO 554
<211> LENGTH: 159
<212> TYPE: DNA
<213> ORGANISM: Bacillus cereus

<400> SEQUENCE: 554
atgagtgaaa ttaaaaaagc attaaatacg cttgaaattg aagattttga tgcaattgaa     60
atggttgatg ttgatgctat gccagaaaac gaagcgcttg aaattatggg agcgtcatgt    120
acgacatgcg tatgtacatg cagttgttgt acaacttga                           159

<210> SEQ ID NO 555
<211> LENGTH: 47
<212> TYPE: PRT
<213> ORGANISM: Bacillus cereus

<400> SEQUENCE: 555

Met Glu Val Met Asn Asn Ala Leu Ile Thr Lys Val Asp Glu Glu Ile
1               5                   10                  15

Gly Gly Asn Ala Ala Cys Val Ile Gly Cys Ile Gly Ser Cys Val Ile
            20                  25                  30

Ser Glu Gly Ile Gly Ser Leu Val Gly Thr Ala Phe Thr Leu Gly
        35                  40                  45

<210> SEQ ID NO 556
<211> LENGTH: 144
<212> TYPE: DNA
<213> ORGANISM: Bacillus cereus

<400> SEQUENCE: 556
atggaagtta tgaacaatgc tttaattaca aaagtagatg aggagattgg aggaaacgct     60
gcttgtgtaa ttggttgtat tggcagttgc gtaattagtg aaggaattgg ttcacttgta    120
ggaacagcat ttactttagg ttaa                                           144

<210> SEQ ID NO 557
<211> LENGTH: 49
<212> TYPE: PRT
<213> ORGANISM: Bacillus cereus

<400> SEQUENCE: 557

Met Glu Val Leu Asn Lys Gln Asn Val Asn Ile Ile Pro Glu Ser Glu
1               5                   10                  15

Glu Val Gly Gly Trp Val Ala Cys Val Gly Ala Cys Gly Thr Val Cys
            20                  25                  30

Leu Ala Ser Gly Gly Val Gly Thr Glu Phe Ala Ala Ala Ser Tyr Phe
        35                  40                  45

Leu

<210> SEQ ID NO 558
<211> LENGTH: 150
<212> TYPE: DNA
<213> ORGANISM: Bacillus cereus

<400> SEQUENCE: 558
atggaagttt taaacaaaca aaatgtaaat attattccag aatctgaaga agtaggtgga     60
tgggtagcat gtgttggagc atgtggtaca gtatgtcttg ctagtggtgg tgttggaaca    120
gagtttgcag ctgcatctta tttcctataa                                     150

<210> SEQ ID NO 559
<211> LENGTH: 40
<212> TYPE: PRT
<213> ORGANISM: Bacillus thuringiensis

<400> SEQUENCE: 559

Met Glu Thr Pro Val Val Gln Pro Arg Asp Trp Thr Cys Trp Ser Cys
1               5                   10                  15

Leu Val Cys Ala Ala Cys Ser Val Glu Leu Leu Asn Leu Val Thr Ala
            20                  25                  30

Ala Thr Gly Ala Ser Thr Ala Ser
        35                  40

<210> SEQ ID NO 560
<211> LENGTH: 123
<212> TYPE: DNA
<213> ORGANISM: Bacillus thuringiensis

<400> SEQUENCE: 560
atggaaacac cagtagtaca accaagggat tggacttgtt ggagttgctt agtatgtgca 60
gcatgttctg tggaattatt aaatttagtt actgcggcaa caggggctag tactgcaagc 120
taa 123

<210> SEQ ID NO 561
<211> LENGTH: 42
<212> TYPE: PRT
<213> ORGANISM: Rhizobium leguminosarum bv. trifolii

<400> SEQUENCE: 561

Met Asp Asn Lys Val Ala Lys Asn Val Glu Val Lys Lys Gly Ser Ile
1 5 10 15

Lys Ala Thr Phe Lys Ala Ala Val Leu Lys Ser Lys Thr Lys Val Asp
20 25 30

Ile Gly Gly Ser Arg Gln Gly Cys Val Ala
35 40

<210> SEQ ID NO 562
<211> LENGTH: 129
<212> TYPE: DNA
<213> ORGANISM: Rhizobium leguminosarum bv. trifolii

<400> SEQUENCE: 562
atggataaca aggttgcgaa gaatgtcgaa gtgaagaagg gctccatcaa ggcgaccttc 60
aaggctgctg ttctgaagtc gaagacgaag gtcgacatcg gaggtagccg tcagggctgc 120
gtcgcttaa 129

<210> SEQ ID NO 563
<211> LENGTH: 70
<212> TYPE: PRT
<213> ORGANISM: Streptococcus uberis

<400> SEQUENCE: 563

Met Asn Thr Ile Glu Lys Phe Glu Asn Ile Lys Leu Phe Ser Leu Lys
1 5 10 15

Lys Ile Ile Gly Gly Lys Thr Val Asn Tyr Gly Asn Gly Leu Tyr Cys
20 25 30

Asn Gln Lys Lys Cys Trp Val Asn Trp Ser Glu Thr Ala Thr Thr Ile
35 40 45

Val Asn Asn Ser Ile Met Asn Gly Leu Thr Gly Gly Asn Ala Gly Trp
50 55 60

His Ser Gly Gly Arg Ala
65 70

<210> SEQ ID NO 564
<211> LENGTH: 213
<212> TYPE: DNA
<213> ORGANISM: Streptococcus uberis

<400> SEQUENCE: 564
atgaatacaa ttgaaaaatt tgaaaatatt aaactttttt cactaaagaa aattatcggt 60
ggcaaaactg taaattatgg taatggcctt tattgtaacc aaaaaaaatg ctgggtaaac 120
tggtcagaaa ctgctacaac aatagtaaat aattccatca tgaacgggct cacaggtggt 180
aatgcgggtt ggcactcagg cgggagagca taa 213

<210> SEQ ID NO 565
<211> LENGTH: 76
<212> TYPE: PRT
<213> ORGANISM: Streptococcus uberis

<400> SEQUENCE: 565

Met Asp Ile Leu Leu Glu Leu Ala Gly Tyr Thr Gly Ile Ala Ser Gly
1 5 10 15

Thr Ala Lys Lys Val Val Asp Ala Ile Asp Lys Gly Ala Ala Ala Phe
20 25 30

Val Ile Ile Ser Ile Ile Ser Thr Val Ile Ser Ala Gly Ala Leu Gly
35 40 45

Ala Val Ser Ala Ser Ala Asp Phe Ile Ile Leu Thr Val Lys Asn Tyr
50 55 60

Ile Ser Arg Asn Leu Lys Ala Gln Ala Val Ile Trp
65 70 75

<210> SEQ ID NO 566
<211> LENGTH: 231
<212> TYPE: DNA
<213> ORGANISM: Streptococcus uberis

<400> SEQUENCE: 566
atggacattt tattagaact cgcaggatat actgggatag cctcaggtac tgcaaaaaaa 60
gttgttgatg ccattgataa aggagctgca gcctttgtta ttatttcaat tatctcaaca 120
gtaattagtg cgggagcatt gggagcagtt tcagcctcag ctgattttat tattttaact 180
gtaaaaaatt acattagtag aaatttaaaa gcacaagctg tcatttggta a 231

<210> SEQ ID NO 567
<211> LENGTH: 64
<212> TYPE: PRT
<213> ORGANISM: Clostridium perfringens

<400> SEQUENCE: 567

Met Asp Ser Glu Leu Phe Lys Leu Met Ala Thr Gln Gly Ala Phe Ala
1 5 10 15

Ile Leu Phe Ser Tyr Leu Leu Phe Tyr Val Leu Lys Glu Asn Ser Lys
20 25 30

Arg Glu Asp Lys Tyr Gln Asn Ile Ile Glu Glu Leu Thr Glu Leu Leu
35 40 45

Pro Lys Ile Lys Glu Asp Val Glu Asp Ile Lys Glu Lys Leu Asn Lys
50 55 60

<210> SEQ ID NO 568
<211> LENGTH: 195
<212> TYPE: DNA
<213> ORGANISM: Clostridium perfringens

<400> SEQUENCE: 568
atggatagtg aattatttaa gttaatggca acacaaggag cctttgcaat attattttcg 60
tatttattgt tttatgtttt aaaagagaat agtaaaagag aagataagta tcaaaatata 120
atagaggagc ttacagaatt attgccaaaa ataaaagaag atgtagaaga tataaaagaa 180
aaacttaata aatag 195

<210> SEQ ID NO 569
<211> LENGTH: 47
<212> TYPE: PRT

<213> ORGANISM: Micrococcus varians

<400> SEQUENCE: 569

Met Thr Asn Ala Phe Gln Ala Leu Asp Glu Val Thr Asp Ala Glu Leu
1 5 10 15

Asp Ala Ile Leu Gly Gly Gly Ser Gly Val Ile Pro Thr Ile Ser His
20 25 30

Glu Cys His Met Asn Ser Phe Gln Phe Val Phe Thr Cys Cys Ser
35 40 45

<210> SEQ ID NO 570
<211> LENGTH: 144
<212> TYPE: DNA
<213> ORGANISM: Micrococcus varians

<400> SEQUENCE: 570
atgacgaacg catttcaggc actggacgaa gtcacggacg ccgagctcga cgccatcctt 60
ggcgggggca gtggtgttat tcccacgatc agccacgagt gccacatgaa ctccttccag 120
ttcgtgttca cctgctgctc ctga 144

<210> SEQ ID NO 571
<211> LENGTH: 285
<212> TYPE: PRT
<213> ORGANISM: Streptococcus equi subsp. zooepidemicus

<400> SEQUENCE: 571

Met Lys Arg Ile Phe Phe Ala Phe Leu Ser Leu Cys Leu Phe Ile Phe
1 5 10 15

Gly Thr Gln Thr Val Ser Ala Ala Thr Tyr Thr Arg Pro Leu Asp Thr
20 25 30

Gly Asn Ile Thr Thr Gly Phe Asn Gly Tyr Pro Gly His Val Gly Val
35 40 45

Asp Tyr Ala Val Pro Val Gly Thr Pro Val Arg Ala Val Ala Asn Gly
50 55 60

Thr Val Lys Phe Ala Gly Asn Gly Ala Asn His Pro Trp Met Leu Trp
65 70 75 80

Met Ala Gly Asn Cys Val Leu Ile Gln His Ala Asp Gly Met His Thr
85 90 95

Gly Tyr Ala His Leu Ser Lys Ile Ser Val Ser Thr Asp Ser Thr Val
100 105 110

Lys Gln Gly Gln Ile Ile Gly Tyr Thr Gly Ala Thr Gly Gln Val Thr
115 120 125

Gly Pro His Leu His Phe Glu Met Leu Pro Ala Asn Pro Asn Trp Gln
130 135 140

Asn Gly Phe Ser Gly Arg Ile Asp Pro Thr Gly Tyr Ile Ala Asn Ala
145 150 155 160

Pro Val Phe Asn Gly Thr Thr Pro Thr Glu Pro Thr Thr Pro Thr Thr
165 170 175

Asn Leu Lys Ile Tyr Lys Val Asp Asp Leu Gln Lys Ile Asn Gly Ile
180 185 190

Trp Gln Val Arg Asn Asn Ile Leu Val Pro Thr Asp Phe Thr Trp Val
195 200 205

Asp Asn Gly Ile Ala Ala Asp Asp Val Ile Glu Val Thr Ser Asn Gly
210 215 220

Thr Arg Thr Ser Asp Gln Val Leu Gln Lys Gly Gly Tyr Phe Val Ile
225 230 235 240

Asn Pro Asn Asn Val Lys Ser Val Gly Thr Pro Met Lys Gly Ser Gly
245 250 255

Gly Leu Ser Trp Ala Gln Val Asn Phe Thr Thr Gly Gly Asn Val Trp
260 265 270

Leu Asn Thr Thr Ser Lys Asp Asn Leu Leu Tyr Gly Lys
275 280 285

<210> SEQ ID NO 572
<211> LENGTH: 858
<212> TYPE: DNA
<213> ORGANISM: Streptococcus equi subsp. zooepidemicus

<400> SEQUENCE: 572
atgaaacgta tattttttgc tttcttaagt ttatgcttat ttatattcgg aacacaaacg 60
gtatctgcag ctacttatac tcggccatta gatacgggaa atatcactac agggtttaac 120 ggatacccctg gtcatgttgg agtcgattat gcagtacccg ttggaactcc ggttagagca 180
gttgcaaatg gtacagtcaa atttgcaggt aatggggcta atcacccatg gatgctttgg 240
atggctggaa actgtgttct aattcaacat gctgacggga tgcatactgg atatgcacac 300
ttatcaaaaa tttcagttag cacagatagt acagttaaac aaggacaaat cataggttat 360
actggtgcca ccggccaagt taccggtcca catttgcatt ttgaaatgtt gccagcaaat 420
cctaactggc aaaatggttt ttctggaaga atagatccaa ccggatacat cgctaatgcc 480
cctgtattta atggaacaac acctacagaa cctactactc ctacaacaaa tttaaaaatc 540
tataaagttg atgatttaca aaaaattaat ggtatttggc aagtaagaaa taacatactt 600
gtaccaactg atttcacatg ggttgataat ggaattgcag cagatgatgt aattgaagta 660
actagcaatg gaacaagaac ctctgaccaa gttcttcaaa aaggtggtta ttttgtcatc 720
aatcctaata atgttaaaag tgttggaact ccgatgaaag gtagtggtgg tctatcttgg 780
gctcaagtaa actttacaac aggtggaaat gtctggttaa atactactag caaagacaac 840
ttactttacg gaaaataa 858

<210> SEQ ID NO 573
<211> LENGTH: 45
<212> TYPE: PRT
<213> ORGANISM: Myxococcus fulvus

<400> SEQUENCE: 573

Ala Asn Cys Ser Cys Ser Thr Ala Ser Asp Tyr Cys Pro Ile Leu Thr
1 5 10 15

Phe Cys Thr Thr Gly Thr Ala Cys Ser Tyr Thr Pro Thr Gly Cys Gly
20 25 30

Thr Gly Trp Val Tyr Cys Ala Cys Asn Gly Asn Phe Tyr
35 40 45

<210> SEQ ID NO 574
<211> LENGTH: 135
<212> TYPE: DNA
<213> ORGANISM: Artificial Sequence
<220> FEATURE:
<223> OTHER INFORMATION: Polynucleotide encoding the polypeptide of SEQ ID NO: 338

<400> SEQUENCE: 574
gcgaactgca gctgcagcac cgcgagcgat tattgcccga ttctgacctt ttgcaccacc 60
ggcaccgcgt gcagctatac cccgaccggc tgcggcaccg gctgggtgta ttgcgcgtgc 120
aacggcaact tttat 135

<210> SEQ ID NO 575
<211> LENGTH: 19
<212> TYPE: PRT
<213> ORGANISM: Streptomyces griseoluteus

<400> SEQUENCE: 575

Cys Ala Asn Ser Cys Ser Tyr Gly Pro Leu Thr Trp Ser Cys Asp Gly
1 5 10 15

Asn Thr Lys

<210> SEQ ID NO 576
<211> LENGTH: 57
<212> TYPE: DNA
<213> ORGANISM: Artificial Sequence
<220> FEATURE:
<223> OTHER INFORMATION: Polynucleotide encoding the polypeptide of SEQ ID NO: 340

<400> SEQUENCE: 576
tgcgcgaaca gctgcagcta tggcccgctg acctggagct gcgatggcaa caccaaa 57

<210> SEQ ID NO 577
<211> LENGTH: 19
<212> TYPE: PRT
<213> ORGANISM: Streptoverticillium griseoverticillatum

<400> SEQUENCE: 577

Cys Lys Gln Ser Cys Ser Phe Gly Pro Phe Thr Phe Val Cys Asp Gly
1 5 10 15

Asn Thr Lys

<210> SEQ ID NO 578
<211> LENGTH: 57
<212> TYPE: DNA
<213> ORGANISM: Artificial Sequence
<220> FEATURE:
<223> OTHER INFORMATION: Polynucleotide encoding the polypeptide of SEQ ID NO: 342

<400> SEQUENCE: 578
tgcaaacaga gctgcagctt tggcccgttt acctttgtgt gcgatggcaa caccaaa 57

<210> SEQ ID NO 579
<211> LENGTH: 7
<212> TYPE: PRT
<213> ORGANISM: Carnobacterium sp.

<400> SEQUENCE: 579

Gly Ser Glu Ile Gln Pro Arg
1 5

<210> SEQ ID NO 580
<211> LENGTH: 21
<212> TYPE: DNA
<213> ORGANISM: Artificial Sequence
<220> FEATURE:
<223> OTHER INFORMATION: Polynucleotide encoding the polypeptide of SEQ ID NO: 344

<400> SEQUENCE: 580
ggcagcgaaa ttcagccgcg c 21

<210> SEQ ID NO 581
<211> LENGTH: 39
<212> TYPE: PRT
<213> ORGANISM: Lactococcus lactis subsp. lactis

<400> SEQUENCE: 581

Gly Thr Trp Asp Asp Ile Gly Gln Gly Ile Gly Arg Val Ala Tyr Trp
1 5 10 15

Val Gly Lys Ala Met Gly Asn Met Ser Asp Val Asn Gln Ala Ser Arg
20 25 30

Ile Asn Arg Lys Lys Lys His
35

<210> SEQ ID NO 582
<211> LENGTH: 117
<212> TYPE: DNA
<213> ORGANISM: Artificial Sequence
<220> FEATURE:
<223> OTHER INFORMATION: Polynucleotide encoding the polypeptide of SEQ ID NO: 346

<400> SEQUENCE: 582
ggcacctggg atgatattgg ccagggcatt ggccgcgtgg cgtattgggt gggcaaagcg 60
atgggcaaca tgagcgatgt gaaccaggcg agccgcatta accgcaaaaa aaaacat 117

<210> SEQ ID NO 583
<211> LENGTH: 35
<212> TYPE: PRT
<213> ORGANISM: Lactococcus lactis subsp. lactis

<400> SEQUENCE: 583

Lys Lys Trp Gly Trp Leu Ala Trp Val Asp Pro Ala Tyr Glu Phe Ile
1 5 10 15

Lys Gly Phe Gly Lys Gly Ala Ile Lys Glu Gly Asn Lys Asp Lys Trp
20 25 30

Lys Asn Ile
35

<210> SEQ ID NO 584
<211> LENGTH: 105
<212> TYPE: DNA
<213> ORGANISM: Artificial Sequence
<220> FEATURE:
<223> OTHER INFORMATION: Polynucleotide encoding the polypeptide of SEQ ID NO: 348

<400> SEQUENCE: 584
aaaaaatggg gctggctggc gtgggtggat ccggcgtatg aatttattaa aggctttggc 60
aaaggcgcga ttaaagaagg caacaaagat aaatggaaaa acatt 105

<210> SEQ ID NO 585
<211> LENGTH: 19
<212> TYPE: PRT
<213> ORGANISM: Streptomyces sp.

<400> SEQUENCE: 585

Cys Val Gln Ser Cys Ser Phe Gly Pro Leu Thr Trp Ser Cys Asp Gly
1 5 10 15

Asn Thr Lys

<210> SEQ ID NO 586

<211> LENGTH: 57
<212> TYPE: DNA
<213> ORGANISM: Artificial Sequence
<220> FEATURE:
<223> OTHER INFORMATION: Polynucleotide encoding the polypeptide of SEQ
ID NO: 350

<400> SEQUENCE: 586
tgcgtgcaga gctgcagctt tggcccgctg acctggagct gcgatggcaa caccaaa 57

<210> SEQ ID NO 587
<211> LENGTH: 19
<212> TYPE: PRT
<213> ORGANISM: Actinoplanes liguriae

<400> SEQUENCE: 587

Ser Ser Gly Trp Val Cys Thr Leu Thr Ile Glu Cys Gly Thr Val Ile
1 5 10 15

Cys Ala Cys

<210> SEQ ID NO 588
<211> LENGTH: 57
<212> TYPE: DNA
<213> ORGANISM: Artificial Sequence
<220> FEATURE:
<223> OTHER INFORMATION: Polynucleotide encoding the polypeptide of SEQ
ID NO: 352

<400> SEQUENCE: 588
agcagcggct gggtgtgcac cctgaccatt gaatgcggca ccgtgatttg cgcgtgc 57

<210> SEQ ID NO 589
<211> LENGTH: 38
<212> TYPE: PRT
<213> ORGANISM: Lactobacillus curvatus
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa = any amino acid

<400> SEQUENCE: 589

Tyr Thr Ala Lys Gln Cys Leu Gln Ala Ile Gly Ser Cys Gly Ile Ala
1 5 10 15

Gly Thr Gly Ala Gly Ala Ala Gly Gly Pro Ala Gly Ala Phe Val Gly
20 25 30

Ala Xaa Val Val Xaa Ile
35

<210> SEQ ID NO 590
<211> LENGTH: 114
<212> TYPE: DNA
<213> ORGANISM: Artificial Sequence
<220> FEATURE:
<223> OTHER INFORMATION: Polynucleotide encoding the polypeptide of SEQ
ID NO: 354
<220> FEATURE:
<221> NAME/KEY: misc_feature
<222> LOCATION: (100)..(102)
<223> OTHER INFORMATION: nnn = any amino acid-coding triplet
<220> FEATURE:
<221> NAME/KEY: misc_feature
<222> LOCATION: (109)..(111)
<223> OTHER INFORMATION: nnn = any amino acid-coding triplet

<400> SEQUENCE: 590
tataccgcga aacagtgcct gcaggcgatt ggcagctgcg gcattgcggg caccggcgcg 60
ggcgcggcgg gcggcccggc gggcgcgttt gtgggcgcgn nngtggtgnn natt 114

<210> SEQ ID NO 591
<211> LENGTH: 42
<212> TYPE: PRT
<213> ORGANISM: Lactobacillus sakei
<220> FEATURE:
<221> NAME/KEY: misc_feature
<222> LOCATION: (32)..(32)
<223> OTHER INFORMATION: Xaa = any amino acid

<400> SEQUENCE: 591

Thr Lys Tyr Tyr Gly Asn Gly Val Tyr Cys Asn Ser Lys Lys Cys Trp
1 5 10 15

Val Asp Trp Gly Gln Ala Ala Gly Gly Ile Gly Gln Thr Val Val Xaa
20 25 30

Gly Trp Leu Gly Gly Ala Ile Pro Gly Lys
35 40

<210> SEQ ID NO 592
<211> LENGTH: 126
<212> TYPE: DNA
<213> ORGANISM: Artificial Sequence
<220> FEATURE:
<223> OTHER INFORMATION: Polynucleotide encoding the polypeptide of SEQ ID NO: 356
<220> FEATURE:
<221> NAME/KEY: misc_feature
<222> LOCATION: (94)..(96)
<223> OTHER INFORMATION: nnn = any amino acid-coding triplet

<400> SEQUENCE: 592
accaaatatt atggcaacgg cgtgtattgc aacagcaaaa aatgctgggt ggattggggc 60
caggcggcgg gcggcattgg ccagaccgtg gtgnnnggct ggctgggcgg cgcgattccg 120
ggcaaa 126

<210> SEQ ID NO 593
<211> LENGTH: 22
<212> TYPE: PRT
<213> ORGANISM: Streptococcus mutans

<400> SEQUENCE: 593

Phe Lys Ser Trp Ser Phe Cys Thr Pro Gly Cys Ala Lys Thr Gly Ser
1 5 10 15

Phe Asn Ser Tyr Cys Cys
20

<210> SEQ ID NO 594
<211> LENGTH: 132
<212> TYPE: DNA
<213> ORGANISM: Artificial Sequence
<220> FEATURE:
<223> OTHER INFORMATION: Polynucleotide encoding the polypeptide of SEQ ID NO: 358

<400> SEQUENCE: 594
tttaaaagct ggagcttttg caccccgggc tgcgcgaaaa ccggcagctt taacagctat 60
tgctgcttta aaagctggag cttttgcacc ccgggctgcg cgaaaaccgg cagctttaac 120
agctattgct gc 132

<210> SEQ ID NO 595
<211> LENGTH: 43
<212> TYPE: PRT
<213> ORGANISM: Enterococcus mundtii

<400> SEQUENCE: 595

Lys Tyr Tyr Gly Asn Gly Val Ser Cys Asn Lys Lys Gly Cys Ser Val
1 5 10 15

Asp Trp Gly Lys Ala Ile Gly Ile Ile Gly Asn Asn Ser Ala Ala Asn
20 25 30

Leu Ala Thr Gly Gly Ala Ala Gly Trp Ser Lys
35 40

<210> SEQ ID NO 596
<211> LENGTH: 129
<212> TYPE: DNA
<213> ORGANISM: Artificial Sequence
<220> FEATURE:
<223> OTHER INFORMATION: Polynucleotide encoding the polypeptide of SEQ ID NO: 360

<400> SEQUENCE: 596
aaatattatg gcaacggcgt gagctgcaac aaaaaaggct gcagcgtgga ttggggcaaa 60
gcgattggca ttattggcaa caacagcgcg gcgaacctgg cgaccggcgg cgcggcgggc 120
tggagcaaa 129

<210> SEQ ID NO 597
<211> LENGTH: 41
<212> TYPE: PRT
<213> ORGANISM: Lactobacillus sakei
<220> FEATURE:
<221> NAME/KEY: misc_feature
<222> LOCATION: (9)..(9)
<223> OTHER INFORMATION: Xaa = any amino acid
<220> FEATURE:
<221> NAME/KEY: misc_feature
<222> LOCATION: (14)..(14)
<223> OTHER INFORMATION: Xaa = any amino acid
<220> FEATURE:
<221> NAME/KEY: misc_feature
<222> LOCATION: (33)..(33)
<223> OTHER INFORMATION: Xaa = any amino acid
<220> FEATURE:
<221> NAME/KEY: misc_feature
<222> LOCATION: (37)..(37)
<223> OTHER INFORMATION: Xaa = any amino acid

<400> SEQUENCE: 597

Lys Tyr Tyr Gly Asn Gly Val His Xaa Gly Lys His Ser Xaa Thr Val
1 5 10 15

Asp Trp Gly Thr Ala Ile Gly Asn Ile Gly Asn Asn Ala Ala Ala Asn
20 25 30

Xaa Ala Thr Gly Xaa Asn Ala Gly Gly
35 40

<210> SEQ ID NO 598
<211> LENGTH: 123
<212> TYPE: DNA
<213> ORGANISM: Artificial Sequence
<220> FEATURE:
<223> OTHER INFORMATION: Polynucleotide encoding the polypeptide of SEQ ID NO: 362
<220> FEATURE:
<221> NAME/KEY: misc_feature
<222> LOCATION: (25)..(27)
<223> OTHER INFORMATION: nnn = any amino acid-coding triplet
<220> FEATURE:
<221> NAME/KEY: misc_feature
<222> LOCATION: (40)..(42)
<223> OTHER INFORMATION: nnn = any amino acid-coding triplet
<220> FEATURE:
<221> NAME/KEY: misc_feature
<222> LOCATION: (97)..(99)
<223> OTHER INFORMATION: nnn = any amino acid-coding triplet
<220> FEATURE:
<221> NAME/KEY: misc_feature
<222> LOCATION: (109)..(111)
<223> OTHER INFORMATION: nnn = any amino acid-coding triplet

<400> SEQUENCE: 598
aaatattatg gcaacggcgt gcatnnnggc aaacatagcn nnaccgtgga ttggggcacc 60
gcgattggca acattggcaa caacgcggcg gcgaacnnng cgaccggcnn naacgcgggc 120
ggc 123

<210> SEQ ID NO 599
<211> LENGTH: 31
<212> TYPE: PRT
<213> ORGANISM: Lactobacillus paracasei

<400> SEQUENCE: 599

Gly Met Ser Gly Tyr Ile Gln Gly Ile Pro Asp Phe Leu Lys Gly Tyr
1 5 10 15

Leu His Gly Ile Ser Ala Ala Asn Lys His Lys Lys Gly Arg Leu
20 25 30

<210> SEQ ID NO 600
<211> LENGTH: 93
<212> TYPE: DNA
<213> ORGANISM: Artificial Sequence
<220> FEATURE:
<223> OTHER INFORMATION: Polynucleotide encoding the polypeptide of SEQ ID NO: 364

<400> SEQUENCE: 600
ggcatgagcg gctatattca gggcattccg gattttctga aaggctatct gcatggcatt 60
agcgcggcga acaaacataa aaaaggccgc ctg 93

<210> SEQ ID NO 601
<211> LENGTH: 31
<212> TYPE: PRT
<213> ORGANISM: Leuconostoc mesenteroides

<400> SEQUENCE: 601

Lys Gly Lys Gly Phe Trp Ser Trp Ala Ser Lys Ala Thr Ser Trp Leu
1 5 10 15

Thr Gly Pro Gln Gln Pro Gly Ser Pro Leu Leu Lys Lys His Arg
20 25 30

<210> SEQ ID NO 602
<211> LENGTH: 93
<212> TYPE: DNA
<213> ORGANISM: Artificial Sequence
<220> FEATURE:
<223> OTHER INFORMATION: Polynucleotide encoding the polypeptide of SEQ ID NO: 366

<400> SEQUENCE: 602
aaaggcaaag gcttttggag ctgggcgagc aaagcgacca gctggctgac cggcccgcag 60
cagccgggca gcccgctgct gaaaaaacat cgc 93

<210> SEQ ID NO 603
<211> LENGTH: 43
<212> TYPE: PRT
<213> ORGANISM: Leuconostoc mesenteroides

<400> SEQUENCE: 603

Lys Asn Tyr Gly Asn Gly Val His Cys Thr Lys Lys Gly Cys Ser Val
1 5 10 15

Asp Trp Gly Tyr Ala Trp Thr Asn Ile Ala Asn Asn Ser Val Met Asn
20 25 30

Gly Leu Thr Gly Gly Asn Ala Gly Trp His Asn
35 40

<210> SEQ ID NO 604
<211> LENGTH: 129
<212> TYPE: DNA
<213> ORGANISM: Artificial Sequence
<220> FEATURE:
<223> OTHER INFORMATION: Polynucleotide encoding the polypeptide of SEQ ID NO: 368

<400> SEQUENCE: 604
aaaaactatg gcaacggcgt gcattgcacc aaaaaaggct gcagcgtgga ttggggctat 60
gcgtggacca acattgcgaa caacagcgtg atgaacggcc tgaccggcgg caacgcgggc 120
tggcataac 129

<210> SEQ ID NO 605
<211> LENGTH: 47
<212> TYPE: PRT
<213> ORGANISM: Bacillus subtilis

<400> SEQUENCE: 605

Ala Ile Lys Leu Val Gln Ser Pro Asn Gly Asn Phe Ala Ala Ser Phe
1 5 10 15

Val Leu Asp Gly Thr Lys Trp Ile Phe Lys Ser Lys Tyr Tyr Asp Ser
20 25 30

Ser Lys Gly Tyr Trp Val Gly Ile Tyr Glu Val Trp Asp Arg Lys
35 40 45

<210> SEQ ID NO 606
<211> LENGTH: 141
<212> TYPE: DNA
<213> ORGANISM: Artificial Sequence
<220> FEATURE:
<223> OTHER INFORMATION: Polynucleotide encoding the polypeptide of SEQ ID NO: 370

<400> SEQUENCE: 606
gcgattaaac tggtgcagag cccgaacggc aactttgcgg cgagctttgt gctggatggc 60
accaaatgga tttttaaaag caaatattat gatagcagca aaggctattg ggtgggcatt 120
tatgaagtgt gggatcgcaa a 141

<210> SEQ ID NO 607
<211> LENGTH: 12
<212> TYPE: PRT
<213> ORGANISM: Bacillus licheniformis
<220> FEATURE:
<221> NAME/KEY: misc_feature
<222> LOCATION: (7)..(7)
<223> OTHER INFORMATION: Xaa = any amino acid

<400> SEQUENCE: 607

Ile Ser Leu Glu Ile Cys Xaa Ile Phe His Asp Asn
1 5 10

<210> SEQ ID NO 608
<211> LENGTH: 36
<212> TYPE: DNA
<213> ORGANISM: Artificial Sequence
<220> FEATURE:
<223> OTHER INFORMATION: Polynucleotide encoding the polypeptide of SEQ ID NO: 372
<220> FEATURE:
<221> NAME/KEY: misc_feature
<222> LOCATION: (19)..(21)
<223> OTHER INFORMATION: nnn = any amino acid-coding triplet

<400> SEQUENCE: 608
attagcctgg aaatttgcnn nattttttcat gataac 36

<210> SEQ ID NO 609
<211> LENGTH: 37
<212> TYPE: PRT
<213> ORGANISM: Lactococcus lactis subsp. lactis

<400> SEQUENCE: 609

Thr Ser Tyr Gly Asn Gly Val His Cys Asn Lys Ser Lys Cys Trp Ile
1 5 10 15

Asp Val Ser Glu Leu Glu Thr Tyr Lys Ala Gly Thr Val Ser Asn Pro
20 25 30

Lys Asp Ile Leu Trp
35

<210> SEQ ID NO 610
<211> LENGTH: 111
<212> TYPE: DNA
<213> ORGANISM: Artificial Sequence
<220> FEATURE:
<223> OTHER INFORMATION: Polynucleotide encoding the polypeptide of SEQ ID NO: 374

<400> SEQUENCE: 610
accagctatg gcaacggcgt gcattgcaac aaaagcaaat gctggattga tgtgagcgaa 60
ctggaaacct ataaagcggg caccgtgagc aacccgaaag atattctgtg g 111

<210> SEQ ID NO 611
<211> LENGTH: 9
<212> TYPE: PRT
<213> ORGANISM: Serratia plymuthica

<400> SEQUENCE: 611

Asp Tyr His His Gly Val Arg Val Leu
1 5

<210> SEQ ID NO 612
<211> LENGTH: 27
<212> TYPE: DNA
<213> ORGANISM: Artificial Sequence
<220> FEATURE:
<223> OTHER INFORMATION: Polynucleotide encoding the polypeptide of SEQ ID NO: 376

<400> SEQUENCE: 612
gattatcatc atggcgtgcg cgtgctg 27

<210> SEQ ID NO 613

<211> LENGTH: 15
<212> TYPE: PRT
<213> ORGANISM: Halobacterium sp.

<400> SEQUENCE: 613

Asp Ile Asp Ile Thr Gly Cys Ser Ala Cys Lys Tyr Ala Ala Gly
1 5 10 15

<210> SEQ ID NO 614
<211> LENGTH: 45
<212> TYPE: DNA
<213> ORGANISM: Artificial Sequence
<220> FEATURE:
<223> OTHER INFORMATION: Polynucleotide encoding the polypeptide of SEQ ID NO: 378

<400> SEQUENCE: 614
gatattgata ttaccggctg cagcgcgtgc aaatatgcgg cgggc 45

<210> SEQ ID NO 615
<211> LENGTH: 12
<212> TYPE: PRT
<213> ORGANISM: Bacillus subtilis
<220> FEATURE:
<221> NAME/KEY: misc_feature
<222> LOCATION: (1)..(2)
<223> OTHER INFORMATION: Xaa = any amino acid
<220> FEATURE:
<221> NAME/KEY: misc_feature
<222> LOCATION: (6)..(6)
<223> OTHER INFORMATION: Xaa = any amino acid

<400> SEQUENCE: 615

Xaa Xaa Lys Glu Ile Xaa His Ile Phe His Asp Asn
1 5 10

<210> SEQ ID NO 616
<211> LENGTH: 36
<212> TYPE: DNA
<213> ORGANISM: Artificial Sequence
<220> FEATURE:
<223> OTHER INFORMATION: Polynucleotide encoding the polypeptide of SEQ ID NO: 380
<220> FEATURE:
<221> NAME/KEY: misc_feature
<222> LOCATION: (1)..(6)
<223> OTHER INFORMATION: nnn = any amino acid-coding triplet
<220> FEATURE:
<221> NAME/KEY: misc_feature
<222> LOCATION: (16)..(18)
<223> OTHER INFORMATION: nnn = any amino acid-coding triplet

<400> SEQUENCE: 616
nnnnnnaaag aaattnnnca tatttttcat gataac 36

<210> SEQ ID NO 617
<211> LENGTH: 12
<212> TYPE: PRT
<213> ORGANISM: Lactobacillus curvatus

<400> SEQUENCE: 617

Thr Pro Val Val Asn Pro Pro Phe Leu Gln Gln Thr
1 5 10

<210> SEQ ID NO 618
<211> LENGTH: 36
<212> TYPE: DNA
<213> ORGANISM: Artificial Sequence
<220> FEATURE:

<223> OTHER INFORMATION: Polynucleotide encoding the polypeptide of SEQ ID NO: 382

<400> SEQUENCE: 618
accccggtgg tgaacccgcc gtttctgcag cagacc 36

<210> SEQ ID NO 619
<211> LENGTH: 10
<212> TYPE: PRT
<213> ORGANISM: Lactobacillus curvatus
<220> FEATURE:
<221> NAME/KEY: misc_feature
<222> LOCATION: (10)..(10)
<223> OTHER INFORMATION: Xaa = any amino acid

<400> SEQUENCE: 619

Val Ala Pro Phe Pro Glu Gln Phe Leu Xaa
1 5 10

<210> SEQ ID NO 620
<211> LENGTH: 30
<212> TYPE: DNA
<213> ORGANISM: Artificial Sequence
<220> FEATURE:
<223> OTHER INFORMATION: Polynucleotide encoding the polypeptide of SEQ ID NO: 384
<220> FEATURE:
<221> NAME/KEY: misc_feature
<222> LOCATION: (28)..(30)
<223> OTHER INFORMATION: nnn = any amino acid-coding triplet

<400> SEQUENCE: 620
gtggcgccgt ttccggaaca gtttctgnnn 30

<210> SEQ ID NO 621
<211> LENGTH: 9
<212> TYPE: PRT
<213> ORGANISM: Lactobacillus curvatus

<400> SEQUENCE: 621

Asn Ile Pro Gln Leu Thr Pro Thr Pro
1 5

<210> SEQ ID NO 622
<211> LENGTH: 27
<212> TYPE: DNA
<213> ORGANISM: Artificial Sequence
<220> FEATURE:
<223> OTHER INFORMATION: Polynucleotide encoding the polypeptide of SEQ ID NO: 386

<400> SEQUENCE: 622
aacattccgc agctgacccc gaccccg 27

<210> SEQ ID NO 623
<211> LENGTH: 18
<212> TYPE: PRT
<213> ORGANISM: Bacillus thuringiensis subsp. entomocidus
<220> FEATURE:
<221> NAME/KEY: misc_feature
<222> LOCATION: (4)..(4)
<223> OTHER INFORMATION: Xaa = any amino acid
<220> FEATURE:
<221> NAME/KEY: misc_feature
<222> LOCATION: (7)..(7)
<223> OTHER INFORMATION: Xaa = any amino acid
<220> FEATURE:
<221> NAME/KEY: misc_feature
<222> LOCATION: (10)..(10)

<223> OTHER INFORMATION: Xaa = any amino acid

<400> SEQUENCE: 623

Asp Trp Thr Xaa Trp Ser Xaa Leu Val Xaa Ala Ala Cys Ser Val Glu
1 5 10 15

Leu Leu

<210> SEQ ID NO 624
<211> LENGTH: 54
<212> TYPE: DNA
<213> ORGANISM: Artificial Sequence
<220> FEATURE:
<223> OTHER INFORMATION: Polynucleotide encoding the polypeptide of SEQ ID NO: 388
<220> FEATURE:
<221> NAME/KEY: misc_feature
<222> LOCATION: (10)..(12)
<223> OTHER INFORMATION: nnn = any amino acid-coding triplet
<220> FEATURE:
<221> NAME/KEY: misc_feature
<222> LOCATION: (19)..(21)
<223> OTHER INFORMATION: nnn = any amino acid-coding triplet
<220> FEATURE:
<221> NAME/KEY: misc_feature
<222> LOCATION: (28)..(30)
<223> OTHER INFORMATION: nnn = any amino acid-coding triplet

<400> SEQUENCE: 624
gattggaccn nntggagcnn nctggtgnnn gcggcgtgca gcgtggaact gctg 54

<210> SEQ ID NO 625
<211> LENGTH: 30
<212> TYPE: PRT
<213> ORGANISM: Lactobacillus curvatus

<400> SEQUENCE: 625

Ala Tyr Pro Gly Asn Gly Val His Cys Gly Lys Tyr Ser Cys Thr Val
1 5 10 15

Asp Lys Gln Thr Ala Ile Gly Asn Ile Gly Asn Asn Ala Ala
20 25 30

<210> SEQ ID NO 626
<211> LENGTH: 90
<212> TYPE: DNA
<213> ORGANISM: Artificial Sequence
<220> FEATURE:
<223> OTHER INFORMATION: Polynucleotide encoding the polypeptide of SEQ ID NO: 390

<400> SEQUENCE: 626
gcgtatccgg gcaacggcgt gcattgcggc aaatatagct gcaccgtgga taaacagacc 60
gcgattggca acattggcaa caacgcggcg 90

<210> SEQ ID NO 627
<211> LENGTH: 43
<212> TYPE: PRT
<213> ORGANISM: Carnobacterium divergens

<400> SEQUENCE: 627

Thr Lys Tyr Tyr Gly Asn Gly Val Tyr Cys Asn Ser Lys Lys Cys Trp
1 5 10 15

Val Asp Trp Gly Thr Ala Gln Gly Cys Ile Asp Val Val Ile Gly Gln
20 25 30

Leu Gly Gly Gly Ile Pro Gly Lys Gly Lys Cys
35 40

<210> SEQ ID NO 628
<211> LENGTH: 129
<212> TYPE: DNA
<213> ORGANISM: Artificial Sequence
<220> FEATURE:
<223> OTHER INFORMATION: Polynucleotide encoding the polypeptide of SEQ ID NO: 392

<400> SEQUENCE: 628
accaaatatt atggcaacgg cgtgtattgc aacagcaaaa aatgctgggt ggattggggc 60
accgcgcagg gctgcattga tgtggtgatt ggccagctgg gcggcggcat tccgggcaaa 120
ggcaaatgc 129

<210> SEQ ID NO 629
<211> LENGTH: 62
<212> TYPE: PRT
<213> ORGANISM: Enterococcus sp.

<400> SEQUENCE: 629

Asn Arg Trp Tyr Cys Asn Ser Ala Ala Gly Gly Val Gly Gly Ala Ala
1 5 10 15

Val Cys Gly Leu Ala Gly Tyr Val Gly Glu Ala Lys Glu Asn Ile Ala
20 25 30

Gly Glu Val Arg Lys Gly Trp Gly Met Ala Gly Gly Phe Thr His Asn
35 40 45

Lys Ala Cys Lys Ser Phe Pro Gly Ser Gly Trp Ala Ser Gly
50 55 60

<210> SEQ ID NO 630
<211> LENGTH: 186
<212> TYPE: DNA
<213> ORGANISM: Artificial Sequence
<220> FEATURE:
<223> OTHER INFORMATION: Polynucleotide encoding the polypeptide of SEQ ID NO: 394

<400> SEQUENCE: 630
aaccgctggt attgcaacag cgcggcgggc ggcgtgggcg gcgcggcggt gtgcggcctg 60
gcgggctatg tgggcgaagc gaaagaaaac attgcgggcg aagtgcgcaa aggctggggc 120
atggcgggcg gctttaccca taacaaagcg tgcaaaagct ttccgggcag cggctgggcg 180
agcggc 186

<210> SEQ ID NO 631
<211> LENGTH: 39
<212> TYPE: PRT
<213> ORGANISM: Enterococcus faecium

<400> SEQUENCE: 631

Thr Thr Lys Asn Tyr Gly Asn Gly Val Cys Asn Ser Val Asn Trp Cys
1 5 10 15

Gln Cys Gly Asn Val Trp Ala Ser Cys Asn Leu Ala Thr Gly Cys Ala
20 25 30

Ala Trp Leu Cys Lys Leu Ala
35

<210> SEQ ID NO 632
<211> LENGTH: 117
<212> TYPE: DNA
<213> ORGANISM: Artificial Sequence
<220> FEATURE:
<223> OTHER INFORMATION: Polynucleotide encoding the polypeptide of SEQ ID NO: 396

<400> SEQUENCE: 632
accaccaaaa actatggcaa cggcgtgtgc aacagcgtga actggtgcca gtgcggcaac 60
gtgtgggcga gctgcaacct ggcgaccggc tgcgcggcgt ggctgtgcaa actggcg 117

<210> SEQ ID NO 633
<211> LENGTH: 30
<212> TYPE: PRT
<213> ORGANISM: Paenibacillus polymyxa

<400> SEQUENCE: 633

Ala Ser Ile Ile Lys Thr Thr Ile Lys Val Ser Lys Ala Val Cys Lys
1 5 10 15

Thr Leu Thr Cys Ile Cys Thr Gly Ser Cys Ser Asn Cys Lys
20 25 30

<210> SEQ ID NO 634
<211> LENGTH: 90
<212> TYPE: DNA
<213> ORGANISM: Artificial Sequence
<220> FEATURE:
<223> OTHER INFORMATION: Polynucleotide encoding the polypeptide of SEQ ID NO: 398

<400> SEQUENCE: 634
gcgagcatta ttaaaaccac cattaaagtg agcaaagcgg tgtgcaaaac cctgacctgc 60
atttgcaccg gcagctgcag caactgcaaa 90

<210> SEQ ID NO 635
<211> LENGTH: 31
<212> TYPE: PRT
<213> ORGANISM: Staphylococcus epidermidis

<400> SEQUENCE: 635

Ser Ala Ser Ile Val Lys Thr Thr Ile Lys Ala Ser Lys Lys Leu Cys
1 5 10 15

Arg Gly Phe Thr Leu Thr Cys Gly Cys His Phe Thr Gly Lys Lys
20 25 30

<210> SEQ ID NO 636
<211> LENGTH: 93
<212> TYPE: DNA
<213> ORGANISM: Artificial Sequence
<220> FEATURE:
<223> OTHER INFORMATION: Polynucleotide encoding the polypeptide of SEQ ID NO: 400

<400> SEQUENCE: 636
agcgcgagca ttgtgaaaac caccattaaa gcgagcaaaa aactgtgccg cggctttacc 60
ctgacctgcg gctgccattt taccggcaaa aaa 93

<210> SEQ ID NO 637
<211> LENGTH: 43
<212> TYPE: PRT
<213> ORGANISM: Enterococcus faecium

<400> SEQUENCE: 637

Lys Tyr Tyr Gly Asn Gly Val Ser Cys Asn Lys Lys Gly Cys Ser Val
1 5 10 15

```
Asp Trp Gly Lys Ala Ile Gly Ile Ile Gly Asn Asn Ala Ala Ala Asn
            20                  25                  30

Leu Thr Thr Gly Gly Lys Ala Ala Trp Ala Cys
        35                  40


<210> SEQ ID NO 638
<211> LENGTH: 129
<212> TYPE: DNA
<213> ORGANISM: Artificial Sequence
<220> FEATURE:
<223> OTHER INFORMATION: Polynucleotide encoding the polypeptide of SEQ
      ID NO: 402

<400> SEQUENCE: 638

aaatattatg gcaacggcgt gagctgcaac aaaaaaggct gcagcgtgga ttggggcaaa      60

gcgattggca ttattggcaa caacgcggcg gcgaacctga ccaccggcgg caaagcggcg     120

tgggcgtgc                                                             129


<210> SEQ ID NO 639
<211> LENGTH: 39
<212> TYPE: PRT
<213> ORGANISM: Paenibacillus polymyxa

<400> SEQUENCE: 639

Ala Thr Tyr Tyr Gly Asn Gly Leu Tyr Cys Asn Lys Gln Lys His Tyr
1               5                   10                  15

Thr Trp Val Asp Trp Asn Lys Ala Ser Arg Glu Ile Gly Lys Ile Thr
            20                  25                  30

Val Asn Gly Trp Val Gln His
        35


<210> SEQ ID NO 640
<211> LENGTH: 117
<212> TYPE: DNA
<213> ORGANISM: Artificial Sequence
<220> FEATURE:
<223> OTHER INFORMATION: Polynucleotide encoding the polypeptide of SEQ
      ID NO: 404

<400> SEQUENCE: 640

gcgacctatt atggcaacgg cctgtattgc aacaaacaga aacattatac ctgggtggat      60

tggaacaaag cgagccgcga aattggcaaa attaccgtga acggctgggt gcagcat       117


<210> SEQ ID NO 641
<211> LENGTH: 35
<212> TYPE: PRT
<213> ORGANISM: Bacillus circulans

<400> SEQUENCE: 641

Val Asn Tyr Gly Asn Gly Val Ser Cys Ser Lys Thr Lys Cys Ser Val
1               5                   10                  15

Asn Trp Gly Ile Ile Thr His Gln Ala Phe Arg Val Thr Ser Gly Val
            20                  25                  30

Ala Ser Gly
        35


<210> SEQ ID NO 642
<211> LENGTH: 105
<212> TYPE: DNA
<213> ORGANISM: Artificial Sequence
<220> FEATURE:
<223> OTHER INFORMATION: Polynucleotide encoding the polypeptide of SEQ
```

ID NO: 406

<400> SEQUENCE: 642
gtgaactatg gcaacggcgt gagctgcagc aaaaccaaat gcagcgtgaa ctggggcatt 60
attacccatc aggcgtttcg cgtgaccagc ggcgtggcga gcggc 105

<210> SEQ ID NO 643
<211> LENGTH: 30
<212> TYPE: PRT
<213> ORGANISM: Paenibacillus polymyxa

<400> SEQUENCE: 643

Phe Val Tyr Gly Asn Gly Val Thr Ser Ile Leu Val Gln Ala Gln Phe
1 5 10 15

Leu Val Asn Gly Gln Arg Arg Phe Phe Tyr Thr Pro Asp Lys
20 25 30

<210> SEQ ID NO 644
<211> LENGTH: 90
<212> TYPE: DNA
<213> ORGANISM: Artificial Sequence
<220> FEATURE:
<223> OTHER INFORMATION: Polynucleotide encoding the polypeptide of SEQ ID NO: 408

<400> SEQUENCE: 644
tttgtgtatg gcaacggcgt gaccagcatt ctggtgcagg cgcagtttct ggtgaacggc 60
cagcgccgct ttttttatac cccggataaa 90

<210> SEQ ID NO 645
<211> LENGTH: 13
<212> TYPE: PRT
<213> ORGANISM: Lactobacillus rhamnosus

<400> SEQUENCE: 645

Ala Val Pro Ala Val Arg Lys Thr Asn Glu Thr Leu Asp
1 5 10

<210> SEQ ID NO 646
<211> LENGTH: 39
<212> TYPE: DNA
<213> ORGANISM: Artificial Sequence
<220> FEATURE:
<223> OTHER INFORMATION: Polynucleotide encoding the polypeptide of SEQ ID NO: 410

<400> SEQUENCE: 646
gcggtgccgg cggtgcgcaa aaccaacgaa accctggat 39

<210> SEQ ID NO 647
<211> LENGTH: 69
<212> TYPE: PRT
<213> ORGANISM: Bacillus licheniformis

<400> SEQUENCE: 647

Met Lys Asn Ser Ala Ala Arg Glu Ala Phe Lys Gly Ala Asn His Pro
1 5 10 15

Ala Gly Met Val Ser Glu Glu Glu Leu Lys Ala Leu Val Gly Gly Asn
20 25 30

Asp Val Asn Pro Glu Thr Thr Pro Ala Thr Thr Ser Ser Trp Thr Cys
35 40 45

Ile Thr Ala Gly Val Thr Val Ser Ala Ser Leu Cys Pro Thr Thr Lys 50 55 60

Cys Thr Ser Arg Cys
65

<210> SEQ ID NO 648
<211> LENGTH: 207
<212> TYPE: DNA
<213> ORGANISM: Artificial Sequence
<220> FEATURE:
<223> OTHER INFORMATION: Polynucleotide encoding the polypeptide of SEQ ID NO: 412

<400> SEQUENCE: 648
atgaaaaaca gcgcggcgcg cgaagcgttt aaaggcgcga accatccggc gggcatggtg 60
agcgaagaag aactgaaagc gctggtgggc ggcaacgatg tgaacccgga aaccaccccg 120
gcgaccacca gcagctggac ctgcattacc gcgggcgtga ccgtgagcgc gagcctgtgc 180
ccgaccacca aatgcaccag ccgctgc 207

<210> SEQ ID NO 649
<211> LENGTH: 36
<212> TYPE: PRT
<213> ORGANISM: Lactobacillus plantarum

<400> SEQUENCE: 649

Lys Tyr Tyr Gly Asn Gly Leu Ser Cys Ser Lys Lys Gly Cys Thr Val
1 5 10 15

Asn Trp Gly Gln Ala Phe Ser Cys Gly Val Asn Arg Val Ala Thr Ala
20 25 30

Gly His Gly Lys
35

<210> SEQ ID NO 650
<211> LENGTH: 108
<212> TYPE: DNA
<213> ORGANISM: Artificial Sequence
<220> FEATURE:
<223> OTHER INFORMATION: Polynucleotide encoding the polypeptide of SEQ ID NO: 414

<400> SEQUENCE: 650
aaatattatg gcaacggcct gagctgcagc aaaaaaggct gcaccgtgaa ctggggccag 60
gcgtttagct gcggcgtgaa ccgcgtggcg accgcgggcc atggcaaa 108

<210> SEQ ID NO 651
<211> LENGTH: 24
<212> TYPE: PRT
<213> ORGANISM: Lactobacillus acidophilus

<400> SEQUENCE: 651

Gly Asn Pro Lys Val Ala His Cys Ala Ser Gln Ile Gly Arg Ser Thr
1 5 10 15

Ala Trp Gly Ala Val Ser Gly Ala
20

<210> SEQ ID NO 652
<211> LENGTH: 72
<212> TYPE: DNA
<213> ORGANISM: Artificial Sequence
<220> FEATURE:
<223> OTHER INFORMATION: Polynucleotide encoding the polypeptide of SEQ ID NO: 416

<400> SEQUENCE: 652
ggcaacccga aagtggcgca ttgcgcgagc cagattggcc gcagcaccgc gtggggcgcg 60
gtgagcggcg cg 72

<210> SEQ ID NO 653
<211> LENGTH: 40
<212> TYPE: PRT
<213> ORGANISM: Enterococcus faecalis

<400> SEQUENCE: 653

Trp Leu Pro Pro Ala Gly Leu Leu Gly Arg Cys Gly Arg Trp Phe Arg
1 5 10 15

Pro Trp Leu Leu Trp Leu Gln Ser Gly Ala Gln Tyr Lys Trp Leu Gly
20 25 30

Asn Leu Phe Gly Leu Gly Pro Lys
35 40

<210> SEQ ID NO 654
<211> LENGTH: 120
<212> TYPE: DNA
<213> ORGANISM: Artificial Sequence
<220> FEATURE:
<223> OTHER INFORMATION: Polynucleotide encoding the polypeptide of SEQ ID NO: 418

<400> SEQUENCE: 654
tggctgccgc cggcgggcct gctgggccgc tgcggccgct ggtttcgccc gtggctgctg 60
tggctgcaga gcggcgcgca gtataaatgg ctgggcaacc tgtttggcct gggcccgaaa 120

<210> SEQ ID NO 655
<211> LENGTH: 40
<212> TYPE: PRT
<213> ORGANISM: Anabaena variabilis

<400> SEQUENCE: 655

Asn Leu Asp Gln Trp Leu Thr Glu Gln Val His Glu Phe Gln Asp Met
1 5 10 15

Tyr Leu Glu Pro Gln Ala Ile Ser Asn Gln Asp Ile Thr Phe Lys Leu
20 25 30

Ser Asp Leu Asp Phe Ile His Asn
35 40

<210> SEQ ID NO 656
<211> LENGTH: 124
<212> TYPE: DNA
<213> ORGANISM: Anabaena variabilis

<400> SEQUENCE: 656
taatttagat cagtggttaa cagaacaagt tcatgagttt caagatatgt acttggaacc 60
acaagcaata tccaatcaag acattacctt caaactatct gacctagatt ttattcataa 120
ttga 124

<210> SEQ ID NO 657
<211> LENGTH: 40
<212> TYPE: PRT
<213> ORGANISM: Nostoc sp

<400> SEQUENCE: 657

Asn Leu Asp Gln Trp Leu Thr Glu Gln Val His Glu Phe Gln Asp Met
1 5 10 15

Tyr Leu Glu Pro Gln Ala Ile Ser Asn Gln Asp Ile Thr Phe Lys Leu
20 25 30

Ser Asp Leu Asp Phe Ile His Asn
35 40

<210> SEQ ID NO 658
<211> LENGTH: 123
<212> TYPE: DNA
<213> ORGANISM: Nostoc sp

<400> SEQUENCE: 658
aatttagatc aatggttaac agaacaagtt catgagtttc aagatatgta cttggaacca 60
caagcaatat ccaatcaaga cattaccttc aaactgtcag acctagattt tattcataat 120
tga 123

<210> SEQ ID NO 659
<211> LENGTH: 7
<212> TYPE: PRT
<213> ORGANISM: Nostoc azollae

<400> SEQUENCE: 659

His Arg Glu Lys Lys Ser Ala
1 5

<210> SEQ ID NO 660
<211> LENGTH: 24
<212> TYPE: DNA
<213> ORGANISM: Nostoc azollae

<400> SEQUENCE: 660
cacagagaga aaaaatcagc atag 24

<210> SEQ ID NO 661
<211> LENGTH: 23
<212> TYPE: PRT
<213> ORGANISM: Acaryochloris marina

<400> SEQUENCE: 661

Thr Ser Asn Asn Trp Leu Ala Lys Asn Tyr Leu Ser Met Trp Asn Lys
1 5 10 15

Lys Ser Ser Asn Pro Asn Leu
20

<210> SEQ ID NO 662
<211> LENGTH: 72
<212> TYPE: DNA
<213> ORGANISM: Acaryochloris marina

<400> SEQUENCE: 662
acaagcaata actggctagc caaaaactat ctttctatgt ggaataaaaa gagcagtaat 60
ccaaaccttt ag 72

<210> SEQ ID NO 663
<211> LENGTH: 6
<212> TYPE: PRT
<213> ORGANISM: Cyanothece

<400> SEQUENCE: 663

Phe Arg Tyr Phe Trp Trp
1 5

<210> SEQ ID NO 664
<211> LENGTH: 21
<212> TYPE: DNA
<213> ORGANISM: Cyanothece

<400> SEQUENCE: 664
tttagatatt tttggtggta a 21

<210> SEQ ID NO 665
<211> LENGTH: 6
<212> TYPE: PRT
<213> ORGANISM: Cyanothece

<400> SEQUENCE: 665

Phe Arg Tyr Phe Trp Trp
1 5

<210> SEQ ID NO 666
<211> LENGTH: 21
<212> TYPE: DNA
<213> ORGANISM: Cyanothece

<400> SEQUENCE: 666
tttagatatt tttggtggta a 21

<210> SEQ ID NO 667
<211> LENGTH: 9
<212> TYPE: PRT
<213> ORGANISM: Cyanothece

<400> SEQUENCE: 667

Cys Gly Glu Lys Trp Arg Ile Phe Ser
1 5

<210> SEQ ID NO 668
<211> LENGTH: 27
<212> TYPE: DNA
<213> ORGANISM: Cyanothece

<400> SEQUENCE: 668
tgtggagaaa aatggagaat ttttagc 27

<210> SEQ ID NO 669
<211> LENGTH: 8
<212> TYPE: PRT
<213> ORGANISM: Cyanothece

<400> SEQUENCE: 669

Phe Arg Leu Gln Leu Trp Gln Phe
1 5

<210> SEQ ID NO 670
<211> LENGTH: 24
<212> TYPE: DNA
<213> ORGANISM: Cyanothece

<400> SEQUENCE: 670
tttcgcttac aactgtggca attt 24

<210> SEQ ID NO 671
<211> LENGTH: 16
<212> TYPE: PRT
<213> ORGANISM: Cyanothece

<400> SEQUENCE: 671

Leu Gly Cys Asn Gln Ser Ser Ile Trp Ser Ile Phe Phe Trp Asn His
1 5 10 15

<210> SEQ ID NO 672
<211> LENGTH: 51
<212> TYPE: DNA
<213> ORGANISM: Cyanothece

<400> SEQUENCE: 672
ctaggatgta accagagcag tatctggtca atttttttct ggaatcatta a 51

<210> SEQ ID NO 673
<211> LENGTH: 40
<212> TYPE: PRT
<213> ORGANISM: Microcoleus chthonoplastes

<400> SEQUENCE: 673

Tyr Asn Leu Gln Gly Leu Pro Ala Ile Glu Ser Glu Asp Cys Ile Pro
1 5 10 15

Asp Ser Val Ala Pro Ser Asp Asp Trp Phe Ser Gly Val Ser Ser Leu
20 25 30

Phe Asn Arg Leu Thr Gly Leu Gly
35 40

<210> SEQ ID NO 674
<211> LENGTH: 123
<212> TYPE: DNA
<213> ORGANISM: Microcoleus chthonoplastes

<400> SEQUENCE: 674
tataacctac aggggttgcc agcaattgag tcagaagact gtatcccaga ttctgtagcg 60
ccttcggatg attggttttc aggcgtatcg tctctgttta accgcttgac tgggttgggt 120
tag 123

<210> SEQ ID NO 675
<211> LENGTH: 37
<212> TYPE: PRT
<213> ORGANISM: Nostoc sp

<400> SEQUENCE: 675

Trp Met Ala Ile Arg Arg Ile Leu Arg Cys His Pro Phe His Pro Gly
1 5 10 15

Gly Tyr Asp Pro Val Pro Glu Leu Gly Glu His Cys Cys His His Asp
20 25 30

Ser Gly Asn Lys Gly
35

<210> SEQ ID NO 676
<211> LENGTH: 114
<212> TYPE: DNA
<213> ORGANISM: Nostoc sp

<400> SEQUENCE: 676
tggatggcga ttcgccgcat tttgcgttgt catccattcc acccaggggg ttatgatcct 60
gtaccagagt tgggtgagca ttgttgtcat catgatagcg ggaataaggg gtga 114

<210> SEQ ID NO 677
<211> LENGTH: 35
<212> TYPE: PRT

<213> ORGANISM: Anabaena variabilis

<400> SEQUENCE: 677

```
Trp Met Gly Ile Arg Arg Ile Leu Arg Cys His Pro Phe His Pro Gly
1               5                   10                  15

Gly Tyr Asp Pro Val Pro Glu Val Gly Glu His Cys Cys His His Asp
            20                  25                  30

Ser Gly Lys
        35
```

<210> SEQ ID NO 678
<211> LENGTH: 108
<212> TYPE: DNA
<213> ORGANISM: Anabaena variabilis

<400> SEQUENCE: 678

```
tggatgggga ttcgccgcat tttgcgttgt catccattcc acccaggcgg ttatgatcct     60

gtaccagagg tgggtgagca ttgttgtcat catgatagcg ggaagtag                 108
```

<210> SEQ ID NO 679
<211> LENGTH: 48
<212> TYPE: PRT
<213> ORGANISM: Nodularia spumigena

<400> SEQUENCE: 679

```
Trp Met Ala Thr Arg Arg Ile Leu Arg Cys His Pro Phe His Pro Gly
1               5                   10                  15

Gly Tyr Asp Pro Val Pro Glu Val Lys His Asn Cys Cys Asp Gln His
            20                  25                  30

Leu Ser Asp Ser Gly Lys Gln Thr Thr Glu Asp His His Lys Gly Ser
        35                  40                  45
```

<210> SEQ ID NO 680
<211> LENGTH: 147
<212> TYPE: DNA
<213> ORGANISM: Nodularia spumigena

<400> SEQUENCE: 680

```
tggatggcga ctcggcggat tttgcgttgt catcccttcc atcctggtgg atatgatcca     60

gttccagagg taaaacacaa ttgctgcgat cagcatctgt ccgattctgg gaaacagacc    120

acagaagacc atcacaaagg ctcgtag                                        147
```

<210> SEQ ID NO 681
<211> LENGTH: 34
<212> TYPE: PRT
<213> ORGANISM: Nostoc azollae

<400> SEQUENCE: 681

```
Trp Met Ala Thr Leu Arg Ile Leu Arg Cys His Pro Phe His Pro Gly
1               5                   10                  15

Gly Tyr Asp Pro Val Pro Gly Leu Ala Glu Lys Ser Cys Cys Asp His
            20                  25                  30

His Asp
```

<210> SEQ ID NO 682
<211> LENGTH: 105
<212> TYPE: DNA
<213> ORGANISM: Nostoc azollae

<400> SEQUENCE: 682
tggatggcaa ctttgcggat tttacgctgt catcctttcc atcctggtgg ttatgatcct 60
gtaccaggac tagcggaaaa atcctgttgt gaccatcatg attga 105

<210> SEQ ID NO 683
<211> LENGTH: 28
<212> TYPE: PRT
<213> ORGANISM: Synechococcus

<400> SEQUENCE: 683

Trp Leu Thr Ala Lys Arg Phe Cys Arg Cys His Pro Leu His Pro Gly
1 5 10 15

Gly Tyr Asp Pro Val Pro Glu Lys Lys Ser Val Leu
20 25

<210> SEQ ID NO 684
<211> LENGTH: 87
<212> TYPE: DNA
<213> ORGANISM: Synechococcus

<400> SEQUENCE: 684
tggctaacag ccaagcgctt ttgtcgctgt catccgcttc atcctggcgg gtatgatccg 60
gtaccggaga agaaatcggt actctaa 87

<210> SEQ ID NO 685
<211> LENGTH: 23
<212> TYPE: PRT
<213> ORGANISM: Prochlorococcus marinus

<400> SEQUENCE: 685

Trp Leu Thr Leu Arg Arg Leu Ser Arg Cys His Pro Phe Thr Pro Cys
1 5 10 15

Gly Cys Asp Pro Val Pro Asp
20

<210> SEQ ID NO 686
<211> LENGTH: 72
<212> TYPE: DNA
<213> ORGANISM: Prochlorococcus marinus

<400> SEQUENCE: 686
tggctcaccc tgcggcgcct gtctcgttgc catcctttta ccccctgtgg ttgcgacccg 60
gtgcctgatt aa 72

<210> SEQ ID NO 687
<211> LENGTH: 9
<212> TYPE: PRT
<213> ORGANISM: Lactobacillus curvatus

<400> SEQUENCE: 687

Asn Ile Pro Gln Leu Thr Pro Thr Pro
1 5

<210> SEQ ID NO 688
<211> LENGTH: 27
<212> TYPE: DNA
<213> ORGANISM: Lactobacillus curvatus

<400> SEQUENCE: 688
aacattccgc agctgacccc gaccccg 27

<210> SEQ ID NO 689
<211> LENGTH: 18
<212> TYPE: PRT
<213> ORGANISM: Bacillus thuringiensis
<220> FEATURE:
<221> NAME/KEY: misc_feature
<222> LOCATION: (4)..(4)
<223> OTHER INFORMATION: Xaa = any amino acid
<220> FEATURE:
<221> NAME/KEY: misc_feature
<222> LOCATION: (7)..(7)
<223> OTHER INFORMATION: Xaa = any amino acid
<220> FEATURE:
<221> NAME/KEY: misc_feature
<222> LOCATION: (10)..(10)
<223> OTHER INFORMATION: Xaa = any amino acid

<400> SEQUENCE: 689

```
Asp Trp Thr Xaa Trp Ser Xaa Leu Val Xaa Ala Ala Cys Ser Val Glu
1               5                   10                  15

Leu Leu
```

<210> SEQ ID NO 690
<211> LENGTH: 54
<212> TYPE: DNA
<213> ORGANISM: Bacillus thuringiensis
<220> FEATURE:
<221> NAME/KEY: misc_feature
<222> LOCATION: (10)..(12)
<223> OTHER INFORMATION: n = A,T,C or G
<220> FEATURE:
<221> NAME/KEY: misc_feature
<222> LOCATION: (19)..(21)
<223> OTHER INFORMATION: n = A,T,C or G
<220> FEATURE:
<221> NAME/KEY: misc_feature
<222> LOCATION: (28)..(30)
<223> OTHER INFORMATION: n = A,T,C or G

<400> SEQUENCE: 690

```
gattggaccn nntggagcnn nctggtgnnn gcggcgtgca gcgtggaact gctg           54
```

<210> SEQ ID NO 691
<211> LENGTH: 30
<212> TYPE: PRT
<213> ORGANISM: Lactobacillus curvatus L442

<400> SEQUENCE: 691

```
Ala Tyr Pro Gly Asn Gly Val His Cys Gly Lys Tyr Ser Cys Thr Val
1               5                   10                  15

Asp Lys Gln Thr Ala Ile Gly Asn Ile Gly Asn Asn Ala Ala
            20                  25                  30
```

<210> SEQ ID NO 692
<211> LENGTH: 90
<212> TYPE: DNA
<213> ORGANISM: Lactobacillus curvatus L442

<400> SEQUENCE: 692

```
gcgtatccgg gcaacggcgt gcattgcggc aaatatagct gcaccgtgga taaacagacc     60

gcgattggca acattggcaa caacgcggcg                                       90
```

<210> SEQ ID NO 693
<211> LENGTH: 43
<212> TYPE: PRT
<213> ORGANISM: Carnobacterium divergens

<400> SEQUENCE: 693

```
Thr Lys Tyr Tyr Gly Asn Gly Val Tyr Cys Asn Ser Lys Lys Cys Trp
1               5                   10                  15

Val Asp Trp Gly Thr Ala Gln Gly Cys Ile Asp Val Val Ile Gly Gln
            20                  25                  30

Leu Gly Gly Gly Ile Pro Gly Lys Gly Lys Cys
        35                  40


<210> SEQ ID NO 694
<211> LENGTH: 129
<212> TYPE: DNA
<213> ORGANISM: Carnobacterium divergens

<400> SEQUENCE: 694

accaaatatt atggcaacgg cgtgtattgc aacagcaaaa aatgctgggt ggattggggc      60

accgcgcagg gctgcattga tgtggtgatt ggccagctgg gcggcggcat tccgggcaaa     120

ggcaaatgc                                                              129


<210> SEQ ID NO 695
<211> LENGTH: 24
<212> TYPE: PRT
<213> ORGANISM: Microbispora sp. (strain 107891

<400> SEQUENCE: 695

Val Thr Ser Trp Ser Leu Cys Thr Pro Gly Cys Thr Ser Pro Gly Gly
1               5                   10                  15

Gly Ser Asn Cys Ser Phe Cys Cys
            20


<210> SEQ ID NO 696
<211> LENGTH: 72
<212> TYPE: DNA
<213> ORGANISM: Microbispora sp. (strain 107891

<400> SEQUENCE: 696

gtgaccagct ggagcctgtg caccccgggc tgcaccagcc cgggcggcgg cagcaactgc      60

agcttttgct gc                                                           72


<210> SEQ ID NO 697
<211> LENGTH: 62
<212> TYPE: PRT
<213> ORGANISM: Enterococcus sp.

<400> SEQUENCE: 697

Asn Arg Trp Tyr Cys Asn Ser Ala Ala Gly Gly Val Gly Gly Ala Ala
1               5                   10                  15

Val Cys Gly Leu Ala Gly Tyr Val Gly Glu Ala Lys Glu Asn Ile Ala
            20                  25                  30

Gly Glu Val Arg Lys Gly Trp Gly Met Ala Gly Gly Phe Thr His Asn
        35                  40                  45

Lys Ala Cys Lys Ser Phe Pro Gly Ser Gly Trp Ala Ser Gly
    50                  55                  60


<210> SEQ ID NO 698
<211> LENGTH: 186
<212> TYPE: DNA
<213> ORGANISM: Enterococcus sp.

<400> SEQUENCE: 698

aaccgctggt attgcaacag cgcggcgggc ggcgtgggcg gcgcggcggt gtgcggcctg      60
```

gcgggctatg tgggcgaagc gaaagaaaac attgcgggcg aagtgcgcaa aggctggggc 120
atggcgggcg gctttaccca taacaaagcg tgcaaaagct ttccgggcag cggctgggcg 180
agcggc 186

<210> SEQ ID NO 699
<211> LENGTH: 39
<212> TYPE: PRT
<213> ORGANISM: Enterococcus faecium

<400> SEQUENCE: 699

Thr Thr Lys Asn Tyr Gly Asn Gly Val Cys Asn Ser Val Asn Trp Cys
1 5 10 15

Gln Cys Gly Asn Val Trp Ala Ser Cys Asn Leu Ala Thr Gly Cys Ala
20 25 30

Ala Trp Leu Cys Lys Leu Ala
35

<210> SEQ ID NO 700
<211> LENGTH: 117
<212> TYPE: DNA
<213> ORGANISM: Enterococcus faecium

<400> SEQUENCE: 700
accaccaaaa actatggcaa cggcgtgtgc aacagcgtga actggtgcca gtgcggcaac 60
gtgtgggcga gctgcaacct ggcgaccggc tgcgcggcgt ggctgtgcaa actggcg 117

<210> SEQ ID NO 701
<211> LENGTH: 30
<212> TYPE: PRT
<213> ORGANISM: Paenibacillus polymyxa

<400> SEQUENCE: 701

Ala Ser Ile Ile Lys Thr Thr Ile Lys Val Ser Lys Ala Val Cys Lys
1 5 10 15

Thr Leu Thr Cys Ile Cys Thr Gly Ser Cys Ser Asn Cys Lys
20 25 30

<210> SEQ ID NO 702
<211> LENGTH: 90
<212> TYPE: DNA
<213> ORGANISM: Paenibacillus polymyxa

<400> SEQUENCE: 702
gcgagcatta ttaaaaccac cattaaagtg agcaaagcgg tgtgcaaaac cctgacctgc 60
atttgcaccg gcagctgcag caactgcaaa 90

<210> SEQ ID NO 703
<211> LENGTH: 31
<212> TYPE: PRT
<213> ORGANISM: Staphylococcus epidermidis

<400> SEQUENCE: 703

Ser Ala Ser Ile Val Lys Thr Thr Ile Lys Ala Ser Lys Lys Leu Cys
1 5 10 15

Arg Gly Phe Thr Leu Thr Cys Gly Cys His Phe Thr Gly Lys Lys
20 25 30

<210> SEQ ID NO 704
<211> LENGTH: 93

<212> TYPE: DNA
<213> ORGANISM: Staphylococcus epidermidis

<400> SEQUENCE: 704
agcgcgagca ttgtgaaaac caccattaaa gcgagcaaaa aactgtgccg cggctttacc 60
ctgacctgcg gctgccattt taccggcaaa aaa 93

<210> SEQ ID NO 705
<211> LENGTH: 58
<212> TYPE: PRT
<213> ORGANISM: Enterococcus faecium

<400> SEQUENCE: 705

Met Glu Lys Leu Thr Val Lys Glu Met Ser Gln Val Val Gly Gly Lys
1 5 10 15

Tyr Tyr Gly Asn Gly Val Ser Cys Asn Lys Lys Gly Cys Ser Val Asp
20 25 30

Trp Gly Lys Ala Ile Gly Ile Ile Gly Asn Asn Ala Ala Ala Asn Leu
35 40 45

Thr Thr Gly Gly Lys Ala Gly Trp Lys Gly
50 55

<210> SEQ ID NO 706
<211> LENGTH: 178
<212> TYPE: DNA
<213> ORGANISM: Enterococcus faecium

<400> SEQUENCE: 706
atggaaaaat taactgtgaa agaaatgtcg caagtagttg gcggaaagta ctatggtaac 60
ggagtatcat gtaataaaaa gggatgtagt gttgattggg gaaaagctat tggtattatt 120
ggaaataatg ctgctgctaa tttaactact ggcggaaaag cagggtggaa aggttaac 178

<210> SEQ ID NO 707
<211> LENGTH: 39
<212> TYPE: PRT
<213> ORGANISM: Paenibacillus polymyxa

<400> SEQUENCE: 707

Ala Thr Tyr Tyr Gly Asn Gly Leu Tyr Cys Asn Lys Gln Lys His Tyr
1 5 10 15

Thr Trp Val Asp Trp Asn Lys Ala Ser Arg Glu Ile Gly Lys Ile Thr
20 25 30

Val Asn Gly Trp Val Gln His
35

<210> SEQ ID NO 708
<211> LENGTH: 93
<212> TYPE: DNA
<213> ORGANISM: Paenibacillus polymyxa

<400> SEQUENCE: 708
agcgcgagca ttgtgaaaac caccattaaa gcgagcaaaa aactgtgccg cggctttacc 60
ctgacctgcg gctgccattt taccggcaaa aaa 93

<210> SEQ ID NO 709
<211> LENGTH: 35
<212> TYPE: PRT
<213> ORGANISM: Bacillus circulans

<400> SEQUENCE: 709

Val Asn Tyr Gly Asn Gly Val Ser Cys Ser Lys Thr Lys Cys Ser Val
1 5 10 15

Asn Trp Gly Ile Ile Thr His Gln Ala Phe Arg Val Thr Ser Gly Val
20 25 30

Ala Ser Gly
35

<210> SEQ ID NO 710
<211> LENGTH: 105
<212> TYPE: DNA
<213> ORGANISM: Bacillus circulans

<400> SEQUENCE: 710
gtgaactatg gcaacggcgt gagctgcagc aaaaccaaat gcagcgtgaa ctggggcatt 60
attacccatc aggcgtttcg cgtgaccagc ggcgtggcga gcggc 105

<210> SEQ ID NO 711
<211> LENGTH: 30
<212> TYPE: PRT
<213> ORGANISM: Paenibacillus polymyxa

<400> SEQUENCE: 711

Phe Val Tyr Gly Asn Gly Val Thr Ser Ile Leu Val Gln Ala Gln Phe
1 5 10 15

Leu Val Asn Gly Gln Arg Arg Phe Phe Tyr Thr Pro Asp Lys
20 25 30

<210> SEQ ID NO 712
<211> LENGTH: 90
<212> TYPE: DNA
<213> ORGANISM: Paenibacillus polymyxa

<400> SEQUENCE: 712
tttgtgtatg gcaacggcgt gaccagcatt ctggtgcagg cgcagtttct ggtgaacggc 60
cagcgccgct ttttttatac cccggataaa 90

<210> SEQ ID NO 713
<211> LENGTH: 13
<212> TYPE: PRT
<213> ORGANISM: Lactobacillus rhamnosus

<400> SEQUENCE: 713

Ala Val Pro Ala Val Arg Lys Thr Asn Glu Thr Leu Asp
1 5 10

<210> SEQ ID NO 714
<211> LENGTH: 39
<212> TYPE: DNA
<213> ORGANISM: Lactobacillus rhamnosus

<400> SEQUENCE: 714
gcggtgccgg cggtgcgcaa aaccaacgaa accctggat 39

<210> SEQ ID NO 715
<211> LENGTH: 60
<212> TYPE: PRT
<213> ORGANISM: Bacillus licheniformis

<400> SEQUENCE: 715

Met Lys Asn Ser Ala Ala Arg Glu Ala Phe Lys Gly Ala Asn His Pro
1 5 10 15

```
Ala Gly Met Val Ser Glu Glu Glu Leu Lys Ala Leu Val Gly Gly Asn
            20                  25                  30

Asp Val Asn Pro Glu Thr Thr Pro Ala Thr Thr Ser Ser Trp Thr Cys
        35                  40                  45

Ile Thr Ala Gly Val Thr Val Ser Ala Ser Leu Cys
    50                  55                  60


<210> SEQ ID NO 716
<211> LENGTH: 180
<212> TYPE: DNA
<213> ORGANISM: Bacillus licheniformis

<400> SEQUENCE: 716

atgaaaaaca gcgcggcgcg cgaagcgttt aaaggcgcga accatccggc gggcatggtg      60

agcgaagaag aactgaaagc gctggtgggc ggcaacgatg tgaacccgga aaccaccccg     120

gcgaccacca gcagctggac ctgcattacc gcgggcgtga ccgtgagcgc gagcctgtgc     180


<210> SEQ ID NO 717
<211> LENGTH: 689
<212> TYPE: PRT
<213> ORGANISM: Pseudomonas aeruginosa

<400> SEQUENCE: 717

Met Ala Val Asn Asp Tyr Glu Pro Gly Ser Met Val Ile Thr His Val
1               5                   10                  15

Gln Gly Gly Gly Arg Asp Ile Ile Gln Tyr Ile Pro Ala Arg Ser Ser
            20                  25                  30

Tyr Gly Thr Pro Pro Phe Val Pro Pro Gly Pro Ser Pro Tyr Val Gly
        35                  40                  45

Thr Gly Met Gln Glu Tyr Arg Lys Leu Arg Ser Thr Leu Asp Lys Ser
    50                  55                  60

His Ser Glu Leu Lys Lys Asn Leu Lys Asn Glu Thr Leu Lys Glu Val
65                  70                  75                  80

Asp Glu Leu Lys Ser Glu Ala Gly Leu Pro Gly Lys Ala Val Ser Ala
                85                  90                  95

Asn Asp Ile Arg Asp Glu Lys Ser Ile Val Asp Ala Leu Met Asp Ala
            100                 105                 110

Lys Ala Lys Ser Leu Lys Ala Ile Glu Asp Arg Pro Ala Asn Leu Tyr
        115                 120                 125

Thr Ala Ser Asp Phe Pro Gln Lys Ser Glu Ser Met Tyr Gln Ser Gln
    130                 135                 140

Leu Leu Ala Ser Arg Lys Phe Tyr Gly Glu Phe Leu Asp Arg His Met
145                 150                 155                 160

Ser Glu Leu Ala Lys Ala Tyr Ser Ala Asp Ile Tyr Lys Ala Gln Ile
                165                 170                 175

Ala Ile Leu Lys Gln Thr Ser Gln Glu Leu Glu Asn Lys Ala Arg Ser
            180                 185                 190

Leu Glu Ala Glu Ala Gln Arg Ala Ala Ala Glu Val Glu Ala Asp Tyr
        195                 200                 205

Lys Ala Arg Lys Ala Asn Val Glu Lys Lys Val Gln Ser Glu Leu Asp
    210                 215                 220

Gln Ala Gly Asn Ala Leu Pro Gln Leu Thr Asn Pro Thr Pro Glu Gln
225                 230                 235                 240

Trp Leu Glu Arg Ala Thr Gln Leu Val Thr Gln Ala Ile Ala Asn Lys
                245                 250                 255
```

-continued

```
Lys Lys Leu Gln Thr Ala Asn Asn Ala Leu Ile Ala Lys Ala Pro Asn
            260                 265                 270

Ala Leu Glu Lys Gln Lys Ala Thr Tyr Asn Ala Asp Leu Leu Val Asp
        275                 280                 285

Glu Ile Ala Ser Leu Gln Ala Arg Leu Asp Lys Leu Asn Ala Glu Thr
    290                 295                 300

Ala Arg Arg Lys Glu Ile Ala Arg Gln Ala Ala Ile Arg Ala Ala Asn
305                 310                 315                 320

Thr Tyr Ala Met Pro Ala Asn Gly Ser Val Val Ala Thr Ala Ala Gly
                325                 330                 335

Arg Gly Leu Ile Gln Val Ala Gln Gly Ala Ala Ser Leu Ala Gln Ala
            340                 345                 350

Ile Ser Asp Ala Ile Ala Val Leu Gly Arg Val Leu Ala Ser Ala Pro
        355                 360                 365

Ser Val Met Ala Val Gly Phe Ala Ser Leu Thr Tyr Ser Ser Arg Thr
    370                 375                 380

Ala Glu Gln Trp Gln Asp Gln Thr Pro Asp Ser Val Arg Tyr Ala Leu
385                 390                 395                 400

Gly Met Asp Ala Ala Lys Leu Gly Leu Pro Pro Ser Val Asn Leu Asn
                405                 410                 415

Ala Val Ala Lys Ala Ser Gly Thr Val Asp Leu Pro Met Arg Leu Thr
            420                 425                 430

Asn Glu Ala Arg Gly Asn Thr Thr Thr Leu Ser Val Val Ser Thr Asp
        435                 440                 445

Gly Val Ser Val Pro Lys Ala Val Pro Val Arg Met Ala Ala Tyr Asn
    450                 455                 460

Ala Thr Thr Gly Leu Tyr Glu Val Thr Val Pro Ser Thr Thr Ala Glu
465                 470                 475                 480

Ala Pro Pro Leu Ile Leu Thr Trp Thr Pro Ala Ser Pro Pro Gly Asn
                485                 490                 495

Gln Asn Pro Ser Ser Thr Thr Pro Val Val Pro Lys Pro Val Pro Val
            500                 505                 510

Tyr Glu Gly Ala Thr Leu Thr Pro Val Lys Ala Thr Pro Glu Thr Tyr
        515                 520                 525

Pro Gly Val Ile Thr Leu Pro Glu Asp Leu Ile Ile Gly Phe Pro Ala
    530                 535                 540

Asp Ser Gly Ile Lys Pro Ile Tyr Val Met Phe Arg Asp Pro Arg Asp
545                 550                 555                 560

Val Pro Gly Ala Ala Thr Gly Lys Gly Gln Pro Val Ser Gly Asn Trp
                565                 570                 575

Leu Gly Ala Ala Ser Gln Gly Glu Gly Ala Pro Ile Pro Ser Gln Ile
            580                 585                 590

Ala Asp Lys Leu Arg Gly Lys Thr Phe Lys Asn Trp Arg Asp Phe Arg
        595                 600                 605

Glu Gln Phe Trp Ile Ala Val Ala Asn Asp Pro Glu Leu Ser Lys Gln
    610                 615                 620

Phe Asn Pro Gly Ser Leu Ala Val Met Arg Asp Gly Gly Ala Pro Tyr
625                 630                 635                 640

Val Arg Glu Ser Glu Gln Ala Gly Gly Arg Ile Lys Ile Glu Ile His
                645                 650                 655

His Lys Val Arg Ile Ala Asp Gly Gly Gly Val Tyr Asn Met Gly Asn
            660                 665                 670
```

Leu Val Ala Val Thr Pro Lys Arg His Ile Glu Ile His Lys Gly Gly
675 680 685

Lys

<210> SEQ ID NO 718
<211> LENGTH: 2070
<212> TYPE: DNA
<213> ORGANISM: Pseudomonas aeruginosa

<400> SEQUENCE: 718
atggctgtca atgattacga acctggttcg atggttatta cacatgtgca gggtggtggg 60
cgtgacataa tccagtatat tcctgctcga tcaagctacg gtactccacc atttgtccca 120
ccaggaccaa gtccgtatgt cggtactgga atgcaggagt acaggaagct aagaagtacg 180
cttgataagt cccattcaga actcaagaaa aacctgaaaa atgaaaccct gaaggaggtt 240
gatgaactca agagtgaagc ggggttgcca ggtaaagcgg tcagtgccaa tgacatccgc 300
gatgaaaaga gtatcgttga tgcactcatg gatgccaaag caaaatcgct aaaggccatt 360
gaggatcgcc cggccaatct ttatacggct tcagactttc ctcagaagtc agagtcgatg 420
taccagagtc agttgctggc cagccgaaaa ttctatggag agttcctgga tcgccatatg 480
agtgagctgg ccaaagcgta cagcgccgat atctataagg cgcaaatcgc tatcttgaaa 540
caaacgtctc aagagctgga gaataaagcc cggtcattgg aagcagaagc ccagcgagcc 600
gctgctgagg tggaggcgga ctacaaggcc aggaaggcaa atgtcgagaa aaaagtgcag 660
tccgagcttg accaggctgg gaatgctttg cctcaactga ccaatccaac gccagagcag 720
tggcttgaac gcgctactca actggttacg caggcgatcg ccaataagaa gaaattgcag 780
actgcaaaca atgccttgat tgccaaggca cccaatgcac tggagaaaca aaaggcaacc 840
tacaacgccg atctcctagt ggatgaaatc gccagcctgc aagcacggct ggacaagctg 900
aacgccgaaa cggcaaggcg caaggaaatc gctcgtcaag cggcgatcag ggctgccaat 960
acttatgcca tgccagccaa tggcagcgtt gtcgccaccg ccgcaggccg gggtctgatc 1020
caggtcgcac aaggcgccgc atcccttgct caagcgatct ccgatgcgat tgccgtcctg 1080
ggccgggtcc tggcttcagc accctcggtg atggccgtgg gctttgccag tctgacctac 1140
tcctcccgga ctgccgagca atggcaggac caaacgcccg atagcgttcg ttacgccctg 1200
ggcatggatg ccgctaaatt ggggcttccc ccaagcgtaa acctgaacgc ggttgcaaaa 1260
gccagcggta ccgtcgatct gccgatgcgc ctgaccaacg aggcacgagg caacacgacg 1320
accctttcgg tggtcagcac cgatggtgtg agcgttccga aagccgttcc ggtccggatg 1380
gcggcctaca atgccacgac aggcctgtac gaggttacgg ttccctctac gaccgcagaa 1440
gcgccgccac tgatcctgac ctggacgccg gcgagtcctc caggaaacca gaacccttcg 1500
agtaccactc cggtcgtacc gaagccggtg ccggtatatg agggagcgac ccttacaccg 1560
gtgaaggcta ccccggaaac ctatcctggg gtgattacac taccggaaga cctgatcatc 1620
ggcttcccgg ccgactcggg gatcaagccg atctatgtga tgttcaggga tccgcgggat 1680
gtacctggtg ctgcgactgg caagggacag cccgtcagcg gtaattggct cggcgccgcc 1740
tctcaaggtg agggggctcc aattccaagc cagattgcgg ataaactacg tggtaagaca 1800
ttcaaaaact ggcgggactt tcgggaacaa ttctggatag ctgtggctaa tgatcctgag 1860
ttaagtaaac agtttaatcc tggtagttta gctgtaatga gagatggagg ggctccttat 1920
gtcagagagt cagaacaggc tggcgggaga ataaagatcg aaatccacca caaggttcga 1980
atagcagatg gaggcggcgt ttacaatatg gggaaccttg ttgcagtaac gccaaaacgt 2040
catatagaaa tccacaaggg agggaagtga 2070

<210> SEQ ID NO 719
<211> LENGTH: 36
<212> TYPE: PRT
<213> ORGANISM: Lactobacillus plantarum

<400> SEQUENCE: 719

Lys Tyr Tyr Gly Asn Gly Leu Ser Cys Ser Lys Lys Gly Cys Thr Val
1 5 10 15

Asn Trp Gly Gln Ala Phe Ser Cys Gly Val Asn Arg Val Ala Thr Ala
20 25 30

Gly His Gly Lys
35

<210> SEQ ID NO 720
<211> LENGTH: 108
<212> TYPE: DNA
<213> ORGANISM: Lactobacillus plantarum

<400> SEQUENCE: 720
aaatattatg gcaacggcct gagctgcagc aaaaaaggct gcaccgtgaa ctggggccag 60
gcgtttagct gcggcgtgaa ccgcgtggcg accgcgggcc atggcaaa 108

<210> SEQ ID NO 721
<211> LENGTH: 30
<212> TYPE: PRT
<213> ORGANISM: Lactococcus lactis

<400> SEQUENCE: 721

Met Lys Thr Ile Leu Arg Phe Val Ala Gly Tyr Asp Ile Ala Ser His
1 5 10 15

Lys Lys Lys Thr Gly Gly Tyr Pro Trp Glu Arg Gly Lys Ala
20 25 30

<210> SEQ ID NO 722
<211> LENGTH: 93
<212> TYPE: DNA
<213> ORGANISM: Lactococcus lactis

<400> SEQUENCE: 722
atgaaaacaa tcctacgttt tgttgctggc tacgatattg ctagtcataa aaagaaaact 60
ggcggctatc catgggaacg tggaaaagct taa 93

<210> SEQ ID NO 723
<211> LENGTH: 24
<212> TYPE: PRT
<213> ORGANISM: Lactobacillus acidophilus

<400> SEQUENCE: 723

Gly Asn Pro Lys Val Ala His Cys Ala Ser Gln Ile Gly Arg Ser Thr
1 5 10 15

Ala Trp Gly Ala Val Ser Gly Ala
20

<210> SEQ ID NO 724
<211> LENGTH: 72
<212> TYPE: DNA
<213> ORGANISM: Lactobacillus acidophilus

<400> SEQUENCE: 724
ggcaacccga aagtggcgca ttgcgcgagc cagattggcc gcagcaccgc gtggggcgcg 60
gtgagcggcg cg 72

<210> SEQ ID NO 725
<211> LENGTH: 53
<212> TYPE: PRT
<213> ORGANISM: Lactobacillus salivarius cp400

<400> SEQUENCE: 725

Met Phe Phe Asn Phe Met Lys Lys Val Asp Val Lys Lys Asn Phe Gly
1 5 10 15

Tyr Lys Glu Val Ser Arg Lys Asp Leu Ala Lys Val Asn Gly Gly Lys
20 25 30

Arg Lys Lys His Arg Cys Arg Val Tyr Asn Asn Gly Met Pro Thr Gly
35 40 45

Met Tyr Arg Trp Cys
50

<210> SEQ ID NO 726
<211> LENGTH: 162
<212> TYPE: DNA
<213> ORGANISM: Lactobacillus salivarius cp400

<400> SEQUENCE: 726
atgtttttta attttatgaa aaaagtagat gtgaagaaga attttggata taaagaagtt 60
tctagaaaag atctagctaa agtaaatggt ggaaagagaa agaaacatcg ttgcagagtt 120
tataataatg gaatgcctac aggaatgtat cgttggtgct aa 162

<210> SEQ ID NO 727
<211> LENGTH: 40
<212> TYPE: PRT
<213> ORGANISM: Artificial sequence
<220> FEATURE:
<223> OTHER INFORMATION: Enterococcus faecalis peptide

<400> SEQUENCE: 727

Trp Leu Pro Pro Ala Gly Leu Leu Gly Arg Cys Gly Arg Trp Phe Arg
1 5 10 15

Pro Trp Leu Leu Trp Leu Gln Ser Gly Ala Gln Tyr Lys Trp Leu Gly
20 25 30

Asn Leu Phe Gly Leu Gly Pro Lys
35 40

<210> SEQ ID NO 728
<211> LENGTH: 8
<212> TYPE: PRT
<213> ORGANISM: Artificial sequence
<220> FEATURE:
<223> OTHER INFORMATION: Consensus motif

<400> SEQUENCE: 728

Leu Pro Phe Trp Leu Val Leu Gly
1 5

<210> SEQ ID NO 729
<211> LENGTH: 8
<212> TYPE: PRT
<213> ORGANISM: Artificial sequence
<220> FEATURE:
<223> OTHER INFORMATION: sBH6

<400> SEQUENCE: 729

Leu Ala Phe Trp Leu Ile Leu Gly
1               5

<210> SEQ ID NO 730
<211> LENGTH: 8
<212> TYPE: PRT
<213> ORGANISM: Artificial sequence
<220> FEATURE:
<223> OTHER INFORMATION: sBI7

<400> SEQUENCE: 730

Leu Pro Phe Trp Leu Ile Leu Gly
1               5

<210> SEQ ID NO 731
<211> LENGTH: 8
<212> TYPE: PRT
<213> ORGANISM: Artificial sequence
<220> FEATURE:
<223> OTHER INFORMATION: sBI10

<400> SEQUENCE: 731

Leu Pro Tyr Trp Leu Leu Ile Gly
1               5

<210> SEQ ID NO 732
<211> LENGTH: 8
<212> TYPE: PRT
<213> ORGANISM: Artificial sequence
<220> FEATURE:
<223> OTHER INFORMATION: sBJ1

<400> SEQUENCE: 732

Leu Pro Phe Trp Leu Ser Val Gly
1               5

<210> SEQ ID NO 733
<211> LENGTH: 8
<212> TYPE: PRT
<213> ORGANISM: Artificial sequence
<220> FEATURE:
<223> OTHER INFORMATION: sBK1

<400> SEQUENCE: 733

Leu Pro Tyr Trp Leu Asp Met Gly
1               5

<210> SEQ ID NO 734
<211> LENGTH: 8
<212> TYPE: PRT
<213> ORGANISM: Artificial sequence
<220> FEATURE:
<223> OTHER INFORMATION: sBK3

<400> SEQUENCE: 734

Ile Leu Trp Trp Gly Thr Met Ile
1               5

<210> SEQ ID NO 735
<211> LENGTH: 8
<212> TYPE: PRT
<213> ORGANISM: Artificial sequence
<220> FEATURE:
<223> OTHER INFORMATION: sBK4

<400> SEQUENCE: 735

Leu Tyr Trp Ala Thr Thr Gly Leu
1               5

<210> SEQ ID NO 736
<211> LENGTH: 8
<212> TYPE: PRT
<213> ORGANISM: Artificial sequence
<220> FEATURE:
<223> OTHER INFORMATION: sBK8

<400> SEQUENCE: 736

Leu Pro Tyr Trp Val Thr Met Gly
1               5

<210> SEQ ID NO 737
<211> LENGTH: 8
<212> TYPE: PRT
<213> ORGANISM: Artificial sequence
<220> FEATURE:
<223> OTHER INFORMATION: sBO2

<400> SEQUENCE: 737

Leu Pro Phe Trp Cys Val Leu Gly
1               5

<210> SEQ ID NO 738
<211> LENGTH: 52
<212> TYPE: DNA
<213> ORGANISM: Artificial sequence
<220> FEATURE:
<223> OTHER INFORMATION: PcomX

<400> SEQUENCE: 738
ttttatagtg acatatatgt cgctatttta tttcttattt atctcttata at            52

<210> SEQ ID NO 739
<211> LENGTH: 52
<212> TYPE: DNA
<213> ORGANISM: Artificial sequence
<220> FEATURE:
<223> OTHER INFORMATION: PcomS

<400> SEQUENCE: 739
aatggtggtg acataaatgt cactactttt ttaatggtta aatgtttact at            52

<210> SEQ ID NO 740
<211> LENGTH: 52
<212> TYPE: DNA
<213> ORGANISM: Artificial sequence
<220> FEATURE:
<223> OTHER INFORMATION: PslvX

<400> SEQUENCE: 740
ctccatagtg acatttatgt cactattttt tattggccat cttacctata at            52

<210> SEQ ID NO 741
<211> LENGTH: 56
<212> TYPE: DNA
<213> ORGANISM: Artificial sequence
<220> FEATURE:
<223> OTHER INFORMATION: PsptA

<400> SEQUENCE: 741
taacgagtca aagtgacata gatgtccttt tgattcgtta tttttttgtt tatact        56

<210> SEQ ID NO 742
<211> LENGTH: 52
<212> TYPE: DNA
<213> ORGANISM: Artificial sequence
<220> FEATURE:
<223> OTHER INFORMATION: P00176

<400> SEQUENCE: 742
tgccatagtg acatttatgt cactattttt ataatcattt aatgattata at 52

<210> SEQ ID NO 743
<211> LENGTH: 52
<212> TYPE: DNA
<213> ORGANISM: Artificial sequence
<220> FEATURE:
<223> OTHER INFORMATION: P01584

<400> SEQUENCE: 743
gcgagtagtg acatttatgt cactactttt ttatcggctt ccaatctata at 52

<210> SEQ ID NO 744
<211> LENGTH: 52
<212> TYPE: DNA
<213> ORGANISM: Artificial sequence
<220> FEATURE:
<223> OTHER INFORMATION: PblpK

<400> SEQUENCE: 744
tcgagtagtg acatttatgt cactactttt ttgttggcct acaacttata at 52

<210> SEQ ID NO 745
<211> LENGTH: 52
<212> TYPE: DNA
<213> ORGANISM: Artificial sequence
<220> FEATURE:
<223> OTHER INFORMATION: PslvV

<400> SEQUENCE: 745
tcaggtagtg acatttatgt cactactttt ttgttggctt tctatctata at 52

<210> SEQ ID NO 746
<211> LENGTH: 52
<212> TYPE: DNA
<213> ORGANISM: Artificial sequence
<220> FEATURE:
<223> OTHER INFORMATION: PblpG

<400> SEQUENCE: 746
tggaatggtg acatctatgt cactattttt tatcttgtta agctcttata at 52

<210> SEQ ID NO 747
<211> LENGTH: 52
<212> TYPE: DNA
<213> ORGANISM: Artificial sequence
<220> FEATURE:
<223> OTHER INFORMATION: PslvW

<400> SEQUENCE: 747
agtgatagtg acatttatgt cactattttt ttgaaaagag agaacctata at 52

<210> SEQ ID NO 748
<211> LENGTH: 52
<212> TYPE: DNA
<213> ORGANISM: Artificial sequence
<220> FEATURE:
<223> OTHER INFORMATION: PslvY -continued

```
<400> SEQUENCE: 748

taccatggtg acatttatgt cactactttt ttatttctcg acaccttata at            52


<210> SEQ ID NO 749
<211> LENGTH: 8
<212> TYPE: PRT
<213> ORGANISM: Artificial sequence
<220> FEATURE:
<223> OTHER INFORMATION: Peptide

<400> SEQUENCE: 749

Leu Ala Phe Trp Asp Ser Leu Gly
1               5


<210> SEQ ID NO 750
<211> LENGTH: 11
<212> TYPE: PRT
<213> ORGANISM: Artificial sequence
<220> FEATURE:
<223> OTHER INFORMATION: Peptide

<400> SEQUENCE: 750

Leu Ala Phe Trp Asp Ser Leu Gly Leu Leu Leu
1               5                   10


<210> SEQ ID NO 751
<211> LENGTH: 30
<212> TYPE: PRT
<213> ORGANISM: Artificial sequence
<220> FEATURE:
<223> OTHER INFORMATION: Peptide

<400> SEQUENCE: 751

Thr Asn Val Thr Lys Ser Trp Trp Val Leu Ala Gly Cys Asn Gln Val
1               5                   10                  15

Val Ala Ser Asn Cys Asn Cys Gly Asn Val Lys Gly Leu Thr
            20                  25                  30


<210> SEQ ID NO 752
<211> LENGTH: 5
<212> TYPE: PRT
<213> ORGANISM: Artificial sequence
<220> FEATURE:
<223> OTHER INFORMATION: Peptide

<400> SEQUENCE: 752

Val Lys Gly Leu Thr
1               5
```